United States Patent
Bailey et al.

(10) Patent No.: US 8,633,009 B2
(45) Date of Patent: Jan. 21, 2014

(54) PRODUCTION OF QUINONE DERIVED COMPOUNDS IN OLEAGINOUS YEAST AND FUNGI

(75) Inventors: Richard B. Bailey, South Natick, MA (US); Kevin T. Madden, Arlington, MA (US); Joshua Trueheart, Concord, MA (US)

(73) Assignee: DSM IP Assets B.V., Heerlen (NL)

( * ) Notice: Subject to any disclaimer, the term of this patent is extended or adjusted under 35 U.S.C. 154(b) by 673 days.

(21) Appl. No.: 12/293,237

(22) PCT Filed: Mar. 20, 2007

(86) PCT No.: PCT/US2007/006834
§ 371 (c)(1),
(2), (4) Date: Mar. 9, 2009

(87) PCT Pub. No.: WO2007/120423
PCT Pub. Date: Oct. 25, 2007

(65) Prior Publication Data
US 2009/0324800 A1    Dec. 31, 2009

Related U.S. Application Data

(60) Provisional application No. 60/784,499, filed on Mar. 20, 2006, provisional application No. 60/848,064, filed on Sep. 28, 2006.

(51) Int. Cl.
*C12N 9/00* (2006.01)
*C12N 9/10* (2006.01)
*C12N 1/00* (2006.01)
*C12N 15/00* (2006.01)
*C07H 21/04* (2006.01)

(52) U.S. Cl.
USPC ... 435/254.11; 435/183; 435/193; 435/320.1; 536/23.2

(58) Field of Classification Search
None
See application file for complete search history.

(56) References Cited

U.S. PATENT DOCUMENTS 6,306,636 B1   10/2001  Haselkorn et al.
6,410,827 B1 *  6/2002  Cahoon et al. ............... 800/278
2007/0026484 A1  2/2007  Kinney et al.

FOREIGN PATENT DOCUMENTS

| EP | 1 227 155 A1 | 7/2002 |
| EP | 1 273 664 A1 | 1/2003 |
| WO | 02/31173 A2 | 4/2002 |
| WO | 02/063016 A1 | 8/2002 |
| WO | 2006/102342 A2 | 9/2006 |

OTHER PUBLICATIONS

Madzak et al. J Biotechnol. Apr. 8, 2004;109(1-2):63-81.*
Kerscher et al. J Cell Sci. Nov. 2001;114(Pt 21):3915-21.*
Holden et al. Biochim Biophys Acta. Jan. 31, 2002;1594(1):160-7.*
Meesters et al. Yeast. Jun. 30, 1996;12(8):723-30.*
Zhang et al., "Phenotypesand fed-batch fermentation of ubiquinone-overproducing fission yeast using pptl gene", Journal of Biotechnology, 128:120-131 (2007).
International Search Report for PCT/US2007/006834, mailed Apr. 14, 2008.

* cited by examiner

*Primary Examiner* — Christian Fronda
(74) *Attorney, Agent, or Firm* — Choate, Hall & Stewart, LLP

(57) ABSTRACT

The present invention provides systems for producing engineered oleaginous yeast or fungi that express quinone derived compounds.

3 Claims, 38 Drawing Sheets

FIG. 1B
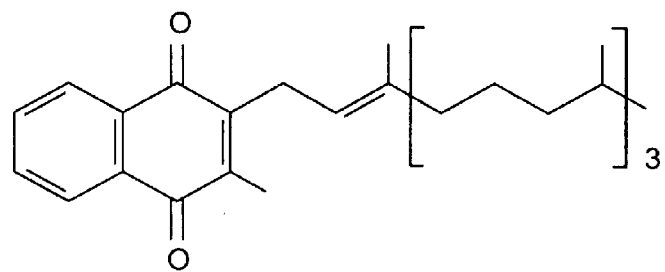
PHYLLOQUINONE
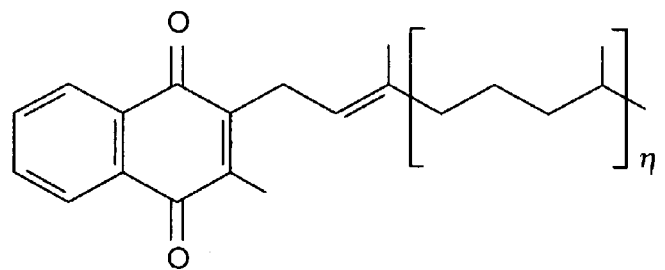
MENAQUINONES
VITAMIN K

FIG. 1C
Vitamin E - Structures and Chemistry
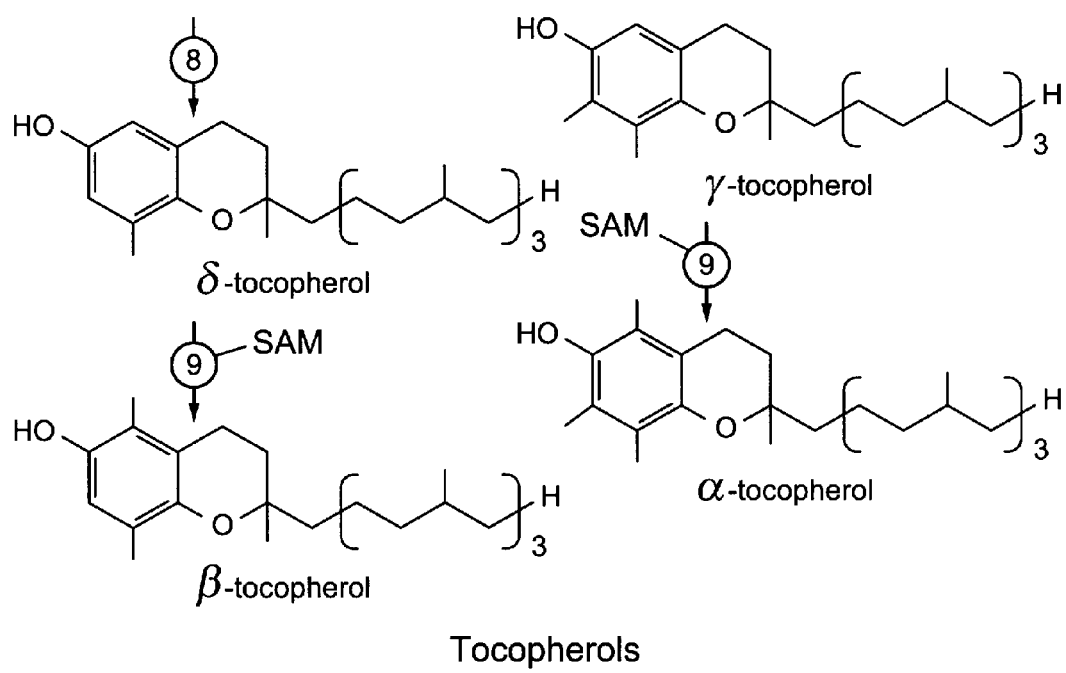
Tocopherols
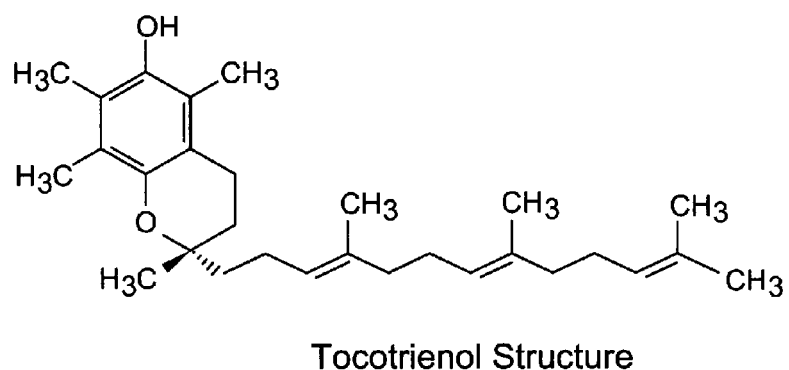
Tocotrienol Structure

PHENYLALANINE, TYROSINE AND TRYPTOPHAN BIOSYNTHESIS

See FIG. 4C

Fig. 7A

| Fig.7A-1 |
| Fig.7A-2 |
| Fig.7A-3 |

Fig.7A-1

Alignment of representative fungal HMG-CoA reductase polypeptides.

```
                          1                                                    50
A. nidulans HMG    (1)  -MASVLIRRKFGTE--GGSDAEPSWLKRQVTGCIQSISRRACIHPTHTIV
G. zeae HMG        (1)  -MASILHPKKFERGETAPAEKTTPSWASKRLTPIAQFISRLACSHPIHTV
N. crassa HMG      (1)  MIASSLLPSKFRGEQPATQAATPSWINKKVTPPLQKLSKITSNPIHTIV
S. cerevisea HMG2  (1)  ---------------------------------MSLPLKTIVHLVKPFACTARFSARYPIHVIV
S. cereviseae HMG1 (1)  ---------------------------------MPPLFKGLKQMAKPIAYMSRFSAKPPIHIIL
Y. lipolytica HMG  (1)  ---------------------------------MLQAAIGKIVGFAVNRPIHTIV
Consensus          (1)         MAS LL RF  E        A PSW   K LT PIQ ISRFAA HPIHTIV
                          51                                                   100
A. nidulans HMG    (48) VIALLASTTYVGLLEGSLFDSFRNSNNVAGHVDVDSLLLGNRSLRLGEGT
G. zeae HMG        (50) IVAVLASTSYVGLLQESFFSTDLP---TVGKADWSSLVEGSRVLRAGPET
N. crassa HMG      (51) IVALLASSSYIGLLQNSLFNVTR----SVRKAEWESLQAGSRMLRAGANT
S. cerevisea HMG2  (32) MAVLLSAAAYLSVTQSYLNEMKLDSN----QYSTYLSIKPDELFEKCTH
S. cereviseae HMG1 (32) ESLIISAFAYLSVIQYYENGWQLDSNS----VFETAPNKDSNTLFQECSH
Y. lipolytica HMG  (23) LTSIVASTAYLALLDIAIPGEEG-----TQPISYYHPAAKSYDNPAD
Consensus          (51) LVALLASTAYLGLLQ SLF W L SN       D TSL GSR LR G  T
``` continued on sheet 14/38

Fig.7A-2  continued from sheet 13/38

```
                      101                                                    150
A. nidulans HMG  (98)  SWKQVEDSLNQDDQKVGNPELKREVDQHLALTTLIFPDSISKS-ASTAP
      G. zeae HMG  (97)  AWNWKATEQDSIQ----------HAGADADHLALLTLMFPDTHSAESSSTAP
   N. crassa HMG  (97)  EWNWQNHDPEAP----------VPANANHLALLTLVFPDTAES--GPVVA
S. cereviseA HMG2  (77)  YVRSPVSDTWKLLS------SKEAADIYTPFHYYLSTISFQSKDNSTILP
S. cereviseae HMG1 (78)  YLRDSSLDGWVSIT------AHEASELPAPHHYLLNLNFSPNETDSIP
  Y. lipolytica HMG (65)  ---WTHIAEADIP-----------SDAYRLAFAQIRVSDVQGE-APTIP
        Consensus (101)  WRW   ID    I         AADA HLAL TLVFPDTQS E ASTIP
                      151                                                    200
A. nidulans HMG  (147) AADALPVPANASAQLLPHTPNLESFLSHDSSLVFTLPFDQVPQFLRAVQE
      G. zeae HMG  (139) RSSHVPVPQNLSITPLPSTKNSFTAYSQDSILAYSLPYAEG--------
   N. crassa HMG  (135) QTNTVPLPSNLSTTPLPSTAISFT-YSQDSALAFSLPYSQAPEFLANAQE
S. cereviseA HMG2  (121) SLDDVIYSVDHTRYLLSEEPKIPTELVSENGTKWRLRNNSN--------
S. cereviseae HMG1 (122) ELANTVFEKDNTKYLLQEDLSVSKEISSTDGTKWRLRSDRK--------
  Y. lipolytica HMG (100) GAVAVSDLDHRIVMDYKQWAPWTASNEQASENHIWKHSFK------D-
        Consensus (151) A    VPVP N SI LLP T   IFT YSQDSSL FSLPYS
                      201                                                    250
A. nidulans HMG  (197) LPDPTLEDDEGEQKR---WIMRATRGPVSGPNGTSSWLSDAWSSFVDLL
      G. zeae HMG  (180) ----------------PDVVQWANNAWTEFLDLL
   N. crassa HMG  (184) IPNAVSSQETIETERGHEKKMWIMKAARVQTRSSTVKWVQNAWVEFTDLL
S. cereviseA HMG2  (162) ----------------FILDLHNIYRNMVKQFSNKT
S. cereviseae HMG1 (163) ----------------SLFDVKTLAYSLYDVFSENM
  Y. lipolytica HMG (142) ----------------HVAFSWIKWFRWAYLRLSTLI
        Consensus (201)                 DIV W   NAW   FSDLI
``` continued on sheet 15/38

Fig.7A-3    continued from sheet 14/38

```
                        251                                                          300
A. nidulans HMG  (244)  KHAETIDIIMTLGYLAMYLSFASLEFSMKQLGSKFWLATTVLFSGMFAF
G. zeae HMG      (198)  KNAETLDIVIMFLGYTAMHLTFVSLELSMRKIGSKFWLGICTLFSSVFAF
N. crassa HMG    (234)  RNAETLDIIMALGYISMHLTFVSLFLSMRRMGSNFWLATSVFSSIFAF
S. cereviseae HMG2 (182) SEFDQFDLEIILAAYLTIFYTLCCLFNDMRKIGSKFWLSFSALSNSACAL
S. cereviseae HMG1 (183) TQADPFDVLIMVTAYLMMFYTIFGLFNDMRKIGSNFWLSASTVNSASSL
Y. lipolytica HMG  (163) QGADNFDIAVVALGYLAMHYTFFSLERSKRKVGSHEWLASMALVSSFFAF
Consensus        (251)  KNADTFDIIIM LGYLAMHYTF SLF SMRKLGSKFWLATS LFSSIFAF
                        301                                                          350
A. nidulans HMG  (294)  LFGLIVTTKFG-VPINLLLSEGLPFIVTTIGFEKPIILTRAVLSASIDK
G. zeae HMG      (248)  LFGLIVTTKLG-VPIISVILLSEGLPFLVTIGFEKNIVLTRAVMSHAIEH
N. crassa HMG    (284)  LFGLLVTTKLG-VPMNMVLLSEGLPFLVTIGFEKNIVLTRAVLSHAIDH
S. cereviseae HMG2 (232) YLSLYTTHSLLKKPASLLSLVIGLPFTVVIGEKHKVRLAAFSLQKFHRI
S. cereviseae HMG1 (233) FLALYVTQCILGKEVSALTLFEGLPFLVVVGEKHKIKIAQYALEKFERV
Y. lipolytica HMG  (213) LLAVVASSSLG-YRPSMITMSEGLPFLVAIGEDRVNLASEVLSKSSQ
Consensus        (301)  LLGLLVTTKLG VPISMLLLSEGLPFLVVTIGEKKIVLTRAVLS AID
                        351                                                          400
A. nidulans HMG  (343)  KRQGS------ATSTPSSIQDSIQTAIREQGFEIIRDYCIEISLIA
G. zeae HMG      (297)  RRQIQNSKSGKGSPERSMQNVIQYAVQSAIKEKGFEIMRDYAIEIVILAL
N. crassa HMG    (333)  RRPTE--KSGKPSKQADSAHSIQSAIQLAIKEKGEDIVBDYAIEAGIIML
S. cereviseae HMG2 (282) S------IDKKITVSNIIYEAMFQEGAYIRDYLFYISSFIG
S. cereviseae HMG1 (283) G------LSKRIITDEIMFESVSEEGGRLIQDHLLCIFAFIG
Y. lipolytica HMG  (262) ------LARMVQVITKIASKALFEYSLEVAALFA
Consensus        (351) RR        S   SIQ AIQ AIKE GFEIIRDYAIEISILIA
                        401                                                          450
A. nidulans HMG  (384)  GAASGVQGG-LQQFCFLAAWILFDCILLFTFYTTICIKLEITRIRRHV
G. zeae HMG      (347)  GAASGVQGG-LQHFCFLAAWTLFDFILLFTFYTAILSIKLEINRIKRHV
```

Fig.7B

| Fig.7B-1 |
| Fig.7B-2 |
| Fig.7B-3 |

Fig.7B-1

```
N. crassa HMG      (381)  GAASGVQGG-LQQFCFLAAWILFFDCILLFSFYTAIICIKLFINRIKRHV
S. cerevisea HMG2  (318)  CAIYARHLPGLVNFCILSTFMIVFDILSATFYSAILSMKLFINIIHRST
S. cereviseae HMG1 (319)  CSMYAHQLKTLTNFGILSAFIHIFELILTPTFYSAILALRLFMNVIHRST
Y. lipolytica HMG  (290)  GAYTGVPR--LSQFCFLSAWILIEDYMFLLTEYSAVIAIKFIINHIKENR
Consensus          (401)  GAASGVQGG L QFCFLAAWILFFD ILLFTFYSAILAIKLEINRIKRHV
                    451                                              500
A. nidulans HMG    (433)  TLRKALEEDGTTQSVAEKVASSN-DWFGAGSDNSDADDASVFGRKIKSNN
G. zeae HMG        (396)  DMRMALFDDQVSRRVAENVAKGIGDWTRVKGDSSLFG------RKSSS
N. crassa HMG      (430)  QMRKALEEDGVSRRVAQSN-DWPRADGKDQPGTTI--FGRQLKSTH
S. cerevisea HMG2  (368)  VIRQTLEEDGVVPITADIIYKDE------TASEPHFLR------SNVA
S. cereviseae HMG1 (369)  IIKQTLEEDGVVPSTARIISKAE------KKSVSSFLN------LSVV
Y. lipolytica HMG  (338)  MIQDALKEDGVSAAVAEKVADSSPDAKLDRKSDVSLFG------ASGA
Consensus          (451)  IIR ALEEDGVS SVAEKVAKSE DW       KGSDS F       KS A
                    501                                              550
A. nidulans HMG    (482)  VRRFKEIMGGFVLVNVVNMTAIPFRNG-S------LSPLCNVFSPTPT
G. zeae HMG        (438)  VPTFKVIMLGFFVNIVNICSIPFRNPRSLSTIRTWASSLGGVVAPLSV
N. crassa HMG      (477)  IPKFKVMMVTGFVLINVINLCTIPFRSANSISSISSWARGLGVTIPPPV
S. cerevisea HMG2  (404)  IILGKASVIGLILINJYVFTDKLNATILN------TVYFD
S. cereviseae HMG1 (405)  VITMKLSVILLFVFINEYNFGANWVNDAFN------SLYFD
Y. lipolytica HMG  (380)  IAMFKIFMVLGEIGLNLINITAIPHLGK------AAAAQSV
Consensus          (501)  I IFKVLMLGFVLINLVNLTAIPFR A S         L GV SP V
``` continued on sheet 17/38

Fig.7B-2 continued from sheet 16/38

```
                              551                                                        600
A. nidulans HMG   (524) DPFKVAENGLDATYVSAKSQKLETLVTVPPIKVKLEYPSVHYAKLGES-
     G. zeae HMG   (488) DPFKVASNGLDAILAAAKSNNRPTLVTVLTPIKYELEYPSIHYALGSAIN
   N. crassa HMG   (527) DPFKVASNGLDIILEAARADGRETTVTVLTPIRYELEYPSTHYDLPQKS-
S. cereviseae HMG2 (439) S---TIYSLPNFINYKDIGNLSNQVIISVLPKQMYTPLKKYHQIEDSVL-
S. cereviseae HMG1 (440) K---ERVSLPDEITSNASENFKEQAIVSVTPLLMYKPIKSYQRIEDMVL-
 Y. lipolytica HMG (416) TPITLSPELLHAIFASVP----VVVTFVPSVVHEHSQLIEQLEDALTE-
         Consensus (551) DPFKVA NLLDAI AAAKSN RETLVTVTPIKYELEYPSIHY E    S
                              601                                                        650
A. nidulans HMG   (573) ---QSIEIEYTDQLLDAVGGHVLNGVLKSIEDPVISKWITAVLTISIVL
     G. zeae HMG   (538) GNNAEYTDAFHHHFQGYGVGGRMVGGILKSLEDPVLSKWIVIALAISVAL
   N. crassa HMG   (576) ------AEVEGGDYANLGGYGGRMVGSILKSILEDPTLSKWIVVALALSVAL
S. cereviseae HMG2 (485) -----------IIDSVSNAIRDQFISKLIFFAFAVSISI-
S. cereviseae HMG1 (486) -----------LLRNVSVAIRDRFVSKLVISALVCSAVI-
 Y. lipolytica HMG (460) -----------FIAACSKTIGDPVISKYIFLCLMVSTAL-
         Consensus (601)              G  GG MLGSVSKSIEDPVISKWIVIALALSIAL
                              651                                                        700
A. nidulans HMG   (619) NGYLFNAARWSIKEPQAAPAPKEP---------------
     G. zeae HMG   (588) NGYLFNVARWGIKDPNVPEHNIDRNELARAQQFNDTGSATLPLGEYVPPT
   N. crassa HMG   (621) NGYLFNAARWGIKDPNVPDHPINPKELDEAQKFNDTASATLPLGEYMKPI
S. cereviseae HMG2 (514) NVYILNAAKIHTGYMNFQPQSNKIDLVVQQKSATIEFSETRSMPLASGL
S. cereviseae HMG1 (515) NVYLLNAARIHTSYTADQLVKTEVTKKSFTAPVQKASTPVLTNKTVISGS
 Y. lipolytica HMG (488) NVYIFGATREVRTQSVKVVEKHMPIMIE----K---------------
         Consensus (651) NVYLFNAARW IKDPNV        EV EL  Q   N   SA  L   I    T
``` continued on sheet 18/38

Fig.7B-3 continued from sheet 17/38

```
                    701                                                    750
A. nidulans HMG  (643) ------------------------------AKPKVYPKTDLNAGPKRSMECEAMLKA
G. zeae HMG      (638) PMR--TEPSTEAITDEAEGLQMTKARSDKLPNRPNEE-----LEKLLAE
N. crassa HMG    (671) APSSPVAPILRSSTDDENDAQAKENRAVTLAAQRATTIRSQGELDKMIAE
S. cerevisea HMG2 (564) E-----TPVTAKDIISEEIQNN---ECVYALSSQDEPIRPLSNLVELMEK
S. cereviseae HMG1 (565) K-----VKSLSSAQSSSSGFSSSSFEDDSRDIESLDKKIRPLEELEALLSS
Y. lipolytica HMG (518) ------PSEKEEDTSSEDSIELTVGKQPKPVTETRSLDDLEATMKA
Consensus         (701)              TPA TDDE S S        V KI   IRSLEELEALLAA 751                                                    800
A. nidulans HMG  (671) KKAAYLSDELLIELSLSGKLPGYALLKSIENEELMSRVDAFLRAVKLRRA
G. zeae HMG      (681) KRVKEMSDEEIVSLMRCKIPGYALLKTLG------DFTRAVKIRRS
N. crassa HMG    (721) KRTHELNDEETVHISLKGKIPGYALEKTLK------DFTRAVKVRRS
S. cerevisea HMG2 (607) EQLKNMNNTEVSNIVNGKLPLYSLEKKLE------DTLRAVLVRRK
S. cereviseae HMG1 (611) GNTKQLKNKEVAALVTHGKLPLYALEKKLG------DTTRAVAVRRK
Y. lipolytica HMG (558) GKTKLLEDHEVVKISLEGKLPLYALFKQLG------DNTRAVGIRRS
Consensus         (751) KKTK L DEEVV LSL GKLPLYALEKTLG       DFTRAVKIRRS 801                                                    850
A. nidulans HMG  (721) VVISRTPATSAVTSSLETSKLEYKDYNYALVHGACCENVIGTLPLPLGVAG
G. zeae HMG      (722) IIARNRATSDLITHSIERSKLPFEKYNWERVFCACCENVIGYMPLPVGVAG
N. crassa HMG    (762) IISRTKATTELTNILDRSKLEYQNVNWAQVMHGACCENVIGYMPLPVGVAG
S. cerevisea HMG2 (648) ALIST----L-AESPILWSEKLPFRNYDYDRVFGACCENVIGYMPIPVGVIG
S. cereviseae HMG1 (652) ALISI----L-AEAPVLASDRLEYKNYDYDRVFGACCENVIGYMPLPVGVIG
Y. lipolytica HMG (599) IISQ---Q-SNTKTLETSKLEYLHYDRVFGACCENVIGYMPLPVGVAG
Consensus         (801) IISR  ATSALT SLESSKLPYKNYNYDRVFGACCENVIGYMPLPVGVAG 851                                                    900
A. nidulans HMG  (771) PLVFTDGQSYFIPMATIEGVLVASASRGAKAINAFGGAVIVLTGDGMTRGE
```

Fig.7C

| Fig.7C-1 |
| Fig.7C-2 |
| Fig.7C-3 |

Fig.7C-1

```
G. zeae HMG       (772) RLVTDGQSYFIPMATTEGVLVASASRGCKAINAGGAVTVLTADGMTRGP
N. crassa HMG     (812) PLVTDGQSFFVPMATTEGVLVASASRGCKAINSGGAVTVLTADGMTRGP
S. cereviseae HMG2(694) PLITDGTSYHIPMATTEGCLVASAMPGCKAINAGGATTVLTKDGMTRGP
S. cereviseae HMG1(698) PLVTDGTSYHIPMATTEGCLVASAMRGCKAINAGGATTVLTKDGMIRGP
Y. lipolytica HMG (645) PMNTDGKNYHIPMATTEGCLVASTMRGCKAINAGGVTVLTQDGMTRGP
Consensus         (851) PLVIDGQSYHIPMATTEGVLVASASRGCKAINAGGAVTVLTADGMTRGP
                         901                                              950
A. nidulans HMG   (821) CVGFFPTIARAAAKVWLDSFEGKSVMTAAFNSTSRFARLQHIKTALAGTY
G. zeae HMG       (822) CVAFETIERAGAAAKLWIDSEAGSDIMKKAFNSTSRFARLQSMKTALAQTN
N. crassa HMG     (862) CVQFETIERAGAAAKLWLDSEKGQSIMKKAFNSTSRFARLETMKTALAQTN
S. cereviseae HMG2(744) VVRFPTILRSGACKIWLDSEEGQNSIKKAFNSTSRFARLQHIQTCLAQDL
S. cereviseae HMG1(748) VVRFPTILKRSGACKIWLDSEEGQNALKKAFNSTSRFARLQHIQTCLAQDL
Y. lipolytica HMG (695) CVSEFSLKRAGAAKIWLDESEGLKSMRKAFNSTSRFARLQSLHSTIAGNL
Consensus         (901) CV FPTL RAGAAKIWLDSEEGQ SMKKAFNSTSRFARLQHIKTALAGTL
                         951                                             1000
A. nidulans HMG   (871) LYIRFKTTTGDAMGMNMISKGVEKALHVMATECGFDDMATISVSGNFCTD
G. zeae HMG       (872) LYIRFKITTGDAMGMNIISKGVEHALSVMSNEAGFDDMQIVSVSGNYCTD
N. crassa HMG     (912) LYIRFKITTGDAMGMNIISKGVEHALSVMYNEG-FEDMNIVSLSGNYCTD
S. cereviseae HMG2(794) LFMRFRTTTSDAMGMNMISKGVEYSLKQMVEEYGMEDMEVVSVSGNYCTD
S. cereviseae HMG1(798) LFMRFRTTTSDAMGMNMISKGVEYSLKQMVEEYGMEDMEVVSVSGNYCTD
Y. lipolytica HMG (745) LFTRFRTTTGDAMGMNMISKGVEHSLAVMVKEYGFPLMDIVSVSGNYCTD
Consensus         (951) LFIRFKTTTGDAMGMNMISKGVEHALSVMV  EYGFEDMEIVSVSGNYCTD
``` continued on sheet 20/38

Fig.7C-2

```
                                         1001                                               1050
A. nidulans HMG  ( 921)  KKAAALNWIDGRGKSVVAEAIIFGDVVRNVLKSDVDALVELNTSKNLIGS
     G. zeae HMG ( 922)  KKAAALNWIDGRGKSVVAEAIIFGDVVRSVLKSDVDALVELNISKNIIGS
   N. crassa HMG ( 961)  KKAAAINVIDGRGKSVVAEAIIFGDVVKNVLKTDVDTLVELNVKNTIGS
  S. cereviseaHMG2( 844) KKPAAINWIEGRGKSVVAEAIIPADVKVKSDVSALVELNISKNIVGS
  S. cereviseaeHMG1( 848) KKPAAINWIEGRGKSVVAEAIIFGDVVRKVLKSDVSALVELNIAKNLVGS
  Y. lipolytica HMG( 795) KKPAAINWIEGRGKSVVAEAIIPAHIVKSVLKSEVDALVELNISKNLIGS
        Consensus (1001) KKPAAINWIDGRGKSVVAEAIIPGDVVKSVLKSDVDALVELNISKNLIGS
                                         1051                                               1100
A. nidulans HMG  ( 971)  AMAGSLGGFNAHASNIVTAIFLATGQDPAQNVESSCITTMKNTNGNIQT
     G. zeae HMG ( 972)  AMAGSVGGFNAHAANIVAAIFLATGQDPAQNVESSANCITLMKNIRGALQT
   N. crassa HMG (1011)  AMAGSMGGFNAHAANIVAAIFLATGQDPAQNVESSNCITLMRNLRGNLQI
  S. cereviseaHMG2( 894) AMAGSVGGFNAHAANLVTAVELALGQDPAQNVESSNCITLMKEVDGDLRI
  S. cereviseaeHMG1( 898) AMAGSVGGENAHAANLVTAVELALGQDPAQNVESSNCITLMKEVDGDLRI
  Y. lipolytica HMG( 845) AMAGSVGGFNAHAANLVTAIYLATGQDPAQNVESSNCITLMSNVDGNLLI
        Consensus (1051) AMAGSVGGFNAHAANIVTAIFLATGQDPAQNVESSNCITLMKNVDGNLQI
                                         1101                                               1150
A. nidulans HMG  (1021)  AVSMPSIEVGTIGGGTILEAQGAMIDILGVRGSHPTNPGDNARQLARIVA
     G. zeae HMG (1022)  SVSMPSIEVGTLGGGTILEPQSAMIDLLGVRGSHPTNPGDNSRRLARIIG
   N. crassa HMG (1061)  SVSMPSIEVGTLGGGTILEPQGAMIDMLGVRGPHPTNPGENARRLARIVA
  S. cereviseaHMG2( 944) SVSMPSIEVGTLGGGTVLEPQGAMIDILGVRGPHPTEPGANARQLARIIA
  S. cereviseaeHMG1( 948) SVSMPSIEVGTLGGGTVLEPQGAMIDLLSVRGPHATAPGTNARQLARIVA
  Y. lipolytica HMG( 895) SVSMPSIEVGTLGGGTMLEPQGAMLEMLGVRGPHIETPGANAQQLARIIA
        Consensus (1101) SVSMPSIEVGTIGGGTILEPQGAMLDLLGVRGPHPTNPGDNARQLARIIA
```

Fig.7C-3 (continued from sheet 20/38)

```
                           1151                                                      1200
A. nidulans HMG    (1071)  AAVLAGELSLQSALAAGHLVRAHMAHNRSAAPTRSATPVSAAVGATRGLS
G. zeae HMG        (1072)  ASVLAGELSLQSALAAGHLVRAHMQHNRSAAPSRSTTPAPMTPVRSFDTK
N. crassa HMG      (1111)  AAVLAGELSLQSALAAGHLVKAHMAHNRSAPPTRTSTPAPAAAAGLTMIS
S. cereviseae HMG2 (994)   CAVLAGELSLCSALAAGHLVQSHMTHNRKTNKANELP---QPSNKGPPC
S. cereviseae HMG1 (998)   CAVLAGELSLCAALAAGHLVQSHMTHNRKPAEPTKPNNLDATDINRLKDG
Y. lipolytica HMG  (945)   SGVLAAELSLQSALAAGHLVQSHMTHNRSQAPTPAKQSADLQRLQNGSN
Consensus          (1151)  AAVLAGELSLCSALAAGHLVQAHMTHNRSAAPTRS TP  A       T
                           1201                                                      1250
A. nidulans HMG    (1121)  MTSSR---------------------------------------------
G. zeae HMG        (1172)  VRCQPNNKDIRNILLTQHPSKPTITYSKRVIKSTIHLNPLILALFDNSVQ
N. crassa HMG      (1161)  S-----------N---PNAAAVERSRR-----------------------
S. cereviseae HMG2 (1040)  KTSALL--------------------------------------------
S. cereviseae HMG1 (1048)  SVTCIKS-------------------------------------------
Y. lipolytica HMG  (995)   ICIRS---------------------------------------------
Consensus          (1201)   S
                           1251                                              1289
A. nidulans HMG    (1126)  --------------------------------------
G. zeae HMG        (1172)  TRDVQLGDQVSTRGTLDAVGGPQGGGVAAGGVARRVVGS
N. crassa HMG      (1174)  --------------------------------------
S. cereviseae HMG2 (1046)  --------------------------------------
S. cereviseae HMG1 (1055)  --------------------------------------
Y. lipolytica HMG  (1000)  --------------------------------------
Consensus          (1251)
```

FIG. 11A  Y. Lipolytica Genes

| Genbank protein GI number | Genbank protein Accession Number | polypeptide | Y.lipolytica gene | Oligo 1 | Oligo 2 |
|---|---|---|---|---|---|
| 50557288 | XP_506052 | HMG-CoA synthase | YALI0F30481g | MO4890-<br>5'ctctagacacaaaaatgtcgcaaccccagaacgt | MO4981-<br>5'cacgcgtctactgctgcttgatctgtact |
| 50546973 | XP_500956 | Mevalonate Kinase | YALI0B16038g | MO4982-<br>5'cgctagccacaaaaatggactacatcatttcggcg | MO4983-<br>5'cacgcgtctaatgggtcagggaccga |
| 50552418 | XP_503619 | Phosphomevalonate kinase | YALI0E06193g | MO4984-<br>5'ctctagacacaaaaatgaccaccattggctccg | MO4985-<br>5'cggcgcgcccacttgaacccttctcga |
| 50555265 | XP_505041 | Mevalonate Pyrophosphate Decarboxylase | YALI0F05632g | MO4986-<br>5'ctctagacacaaaaatgatccaccaggcctccacc<br>a | MO4987-<br>5'cacgcgtctactgctgttcttcagag |
| 50555131 | XP_504974 | IPP Isomerase | YALI0F04015g | MO4988-<br>5'ctctagacacaaaaatgacgacgtcttacagcga | MO4989-<br>5'cacgcgtctacttgatccaccgcgaa |
| 50552378 | XP_503599 | FPP synthase | YALI0E05753 | MO4990-<br>5'ctctagacacaaaaatgtcaaggcgaaattcgaa | MO4991-<br>5'cacgcgtctacttctgtcgcttgtaaa |
| 50553402 | XP_504112 | Malic Enzyme | YALI0E18634g | MO4992-<br>5'ctctagacacaaaaatgttacgactacgaaccat | MO4993-<br>5'cacgcgtctagtcgtaacccgcacat |

FIG. 11B    Y. Lipolytica Genes

| | | | | |
|---|---|---|---|---|
| 50552824 | XP_503822 | AMP Deaminase | YALI0E11495g | MO4996-5'cgtagcacacaaaatgccgcagcaagcaatgga | MO4997-5'cacgcgtttaaccatgcagccgctcaa |
| 50550873 | XP_502909 | Malate Dehydrogenase Homolog | YALI0D16753g | MO5000-5'ctctagacacaaaaatgttccgaaccgagttac | MO5001-5'cacgcgtttaagggttctgcttgacaa |
| 50550839 | XP_502892 | Isocitrate Dehydrogenase | YALI0D16247g | MO5004-5'ctctagacacaaaaatgacacaaaacgcacaatct | MO5005-5'caacgcgtttacatcttgtacgcaggt |
| 50545147 | XP_500111 | Fructose 1,6 bisphosphatase | YALI0A15972g | MO5008-5'ctctagacacacaaaatggaagccaaccccgaagt | MO5009-5'caacgcgttcatttcagaaggtactct |
| 50552796 | XP_503808 | Acetoacetyl CoA thiolase | YALI0E11099g | MO4852-5'ctctagacacacaaaatgcgactcactctgccc | MO4853-5'caacgcgtcactgacagaagagaccttc |
| 50554757 | XP_504787 | ATP citrate lyase subunit 1 | YALI0E34793g | MO4741-5'ttctagaccccaaaaatgtctgccaacgagaacatct c | MO4743-5'aacgcgtctatgagtcttggccttg |
| 50551515 | XP_503231 | ATP citrate lyase subunit 2 | YALI0D24431g | MO4760-5'ttctagacacaaaaatgcagcgaaatcattcacg a | MO4861-5'cacgcgttaaactccgagagagtgg |
| 50553046 | XP_503933 | Malate Dehydrogenase | YALI0E14190g | MO4994-5'ctctagacacaaagtggtaaagctgtcgttgc | MO4995-5'cacgcgtttacttggcagagaggaggt |

FIG. 11C

Y. Lipolytica Genes

| | | | | |
|---|---|---|---|---|
| 50553728 | XP_504275 | Glucose 6 Phosphate Dehydrogenase | YALI0E22649g | MO4998-5'ctctagacacaaaaatgactggcacttacccaa | MO4999-5'cacgcgttcacgaggagcccttggtga |
| 50546937 | XP_500938 | 6-phosphogluconate dehydrogenase | YALI0B15598g | MO5002-5'ctctagacacaaaaatgactgacacttcaaacat | MO5003-5'cacgcgttaagcatcgtaagtggaag |
| 50550013 | XP_502479 | Isocitrate dehydrogenase | YALI0D06303g | MO5006-5'ctctagacacaaaaatgctcaacttagaaccgc | MO5007-5'cacgcgtctacttgagtcgcttgataa |

FIG. 12A
Schematic diagram of certain plasmids used herin
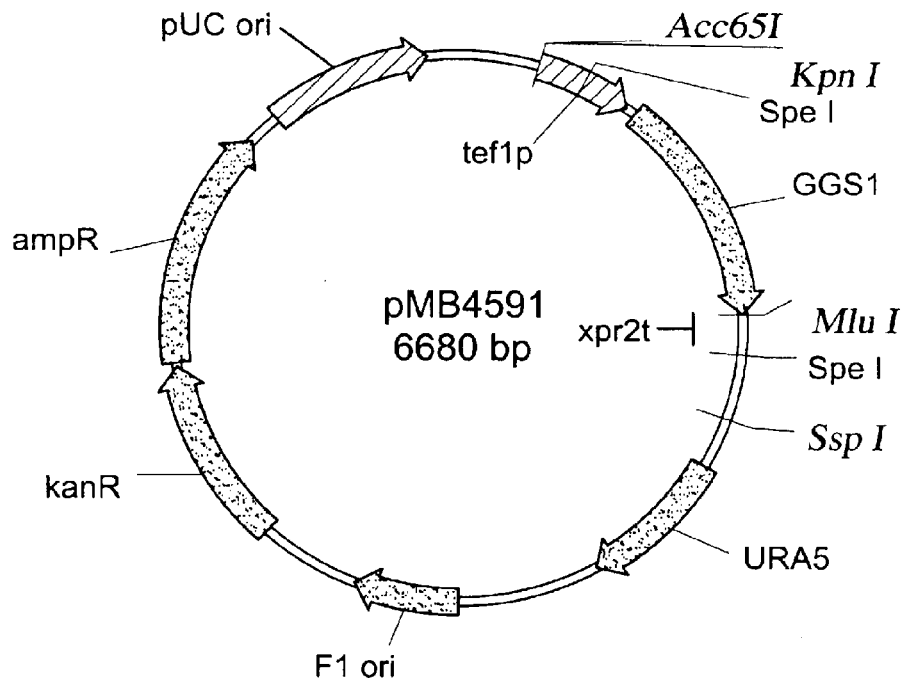
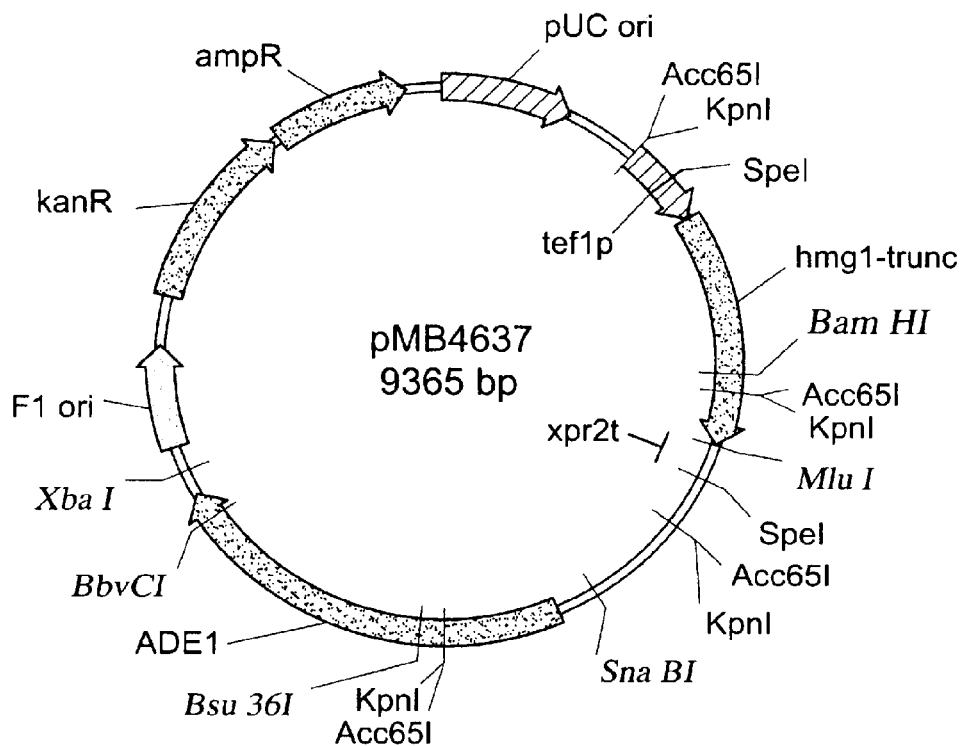

Schematic diagram of certain plasmids used herin

Schematic diagram of certain plasmids used herin

US 8,633,009 B2

PRODUCTION OF QUINONE DERIVED COMPOUNDS IN OLEAGINOUS YEAST AND FUNGI

CROSS REFERENCE TO RELATED APPLICATIONS

The present application is a national phase application under 35 U.S.C. §371 of PCT International Application No. PCT/US2007/006834, filed Mar. 20, 2007, which is copending with, shares at least one common inventor with and claims priority to U.S. provisional patent application Ser. No. 60/784,499, filed Mar. 20, 2006, the entire contents of which are incorporated herein by reference. The present application is also copending with, shares at least one common inventor with and claims priority to U.S. provisional patent application Ser. No. 60/848,064, filed Sep. 28, 2006, the entire contents of which are incorporated herein by reference.

BACKGROUND OF THE INVENTION

Compounds containing or derived from quinone structures (i.e., "quinone derived compounds") play a variety of important roles in biological systems. Certain vitamins, for example, have quinone moieties (e.g., vitamin K) or are derived from such structures (e.g., vitamin E). Ubiquinones also represent an important class of quinone derived compounds. Ubiquinones play a critical function in the production of cellular ATP, serving as electron carriers in the respiratory chain. Furthermore, ubiquinones are lipophilic antioxidants that are capable of regenerating other antioxidants such as ascorbate and tocopherols.

Although many quinone derived compounds are naturally produced by the human body, they are often produced at levels lower than are required for optimal cell function. Accordingly, they must be obtained through the diet or by other means. There is a rapidly growing market for nutritional supplements and other products containing quinone derived compounds. Improved systems for enabling cost effective production, isolation, and/or formulation of such compounds are needed to effectively meet the growing demand.

SUMMARY OF THE INVENTION

The present invention provides improved systems for the biological production of quinone derived compounds. In particular, the present invention provides improved systems for the biological production of ubiquinone(s) (e.g., CoQ10 and/or $C_{5-9}$ quinone compounds), vitamin K compounds, and vitamin E compounds.

In one aspect, the invention encompasses the discovery that it is desirable to produce such quinone derived compounds in oleaginous organisms. The present invention thus provides biological systems able to accumulate one or more quinone derived compounds (e.g., ubiquinones, vitamin K compounds, and/or vitamin E compounds) in lipid bodies. In some embodiments, the biological systems may produce higher levels of quinone derived compounds when the compound(s) is/are sequestered in lipid bodies. Regardless of whether absolute levels are higher; however, compounds that are accumulated within lipid bodies in oleaginous organisms are readily isolatable through isolation of the lipid bodies.

The present invention therefore provides oleaginous fungi (including, for example, yeast or other unicellular fungi) that produce one or more quinone derived compounds (e.g., ubiquinones, vitamin K compounds, and/or vitamin E compounds). The present invention also provides methods of constructing such yeast and fungi and methods of using such yeast and fungi to produce the quinone derived compounds. The present invention further provides methods of preparing quinone derived compounds, as well as compositions containing them, such as food or feed additives, nutritional supplements, or compositions for nutraceutical, pharmaceutical and/or cosmetic applications. In particular, the present invention provides systems and methods for generating yeast and fungi containing one or more oleaginic and/or quinonogenic modifications that increase the oleaginicity and/or alter their ability to produce one or more quinone derived compounds as compared with otherwise identical organisms that lack the modification(s). In some embodiments, the present invention provides a recombinant fungus. In certain embodiments, the recombinant fungus is oleaginous in that it can accumulate lipid to at least about 20% of its dry cell weight; and produces at least one quinone derived compound, and can accumulate the produced quinone derived compound to at least about 1% of its dry cell weight; wherein the recombinant fungus comprises at least one modification as compared with a parental fungus, which parental fungus both is not oleaginous and does not accumulate the quinone derived compound to at least about 1% of its dry cell weight, the at least one modification being selected from the group consisting of: quinonogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one quinone derived compound to a level at least about 1% of its dry cell weight, or confers to the recombinant fungus the ability to produce at least one quinone derived compound which the parental fungus does not produce.

In other embodiments, the recombinant fungus is oleaginous in that it can accumulate lipid to at least about 20% of its dry cell weight; and the recombinant fungus produces at least one quinone derived compound selected from the group consisting of: a ubiquinone (including, but not limited to, coenzyme Q10 and/or a $C_{5-9}$ quinone compound), a vitamin K compound, a vitamin E compound, and combinations thereof, and can accumulate the produced quinone derived compound to at least about 1% of its dry cell weight; wherein the recombinant fungus comprises at least one modification as compared with a parental fungus, the at least one modification being selected from the group consisting of quinonogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one quinone derived compound to a level at least about 1% of its dry cell weight, or confers to the recombinant fungus the ability to produce at least one quinone derived compound which the parental fungus does not naturally produce.

In some embodiments, the recombinant fungus is oleaginous in that it can accumulate lipid to at least about 20% of its dry cell weight; and the recombinant fungus produces at least one quinone derived compound, and can accumulate the produced quinone derived compound to at least about 1% of its dry cell weight; wherein the recombinant fungus is a member of a genus selected from the group consisting of: *Aspergillus, Blakeslea, Botrytis, Candida, Cercospora, Cryptococcus, Cunninghamella, Fusarium (Gibberella), Kluyveromyces, Lipomyces, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Xanthophyllomyces (Phaffia)*, and

*Yarrowia*; or is a species selected from the group consisting of: *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvalus, Cunninghamella echinulata, Cunninghamella elegans, Fusarium fujikuroi* (*Gibberelia zeae*), *Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Xanthophyllomyces dendrorhous* (*Phaffia rhodozyma*), and *Yarrowia lipolytica*; wherein the recombinant fungus comprises at least one modification as compared with a parental fungus, the at least one modification being selected from the group consisting of quinonogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one quinone derived compound to a level at least about 1% of its dry cell weight, or confers to the recombinant fungus the ability to produce at least one quinone derived compound which the parental fungus does not naturally produce.

In some embodiments, the recombinant fungus is oleaginous in that it can accumulate lipid to at least about 20% of its dry cell weight; and the recombinant fungus produces at least one quinone derived compound selected from the group consisting of: a ubiquinone (including, but not limited to, coenzyme Q10 and/or a $C_{5-9}$ quinone compound), a vitamin K compound, a vitamin E compound, and combinations thereof, and can accumulate the produced quinone derived compound to at least about 1% of its dry cell weight; wherein the recombinant fungus is a member of a genus selected from the group consisting of: *Aspergillus, Blakeslea, Botrytis, Candida, Cercospora, Cryptococcus, Cunninghamella, Fusarium* (*Gibberella*), *Kluyveromyces, Lipomyces, Mortierella, Mucor, Neurospora, Penicillium, Phycomyces, Pichia* (*Hansenula*), *Puccinia, Pythium, Rhodosporidium, Rhodotorula, Saccharomyces, Sclerotium, Trichoderma, Trichosporon, Xanthophyllomyces* (*Phaffia*), and *Yarrowia*; or is of a species selected from the group consisting of: *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujikuroi* (*Gibberella zeae*), *Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Xanthophyllomyces dendrorhous* (*Phaffia rhodozyma*), and *Yarrowia lipolytica*; wherein the recombinant fungus comprises at least one modification as compared with a parental fungus, the at least one modification being selected from the group consisting of quinonogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one quinone derived compound to a level at least about 1% of its dry cell weight, or confers to the recombinant fungus the ability to produce at least one quinone derived compound which the parental fungus does not naturally produce.

In some embodiments, the recombinant fungus accumulates the produced at least one quinone derived compound to a level selected from the group consisting of: above about 1%, above about 2%, above about 3%, above about 5%, and above about 10% of the fungus' dry cell weight.

In some embodiments, the present invention provides an engineered *S. cerevisiae* strain, comprising one or more quinonogenic modifications, wherein the one or more quinonogenic modifications are selected from the group consisting of: increased expression or activity of a decaprenyl diphosphate synthase polypeptide; increased expression or activity of an 4-hydroxybenzoate polyprenyl polypeptide; increased expression or activity of a GGPP synthase polypeptide; increased expression or activity of an FPP synthase polypeptide; increased expression or activity of an HMG CoA reductase polypeptide; decreased expression or activity of a squalene synthase polypeptide; decreased expression of activity of a prenyldiphosphate synthase polypeptide; increased expression or activity of a DAHP synthase polypeptide; increased expression or activity of a chorismate lyase polypeptide; increased expression or activity of a chorismate synthase polypeptide; increased expression or activity of an ATP-citrate lyase polypeptide; increased expression or activity of an AMP deaminase polypeptide; increased expression or activity of a cytosolic malic enzyme polypeptide; and combinations thereof.

In some embodiments, the present invention provides an engineered *Y. lipolytica* strain containing a truncated HMG CoA reductase polypeptide.

In some embodiments, the present invention provides an engineered *Y. lipolytica* strain having increased expression or activity of a decaprenyl diphosphate synthase gene. In some embodiments, the present invention provides an engineered *Y. lipolytica* strain having decreased expression or activity of a squalene synthase polypeptide. In some embodiments, the present invention provides an engineered *Y. lipolytica* strain having decreased expression or activity of a squalene synthase polypeptide. In some embodiments, the present invention provides an engineered *Y. lipolytica* strain having increased expression or activity of a 4-hydroxybenzoate polyprenyl polypeptide. In some embodiments, the present invention provides an engineered *Y. lipolytica* strain having increased expression or activity of a DAHP synthase polypeptide. In some embodiments, the present invention provides an engineered *Y. lipolytica* strain having increased expression or activity of a chorismate lyase polypeptide. In some embodiments, the present invention provides an engineered *Y. lipolytica* strain having increased expression or activity of an ATP-citrate lyase polypeptide. In some embodiments, the present invention provides an engineered *Y. lipolytica* strain having increased expression or activity of a AMP deaminase polypeptide. In some embodiments, the present invention provides an engineered *Y. lipolytica* strain having increased expression or activity of a cytosolic malic polypeptide. In some embodiments, the present invention provides an engineered *Y. lipolytica* strain having increased expression or activity of a GGPP synthase polypeptide. In some embodiments, the present invention provides an engineered *Y. lipoly-*

*tica* strain having increased expression or activity of an FPP synthase polypeptide. In some embodiments, the present invention provides an engineered *Y. lipolytica* strain having increased expression or activity of a chorismate synthase polypeptide.

In some embodiments, the present invention provides a strain of *Y. lipolytica* comprising one or more modifications selected from the group consisting of an oleaginic modification, a quinonogenic modification, and combinations thereof, such that the strain accumulates from 1% to 15% of its dry cell weight as at least one quinone derived compound.

In certain embodiments, the present invention provides an engineered *Y. lipolytica* strain that produces a ubiquinone, the strain containing one or more quinonogenic modifications selected from the group consisting of: increased expression or activity of a *Y. lipolytica* GGPP synthase polypeptide; expression or activity of a truncated HMG CoA reductase polypeptide; increased expression or activity of a 4-hydroxybenzoate polyprenyl transferase polypeptide; increased expression or activity of a decaprenyl diphosphate synthase polypeptide; increased expression or activity of a DAHP synthase polypeptide; increased expression or activity of a chorismate lyase polypeptide; increased expression or activity of a shikimate pathway polypeptide; increased expression or activity of a chorismate mutase polypeptide; increased expression or activity of a transketolase polypeptide; increased expression or activity of an FPP synthase polypeptide; increased expression or activity of an IPP isomerase polypeptide; increased expression or activity of an HMG-CoA synthase polypeptide; increased expression or activity of a mevalonate kinase polypeptide; increased expression or activity of a phosphomevalonate kinase polypeptide; increased expression or activity of a mevalonate pyrophosphate decarboxylate polypeptide; increased expression or activity of a cytosolic malic enzyme polypeptide; increased expression or activity of a malate dehydrogenase polypeptide; increased expression or activity of an AMP deaminase polypeptide; increased expression or activity of a glucose 6 phosphate dehydrogenase polypeptide; increased expression or activity of a malate dehydrogenase homolog 2 polypeptide; increased expression or activity of a GND1-6-phosphogluconate dehydrogenase polypeptide; increased expression or activity of a isocitrate dehydrogenase polypeptide; increased expression or activity of a IDH2-isocitrate dehydrogenase polypeptide; increased expression or activity of a fructose 1,6 bisphosphatase polypeptide; increased expression or activity of a Erg10-acetoacetyl CoA thiolase polypeptide; increased expression or activity of a ATP citrate lyase subunit 2 polypeptide; increased expression or activity of a ATP citrate lyase subunit 1 polypeptide; decreased expression or activity of a squalene synthase polypeptide; decreased expression or activity of a prenyldiphosphate synthase polypeptide; or decreased expression or activity of a PHB polyprenyltransferase polypeptide; and combinations thereof.

In certain embodiments, the present invention provides a recombinant fungus characterized in that the fungus accumulates lipid in the form of cytoplasmic oil bodies.

In some embodiments, the present invention provides a composition comprising: lipid bodies; at least one quinone derived compound; and intact fungal cells.

In some embodiments, the present invention provides a method of producing a quinone derived compound, the method comprising steps of cultivating a fungus under conditions that allow production of the quinone derived compound; and isolating the produced quinone derived compound.

In some embodiments, the present invention provides a composition comprising: an oil suspension comprising: lipid bodies; at least one quinone derived compound; and intact fungal cells; and a binder or filler.

In some embodiments, the present invention provides a composition comprising: an oil suspension comprising: lipid bodies; at least one quinone derived compound; and intact fungal cells; and one or more other agents selected from the group consisting of chelating agents, pigments, salts, surfactants, moisturizers, viscosity modifiers, thickeners, emollients, fragrances, preservatives, and combinations thereof.

In some embodiments, the present invention provides an isolated quinone derived compound composition, prepared by a method comprising steps of cultivating a fungus under conditions that allow production of a quinone derived compound; and isolating the produced quinone derived compound.

In some embodiments, the present invention provides a quinone derived compound composition comprising a *Y. lipolytica* cell containing at least 1% quinone derived compounds by weight.

In some embodiments, the present invention provides a quinone derived compound comprising *Y. lipolytica* lipid bodies; and at least one quinone derived compound, wherein the at least one quinone derived compound is present at a level that is at least 1% by weight of the lipid bodies. In some embodiments, the present invention provides a composition comprising a quinone derived compound and one or more additional compounds (e.g., binders, fillers, chelating agents, pigments, salts, surfactants, moisturizers, viscosity modifiers, thickeners, emollients, fragrances, preservatives, etc. and combinations thereof).

In some embodiments, the present invention provides a feedstuff comprising a quinone derived compound in lipid bodies.

In some embodiments, the present invention provides methods comprising steps of cultivating the recombinant fungus under conditions that allow production of a quinone derived compound (e.g., ubiquinones, vitamin K compounds, and/or vitamin E compounds) and isolating the produced quinone derived compound (e.g., extracting with an organic or non-organic solvent). In certain embodiments, the recombinant fungus is cultured by growing under conditions of limiting nutrient (e.g., one or more of carbon, nitrogen, phosphate, magnesium, etc.) and/or by controlling at least one environmental parameter (e.g. one or more of nutrients, pH, temperature, pressure, oxygen concentration, timing of feeds, content of feeds, etc.) for at least a portion of the cultivation. In certain embodiments, the recombinant fungus is cultivated at a temperature of 20, 20.5, 21, 21.5, 22, 22.5, 23, 23.5, 24, 24.5, 25, 25.5, 26, 26.5, 27, 27.5, 28, 28.5, 29, 29.5, 30° C. or above, and/or at one or more ranges within these temperatures. In certain embodiments, the recombinant fungus is cultivated at a pH of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5 or above, and/or at one or more ranges within these pH's. In certain embodiments, the temperature, the pH, or both is varied during the culture period. In certain embodiments, the recombinant fungus is cultivated at an oxygen concentration within the rage of about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or more, and/or at one or more ranges within these concentrations. In certain embodiments, the produced quinone derived compound is isolated by crystallization.

Additional aspects of the present invention will be apparent to those of ordinary skill in the art from the present description, including the appended claims. Various polypeptides are listed in Tables 1-101; as one of ordinary skill in the art will understand, the order in which these polypeptides are listed is not indicative of their importance to the present invention. Various patent and non-patent publications are referenced throughout the present application. Unless otherwise indicated, each of these references is hereby incorporated by reference in its entirety.

BRIEF DESCRIPTION OF THE DRAWING

FIG. 4 depicts ubiquinone biosynthesis pathways.

FIGS. 7A-7C show an alignment of certain representative fungal HMG-CoA reductase polypeptides. As can be seen, these polypeptides show very high identity across the catalytic region, and also have complex membrane spanning domains. In some embodiments of the invention, these membrane-spanning domains are disrupted or are removed, so that, for example, a hyperactive version of the polypeptide may be produced.

FIG. 11 is a Table listing certain *Y. lipolytica* genes representing various polypeptides useful in engineering cells in accordance with the present invention.

DEFINITIONS

Figure 1A:
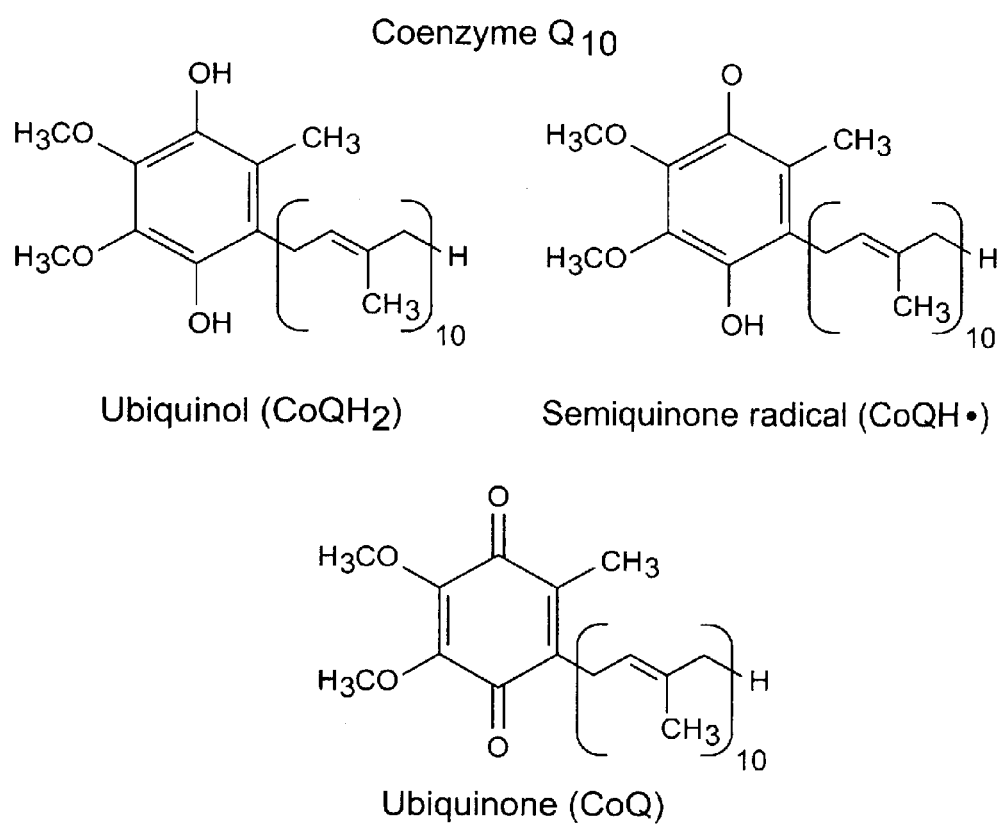
FIG. 1 depicts various quinone derived compounds including ubiquinone/Coenzyme Q10 in its various oxidized forms (Panel A); vitamin K (Panel B); and vitamin E (Panel C).

Aromatic amino acid biosynthesis polypeptide: The term "aromatic amino acid biosynthesis polypeptide" refers to any polypeptide that is involved in the synthesis of aromatic amino acids in yeast and/or bacteria through chorismate and the shikimate pathway. For example, as discussed herein, anthranilate synthase, enzymes of the shikimate pathway, chorismate mutase, chorismate synthase, DAHP synthase, and transketolase are all aromatic amino acid biosynthesis polypeptides. Each of these polypeptides is also a ubiquinone biosynthesis polypeptide or a ubiquinone biosynthesis competitor for purposes of the present invention, as production of chorismate is a precursor in the synthesis of para-hydroxybenzoate for the biosynthesis of a ubiquinone. Representative examples of some of these enzymes are provided in Tables 32-37.

Aromatic amino acid pathway: The "aromatic amino acid pathway" is understood in the art to refer to a metabolic pathway that produces or utilizes shikimate pathway enzymes and chorismate in the production of phenylalanine, tryptophan or tyrosine. As discussed herein, two different pathways can produce the ubiquinoid precursor para-hydroxybenzoate—the first, the "shikimate pathway" is utilized in prokaryotes and induces conversion of chorismate to para-hydroxybenzoate through the action of chorismate pyruvate lyase; the second is utilized in mammalian systems and induces induction of para-hydroxybenzoate by derivation of tyrosine or phenylalanine. The term "aromatic amino acid pathway" encompasses both of these pathways. Lower eukaryotes such as yeast can utilize either method for production of para-hydroxybenzoate.

Biosynthesis polypeptide: The term "biosynthesis polypeptide" as used herein (typically in reference to a particular compound or class of compounds), refers to polypeptides involved in the production of the compound or class of compounds. In some embodiments of the invention, biosynthesis polypeptides are synthetic enzymes that catalyze particular steps in a synthesis pathway that ultimately produces a relevant compound. In some embodiments, the term "biosynthesis polypeptide" may also encompass polypeptides that do not themselves catalyze synthetic reactions, but that regulate expression and/or activity of other polypeptides that do so.

$C_{5-9}$ quinone biosynthesis polypeptide: The term "$C_{5-9}$ quinone biosynthesis polypeptide" refers to any polypeptide that is involved in the synthesis of a $C_{5-9}$ quinone, for example a polyprenyldiphosphate synthase polypeptide. To mention but a few, these include, for example, pentaprenyl, hexaprenyl, heptaprenyl, octaprenyl, and/or solanesyl(nonaprenyl) diphosphate synthase polypeptides (i.e., polypeptides that perform the chemical reactions performed by the pentaprenyl, hexaprenyl, heptaprenyl, octaprenyl, and solanesyl (nonaprenyl) polypeptides, respectively, listed in Tables 61-65 (see also Okada et al., Biochim. Biophys. Acta 1302: 217, 1996; Okada et al., J. Bacteriol. 179:5992, 1997). As will be appreciated by those of ordinary skill in the art, in some embodiments of the invention, $C_{5-9}$ quinone biosynthesis polypeptides include polypeptides that affect the expression and/or activity of one or more other $C_{5-9}$ quinone biosynthesis polypeptides.

$C_{5-9}$ quinone compound: The term "$C_{5-9}$ quinone compound", as used herein, refers to a family of ubiquinone compounds having 5-9 isoprenoid units in the side chain.

$C_{5-9}$ quinone production modification: The term "$C_{5-9}$ quinone production modification", as used herein, refers to a modification of a host organism that adjusts production of one or more $C_{5-9}$ quinones, as described herein. For example, a $C_{5-9}$ quinone production modification may increase the production level of one or more $C_{5-9}$ quinones, and/or may alter relative production levels of different $C_{5-9}$ quinones. In principle, an inventive $C_{5-9}$ quinone production modification may be any chemical, physiological, genetic, or other modification that appropriately alters production of one or more $C_{5-9}$ quinones in a host organism produced by that organism as compared with the level produced in an otherwise identical organism not subject to the same modification. In most embodiments, however, the $C_{5-9}$ quinone production modification will comprise a genetic modification, typically resulting in increased production of one or more selected $C_{5-9}$ quinones. In some embodiments, the $C_{5-9}$ quinone production modification comprises at least one chemical, physiological, genetic, or other modification; in other embodiments, the $C_{5-9}$ quinone production modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Carotenogenic modification: The term "carotenogenic modification", as used herein, refers to a modification of a host organism that adjusts production of one or more carotenoids, as described herein. For example, a carotenogenic modification may increase the production level of one or more carotenoids, and/or may alter relative production levels of different carotenoids. In principle, an inventive carotenogenic modification may be any chemical, physiological, genetic, or other modification that appropriately alters production of one or more carotenoids in a host organism produced by that organism as compared with the level produced in an otherwise identical organism not subject to the same modification. In most embodiments, however, the carotenogenic modification will comprise a genetic modification, typically resulting in increased production of one or more selected carotenoids. In some embodiments, the carotenogenic modification comprises at least one chemical, physiological, genetic, or other modification; in other embodiments, the carotenogenic modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)). In some embodiments, the selected carotenoid is one or more of astaxanthin, β-carotene, canthaxanthin, lutein, lycopene, phytoene, zeaxanthin, and/or modifications of zeaxanthin or astaxanthin (e. g., glucoside, or other ester of zeaxanthin or astaxanthin). In some embodiments, the selected carotenoid is astaxanthin. In some embodiments, the selected carotenoid is other than β-carotene.

Carotenogenic polypeptide: The term "carotenogenic polypeptide", as used herein, refers to any polypeptide that is involved in the process of producing carotenoids in a cell, and may include polypeptides that are involved in processes other than carotenoid production but whose activities affect the extent or level of production of one or more carotenoids, for example by scavenging a substrate or reactant utilized by a carotenoid polypeptide that is directly involved in carotenoid production. Carotenogenic polypeptides include isoprenoid biosynthesis polypeptides, carotenoid biosynthesis polypeptides, and isoprenoid biosynthesis competitor polypeptides, as those terms are defined herein. The term also encompasses polypeptides that may affect the extent to which carotenoids are accumulated in lipid bodies.

Carotenoid: The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound IPP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $C_{60}$, $C_{70}$, $C_{80}$ in length or other lengths. Many carotenoids have strong light absorbing properties and may range in length in excess of $C_{200}$. $C_{30}$ diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature; carotenoids include but are not limited to: antheraxanthin, adonirubin, adonixanthin, astaxanthin, canthaxanthin, capsorubrin, β-cryptoxanthin, α-carotene, β-carotene, β,ψ-carotene, δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e. g., glycoside ester, fatty acid ester) and sulfate derivatives (e. g., esterified xanthophylls).

Carotenoid biosynthesis polypeptide: The term "carotenoid biosynthesis polypeptide" refers to any polypeptide that is involved in the synthesis of one or more carotenoids. To mention but a few, these carotenoid biosynthesis polypeptides include, for example, polypeptides of phytoene synthase, phytoene dehydrogenase (or desaturase), lycopene cyclase, carotenoid ketolase, carotenoid hydroxylase, astaxanthin synthase, carotenoid epsilon hydroxylase, lycopene cyclase (beta and epsilon subunits), carotenoid glucosyltransferase, and Acyl CoA:diacylglycerol acyltransferase. In some instances, a single gene may encode a protein with multiple carotenoid biosynthesis polypeptide activities. Representative examples of carotenoid biosynthesis polypeptide sequences are presented in Tables 17-21 and Tables 38-41. As will be appreciated by those of ordinary skill in the art, in some embodiments of the invention, carotenoid biosynthesis polypeptides include polypeptides that affect the expression and/or activity of one or more other carotenoid biosynthesis polypeptides.

Effective amount. The term "effective amount" is used herein to describe concentrations or amounts of compounds and/or compositions that, when administered to a subject, achieve a desired therapeutic or physiological effect.

FPP biosynthesis polypeptides: The term "FPP biosynthesis polypeptide" refers to any polypeptide that is involved in the synthesis of farnesyl pyrophosphate. As discussed herein, farnesyl pyrophosphate represents the branchpoint between the sterol biosynthesis pathway and the carotenoid and other biosynthesis pathways. One specific example of an FPP biosynthesis polypeptide is FPP synthase. Representative examples of FPP synthase polypeptide sequences are presented in Table 14. As will be appreciated by those of ordinary skill in the art, in some embodiments of the invention, FPP biosynthesis polypeptides include polypeptides that affect the expression and/or activity of one or more other FPP biosynthesis polypeptides.

Gene: The term "gene", as used herein, generally refers to a nucleic acid encoding a polypeptide, optionally including certain regulatory elements that may affect expression of one or more gene products (i. e., RNA or protein).

Heterologous: The term "heterologous", as used herein to refer to genes or polypeptides, refers to a gene or polypeptide that does not naturally occur in the organism in which it is being expressed. It will be understood that, in general, when a heterologous gene or polypeptide is selected for introduction into and/or expression by a host cell, the particular source organism from which the heterologous gene or polypeptide may be selected is not essential to the practice of the present invention. Relevant considerations may include, for example, how closely related the potential source and host organisms are in evolution, or how related the source organism is with other source organisms from which sequences of other relevant polypeptides have been selected. Where a plurality of different heterologous polypeptides are to be introduced into and/or expressed by a host cell, different polypeptides may be from different source organisms, or from the same source organism. To give but one example, in some cases, individual polypeptides may represent individual subunits of a complex protein activity and/or may be required to work in concert with other polypeptides in order to achieve the goals of the present invention. In some embodiments, it will often be desirable for such polypeptides to be from the same source organism, and/or to be sufficiently related to function appropriately when expressed together in a host cell. In some embodiments, such polypeptides may be from different, even unrelated source organisms. It will further be understood that, where a heterologous polypeptide is to be expressed in a host cell, it will often be desirable to utilize nucleic acid sequences encoding the polypeptide that have been adjusted to accommodate codon preferences of the host cell and/or to link the encoding sequences with regulatory elements active in the host cell.

Host cell: As used herein, the "host cell" is a fungal cell or yeast cell that is manipulated according to the present invention to accumulate lipid and/or to express one or more quinone derived compounds as described herein. A "modified host cell", as used herein, is any host cell which has been modified, engineered, or manipulated in accordance with the present invention as compared with a parental cell. In some embodiments, the modified host cell has at least one quinonogenic and/or at least one oleagenic modification. In some embodiments, the modified host cell containing at least one oleaginic modification and/or one quinonogenic modification further has at least one sterologenic modification and/or or at least one carotenogenic modification. In some embodiments, the parental cell is a naturally occurring parental cell.

Isolated: The term "isolated", as used herein, means that the isolated entity has been separated from at least one component with which it was previously associated. When most other components have been removed, the isolated entity is "purified" or "concentrated". Isolation and/or purification and/or concentration may be performed using any techniques known in the art including, for example, fractionation, extraction, precipitation, or other separation.

Isoprenoid biosynthesis polypeptide: The term "isoprenoid biosynthesis polypeptide" refers to any polypeptide that is involved in the synthesis of isoprenoids. For example, as discussed herein, acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase, are all involved in the mevalonate pathway for isoprenoid biosynthesis. Each of these proteins is also an isoprenoid biosynthesis polypeptide for purposes of the present invention, and sequences of representative examples of these enzymes are provided in Tables 7-15. As will be appreciated by those of ordinary skill in the art, in some embodiments of the invention, isoprenoid biosynthesis polypeptides include polypeptides that affect the expression and/or activity of one or more other isoprenoid biosynthesis polypeptides (e.g., of one or more enzymes that participate(s) in isoprenoid synthesis). Thus, for instance, transcription factors that regulate expression of isoprenoid biosynthesis enzymes can be isoprenoid biosynthesis polypeptides for purposes of the present invention. To give but a couple of examples, the *S. cerevisiae* Upc2 and YLR228c genes, and the *Y. lipolytica* YALI0B00660g gene encode transcription factors that are isoprenoid biosynthesis polypeptides according to certain embodiments of the present invention. For instance, the semi-dominant upc2-1 point mutation (G888D) exhibits increased sterol levels (Crowley et al., *J. Bacteriol* 180:4177-4183, 1998). Corresponding YLR228c mutants have been made and tested (Shianna et al., *J Bacteriol* 183:830, 2001); such mutants may be useful in accordance with the present invention, as may be YALI0B00660g derivatives with corresponding upc2-1 mutation(s).

Isoprenoid pathway: The "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP—the "mevalonate pathway" and the "non-mevalonate pathway". The term "isoprenoid pathway" is sufficiently general to encompass both of these types of pathway. Biosynthesis of isoprenoids from IPP occurs by polymerization of several five-carbon isoprene subunits. Isoprenoid metabolites derived from IPP are of varying size and chemical structure, including both cyclic and acyclic molecules. Isoprenoid metabolites include, but are not limited to, monoterpenes, sesquiterpenes, diterpenes, sterols, and polyprenols such as carotenoids.

Oleaginic modification: The term "oleaginic modification", as used herein, refers to a modification of a host organism that adjusts the desirable oleaginy of that host organism, as described herein. In some cases, the host organism will already be oleaginous in that it will have the ability to accumulate lipid to at least about 20% of its dry cell weight. It may nonetheless be desirable to apply an oleaginic modification to such an organism, in accordance with the present invention, for example to increase (or, in some cases, possibly to decrease) its total lipid accumulation, or to adjust the types or amounts of one or more particular lipids it accumulates (e. g., to increase relative accumulation of triacylglycerol). In other cases, the host organism, may be non-oleaginous (though may contain some enzymatic and/or regulatory components used in other organisms to accumulate lipid), and may require oleaginic modification in order to become oleaginous in accordance with the present invention. The present invention also contemplates application of oleaginic modification to non-oleaginous host strains such that their oleaginicity is increased even though, even after being modified, they may not be oleaginous as defined herein. In principle, the oleaginic modification may be any chemical, physiological, genetic, or other modification that appropriately alters oleaginy of a host organism as compared with an otherwise identical organism not subjected to the oleaginic modification. In most embodiments, however, the oleaginic modification will comprise a genetic modification, typically resulting in increased production and/or activity of one or more oleaginic polypeptides. In some embodiments, the oleaginic modification comprises at least one chemical, physiological, genetic, or other modification; in other embodiments, the oleaginic modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Oleaginic polypeptide: The term "oleaginic polypeptide", as used herein, refers to any polypeptide that is involved in the process of lipid accumulation in a cell and may include polypeptides that are involved in processes other than lipid biosynthesis but whose activities affect the extent or level of accumulation of one or more lipids, for example by scavenging a substrate or reactant utilized by an oleaginic polypeptide that is directly involved in lipid accumulation. For example, as discussed herein, acetyl-CoA carboxylase, pyruvate decarboxylase, isocitrate dehydrogenase, ATP-citrate lyase, malic enzyme, malate dehydrogenase, and AMP deaminase, among other proteins, are all involved in lipid accumulation in cells. In general, reducing the activity of pyruvate decarboxylase or isocitrate dehydrogenase, and/or increasing the activity of acetyl CoA carboxylase, ATP-citrate lyase, malic enzyme, malate dehydrogenase, and/or AMP deaminase is expected to promote oleaginy. Each of these proteins is an oleaginic peptide for the purposes of the present invention, and sequences of representative examples of these enzymes are provided in Tables 1-6, 69. Other peptides that can be involved in regenerating NADPH may include, for example, 6-phosphogluconate dehydrogenase (gnd); Fructose 1,6 bisphosphatase (fbp); Glucose 6 phosphate dehydrogenase (g6pd); NADH kinase (EC 2.7.1.86); and/or transhydrogenase (EC 1.6.1.1 and 1.6.1.2). Alternative or additional strategies to promote oleaginy may include one or more of the following: (1) increased or heterologous expression of one or more of acyl-CoA:diacylglycerol acyltransferase (e.g., DGA1; YALI0E32769g); phospholipid:diacylglycerol acyltransferase (e.g., LRO1; YALI0E16797g); and acyl-CoA:cholesterol acyltransferase (e.g., ARE genes such as ARE1, ARE2, YALI0F06578g), which are involved in triglyceride synthesis (Kalscheuer et al. *Appl Environ Microbiol* p. 7119-7125, 2004; Oelkers et al. *J Biol Chem* 277:8877-8881, 2002; and Sorger et al. *J Biol Chem* 279:31190-31196, 2004), (2) decreased expression of triglyceride lipases (e.g., TGL3 and/or TGL4; YALI0D17534g and/or YALI0F10010g (Kurat et al. *J Biol Chem* 281:491-500, 2006); and (3) decreased expression of one or more acyl-coenzyme A oxidase activities, for example encoded by POX genes (e.g. POX1, POX2, POX3, POX4, POX5; YALI0C23859g, YALI0D24750g, YALI0E06567g, YALI0E27654g, YALI0E32835g, YALI0F10857g; see, for example, Mlickova et al. *Appl Environ Microbiol* 70: 3918-3924, 2004; Binns et al. *J Cell Biol* 173:719, 2006). Each of these proteins is an oleaginic peptide for the purposes of the present invention, and sequences of representative examples of these enzymes are provided in Tables 70-85 and Tables 100-101.

Oleaginous: The term "oleaginous", as used herein, refers to ability of an organism to accumulate lipid to at least about 20% of its dry cell weight. In certain embodiments of the invention, oleaginous yeast or fungi accumulate lipid to at least about 25% of their dry cell weight. In other embodiments, inventive oleaginous yeast or fungi accumulate lipid within the range of about 20-45% (e.g., about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, or more) of their dry cell weight. In some embodiments, oleaginous organisms may accumulate lipid to as much as about 70% of their dry cell weight. In some embodiments of the invention, oleaginous organisms may accumulate a large fraction of total lipid accumulation in the form of triacylglycerol. In certain embodiments, the majority of the accumulated lipid is in the form of triacylglycerol. Alternatively or additionally, the lipid may accumulate in the form of intracellular lipid bodies, or oil bodies. In certain embodiments, the present invention utilizes yeast or fungi that are naturally oleaginous. In some aspects, naturally oleaginous organisms are manipulated (e. g., genetically, chemically, or otherwise) so as to further increase the level of accumulated lipid in the organism. For example, for the purposes of the present invention, *Yarrowia lipolytica* is a naturally oleaginous fungi. In other embodiments, yeast or fungi that are not naturally oleaginous are manipulated (e. g., genetically, chemically, or otherwise) to accumulate lipid as described herein. For example, for the purposes of the present invention, *Saccharomyces cerevisiae, Xanthophyllomyces dendrorhous (Phaffia rhodozyma)*, and *Candida utilis* are not naturally oleaginous fungi.

PHB polypeptide or PHB biosynthesis polypeptide: The terms "PHB polypeptide" or "PHB biosynthesis polypeptide" as used herein refers to a polypeptide that is involved in the synthesis of para-hydroxybenzoate from chorismate. In prokaryotes and lower eukaryotes, synthesis of para-hydroxybenzoate occurs by the action of chorismate pyruvate lyase. Biosynthesis of para-hydroxybenzoate from tyrosine or phenylalanine occurs through a five-step process in mammalian cells. Lower eukaryotes such as yeast can utilize either method for production of para-hydroxybenzoate. For example, enzymes of the shikimate pathway, chorismate synthase, DAHP synthase, and transketolase are all PHB biosynthesis polypeptides. Each of these polypeptides is also a ubiquinone biosynthesis polypeptide or a ubiquinone biosynthesis competitor polypeptide for purposes of the present invention. Exemplary PHB polypeptides are provided in Tables 33 and 35-37.

Polypeptide: The term "polypeptide", as used herein, generally has its art-recognized meaning of a polymer of at least three amino acids. However, the term is also used to refer to specific functional classes of polypeptides, such as, for example, aromatic amino acid biosynthesis polypeptides, biosynthesis polypeptides, $C_{5-9}$ quinone biosynthesis polypeptides, carotenogenic polypeptides, carotenoid biosynthesis polypeptides, isoprenoid biosynthesis polypeptides, oleaginic polypeptides, PHB polypeptides, PHB biosynthesis polypeptides, quinone biosynthesis polypeptides, quinonogenic polypeptides, ubiquinone biosynthesis polypeptides, ubiquinone biosynthesis competitor polypeptides, ubiquinogenic polypeptides, Vitamin E biosynthesis polypeptides, Vitamin K biosynthesis polypeptides, etc. For each such class, the present specification provides several examples of known sequences of such polypeptides. Those of ordinary skill in the art will appreciate, however, that the term "polypeptide" is intended to be sufficiently general as to encompass not only polypeptides having the complete sequence recited herein (or in a reference or database specifically mentioned herein), but also to encompass polypeptides that represent functional fragments (i. e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions (e.g., isocitrate dehydrogenase polypeptides often share a conserved AMP-binding motif; HMG-CoA reductase polypeptides typically include a highly conserved catalytic domain [see, for example, FIG. 7]; acetyl coA carboxylase typically has a carboxyl transferase domain; see, for example, Downing et al., *Chem. Abs.* 93:484, 1980; Gil et al., *Cell* 41:249, 1985; Jitrapakdee et al. *Curr Protein Pept Sci.* 4:217, 2003; U.S. Pat. No. 5,349,126, each of which is incorporated herein by reference in its entirety), usually encompassing at least 3-4 and often up to 20 or more amino acids, with another polypeptide of the same class, is encompassed within the relevant term "polypeptide" as used herein. Other regions of similarity and/or identity can be determined by those of ordinary skill in the art by analysis of the sequences of various polypeptides presented in the Tables herein.

Quinone biosynthesis polypeptide: A "quinone biosynthesis polypeptide", as that term is used herein, refers to any polypeptide involved in the synthesis of one or more quinone derived compound, as described herein. In particular, quinone biosynthesis polypeptides include ubiquinone biosynthesis polypeptides (e.g., biosynthesis polypeptides involved in production of coenzyme Q10 and/or a $C_{5-9}$ quinone compound), vitamin K biosynthesis polypeptides, and vitamin E biosynthesis polypeptides.

Quinone derived compounds: The term "quinone derived compounds" is used herein to refer to certain compounds that either contain a quinone moiety or are derived from a precursor that contains a quinone moiety. In particular, quinone derived compounds according to the present invention are ubiquinones (e.g., coenzyme Q10, $C_{5-9}$ quinone compounds, etc.), vitamin E compounds, and/or vitamin K compounds. Structures of representative quinone derived compounds are presented in FIG. 1.

Quinonogenic modification: The term "quinonogenic modification", as used herein, refers to refers to a modification of a host organism that adjusts production of one or more quinone derived compounds (e.g., ubiquinones, vitamin K compounds, vitamin E compounds, etc.), as described herein. For example, a quinonogenic modification may increase the production level of a particular quinone derived compound, or of a variety of different quinone derived compounds. In some embodiments of the invention, production of a particular quinone derived compound may be increased while production of other quinone derived compounds is decreased. In some embodiments of the invention, production of a plurality of different quinone derived compounds is increased. In principle, an inventive quinonogenic modification may be any chemical, physiological, genetic, or other modification that appropriately alters production of one or more quinone derived compounds in a host organism produced by that organism as compared with the level produced in an otherwise identical organism not subject to the same modification. In most embodiments, however, the quinonogenic modification will comprise a genetic modification, typically resulting in increased production of one or more quinone derived compounds (e.g., ubiquinones, vitamin K compounds, vitamin E compounds). In some embodiments, the quinonogenic modification comprises at least one chemical, physiological, genetic, or other modification; in other embodiments, the quinonogenic modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s))

Quinonogenic polypeptide: The term "quinonogenic polypeptide", as used herein, refers to any polypeptide whose activity in a cell increases production of one or more quinone derived compounds (e.g., ubiquinones, vitamin K compounds, vitamin E compounds) in that cell. The term encompasses both polypeptides that are directly involved in quinone derived compound synthesis and those whose expression or activity affects the extent or level of production of one or more quinone derived compounds, for example by scavenging a substrate or reactant utilized by a quinone biosynthetic polypeptide that is directly involved in quinone derived compound production. Quinonogenic polypeptides include isoprenoid biosynthesis polypeptides, ubiquinone biosynthesis polypeptides (e.g., polypeptides involved in production of coenzyme Q10 and/or a C5-9 quinone compound), vitamin E biosynthesis polypeptides, and vitamin K biosynthesis polypeptides. Quinonogenic polypeptides may also include ubiquinogenic polypeptides, etc. The term also encompasses polypeptides that may affect the extent to which one or more quinone derived compounds is accumulated in lipid bodies.

Small Molecule: In general, a small molecule is understood in the art to be an organic molecule that is less than about 5 kilodaltons (Kd) in size. In some embodiments, the small molecule is less than about 3 Kd, 2 Kd, or 1 Kd. In some embodiments, the small molecule is less than about 800 daltons (D), 600 D, 500 D, 400 D, 300 D, 200 D, or 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Source organism: The term "source organism", as used herein, refers to the organism in which a particular polypeptide sequence can be found in nature. Thus, for example, if one or more heterologous polypeptides is/are being expressed in a host organism, the organism in which the polypeptides are expressed in nature (and/or from which their genes were originally cloned) is referred to as the "source organism". Where multiple heterologous polypeptides are being expressed in a host organism, one or more source organism(s) may be utilized for independent selection of each of the heterologous polypeptide(s). It will be appreciated that any and all organisms that naturally contain relevant polypeptide sequences may be used as source organisms in accordance with the present invention. Representative source organisms include, for example, animal, mammalian, insect, plant, fungal, yeast, algal, bacterial, archaebacterial, cyanobacterial, and protozoal source organisms.

Sterol biosynthesis polypeptide: The term "sterol biosynthesis polypeptide", as used herein, refers to any polypeptide that is involved in the synthesis of one or more sterol compounds. Thus, sterol biosynthesis polypeptides can include isoprenoid biosynthesis polypeptides to the extent that they are involved in production of isopentyl pyrophosphate. Moreover, the term refers to any polypeptide that acts downstream of farnesyl pyrophosphate and in involved in the production of one or more sterol compounds. For example, sterol biosynthesis polypeptides include squalene synthase, which catalyses conversion of farnesyl pyrophosphate to presqualene pyrophosphate, and further catalyzes conversion of presqualene pyrophosphate to squalene (i.e., enzyme 2.5.1.21 in FIG. 8). In some embodiments of the invention, sterol biosynthesis polypeptides further include one or more polypeptides involved in metabolizing squalene into a vitamin D compound. Thus, sterol biosynthesis polypeptides can include one or more of the 1.14.99.7, 5.4.99.7, 5.4.99.8, 5.3.3.5, 1.14.21.6, 1.14.15.-, 1.14.13.13 enzyme polypeptides depicted in FIG. 8, as well as other enzyme polypeptides involved in the illustrated pathways. Furthermore, sterol biosynthesis polypeptides can include one or more enzyme polypeptides including, for example, C-14 demethylase (ERG9), squalene monooxygenase (ERG1), 2,3-oxidosqualene-lanosterol synthase (ERG7), C-1 demethylase (ERG11), C-14 reductase (ERG24), C-4 methyloxidase (ERG25), C-4 decarboxylase (ERG26), 3-ketoreductase (ERG27), C-24 methyltransferase (ERG6), Δ8-7 isomerase (ERG2), C-5 desaturase (ERG3), C-22 desaturase (ERG5) and/or C-24 reductase (ERG4) polypeptides, and/or other polypeptides involved in producing one or more vitamin D compounds (e.g., vitamin D2, vitamin D3, or a precursor thereof). As will be appreciated by those of ordinary skill in the art, in some embodiments of the invention, sterol biosynthesis polypeptides include polypeptides that affect the expression and/or activity of one or more other sterol biosynthesis polypeptides. Thus, for instance, transcription factors that regulate expression of sterol biosynthesis enzymes can be sterol biosynthesis polypeptides for purposes of the present invention. To give but a couple of examples, the S. cerevisiae Upc2 and YLR228c genes, and the Y. lipolytica YALI0B00660g gene encode transcription factors that are sterol biosynthesis polypeptides according to certain embodiments of the present invention. For instance, the semidominant upc2-1 point mutation (G888D) exhibits increased sterol levels (Crowley et al., J. Bacteriol 180:4177-4183, 1998). Corresponding YLR228c mutants have been made and tested (Shianna et al., J Bacteriol 183:830, 2001); such mutants may be useful in accordance with the present invention, as may be YALI0B00660g derivatives with corresponding upc2-1 mutation(s). Representative examples of certain sterol biosynthesis polypeptide sequences are presented in Table 16 and 86-99.

Sterologic modification: The term "sterologic modification", as used herein, refers to a modification of a host organism that adjusts production of one or more sterol compounds (e.g., squalene, lanosterol, zymosterol, ergosterol, 7-dehydrocholesterol (provitamin D3), vitamin D compound(s), etc.), as described herein. For example, a sterologenic modification may increase the production level of a particular sterol compound, or of a variety of different sterol compounds. In some embodiments of the invention, production of a particular sterol compound may be increased while production of other sterol compounds is decreased. In some embodiments of the invention, production of a plurality of different sterol compounds is increased. In principle, an inventive sterologenic modification may be any chemical, physiological, genetic, or other modification that appropriately alters production of one or more sterol compounds in a host organism produced by that organism as compared with the level produced in an otherwise identical organism not subject to the same modification. In most embodiments, however, the sterologenic modification will comprise a genetic modification, typically resulting in increased production of one or more sterol compounds (e.g., squalene, lanosterol, zymosterol, ergosterol, 7-dehydrocholesterol (provitamin D3) or vitamin D compound(s)). In certain aspects where more than one modification is utilized, such modifications can comprise any combination of chemical, physiological, genetic, or other modification (e.g., one or more genetic modification and chemical or physiological modification).

Subject: The term "subject" is used throughout the present specification to describe an animal, in most instances a human, to whom inventive compositions are administered.

Ubiquinone: The term "ubiquinone" is understood in the art to refer to a structural class of quinone derivatives with or without isoprenoid side chains. Ubiquinones are described in the Merck Index, 11th Edition, Merck & Co., Inc. Rahway, N.Y., USA, Abstr. 9751 (1989), which is incorporated herein by reference. A dual nomenclature exists for these compounds and is based upon the length of the terpenoid side chain. Those which contain an isoprene side chain are also referred to by the term coenzymes Q. A benzoquinone of this family is therefore properly referred to as either "Coenzyme Qn," where n is an integer from one to twelve and designates the number of isoprenoid units in the side chain, or alternatively, "ubiquinone (x)" where x designates the total number of carbon atoms in the side chain and is a multiple of five. Typically, n is an integer ranging from 0 to 12, in particular from 1 to 12, and more particularly 6, 7, 8, 9, or 10. For example, the most common ubiquinone in animals has a ten isoprenoid side chain and is referred to as either Coenzyme Q10, ubiquinone, or ubidecarenone. In other organisms (e.g. fungi, bacteria), other ubiquinones, for example $C_5$ (CoQ5), $C_6$ (CoQ6), $C_7$ (CoQ7), $C_8$ (CoQ8), or $C_9$ (CoQ9) (collectively $C_{5-9}$) quinones are more prevalent than Coenzyme Q10 (CoQ10). As mentioned, ubiquinones may lack an isoprene side chain, and may be selected from alkylubiquinones in which the alkyl group may contain from 1 to 20 and preferably from 1 to 12 carbon atoms, such as, for example, decylubiquinones such as 6-decylubiquinone or 2,3-dimethoxy-5-decyl-1,4-ubiquinone, derivatives thereof, and mixtures thereof. Ubiquinones may exist in reduced (ubiquinol), oxidized or superoxidized states. For example, the oxidation states of the ubiquinone coenzyme Q10 are depicted in FIG. 1A.

Figure 3:
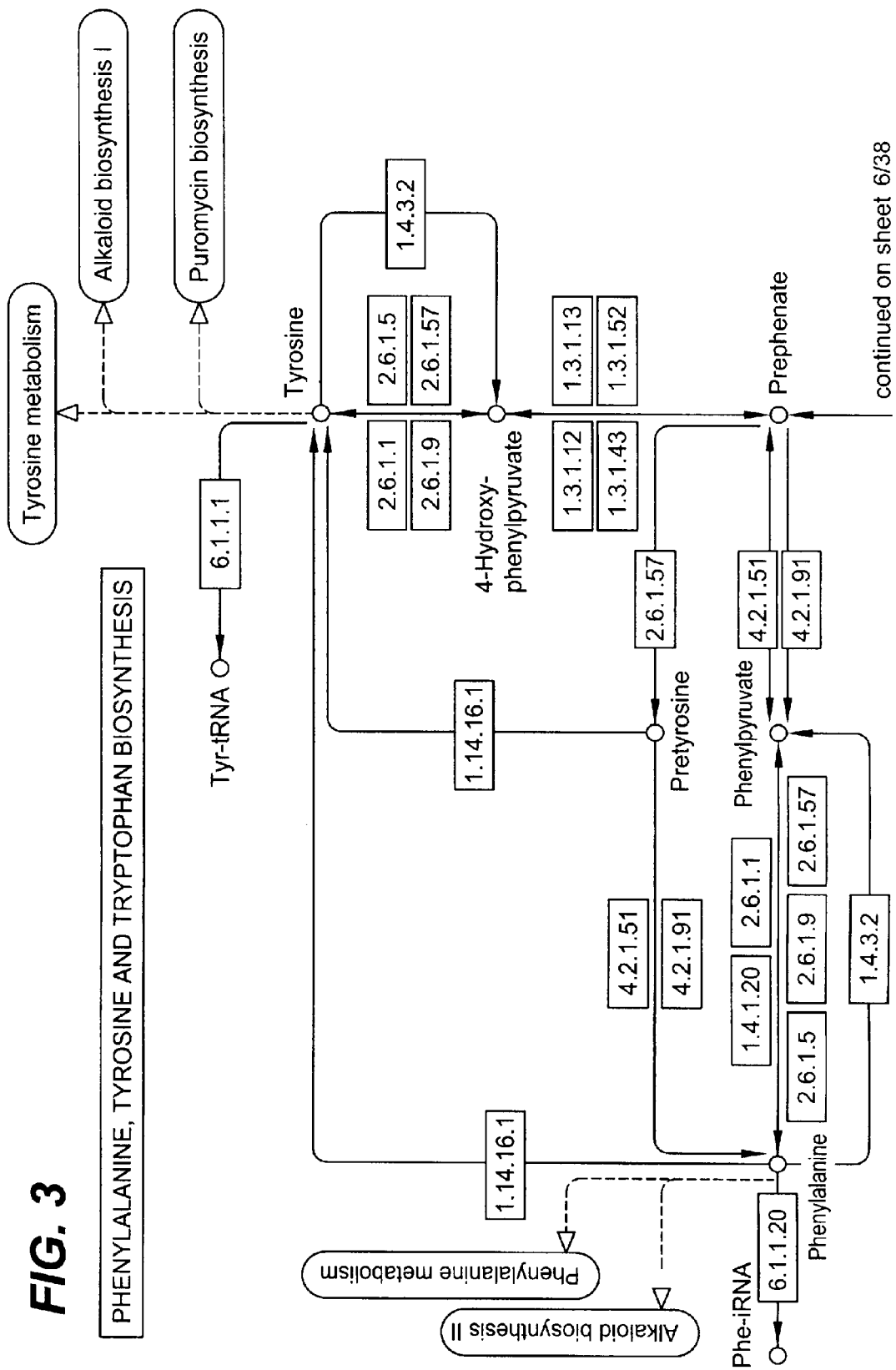
FIG. 3 illustrates biosynthetic pathways of aromatic amino acids, and the shikimate pathway for production of chorismate. A depiction of how these pathways feed into ubiquinone biosynthesis is depicted. Boxed numerical references are IUBMB Enzyme Nomenclature EC numbers for enzymes catalyzing the relevant reaction.
Figure 3:
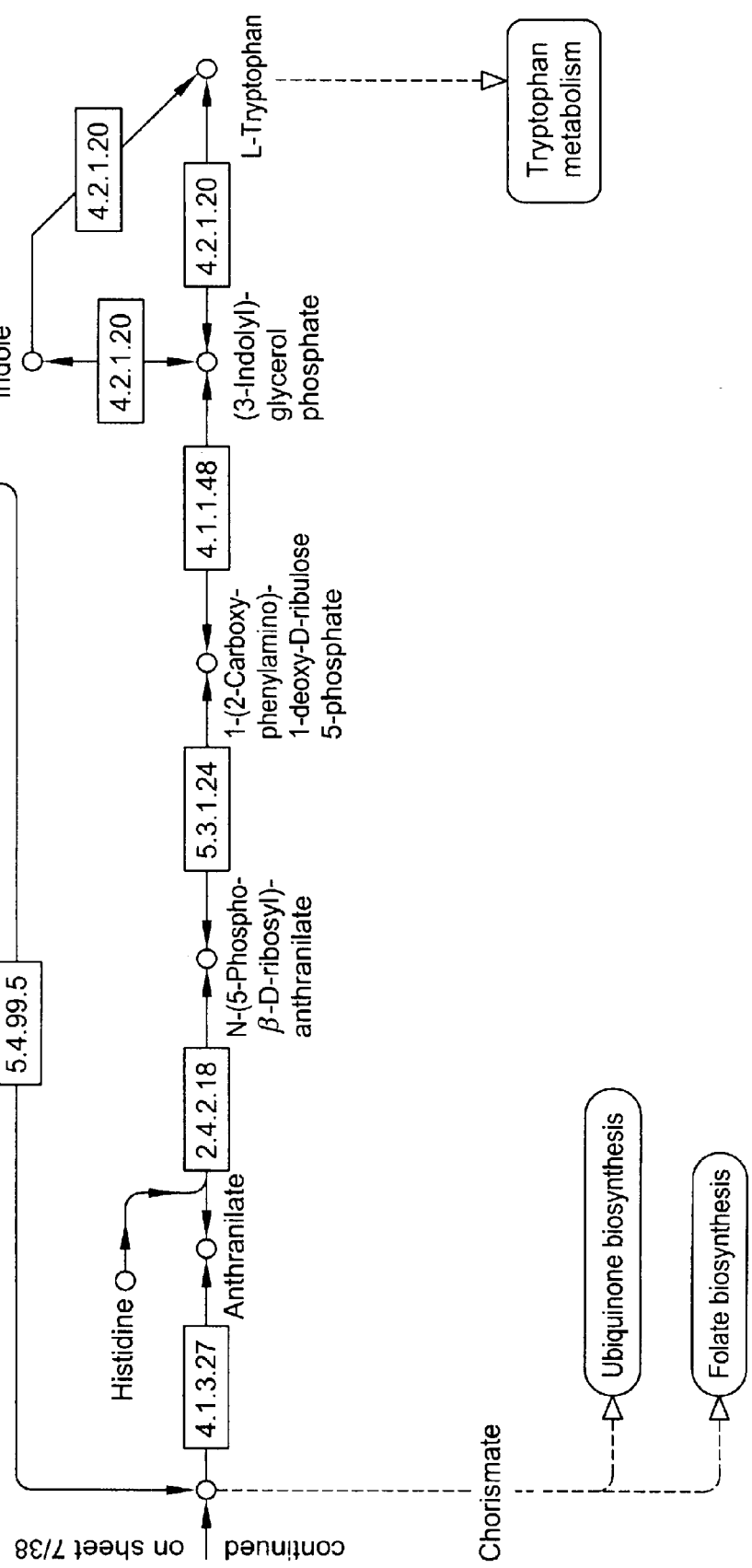
Figure 3:
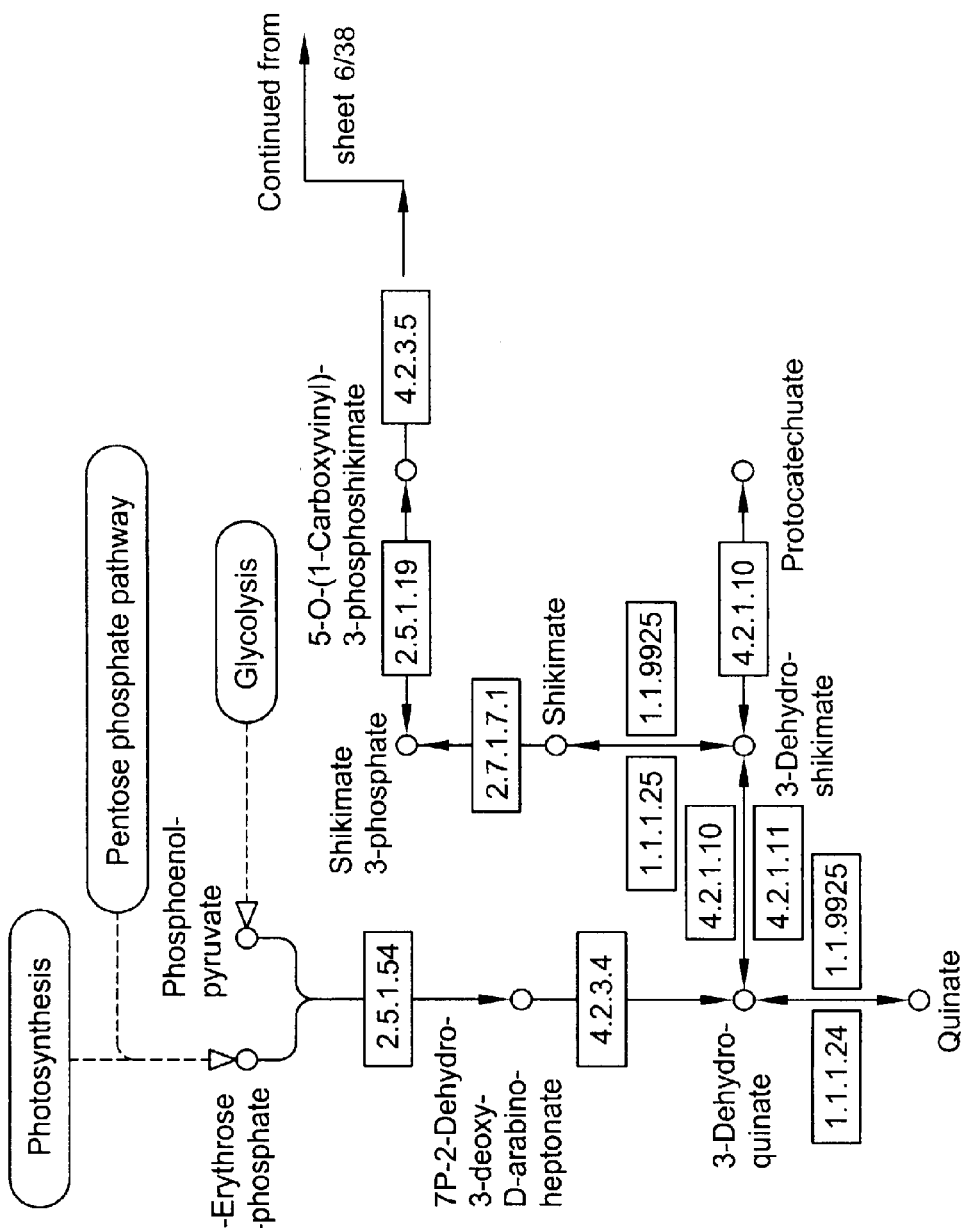
Figure 5:
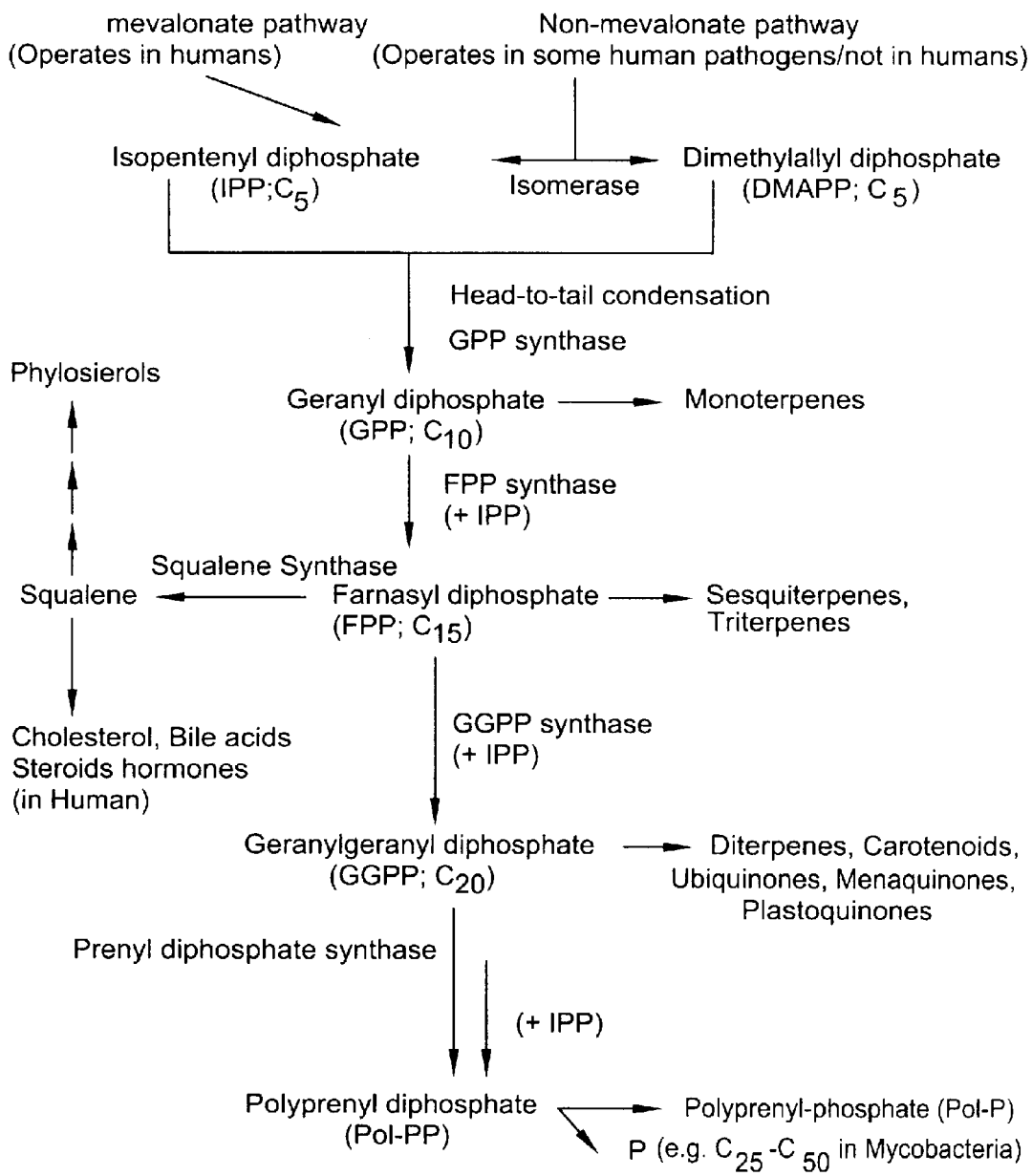
FIG. 5, illustrates how intermediates in the isoprenoid biosynthesis pathway can be processed into biomolecules, including ubiquinones, carotenoids, sterols, steroids, and vitamins, such as vitamin E or vitamin K.
Figure 6:
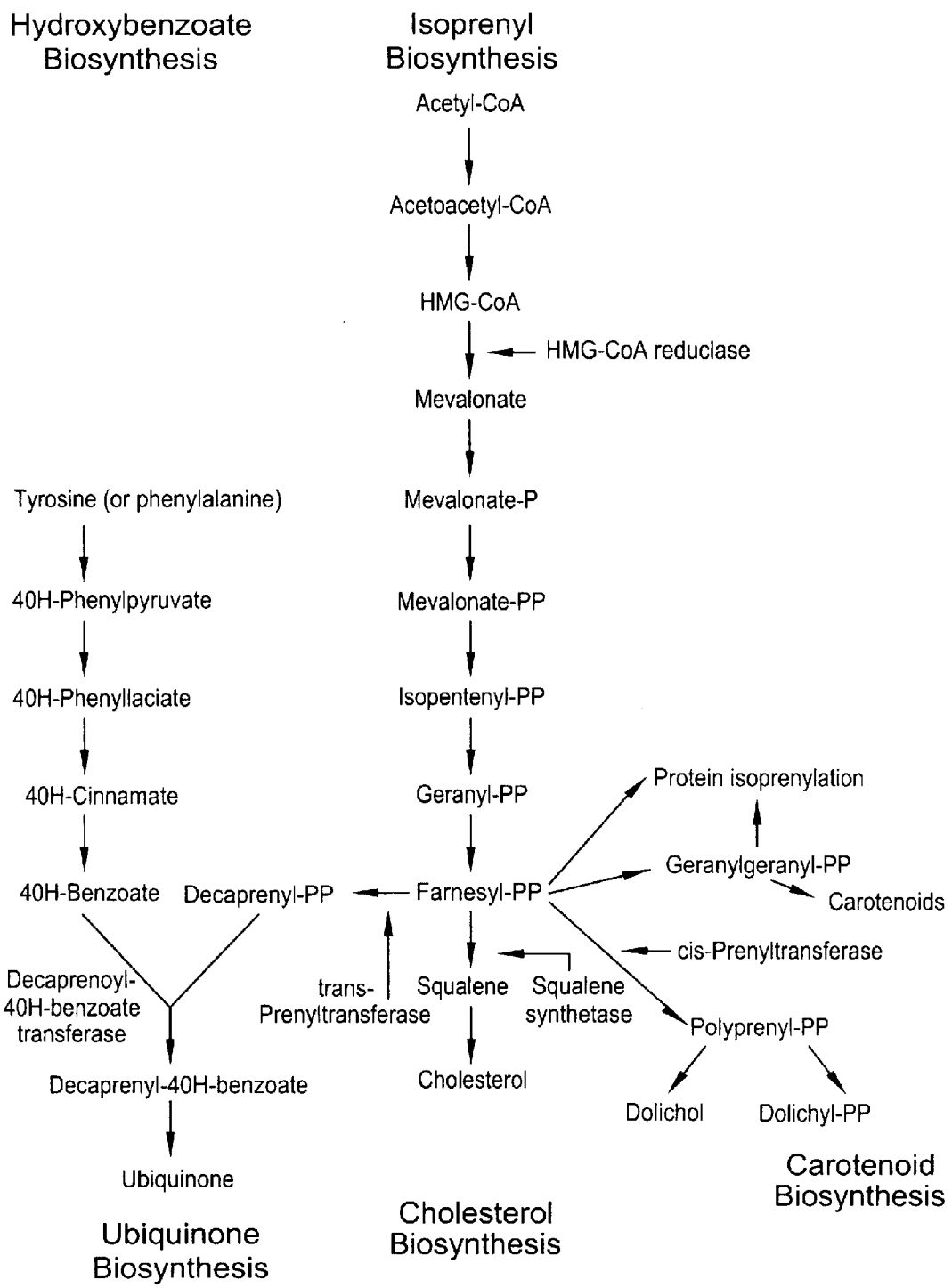
FIG. 6 illustrates how intermediates in ubiquinone biosynthesis feed into the biosynthetic pathway, and how some intermediates can be processed into other molecules.

Ubiquinone biosynthesis competitor: The term "ubiquinone biosynthesis competitor", as used herein, refers to an agent whose presence or activity in a cell reduces the level of farnesyl pyrophosphate (FPP), geranylgeranyl diphosphate (GGPP), chorismate, or any combination thereof that is available to enter the ubiquinogenic biosynthesis pathway. The term "ubiquinone biosynthesis competitor" encompasses both polypeptide (e.g. ubiquinone biosynthesis competitor polypeptides) and non-polypeptide (e.g., small molecule) inhibitor agents. Those of ordinary skill in the art will appreciate that certain competitor agents that do not act as inhibitors of ubiquinone biosynthesis generally can nonetheless act as inhibitors of biosynthesis of a particular ubiquinone compound (e.g. CoQ10 or a $C_{5-9}$ quinone compound). Particular examples of ubiquinone biosynthesis competitor agents act on isoprenoid intermediates prior to FPP or GGPP, such that less FPP or GGPP is generated (see, for example, FIG. 5, FIG. 6). Squalene synthase (also called squalene synthetase) is a ubiquinone biosynthesis competitor according to the present invention; representative squalene synthase sequences are presented in Table 16. In another example, ubiquinone biosynthesis competitors include aromatic amino acid polypeptide enzymes that act on PHB precursors at or prior to chorismate, such that less chorismate is available for synthesis of para-hydroxybenzoate (see, for example FIG. 3). Anthranilate synthase is one ubiquinone biosynthesis competitor according to the present invention, and chorismate mutase another, representative anthranilate synthase and chorismate mutase polypeptides are presented in Table 32, 32B and Table 34, respectively. Those of ordinary skill in the art, considering the known metabolic pathways relating to ubiquinone production and/or metabolism (see, for example, FIG. 1 and other Figures and references herein) will readily appreciate a variety of other particular ubiquinone biosynthesis competitors, including ubiquinone biosynthesis polypeptides.

Ubiquinone biosynthesis polypeptide: The term "ubiquinone biosynthesis polypeptide" refers to any polypeptide that is involved in the synthesis of a ubiquinone (e. g., CoQ10 or a $C_{5-9}$ quinone compound). To mention but a few, these ubiquinone biosynthesis polypeptides include, for example, polypeptides of polyprenyldiphosphate synthase (e.g. penta-, hexa-, hepta, octa-, nona-, deca-prenyldiphosphate synthase, PHB-polyprenyltransferase, and O-methyltransferase. Representative examples of ubiquinone biosynthesis polypeptide sequences are presented in Tables 23 (including 23b and 23c), 24-31, Table 33 as well as 35-37 (see also above PHB biosynthesis, $C_{5-9}$ quinone biosynthesis polypeptides (e.g., Tables 61-65), and isoprenoid biosynthesis polypeptides which are ubiquinone biosynthesis polypeptides).

Ubiquinogenic modification: The term "ubiquinogenic modification", as used herein, refers to a modification of a host organism that adjusts production of a ubiquinone (e. g., CoQ10), as described herein. For example, a ubiquinogenic modification may increase the production level of a ubiquinone (e.g., CoQ10 and/or a $C_{5-9}$ quinone compound), and/or may alter relative levels of a ubiquinone and/or a ubiquinol. In principle, an inventive ubiquinogenic modification may be any chemical, physiological, genetic, or other modification that appropriately alters production of a ubiquinone (e.g., CoQ10 and/or a $C_{5-9}$ quinone compound) in a host organism produced by that organism as compared with the level produced in an otherwise identical organism not subject to the same modification. In most embodiments, however, the ubiquinogenic modification will comprise a genetic modification, typically resulting in increased production of a ubiquinone (e.g., CoQ10 and/or a $C_{5-9}$ quinone compound). In some embodiments, the ubiquinogenic modification comprises at least one chemical, physiological, genetic, or other modification; in other embodiments, the ubiquinogenic modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Ubiquinogenic polypeptide: The term "ubiquinogenic polypeptide," as used herein, refers to any polypeptide that is involved in the process of producing a ubiquinone (e.g., CoQ10 and/or a $C_{5-9}$ quinone compound) in a cell, and may include polypeptides that are involved in processes other than ubiquinone production but whose expression or activity affects the extent or level of production of a ubiquinone and/or a ubiquinol, for example by scavenging a substrate or reactant utilized by a ubiquinone biosynthetic polypeptide that is directly involved in ubiquinone production. Ubiquinogenic polypeptides include isoprenoid biosynthesis polypeptides, ubiquinone biosynthesis polypeptides, and ubiquinonebiosynthesis competitor polypeptides, as those terms are defined herein. The term also encompasses polypeptides that may affect the extent to which a given ubiquinone is accumulated in lipid bodies.

Vitamin D biosynthesis polypeptide: The term "vitamin D biosynthesis polypeptide" refers to any polypeptide that is involved in the synthesis of one or more vitamin D compounds. To mention but a few, these include, for example, the 1.14.99.7, 5.4.99.7, 5.4.99.8, 5.3.3.5, and/or 1.14.21.6, polypeptides depicted in FIG. 8. They further can include the hydroxylases that convert vitamin $D_3$ to calcitriol (e.g., the 1.14.15.- and 1.14.13.13 polypeptides depicted in FIG. 8). As will be appreciated by those of ordinary skill in the art, in some embodiments of the invention, vitamin D biosynthesis polypeptides include polypeptides that affect the expression and/or activity of one or more other vitamin D biosynthesis polypeptides. Particular examples of certain vitamin D biosynthesis polypeptides are presented in Tables 86-99.

Vitamin E biosynthesis polypeptide: The term "vitamin E biosynthesis polypeptide" refers to any polypeptide that is involved in the synthesis of vitamin K. To mention but a few, these include, for example, tyrA, pds1(hppd), VTE1, HPT1 (VTE2), VTE3, VTE4, and/or GGH polypeptides (i.e., polypeptides that perform the chemical reactions performed by tyrA, pds1(hppd), VTE1, HPT1(VTE2), VTE3, VTE4, and/or GGH, respectively). Particular examples of such vitamin E biosynthesis polypeptides are presented in Tables 54-60.

Vitamin E compound: The term "vitamin E compound", as used herein, refers to members of a family of structurally related compounds that have a 6-chromanol ring, an isoprenoid side chain, and the biologic activity of α-tocopherol. The term encompasses the eight known naturally occurring vitamin E compounds, the four tocopherols (α, β, γ, δ) and four tocotrienols (α, β, γ, δ), which all contain a hydrophilic chromanol ring and a hydrophobic side chain. The α, β, γ, and δ forms differ from one another in the number of methyl groups on the chromanol ring. Several synthetic vitamin E compounds have also been prepared, and still others are possible (see, for example, Bramley et al., *J. Sci Food Agric* 80:913, 2000). α-tocopherol is a potent antioxidant, and is generally considered to be the most active vitamin E compound in humans.

Vitamin E production modification: The term "Vitamin E production modification", as used herein, refers to a modification of a host organism that adjusts production of Vitamin E. For example, a Vitamin E production modification may increase the production level of one or more vitamin E compounds, and/or may alter relative production levels of different vitamin E compounds. In principle, an inventive vitamin E production modification may be any chemical, physiological, genetic, or other modification that appropriately alters production of one or more vitamin E compounds in a host organism produced by that organism as compared with the level produced in an otherwise identical organism not subject to the same modification. In most embodiments, however, the vitamin E production modification will comprise a genetic modification, typically resulting in increased production of one or more selected vitamin E compounds. In some embodiments, the vitamin E production modification comprises at least one chemical, physiological, genetic, or other modification; in other embodiments, the vitamin E production modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Vitamin K biosynthesis polypeptide: The term "vitamin K biosynthesis polypeptide" refers to any polypeptide that is involved in the synthesis of vitamin K. To mention but a few, these include, for example, MenF, MenD, MenC, MenE, MenB, MenA, UbiE, and/or MenG polypeptides (i.e., polypeptides that perform the chemical reactions performed by MenF, MenD, MenC, MenE, MenB, MenA, UbiE, and/or MenG, respectively). Particular examples of such vitamin K biosynthesis polypeptides are presented in Tables 46-53.

Vitamin K compounds: The term "vitamin K compounds", as used herein, refers to members of a family of structurally related compounds that share a common biologic activity. In particular, vitamin K compounds are derivatives of 2-methyl-1,4-naphthoquinone that have coagulation activity. The two natural forms of vitamin K differ in the identity of their side chains at position 3. Vitamin $K_1$, also known as phylloquinone (based on its presence in plants), has a phytyl side chain in position 3; vitamin K2, also known as menaquinone, has an isoprenyl side chain at position 3. Different forms of menaquinone, having side chains with different numbers of isoprene units (typically 4-13) are found in different types of cells.

Vitamin K production modification: The term "Vitamin K production modification", as used herein, refers to a modification of a host organism that adjusts production of Vitamin K. For example, a Vitamin K production modification may increase the production level of one or more vitamin K compounds, and/or may alter relative production levels of different vitamin K compounds. In principle, an inventive vitamin K production modification may be any chemical, physiological, genetic, or other modification that appropriately alters production of one or more vitamin K compounds in a host organism produced by that organism as compared with the level produced in an otherwise identical organism not subject to the same modification. In most embodiments, however, the vitamin K production modification will comprise a genetic modification, typically resulting in increased production of one or more selected vitamin K compounds. In some embodiments, the vitamin K production modification comprises at least one chemical, physiological, genetic, or other modification; in other embodiments, the vitamin K production modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

DETAILED DESCRIPTION OF CERTAIN PREFERRED EMBODIMENTS OF THE INVENTION

The present invention embraces the reasoning that quinone derived compound(s) (e.g., ubiquinones, vitamin K compounds, and vitamin E compounds) can effectively be produced in oleaginous yeast and fungi. According to the present invention, strains that both (i) accumulate lipid, often in the form of cytoplasmic oil bodies; and (ii) produce one or more quinone derived compound(s) at a level at least about 1%, of their dry cell weight, are generated through manipulation of host cells (i.e., strains, including, e.g., naturally-occurring strains and strains which have been previously modified). In certain embodiments, strains can accumulate lipid typically to at least about 20% of their dry cell weight. In some embodiments quinone derived compound(s) can be produced in the strains to at least about 2%; at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, or at least about 20% of fungus' dry cell weight Thus, the provided manipulated strains can then be used to produce the quinone derived compound(s). In some embodiments, the compound(s) that partition(s) into the lipid bodies can readily be isolated. In some embodiments the quinone derived compound is Coenzyme Q10 (CoQ10; Ubiquinone 10; Ubiquinone 50). In some embodiments, the quinone derived compound is $C_5$ (CoQ5), $C_6$ (CoQ6), $C_7$ (CoQ7), $C_8$ (CoQ8), or $C_9$ (CoQ9) quinone. In some embodiments, the quinone derived compound is a tocopherol or a tocotrienols. In some embodiments, the quinone derived compound is phylloquinone (vitamin $K_1$), or menaquinone (vitamin $K_2$).

In some embodiments, it will be desirable to balance oleaginy and production of quinone derived compound(s) in cells such that, as soon as a minimum desirable level of oleaginy is achieved, substantially all further carbon is diverted into a metabolic pathway that results in production of one or more quinone derived compounds. In some embodiments of the invention, this strategy involves engineering cells to be oleaginous; in other embodiments, it involves engineering cells to accumulate a higher level of lipid, particularly cytoplasmic lipid, than they would do in the absence of such engineering even though the engineered cells may not become "oleaginous" as defined herein. In other embodiments, the extent to which an oleaginous host cell accumulates lipid is actually reduced so that remaining carbon can be utilized in ubiquinone production.

To give but one example of adjustments that could be made to achieve a desired balance between oleaginy and production of quinone derived compound(s), we note that, while increasing acetyl CoA carboxylase expression (and/or activity) promotes oleaginy, decreasing its expression and/or activity may promote production of quinone derived compound(s). Those of ordinary skill in the art will appreciate that the expression and/or activity of acetyl CoA carboxylase, or of other polypeptides, may be adjusted up or down as desired according to the characteristics of a particular host cell of interest.

We note that engineered cells and processes of using them as described herein may provide one or more advantages as compared with unmodified cells. Such advantages may include, but are not limited to: increased yield (e.g., quinone derived compound expressed as either % dry cell weight (mg/mg) or parts per million), titer (g quinone derived compound/L), specific productivity (mg quinone derived compound $g^{-1}$ biomass $hour^{-1}$), and/or volumetric productivity (g quinone derived compound $liter^{-1}$ $hour^{-1}$)) of the desired quinone derived compound (and/or intermediates thereof), and/or decreased formation of undesirable side products (for example, undesirable intermediates).

Thus, for example, the specific productivity for one or more quinone derived compounds (e.g., ubiquinones, vitamin K compounds, and/or vitamin E compounds) or total quinone derived compounds may be at or about 0.1, at or about 0.11, at or about 0.12, at or about 0.13, at or about 0.14, at or about 0.15, at or about 0.16, at or about 0.17, at or about 0.18, at or about 0.19, at or about 0.2, at or about 0.21, at or about 0.22, at or about 0.23, at or about 0.24, at or about 0.25, at or about 0.26, at or about 0.27, at or about 0.28, at or about 0.29, at or about 0.3, at or about 0.31, at or about 0.32, at or about 0.33, at or about 0.34, at or about 0.35, at or about 0.36, at or about 0.37, at or about 0.38, at or about 0.39, at or about 0.4, at or about 0.41, at or about 0.42, at or about 0.43, at or about 0.44, at or about 0.45, at or about 0.46, at or about 0.47, at or about 0.48, at or about 0.49, at or about 0.5, at or about 0.51, at or about 0.52, at or about 0.53, at or about 0.54, at or about 0.55, at or about 0.56, at or about 0.57, at or about 0.58, at or about 0.59, at or about 0.6, at or about 0.61, at or about 0.62, at or about 0.63, at or about 0.64, at or about 0.65, at or about 0.66, at or about 0.67, at or about 0.68, at or about 0.69, at or about 0.7, at or about 0.71, at or about 0.72, at or about 0.73, at or about 0.74, at or about 0.75, at or about 0.76, at or about 0.77, at or about 0.78, at or about 0.79, at or about 0.8, at or about 0.81, at or about 0.82, at or about 0.83, at or about 0.84, at or about 0.85, at or about 0.86, at or about 0.87, at or about 0.88, at or about 0.89, at or about 0.9, at or about 0.91, at or about 0.92, at or about 0.93, at or about 0.94, at or about 0.95, at or about 0.96, at or about 0.97, at or about 0.98, at or about 0.99, at or about 1, 1.05, at or about 1.1, at or about 1.15, at or about 1.2, at or about 1.25, at or about 1.3, at or about 1.35, at or about 1.4, at or about 1.45, at or about 1.5, at or about 1.55, at or about 1.6, at or about 1.65, at or about 1.7, at or about 1.75, at or about 1.8, at or about 1.85, at or about 1.9, at or about 1.95, at or about 2 mg $g^{-1}$ $hour^{-1}$ or more.

Thus, for example, the volumetric productivity for one or more quinone derived compounds (e.g., ubiquinones, vitamin K compounds, and/or vitamin E compounds) or total quinone derived compounds may be at or about 0.01, at or about 0.011, at or about 0.012, at or about 0.013, at or about 0.014, at or about 0.015, at or about 0.016, at or about 0.017, at or about 0.018, at or about 0.019, at or about 0.02, at or about 0.021, at or about 0.022, at or about 0.023, at or about 0.024, at or about 0.025, at or about 0.026, at or about 0.027, at or about 0.028, at or about 0.029, at or about 0.03, at or about 0.031, at or about 0.032, at or about 0.033, at or about 0.034, at or about 0.035, at or about 0.036, at or about 0.037, at or about 0.038, at or about 0.039, at or about 0.04, at or about 0.041, at or about 0.042, at or about 0.043, at or about 0.044, at or about 0.045, at or about 0.046, at or about 0.047, at or about 0.048, at or about 0.049, at or about 0.05, at or about 0.051, at or about 0.052, at or about 0.053, at or about 0.054, at or about 0.055, at or about 0.056, at or about 0.057, at or about 0.058, at or about 0.059, at or about 0.06, at or about 0.061, at or about 0.062, at or about 0.063, at or about 0.064, at or about 0.065, at or about 0.066, at or about 0.067, at or about 0.068, at or about 0.069, at or about 0.07, at or about 0.071, at or about 0.072, at or about 0.073, at or about 0.074, at or about 0.075, at or about 0.076, at or about 0.077, at or about 0.078, at or about 0.079, at or about 0.08, at or about 0.081, at or about 0.082, at or about 0.083, at or about 0.084, at or about 0.085, at or about 0.086, at or about 0.087, at or about 0.088, at or about 0.089, at or about 0.09, at or about 0.091, at or about 0.092, at or about 0.093, at or about 0.094, at or about 0.095, at or about 0.096, at or about 0.097, at or about 0.098, at or about 0.099, at or about 0.1, 0.105, at or about 0.110, at or about 0.115, at or about 0.120, at or about 0.125, at or about 0.130, at or about 0.135, at or about 0.14, at or about 0.145, at or about 0.15, at or about 0.155, at or about 0.16, at or about 0.165, at or about 0.17, at or about 0.175, at or about 0.18, at or about 0.185, at or about 0.19, at or about 0.195, at or about 0.20 grams $liter^{-1}$ $hour^{-1}$ or more.

Host Cells

Those of ordinary skill in the art will readily appreciate that a variety of yeast and fungal strains exist that are naturally oleaginous or that naturally produce one or more quinone derived compounds (e.g., a ubiquinone, a vitamin K compound and/or a vitamin E compound). Any of such strains may be utilized as host strains according to the present invention, and may be engineered or otherwise manipulated to generate inventive oleaginous, quinone derived-compound-producing strains. Alternatively, strains that naturally are neither oleaginous nor quinone derived-compound-producing may be employed. Furthermore, even when a particular strain has a natural capacity for oleaginy or for production of one or more quinone derived compounds, its natural capabilities may be adjusted as described herein for optimal production of one or more particular desired compounds.

In certain embodiments, engineering or manipulation of a strain results in modification of a type of lipid and/or quinone derived compound produced. For example, a strain may be naturally oleaginous and/or may naturally produce one or more quinone derived compounds (e.g., a ubiquinone, including, e.g., CoQ5, CoQ6, CoQ8, CoQ9, CoQ10; vitamin K, including phylloquinone and/or one or more menaquinones; and/or vitamin E, including one or more tocopherols and/or one or more tocotrienols). However, engineering or modification of the strain may be employed so as to change the type or amount of lipid that is accumulated and/or to adjust production of one or more quinone derived compounds (including, for example, modulating relative amounts of particular quinone derived compounds). In some embodiments, production of CoQ10; phylloquinone; menaquinone; and/or α-tocopherol production will be optimized.

When selecting a particular yeast or fungal strain for use in accordance with the present invention, it will generally be desirable to select one whose cultivation characteristics are amenable to commercial scale production. For example, it will generally (though not necessarily always) be desirable to avoid filamentous organisms, or organisms with particularly unusual or stringent requirements for growth conditions. In some embodiments of the invention, it will be desirable to utilize edible organisms as host cells, as they may optionally be formulated directly into pharmaceutical compositions, food or feed additives, or into nutritional supplements, as desired. Some embodiments of the invention utilize host cells that are genetically tractable, amenable to molecular genetics (e.g., can be efficiently transformed, especially with established or available vectors; optionally can incorporate and/or integrate multiple genes, for example sequentially; and/or have known genetic sequence; etc), devoid of complex growth requirements (e.g., a necessity for light), mesophilic (e.g., prefer growth temperatures within the range of about 20-32° C.) (e.g., 20, 21, 22, 23, 24, 25, 26, 27, 28, 29, 30, 31, 32° C.), able to assimilate a variety of carbon and nitrogen sources and/or capable of growing to high cell density. Alternatively or additionally, various embodiments of the invention utilize host cells that grow as single cells rather than, for example, as mycelia.

In general, when it is desirable to utilize a naturally oleaginous organism in accordance with the present invention, any modifiable and cultivatable oleaginous organism may be employed. In certain embodiments of the invention, yeast or fungi of genera including, but not limited to, *Blakeslea, Candida, Cryptococcus, Cunninghamella, Lipomyces, Mortierella, Mucor, Phycomyces, Pythium, Rhodosporidium, Rhodotorula, Thraustochytrium, Trichosporon*, and *Yarrowia* are employed. In certain particular embodiments, organisms of species that include, but are not limited to, *Blakeslea trispora, Candida pulcherrima, C. revkaufi, C. tropicalis, Cryptococcus curvatus, Cunninghamella echinulata, C. elegans, C. japonica, Lipomyces starkeyi, L. lipoferus, Mortierella alpina, M. isabellina, M. ramanniana, M. vinacea, Mucor circinelloides, Phycomyces blakesleanus, Pythium irregulare, Rhodosporidium toruloides, Rhodotorula glutinis, R. gracilis, R. graminis, R. mucilaginosa, K. pinicola, Thraustochytrium sp, Trichosporon pullans, T. cutaneum*, and *Yarrowia lipolytica* are used.

Of these naturally oleaginous strains, some also naturally produce one or more quinone derived compounds and some do not. In most cases, only low levels (less than about 0.05% dry cell weight) of quinone derived compounds are produced by naturally-occurring oleaginous yeast or fungi.

In general, any organism that is naturally oleaginous but does not naturally produce one or more particular quinone derived compounds of interest (e.g., does not produce a ubiquinone such as CoQ10, vitamin K compounds, vitamin E compounds be utilized as a host cell in accordance with the present invention. In some embodiments, the organism is a yeast or fungus from a genus such as, but not limited to, *Candida, Mortierella*, and *Yarrowia*; in some embodiments, the organism is of a species including, but not limited to, *Mortierella alpina* and *Yarrowia lipolytica*. At least some fungal strains are known not to produce vitamin K.

Comparably, the present invention may utilize any naturally oleaginous organism that does naturally produce one or more quinone derived compounds as a host cell. In general, the present invention may be utilized to increase carbon flow into the isoprenoid pathway organisms that naturally produce a particular quinone derived compounds of interest and/or to shift production of one or more different quinone derived compounds. For example, the present invention may be utilized to shift production from one ubiquinone (e.g., CoQ5, CoQ6, CoQ8, CoQ9) to another (e.g., CoQ10). Introduction of one or more quinonogenic modifications (e.g., one or more ubiquinogenic modifications), such as but not limited to increased expression of one or more endogenous or heterologous quinonogenic polypeptides), in accordance with the present invention, can achieve these goals.

In certain embodiments of the invention, the utilized oleaginous, quinone derived compound-producing organism is a yeast or fungus, for example of a genus such as, but not limited to, *Rhodotorula*; in some embodiments, the organism is of a species such as *Rhodotorula glutinis*.

When it is desirable to utilize strains that are naturally non-oleaginous as host cells in accordance with the present invention, genera of non-oleaginous yeast or fungi include, but are not limited to, *Aspergillus, Botrytis, Cercospora, Fusarium (Gibberella), Kluyveromyces, Neurospora, Penicillium, Pichia (Hansenula), Puccinia, Saccharomyces, Schizosaccharomyces, Sclerotium, Trichoderma*, and *Xanthophyllomyces (Phaffia)*; in some embodiments, the organism is of a species including, but not limited to, *Candida utilis, Aspergillus nidulans, A. niger, A. terreus, Botrytis cinerea, Cercospora nicotianae, Fusarium fujikuroi (Gibberella zeae), Kluyveromyces lactis, K. lactis, Neurospora crassa, Pichia pastoris, Puccinia distincta, Saccharomyces cerevisiae, Schizosaccharomyces pombe, Sclerotium rolfsii, Trichoderma reesei*, and *Xanthophyllomyces dendrorhous (Phaffia rhodozyma)*.

It will be appreciated that the term "non-oleaginous", as used herein, encompasses both strains that naturally have some ability to accumulate lipid, especially cytoplasmically, but do not do so to a level sufficient to qualify as "oleaginous" as defined herein, as well as strains that do not naturally have any ability to accumulate extra lipid, e.g., extra-membranous lipid. It will further be appreciated that, in some embodiments of the invention, it will be sufficient to increase the natural level of oleaginy of a particular host cell, even if the modified cell does not qualify as oleaginous as defined herein. In some embodiments, the cell will be modified to accumulate at least about 19%, 18%, 17%, 16%, 15%, 14%, 13%, 12%, 11%, 10%, 9%, 8%, 7%, 6%, or 5% dry cell weight as lipid, so long as the accumulation level is more than that observed in the unmodified parental cell.

As with the naturally oleaginous organisms, some of the naturally non-oleaginous fungi naturally produce one or more quinone derived compounds, whereas others do not. Genera of naturally non-oleaginous fungi that do not naturally produce quinone derived compounds (such as CoQ10 or other ubiquinone, vitamin K compounds, vitamin E compounds) for instance, but that may desirably be used as host cells in accordance with the present invention include, but are not limited to, *Aspergillus, Kluyveromyces, Penicillium, Saccharomyces*, and *Pichia*, species include, but are not limited to, *Candida utilis, Aspergillus niger, Xanthophyllomyces dendrorhous (Phaffia rhodozyma)* and *Saccharomyces cerevisiae. Saccharomyces cerevisiae*, in particular, is known not to produce vitamin E or vitamin K compounds; other fungi likely also do not produce these compounds. Genera of naturally non-oleaginous fungi that do naturally produce one or more quinone derived compounds (e.g., CoQ10) and that may desirably be used as host cells in accordance with the present invention include, but are not limited to, yeasts of such genera as *Schizosaccharomyces* and *Basidiomycetes*; fungi of such genera as *Tremella* are capable of producing certain quinone derived compounds, and in particular are capable of producing CoQ10.

As discussed above, any of a variety of organisms may be employed as host cells in accordance with the present invention. In certain embodiments of the invention, host cells will be *Y. lipolytica* cells. Advantages of *Y. lipolytica* include, for example, tractable genetics and molecular biology, availability of genomic sequence (see, for example, Sherman et al. *Nucleic Acids Res.* 32(Database issue):D315-8, 2004), suitability to various cost-effective growth conditions, ability to grow to high cell density. In addition, *Y. lipolytica* is naturally oleaginous, such that fewer manipulations may be required to generate an oleaginous, ubiquinone-producing (e. g., CoQ10) *Y. lipolytica* strain than might be required for other organisms. Furthermore, there is already extensive commercial experience with *Y. lipolytica*.

*Saccharomyces cerevisiae* is also a useful host cell in accordance with the present invention, particularly due to its experimental tractability and the extensive experience that researchers have accumulated with the organism. Although cultivation of *Saccharomyces* under high carbon conditions may result in increased ethanol production, this can generally be managed by process and/or genetic alterations.

The edible fungus, *Candida utilis* is also a useful host cell in accordance with the present invention. Molecular biology tools and techniques are available in *C. utilis* (for example, see Iwakiri et al. (2006) Yeast 23:23-34, Iwakiri et al. (2005) Yeast 2005 22:1079-87, Iwakiri et al. (2005) Yeast 22:1049-60, Rodriquez et al. (1998) Yeast 14:1399-406, Rodriquez et al. (1998) FEMS Microbiol Lett. 165:33540, and Kondo et al. (1995) J Bacteriol. 177:7171-7).

Additional useful hosts include *Xanthophyllomyces dendrorhous* (*Phaffia rhodozyma*), which is experimentally tractable and naturally produces isoprenoid compounds.

*Aspergillus niger* and *Mortierella alpina* accumulate large amounts of citric acid and fatty acid, respectively; *Mortierella alpina* is also oleaginous.

*Neurospora* or *Gibberella* are also useful. They are not naturally oleaginous and may require extensive modification to be used in accordance with the present invention. *Neurospora* and *Gibberella* are considered relatively tractable from an experimental standpoint. Both are filamentous fungi, such that production at commercial scales can be a challenge necessary to overcome in utilization of such strains.

*Mucor circinelloides* is another available useful species. While its molecular genetics are generally less accessible than are those of some other organisms, it naturally produces isoprenoids and may require less modification than other species available.

Molecular genetics can be performed in Blakeslea, though significant effort may be required. Furthermore, cost-effective fermentation conditions can be challenging, as, for example, it may be required that the two mating types are mixed. Fungi of the genus *Phycomyces* are also possible sources which have the potential to pose fermentation process challenges, and these fungi may be less amenable to manipulate than several other potential host organisms.

Additional useful hosts include strains, such as *Schizosaccharomyces pombe*, *Saitoella complicata*, and *Sporidiobolus ruineniae*, which can produce certain quinone derived compounds including, for example, CoQ10.

Those of ordinary skill in the art will appreciate that the selection of a particular host cell for use in accordance with the present invention will also affect, for example, the selection of expression sequences utilized with any heterologous polypeptide to be introduced into the cell, and will also influence various aspects of culture conditions, etc. Much is known about the different gene regulatory requirements, protein targeting sequence requirements, and cultivation requirements, of different host cells to be utilized in accordance with the present invention (see, for example, with respect to *Yarrowia*, Barth et al. *FEMS Microbiol Rev.* 19:219, 1997; Madzak et al. *J Biotechnol.* 109:63, 2004; see, for example, with respect to *Xanthophyllomyces*, Verdoes et al. *Appl Environ Microbiol* 69: 3728-38, 2003; Visser et al. FEMS Yeast Res 4: 221-31, 2003; Martinez et al. Antonie Van Leeuwenhoek. 73(2): 147-53, 1998; Kim et al. Appl Environ Microbiol. 64(5):1947-9, 1998; Wery et al. Gene. 184(1):89-97, 1997; see, for example, with respect to *Saccharomyces*, Guthrie and Fink *Methods in Enzymology* 194:1-933, 1991). In certain aspects, for example, targeting sequences of the host cell (or closely related analogs) may be useful to include for directing heterologous proteins to subcellular localization. Thus, such useful targeting sequences can be added to heterologous sequence for proper intracellular localization of activity. In other aspects (e.g., addition of mitochondrial targeting sequences), heterologous targeting sequences may be eliminated or altered in the selected heterologous sequence (e.g., alteration or removal of source organism plant chloroplast targeting sequences).

To give but a few specific examples, of promoters and/or regulatory sequences that may be employed in expression of polypeptides according to the present invention, useful promoters include, but are not limited to, the Leu2 promoter and variants thereof (see, for example, see U.S. Pat. No. 5,786, 212); the EF1alpha protein and ribosomal protein S7 gene promoters (see, for example, PCT Application WO 97/44470); the Gpm (see US20050014270), Xpr2 (see U.S. Pat. No. 4,937,189), Tef1, Gpd1 (see, for example, US Application 2005-0014270A1), Cam1 (YALI0C24420g), YALI0D16467g, Tef4 (YALI0B12562g), Yef3 (YALI0E13277g), Pox2, Yat1 (see, for example US Application 2005-0130280; PCT Application WO 06/052754), Fba1 (see, for example WO05049805), and/or Gpat (see WO06031937) promoters; the sequences represented by SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12, subsequences thereof, and hybrid and tandem derivatives thereof (e.g., as disclosed in US Application 2004-0146975); the sequences represented by SEQ ID NO: 1, 2, or 3 including fragments (e.g. bp 462-1016 and bp 197-1016 of SEQ ID NO: 1; bp 5-523 of SEQ ID NO:3) and complements thereof (e.g., as disclosed in U.S. Pat. No. 5,952,195); CYP52A2A (see, for example, US Application 2002-0034788); promoter sequences from fungal (e.g., *C. tropicalis*) catalase, citrate synthase, 3-ketoacyl-CoA thiolase A, citrate synthase, O-acetylhornserine sulphydrylase, protease, carnitine O-acetyltransferase, hydratase-dehydrogenase, epimerase genes; promoter sequences from Pox4 genes (see, for example, US application 2004-0265980); and/or promoter sequences from Met2, Met3, Met6, Met25 and YALI0D12903g genes. Any such promoters can be used in conjunction with endogenous genes and/or heterologous genes for modification of expression patterns of endogenous polypeptides and/or heterologous polypeptides in accordance with the present invention.

Alternatively or additionally, regulatory sequences useful in accordance with the present invention may include one or more Xpr2 promoter fragments, for example as described in U.S. Pat. No. 6,083,717 (e.g. SEQ ID NOS: 14 also including sequences with 80% or more identity to these SEQ ID NOs) in one or more copies either in single or in tandem. Similarly, exemplary terminator sequences include, but are not limited to, *Y. lipolytica* Xpr2 (see U.S. Pat. No. 4,937,189) and Pox2 (YALI0F10857g) terminator sequences and those listed in example 11 herein.

Engineering Oleaginy

All living organisms synthesize lipids for use in their membranes and various other structures. However, most organisms do not accumulate in excess of about 10% of their dry cell weight as total lipid, and most of this lipid generally resides within cellular membranes.

Significant biochemical work has been done to define the metabolic enzymes necessary to confer oleaginy on microorganisms (primarily for the purpose of engineering single cell oils as commercial sources of arachidonic acid and docosahexaenoic acid; see for example Ratledge *Biochimie* 86:807, 2004, the entire contents of which are incorporated herein by reference). Although this biochemical work is compelling, there only have been a limited number of reports of de novo oleaginy being established through genetic engineering with the genes encoding the key metabolic enzymes. It should be noted that oleaginous organisms typically accumulate lipid only when grown under conditions of carbon excess and nitrogen limitation. The present invention further establishes that the limitation of other nutrients (e.g. phosphate or magnesium) can also induce lipid accumulation. The present invention establishes, for example, that limitation of nutrients such as phosphate and/or magnesium can induce lipid accumulation, much as is observed under conditions of nitrogen limitation. Under these conditions, the organism readily depletes the limiting nutrient but continues to assimilate the carbon source. The "excess" carbon is channeled into lipid biosynthesis so that lipids (usually triacylglycerols) accumulate in the cytosol, typically in the form of bodies.

In general, it is thought that, in order to be oleaginous, an organism must produce both acetyl-CoA and NADPH in the cytosol, which can then be utilized by the fatty acid synthase machinery to generate lipids. In at least some oleaginous organisms, acetyl-CoA is generated in the cytosol through the action of ATP-citrate lyase, which catalyzes the reaction:

citrate+CoA+ATP→acetyl-CoA+oxaloacetate+ADP+ $P_i$. (1)

Of course, in order for ATP-citrate lyase to generate appropriate levels of acetyl-CoA in the cytosol, it must first have an available pool of its substrate citric acid. Citric acid is generated in the mitochondria of all eukaryotic cells through the tricarboxylic acid (TCA) cycle, and can be moved into the cytosol (in exchange for malate) by citrate/malate translocase.

In most oleaginous organisms, and in some non-oleaginous organisms, the enzyme isocitrate dehydrogenase, which operates as part of the TCA cycle in the mitochondria, is strongly AMP-dependent. Thus, when AMP is depleted from the mitochondria, this enzyme is inactivated. When isocitrate dehydrogenase is inactive, isocitrate accumulates in the mitochondria. This accumulated isocitrate is then equilibrated with citric acid, presumably through the action of aconitase. Therefore, under conditions of low AMP, citrate accumulates in the mitochondria. As noted above, mitochondrial citrate is readily transported into the cytosol.

Figure 2:
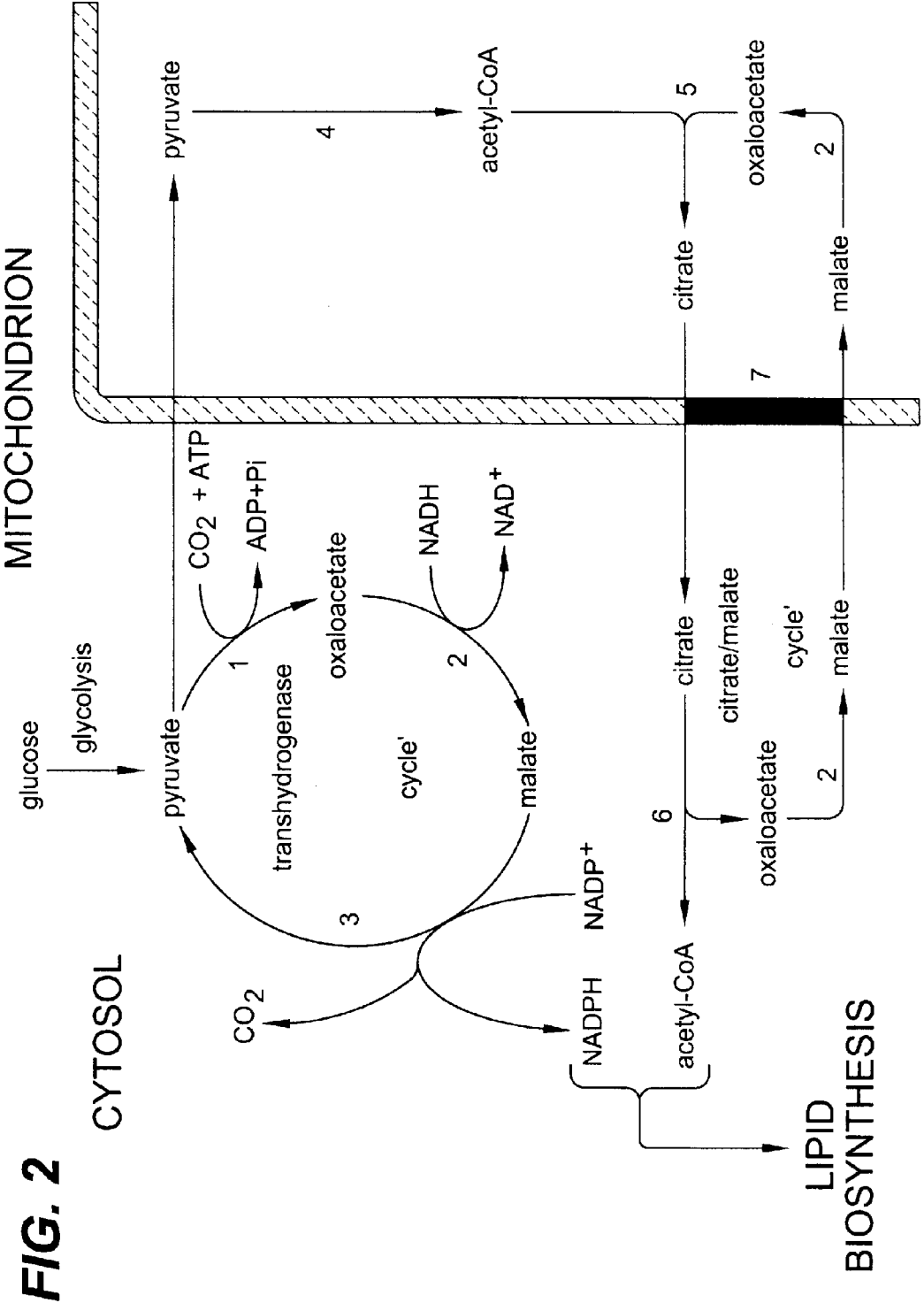
FIG. 2 depicts how sufficient levels of acetyl-CoA and NADPH may be accumulated in the cytosol of oleaginous organisms to allow for production of significant levels of cytosolic lipids. Enzymes: 1, pyruvate decarboxylase; 2, malate dehydrogenase; 3, malic enzyme; 4, pyruvate dehydrogenase; 5, citrate synthase; 6, ATP-citrate lyase; 7, citrate/malate translocase.

AMP depletion, which in oleaginous organisms is believed to initiate the cascade leading to accumulation of citrate (and therefore acetyl-CoA) in the cytoplasm, occurs as a result of the nutrient depletion mentioned above. When oleaginous cells are grown in the presence of excess carbon source but the absence of nitrogen or other nutrient (e.g., phosphate or magnesium), the activity of AMP deaminase, which catalyzes the reaction:

AMP→inosine 5'-monophosphate+$NH_3$ (2)

is strongly induced. The increased activity of this enzyme depletes cellular AMP in both the cytosol and the mitochondria. Depletion of AMP from the mitochondria is thought to inactivate the AMP-dependent isocitrate dehydrogenase, resulting in accumulation of citrate in the mitochondria and, therefore, the cytosol. This series of events is depicted diagrammatically in FIG. 2.

As noted above, oleaginy requires both cytosolic acetyl-CoA and cytosolic NADPH. It is believed that, in many oleaginous organisms, appropriate levels of cytosolic NADPH are provided through the action of malic enzyme (Enzyme 3 in FIG. 2). Some oleaginous organisms (e.g., *Lipomyces* and some *Candida*) do not appear to have malic enzymes, however, so apparently other enzymes can provide comparable activity, although it is expected that a dedicated source of NADPH is probably required for fatty acid synthesis (see, for example, Wynn et al., *Microbiol* 145:1911, 1999; Ratledge *Adv. Appl. Microbiol.* 51:1, 2002, each of which is incorporated herein by reference in its entirety).

Other activities which can be involved in regenerating NADPH include, for example, 6-phosphogluconate dehydrogenase (gnd); Fructose 1,6 bisphosphatase (fbp); Glucose 6 phosphate dehydrogenase (g6pd); NADH kinase (EC 2.7.1.86); and/or transhydrogenase (EC 1.6.1.1 and 1.6.1.2).

Gnd is part of the pentose phosphate pathway and catalyses the reaction:

6-phospho-D-gluconate+NADP+→D-ribulose 5-phosphate+$CO_2$+NADPH

Fbp is a hydrolase that catalyses the gluconeogenic reaction:

D-fructose 1,6-bisphosphate+$H_2O$→D-fructose 6-phosphate+phosphate

Fbp redirects carbon flow from glycolysis towards the pentose phosphate pathway. The oxidative portion of the pentose phosphate pathway, which includes glucose 6 phosphate dehydrogenase and 6-phosphogluconate dehydrogenase, enables the regeneration of NADPH.

G6pd is part of the pentose phosphate pathway and catalyses the reaction:

D-glucose 6phosphate+$NADP^+$→D-glucono-1,5-lactone 6-phosphate+NADPH+$H^+$

NADH kinase catalyzes the reaction:

ATP+NADH→ADP+NADPH

Transhydrogenase catalyzes the reaction:

$NADP+NAD^+$ ↔ $NADP^++NADH$

Thus, enhancing the expression and/or activity of any of these enzymes can increase NADPH levels and promote anabolic pathways requiring NADPH.

Alternative or additional strategies to promote oleaginy may include one or more of the following: (1) increased or heterologous expression of one or more of acyl-CoA:diacylglycerol acyltransferase (e.g., DGA1; YALI0E32769g); phospholipid:diacylglycerol acyltransferase (e.g., LRO1; YALI0E16797g); and acyl-CoA:cholesterol acyltransferase (e.g., ARE genes such as ARE1, ARE2, YALI0F06578g), which are involved in triglyceride synthesis (Kalscheuer et al. *Appl Environ Microbiol p.* 7119-7125, 2004; Oelkers et al. *J Biol Chem* 277:8877-8881, 2002; and Sorger et al. *J Biol Chem* 279:31190-31196, 2004), (2) decreased expression of triglyceride lipases (e.g., TGL3 and/or TGL4; YALI0D17534g and/or YALI0F10010g (Kurat et al. *J Biol Chem* 281:491-500, 2006); and (3) decreased expression of one or more acyl-coenzyme A oxidase activities, for example encoded by POX genes (e.g. POX1, POX2, POX3, POX4, POX5; YALI0C23859g, YALI0D24750g, YALI0E06567g, YALI0E27654g, YALI0E32835g, YALI0F10857g; see for example Mlickova et al. *Appl Environ Microbiol* 70: 3918-3924, 2004; Binns et al. *J Cell Biol* 173:719, 2006).

Thus, according to the present invention, the oleaginy of a host organism may be enhanced by modifying the expression or activity of one or more polypeptides involved in generating cytosolic acetyl-CoA and/or NADPH and/or altering lipid levels through other mechanisms. For example, modification of the expression or activity of one or more of acetyl-CoA carboxylase, pyruvate decarboxylase, isocitrate dehydrogenase, ATP-citrate lyase, malic enzyme, AMP-deaminase, glucose-6-phosphate dehydrogenase, 6-phosphogluconate dehydrogenase, fructose 1,6 bisphosphatase, NADH kinase, transhydrogenase, acyl-CoA:diacylglycerol acyltransferase, phospholipid:diacylglycerol acyltransferase, acyl-CoA:cholesterol acyltransferase, triglyceride lipase, acyl-coenzyme A oxidase can enhance oleaginy in accordance with the present invention. Exemplary polypeptides which can be utilized or derived so as to enhance oleaginy in accordance with the present invention include, but are not limited to those acetyl-CoA carboxylase, pyruvate decarboxylase, isocitrate dehydrogenase, ATP-citrate lyase, malic enzyme, AMP-deaminase, glucose-6-phosphate dehydrogenase, 6-phosphogluconate dehydrogenase, fructose 1,6 bisphosphatase, NADH kinase, transhydrogenase, acyl-CoA:diacylglycerol acyltransferase, phospholipid:diacylglycerol acyltransferase, acyl-CoA:cholesterol acyltransferase, triglyceride lipase, acyl-coenzyme A oxidase polypeptides provided in Tables 1-6 and Tables 69-85 respectively.

In some embodiments of the invention, where an oleaginous host cell is employed, enzymes and regulatory components relevant to oleaginy are already in place but could be modified, if desired, by for example altering expression or activity of one or more oleaginic polypeptides and/or by introducing one or more heterologous oleaginic polypeptides. In those embodiments of the invention where a non-oleaginous host cell is employed, it is generally expected that at least one or more heterologous oleaginic polypeptides will be introduced.

The present invention contemplates not only introduction of heterologous oleaginous polypeptides, but also adjustment of expression or activity levels of heterologous or endogenous oleaginic polypeptides, including, for example, alteration of constitutive or inducible expression patterns. In some embodiments of the invention, expression patterns are adjusted such that growth in nutrient-limiting conditions is not required to induce oleaginy. For example, genetic modifications comprising alteration and/or addition of regulatory sequences (e.g., promoter elements, terminator elements) and/or regulatory factors (e.g., polypeptides that modulate transcription, splicing, translation, modification, etc.) may be utilized to confer particular regulation of expression patterns. Such genetic modifications may be utilized in conjunction with endogenous genes (e.g., for regulation of endogenous oleagenic polypeptide(s)); alternatively, such genetic modifications may be included so as to confer regulation of expression of at least one heterologous polypeptide (e.g., oleaginic polypeptide(s)).

In some embodiments, at least one oleaginic polypeptide is introduced into a host cell. In some embodiments of the invention, a plurality (e.g., two or more) of different oleaginic polypeptides is introduced into the same host cell. In some embodiments, the plurality of oleaginic polypeptides contains polypeptides from the same source organism; in other embodiments, the plurality includes polypeptides independently selected from different source organisms.

Representative examples of a variety of oleaginic polypeptides that may be introduced into or modified within host cells according to the present invention, include, but are not limited to, those provided in Tables 1-6, and Tables 69-85. As noted above, it is expected that at least some of these polypeptides (e.g., malic enzyme and ATP-citrate lyase) should desirably act in concert, and possibly together with one or more components of fatty acid synthase, such that, in some embodiments of the invention, it will be desirable to utilize two or more oleaginic polypeptides from the same source organism.

In general, source organisms for oleaginic polypeptides to be used in accordance with the present invention include, but are not limited to, *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium (Gibberella), Kluyveromyces, Neurospora, Penicillium, Pichia (Hansenula), Puccinia, Saccharomyces, Sclerotium, Trichoderma*, and *Xanthophyllomyces (Phaffia)*. In some embodiments, the source species for acetyl CoA carboxylase, ATP-citrate lyase, malic enzyme and/or AMP deaminase polypeptides include, but are not limited to, *Aspergillus nidulans, Cryptococcus neoformans, Fusarium fujikuroi, Kluyveromyces lactis, Neurospora crassa, Saccharomyces cerevisiae, Schizosaccharomyces pombe, Ustilago maydis*, and *Yarrowia lipolytica*; in some embodiments, source species for pyruvate decarboxylase or isocitrate dehydrogenase polypeptides include, but are not limited to *Neurospora crassa, Xanthophyllomyces dendrorhous (Phaffia rhodozyma), Aspergillus niger, Saccharomyces cerevisiae, Mucor circinelloides, Rhodotorula glutinis, Candida utilis, Mortierella alpina*, and *Yarrowia lipolytica*.

*Aspergillus niger* accumulates large amounts of citric acid, whereas *Mortierella alpina* and *Thraustochytrium* sp. accumulate large amounts of fatty acid, respectively; *Mortierella alpina* and *Thraustochytrium* are also oleaginous. To give but one particular example of a host cell engineered to be oleaginous (or at least to accumulate increased levels of lipid) in accordance with the present invention, *S. cerevisiae* can be engineered to express one or more oleaginic polypeptides, e.g., from heterologous source organisms.

In some embodiments, a plurality of different oleaginic polypeptides are expressed, optionally from different source organisms. For instance, in some embodiments, *S. cerevisiae* cells are engineered to express (and/or to increase expression of) ATP-citrate lyase (e.g., from *N. crassa*), AMP deaminase (e.g., from *S. cerevisiae*), and/or malic enzyme (e.g., from *M. circinelloides*). In other embodiments, *Candida utilis* and *Phaffia rhodozyma* can be similarly modified. Modified *S. cerevisiae, C. utilis*, and *P. rhodozyma* strains can be further modified as described herein to increase production of one or more quinone derived compounds.

Engineering Production of Quinone Derived Compounds

The present invention encompasses the recognition that lipid-accumulating systems are useful for the production and/or isolation of certain quinone derived compounds, and particularly of a ubiquinone (e.g., CoQ10 and/or one or more $C_{5-9}$ quinone compounds such as CoQ5, CoQ6, CoQ7, CoQ8, CoQ9), one or more vitamin K compounds (e.g., phylloquinone and/or one or more menaquinones), and/or one or more vitamin E compounds (e.g., one or more tocopherols and/or tocotrienols). Without wishing to be bound by theory, the present inventors propose that the higher intracellular membrane content may facilitate increased quinone derived compound production and/or accumulation. The present invention therefore encompasses the discovery that certain quinone derived compounds can desirably be produced in oleaginous yeast and fungi.

According to the present invention, strains that both (i) accumulate lipid, often in the form of cytoplasmic lipid bodies and typically to at least about 20% of their dry cell weight; and (ii) produce one or more quinone derived compounds at a level at least about 1%, and in some embodiments at least about 3-20%, of their dry cell weight, are generated through manipulation of generally available strains (e.g., naturally-occurring strains and strains which have been previously genetically modified, whether via recombinant DNA techniques or mutagenesis directed modification). These manipulated strains are then used to produce one or more quinone derived compounds, so that compound(s) that partitions into the lipid bodies can readily be isolated.

In certain embodiments of the invention, host cells are *Yarrowia lipolytica* cells. Advantages of *Y. lipolytica* include, for example, tractable genetics and molecular biology, availability of genomic sequence, suitability to various cost-effective growth conditions, and ability to grow to high cell density. In addition, *Y. lipolytica* is naturally oleaginous, such that fewer manipulations may be required to generate an oleaginous, quinone derived compound-producing *Y. lipolytica* strain than might be required for other organisms. Furthermore, there is already extensive commercial experience with *Y. lipolytica*. In certain embodiments, host cells are *Saccharomyces cerevisiae* cells. In other embodiments, host cells are *Candida utilis* cells.

Figure 4A:
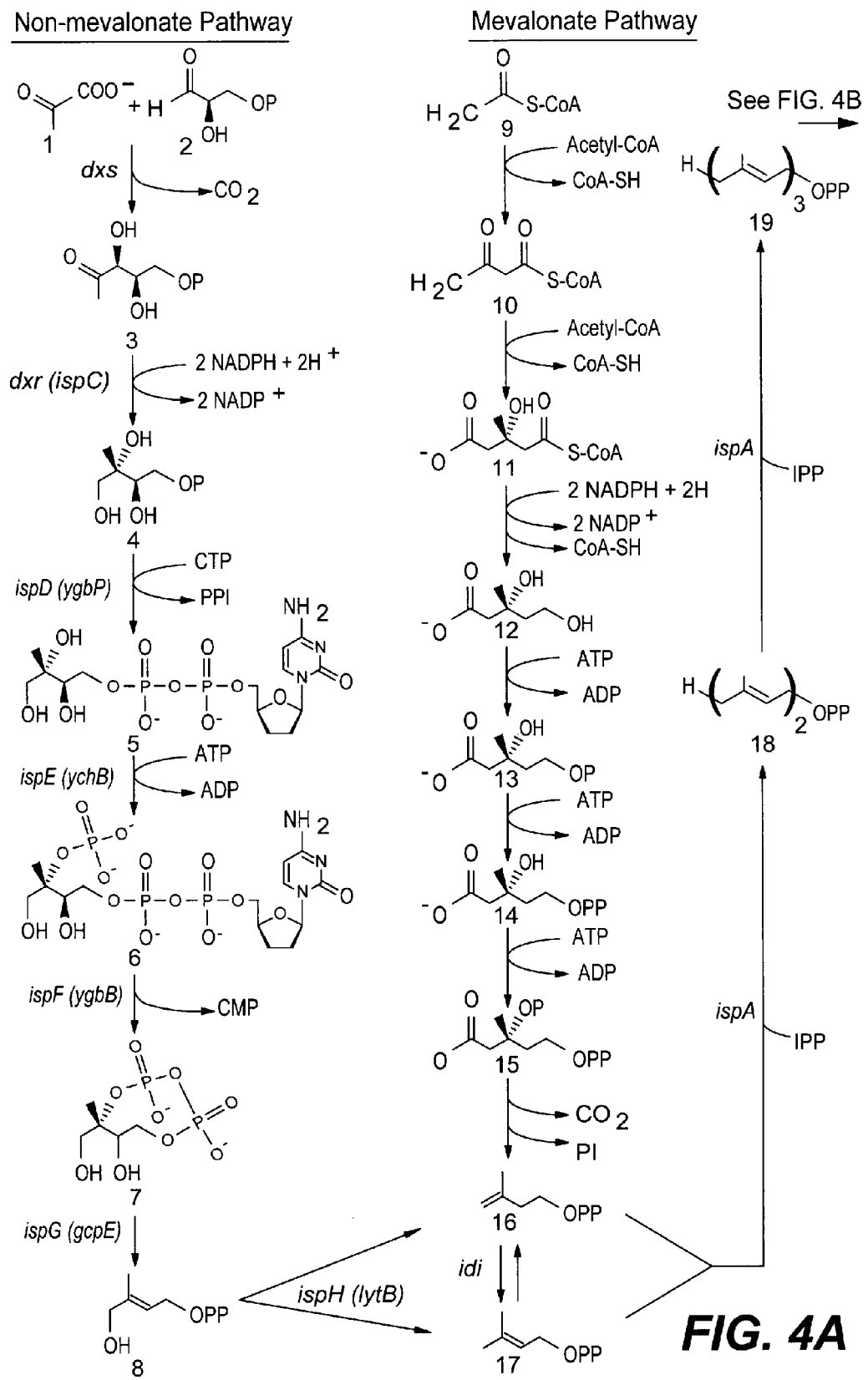
FIG. 4A shows the mevalonate isoprenoid biosynthesis pathway, which typically operates in eukaryotes, including fungi; as well as the mevalonate-independent isoprenoid biosynthesis pathway, also known as the DXP pathway, which typically operates in bacteria and in the plastids of plants and production of isoprenoid precursors.
Figure 8:
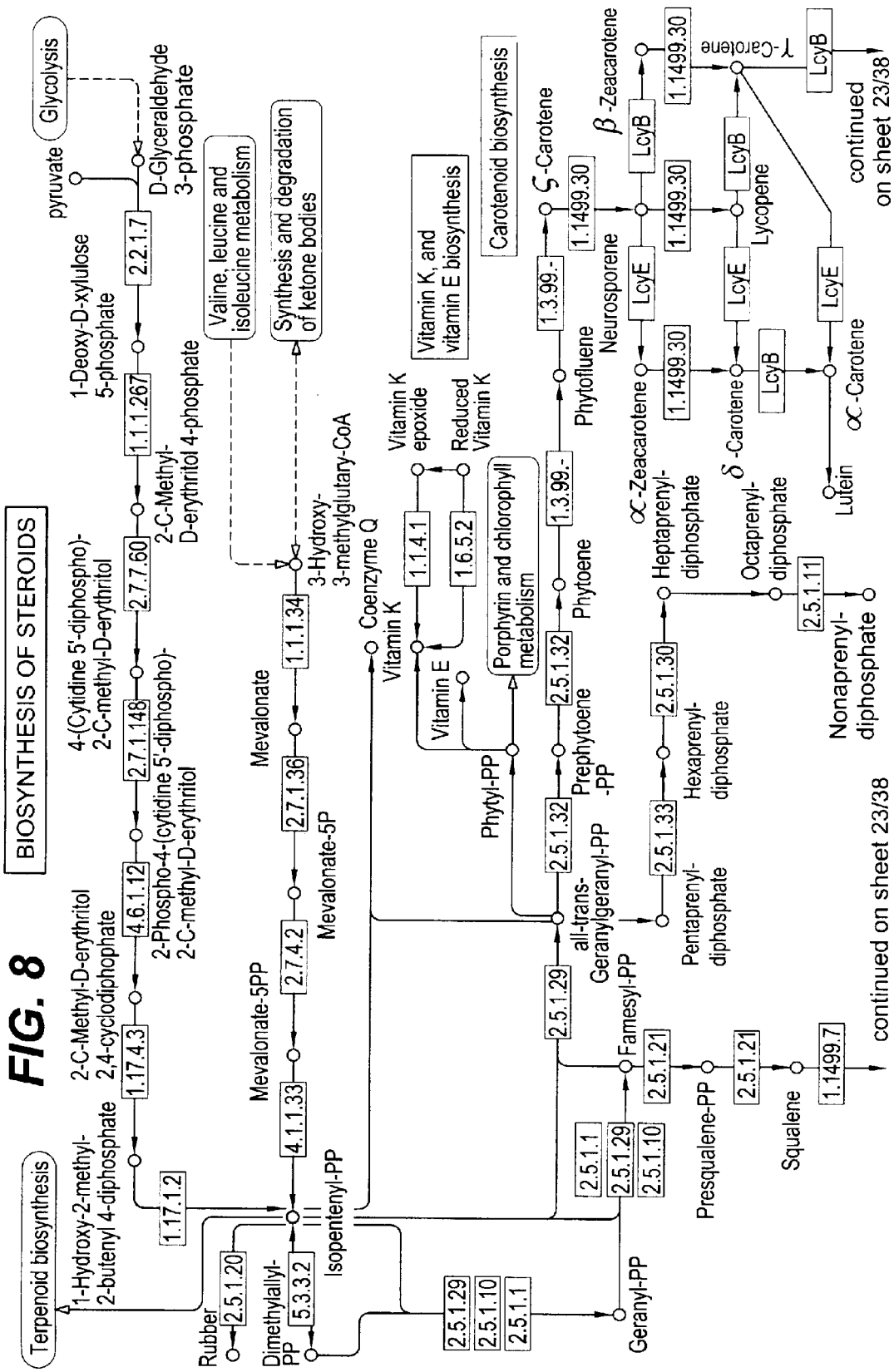
FIG. 8 depicts the steroid biosynthesis pathways, including the isoprenoid biosynthesis pathway, it indicates where certain quinone derived compounds (e.g., a ubiquinone, vitamin E and vitamin K) are produced via geranylgeranyl pyrophosphate.
Figure 8:
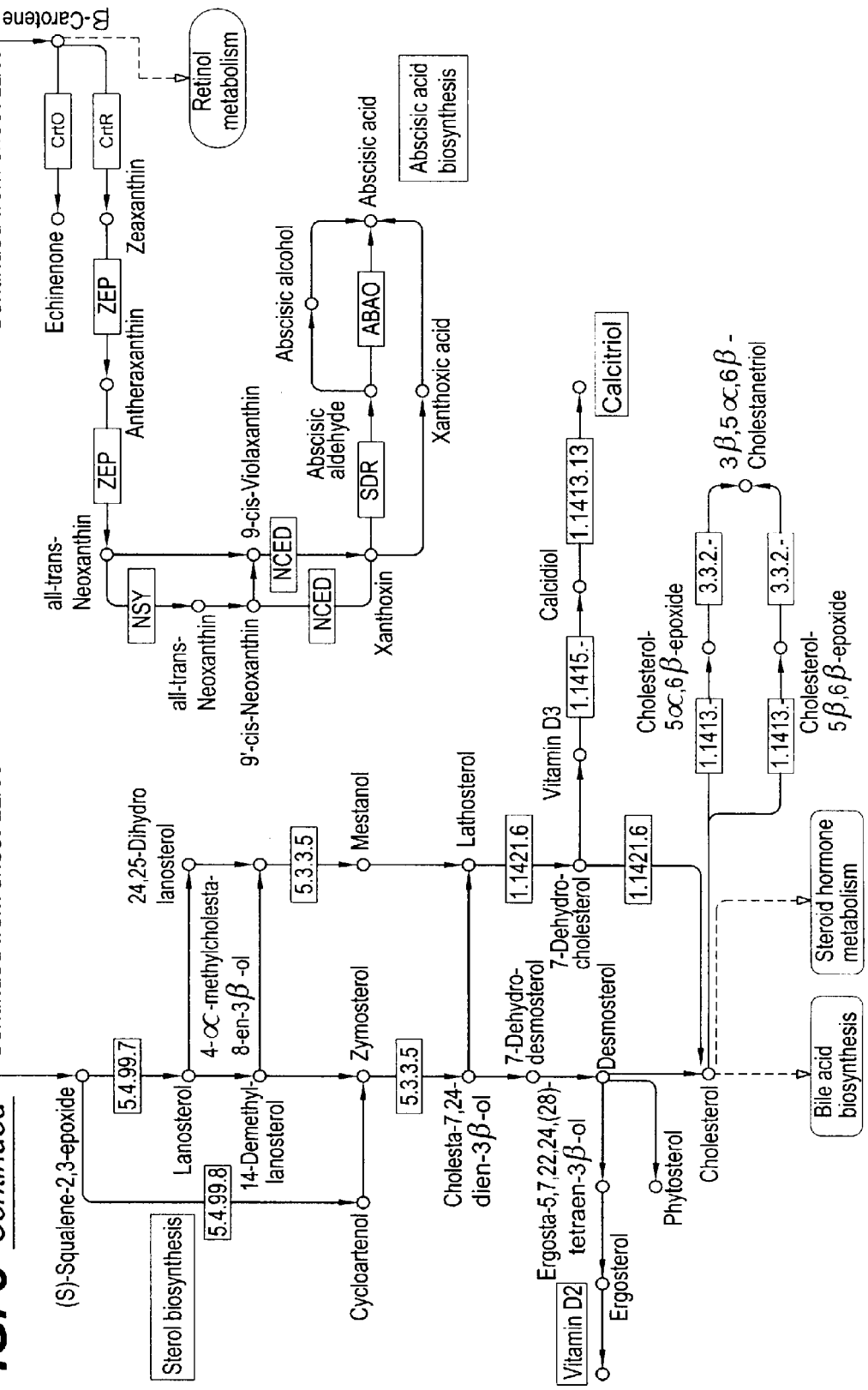

As mentioned, quinone derived compounds are produced from the isoprenoid compound isopentyl pyrophosphate (IPP), via geranylgeranyl pyrophosphate (see, for example, FIG. 8. IPP can be generated through one of two different isoprenoid biosynthesis pathways. The most common isoprenoid biosynthesis pathway, sometimes referred to as the "mevalonate pathway", is generally depicted in FIG. 4A. As shown, acetyl-CoA is converted, via hydroxymethylglutaryl-CoA (HMG-CoA), into mevalonate. Mevalonate is then phosphorylated and converted into the five-carbon compound isopentenyl pyrophosphate (IPP).

Figure 4B:
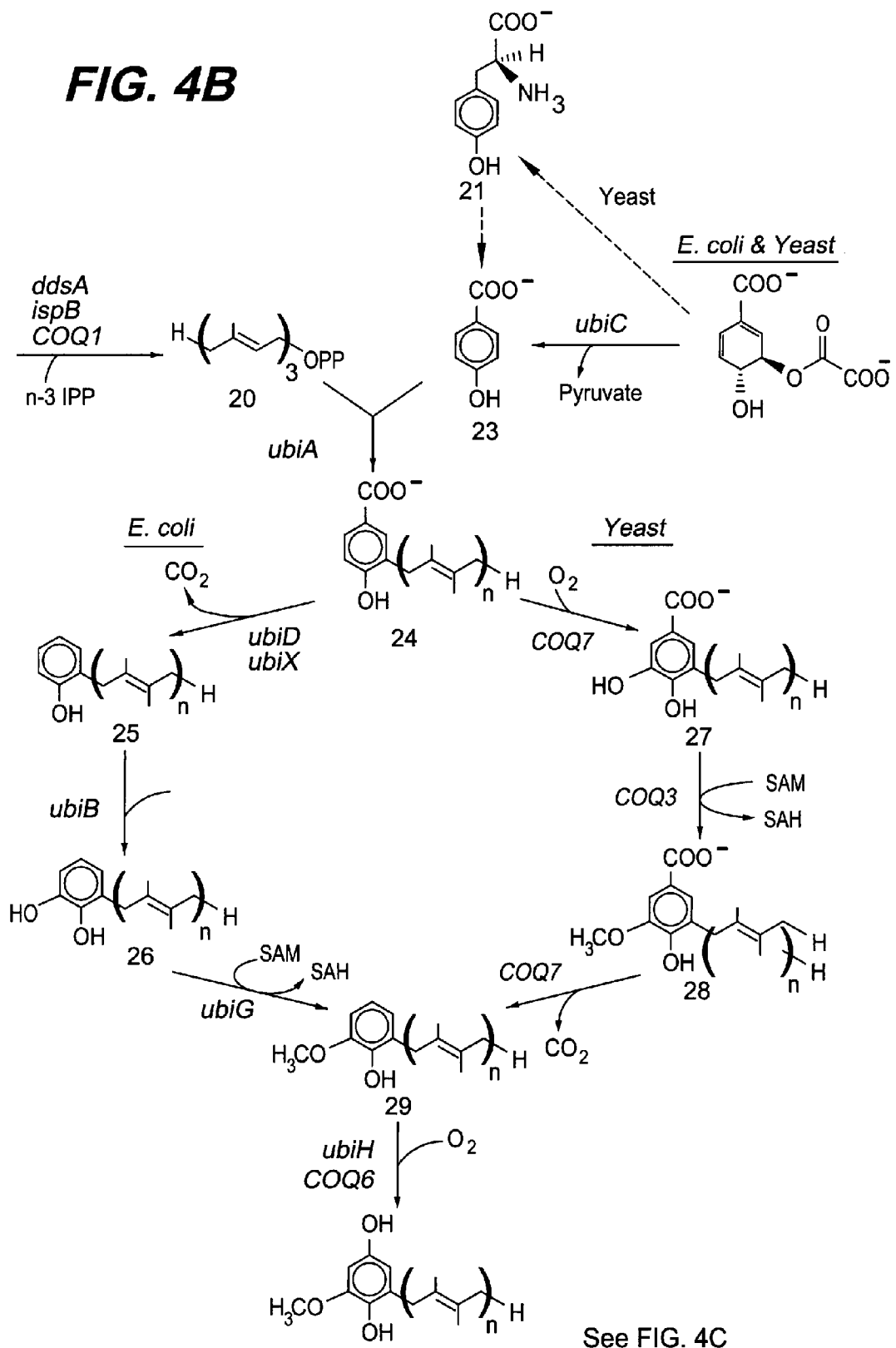
FIG. 4B depicts production of para-hydroxybenzoate (23) from precursor chorismate or tyrosine, and condensation with isoprene, resulting in formation of polyprenylhydroxybenzoate (24), followed by subsequent oxygenation, decarboxylation, and methylation reactions involved in production of quinine compound, polyprenyl-6-methoxy-1,4-benzoquinol (30).
Figure 4C:
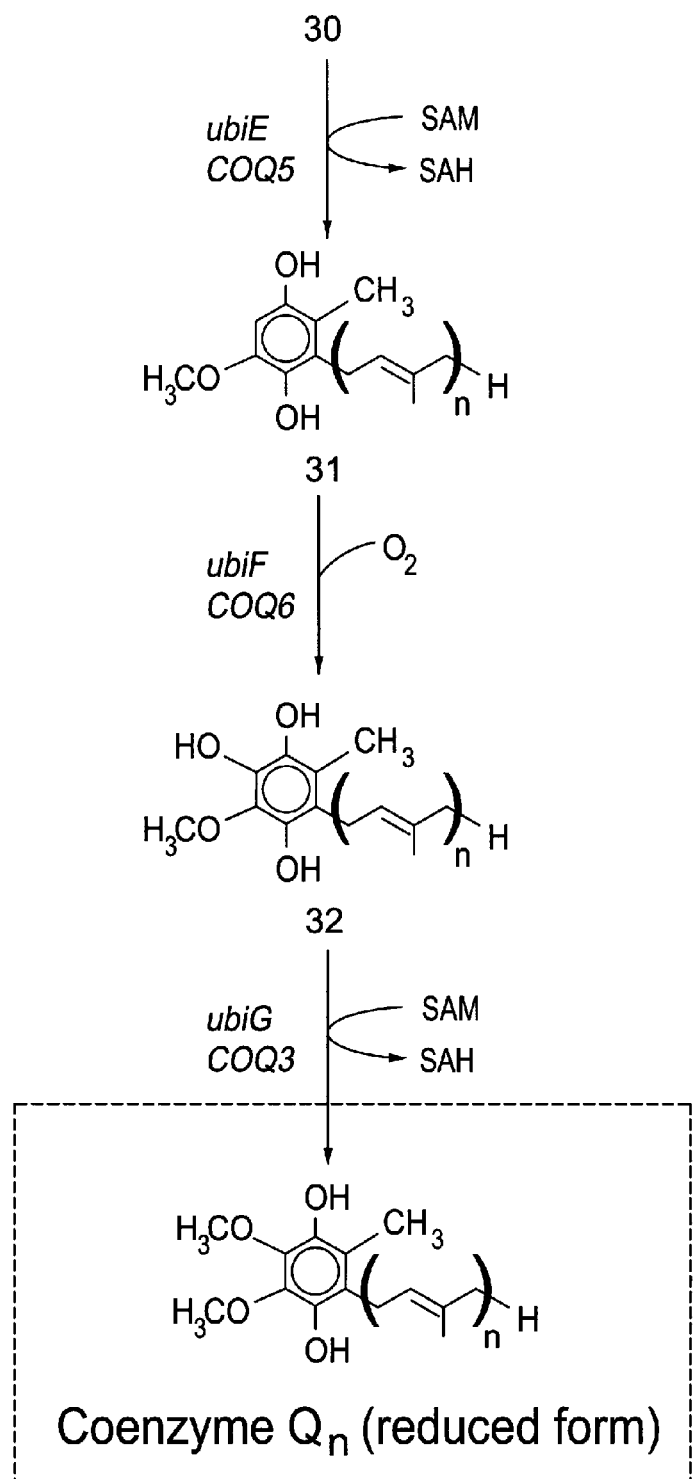
FIG. 4C depicts the final steps of methylation and oxygenation for generation of the ubiquinone CoQ10.

An alternative isoprenoid biosynthesis pathway, that is utilized by some organisms (particularly bacteria) and is sometimes called the "mevalonate-independent pathway", is also depicted in FIG. 4A. This pathway is initiated by the synthesis of 1-deoxy-D-xyloglucose-5-phosphate (DOXP) from pyruvate and glyceraldehyde-3-phosphate. DOXP is then converted, via a series of reactions shown in FIG. 4B, into IPP.

Various proteins involved in isoprenoid biosynthesis have been identified and characterized in a number of organisms. Moreover, isoprenoids are synthesized in many, if not most, organisms. Thus, various aspects of the isoprenoid biosynthesis pathway are conserved throughout the fungal, bacterial, plant and animal kingdoms. For example, polypeptides corresponding to the acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase shown in FIGS. 4-6 and 8 have been identified in and isolated from a wide variety of organisms and cells; representative examples of a wide variety of such polypeptides are provided in Tables 7-15. One or more of the polypeptides selected from those provided in any one of Tables 7-15 may be utilized or derived for use in the methods and compositions in accordance with the present invention.

Alternatively or additionally, modified mevalonate kinase polypeptides that exhibit decreased feedback inhibition properties (e.g., to farnesyl pyrophosphate (FPP)) may be utilized in accordance with the present invention. Such modified mevalonate kinase polypeptides may be of eukaryotic or prokaryotic origin. For example, modified versions of mevalonate kinase polypeptides from animals (including humans), plants, algae, fungi (including yeast), and/or bacteria may be employed; for instance, modified versions of mevalonate kinase polypeptides disclosed in Table 10 herein may be utilized.

Particular examples of modified mevalonate kinase polypeptides include "feedback-resistant mevalonate kinases" disclosed in PCT Application WO 06/063,752. Thus, for example, a modified mevalonate kinase polypeptide may include one or more mutation(s) at one or more amino acid position(s) selected from the group consisting of amino acid positions corresponding to positions 17, 47, 93, 94, 132, 167, 169, 204, and 266 of the amino acid sequence of *Paracoccus zeaxanthinifaciens* mevalonate kinase as shown in SEQ ID NO:1 of PCT Application WO 04/111,214. For example, the modified mevalonate kinase polypeptide may contain one or more substitutions at positions corresponding to one or more of I17T, G47D, K93E, V94I, R204H and C266S.

To give but a few specific examples, when a modified mevalonate kinase polypeptide comprises 2 amino acid changes as compared with a parent mevalonate kinase polypeptide, it may comprise changes at positions corresponding to the following positions 132/375,167/169, 17/47 and/or 17/93 of SEQ ID NO: 1 of WO 04/111,214 (e.g. P132A/P375R, R167W/K169Q, I17T/G47D or I17T/K93E); when a modified mevalonate kinase polypeptide comprises 3 amino acid changes as compared with a parent mevalonate kinase, it may comprise changes at positions corresponding to the following positions 17/167/169, 17/132/375, 93/132/375, and/or 17/47/93 of SEQ ID NO: 1 of WO/2004/111214 (e.g., I17T/R167W/K169Q, I17T/P132A/P375R, K93E/P132A/P375R, I17T/R167W/K169H, I17T/R167T/K169M, I17T/R167T/K169Y, I17T/R167F/K169Q, I17T/R167/K169N, I17T/R167H/K169Y, I17T/G47D/K93E or I17T/G47D/K93Q).

Thus, for example, a modified mevalonate kinase polypeptide may include one or more mutation(s) (particularly substitutions), as compared with a parent mevalonate kinase polypeptide, at one or more amino acid position(s) selected from the group consisting of amino acid positions corresponding to positions 55, 59, 66, 83, 106, 111, 117, 142, 152, 158, 218, 231, 249, 367 and 375 of the amino acid sequence of *Saccharomyces cerevisiae* mevalonate kinase as shown in SEQ ID NO:1 of PCT application WO 06/063,752. For example, such corresponding substitutions may comprise one or more of P55L, F59S, N66K, C117S, or I152M. A modified mevalonate kinase may comprise a substitution corresponding to F59S substitution. A modified mevalonate kinase polypeptide comprising 2 amino acid changes as compared with its parent mevalonate kinase polypeptide may, for example, comprise changes at positions corresponding to the following positions 55/117, 66/152, 83/249, 111/375 or 106/218 of to SEQ ID NO: 1 of WO 06/063,752 (e.g. P55L/C117S, N66K/I152M, K83E/S249P, H111N/K375N or L106P/S218P). A modified mevalonate kinase may comprise a substitution corresponding to N66K/I152M. A modified mevalonate kinase polypeptide comprising 4 amino acid changes as compared with its parent mevalonate kinase polypeptide may have changes at positions corresponding to one or more of the following positions 42/158/231/367 of SEQ ID NO:1 of WO 06/063,752 (e.g., I142N/L158S/L231I/T367S).

According to the present invention, quinone derived compound production in a host organism may be adjusted by modifying the expression or activity of one or more proteins involved in isoprenoid biosynthesis. In some embodiments, such modification involves introduction of one or more heterologous isoprenoid biosynthesis polypeptides into the host cell; alternatively or additionally, modifications may be made to the expression or activity of one or more endogenous or heterologous isoprenoid biosynthesis polypeptides. Given the considerable conservation of components of the isoprenoid biosynthesis polypeptides, it is expected that heterologous isoprenoid biosynthesis polypeptides will often function well even in significantly divergent organisms. Furthermore, should it be desirable to introduce more than one heterologous isoprenoid biosynthesis polypeptide (e.g., more than one version of the same polypeptide and/or more than one different polypeptides), in many cases polypeptides from different source organisms may function well together. In some embodiments of the invention, a plurality of different heterologous isoprenoid biosynthesis polypeptides is introduced into the same host cell. In some embodiments, this plurality contains only polypeptides from the same source organism; in other embodiments the plurality includes polypeptides from different source organisms.

In certain embodiments of the present invention that utilize heterologous isoprenoid biosynthesis polypeptides, the source organisms include, but are not limited to, fungi of the genera *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium (Gibberella), Kluyveromyces, Neurospora, Penicillium, Pichia (Hansenula), Puccinia, Saccharomyces, Schizosaccharomyces, Sclerotium, Trichoderms Ustilago*, and *Xanthophyllomyces (Phaffia)*. In certain embodiments, the source organisms are of a species including, but not limited to, *Cryptococcus neoformans, Fusarium fujikuroi, Kluyverimyces lactis, Neurospora crassa, Saccharomyces cerevisiae, Schizosaccharomyces pombe, Ustilago maydis*, and *Yarrowia lipolytica*.

Ubiquinone-10/Coenzyme Q10

Ubiquinone-10, or coenzyme Q10 (CoQ10), is synthesized de novo in all mammalian tissues, and serves a critical function in mediating electron transport in the mitochondrial respiratory chain. The reduced form of CoQ10 is also thought to function as an antioxidant and to protect against lipid peroxidation as well as against other free radical-induced oxidative damage. Recent studies have confirmed the role of CoQ10 in certain disease states, and additional roles in certain disorders continue to be elucidated. For example, administration of cholesterol lowering drugs, including HMG-CoA reductase inhibitors (e.g., the statins) to patients can result in diminished CoQ10 levels since cholesterol biosynthesis and CoQ10 biosynthesis share many of the same biosynthetic steps. Additionally, several clinical studies have been conducted to examine whether supplemental CoQ10 administration provides protection against, for example, deterioration in cardiac function (e.g., congestive heart failure), slows deterioration in Parkinson's patients, or protects the heart from damage caused by certain chemotherapeutic drugs.

While cells are capable of endogenously producing CoQ10, only about half of the levels required for optimum human cell function are produced in the body; the other half is acquired through dietary sources. Also, cellular levels of CoQ10 decrease under stress, with increasing age, and after certain pharmacological treatments, further increasing the need for exogenous CoQ10 to maintain optimum cell function.

CoQ10 has been used commercially in dietary and nutritional supplements as well as in functional foods, cosmetics and in personal care items. A rapidly growing market exists for CoQ10. The 2005 market for CoQ10 as an ingredient is estimated to be approximate $500 million, which represented approximately 250 metric tonnes of CoQ10. Further market expansion for CoQ10 is expected. Improved systems for enabling cost effective production, isolation, and/or formulation of CoQ10 are needed to effectively meet the growing demand for CoQ10.

Figure 9:
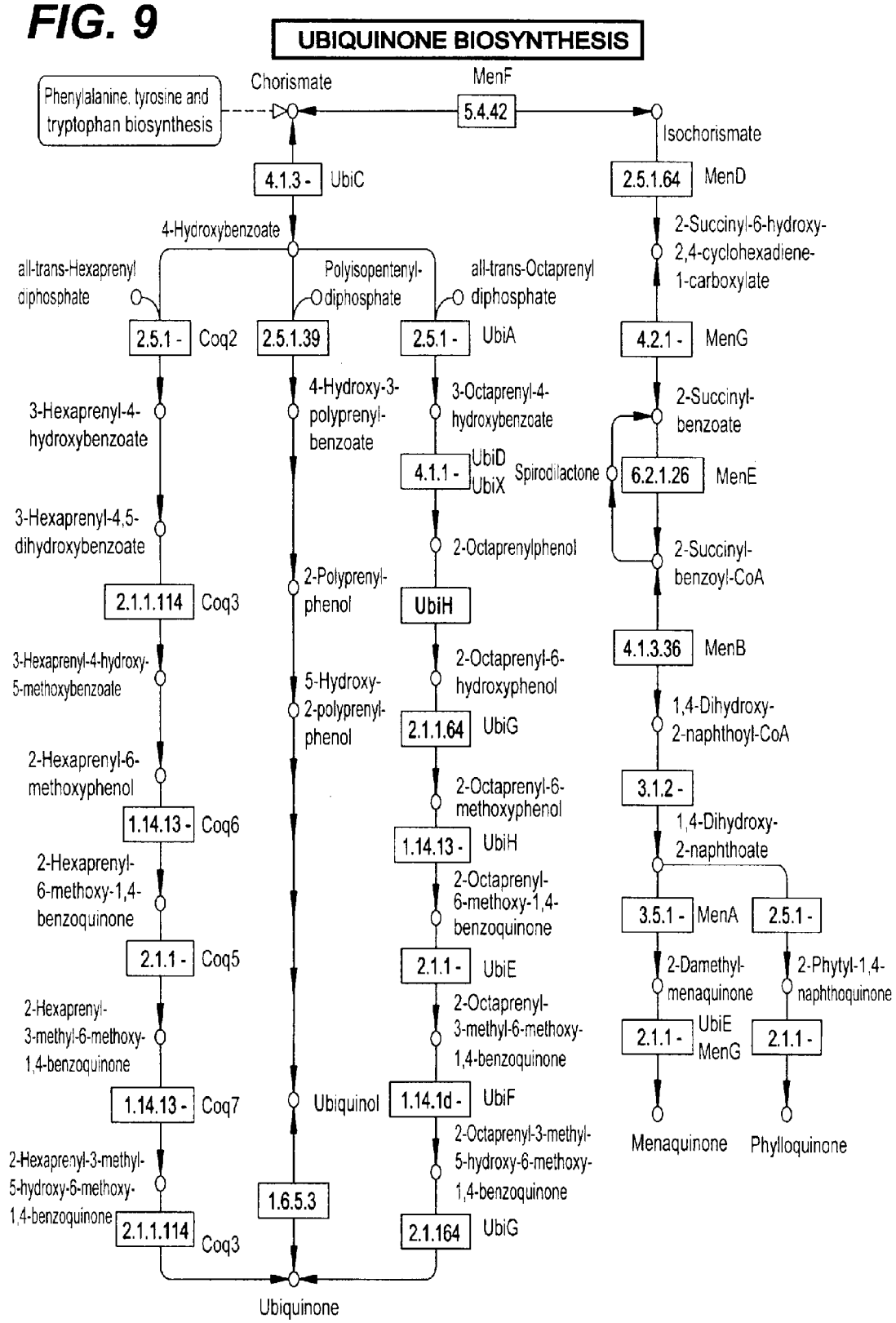
FIG. 9 depicts ubiquinone and vitamin K biosynthesis pathways.

The commitment step in ubiquinone biosynthesis is the formation of para-hydroxybenzoate (PHB) from tyrosine or phenylalanine in mammals or chorismate in bacteria, followed by condensation of PHB and isoprene precursor, resulting in addition of the prenyl group (see FIG. 9). Lower eukaryotes, such as yeast, can synthesize PHB from either tyrosine or chorismate. The 3-decaprenyl-4-hydroxybenzoic acid resulting from the condensation reaction undergoes further modifications, which include hydroxylation, methylation and decarboxylation, in order to form ubiquinone. Ubiquinone biosynthetic enzymes and genes encoding these proteins have been characterized in several organisms. The most extensive analysis has been performed in bacterial systems such as *Escherichia coli* and *Rhodobacter sphaeroides* as well as the yeast, *Saccharomyces cerevisiae*. At least 8 enzymes are required for the synthesis of CoQ10 from PHB and the isoprene precursors.

Biomanufacturing processes for CoQ10 have been developed or attempted using several genera of bacteria and yeast. Bacterial hosts have included *R. sphaeroides, Agrobacterium tumefaciens, Paracoccus denitrificans, Rhodopseudomonas spheroides*, and recombinant strains of *E. coli*, which naturally produces CoQ8. Yeast hosts have included *Saitoella complicata, Sporidiobolus ruineniae, Schizosaccharomyces pombe*, and several species of *Rhodotorula* and *Candida*. In addition, a semi-synthetic process for producing CoQ10 has been developed using solanesol extracted from tobacco leaves as a starting material; this process has economic and environmental disadvantages.

Despite the early identification of several microorganisms as potential hosts for CoQ10 production, only limited progress has been made towards the development of a cost-effective CoQ10 process using fermentation. Without wishing to be bound by any particular theory, the present inventors note that the hydrophobic isoprenoid side chain on CoQ10 causes it to localize to cell membranes, and offer that enhanced CoQ10 concentrations in the membranes might be detrimental to cell growth or viability. Efforts to engineer strains with increased production of CoQ10 have focused primarily in prokaryotes such as *E. coli*. While *E. coli* is a host with facile molecular genetic tools, this organism's fundamental physiology, may limit its ultimate utility as a CoQ10 production system.

The present invention encompasses the recognition that lipid-accumulating systems are useful for the production and/or isolation of ubiquinone(s). Indeed, several of the more productive natural CoQ10 strains (e.g., *P. denitrificans, R. sphaeroides*) display a relatively high intracellular membrane content. Without wishing to be bound by theory, the present inventors propose that the higher intracellular membrane content may facilitate increased CoQ10 production and/or accumulation. The present invention therefore encompasses the discovery that CoQ10 can desirably be produced in oleaginous yeast and fungi. According to the present invention, strains that both (i) accumulate lipid, often in the form of cytoplasmic lipid bodies and typically to at least about 20% of their dry cell weight; and (ii) produce CoQ10 at a level at least about 1%, and in some embodiments at least about 3-20%, of their dry cell weight, are generated through manipulation of generally available strains (e.g., naturally-occurring strains and strains which have been previously genetically modified, whether via recombinant DNA techniques or mutagenesis directed modification). These manipulated strains are then used to produce CoQ10, so that the CoQ10 that partitions into the lipid bodies can readily be isolated.

In certain embodiments of the invention, host cells are *Yarrowia lipolytica* cells. Advantages of *Y. lipolytica* include, for example, tractable genetics and molecular biology, availability of genomic sequence, suitability to various cost-effective growth conditions, and ability to grow to high cell density. In addition, *Y. lipolytica* is naturally oleaginous, such that fewer manipulations may be required to generate an oleaginous, CoQ10-producing *Y. lipolytica* strain than might be required for other organisms. Furthermore, there is already extensive commercial experience with *Y. lipolytica*.

As mentioned, ubiquinone is formed by the combination of para-hydroxybenzoate and isoprenoid chains produced, for example, via the isoprenoid biosynthesis pathways discussed above. Once IPP is formed according to that pathway, it isomerizes into dimethylallyl pyrophophate (DMAPP). Three sequential condensation reactions with additional molecules of IPP generate the ten-carbon molecule geranyl pyrophosphate (GPP), followed by the fifteen-carbon molecule farnesyl pyrophosphate (FPP), which can be used to form the twenty-carbon compound geranylgeranyl pyrophosphate (GGPP). In many instances, FPP appears to be the predominant substrate used by polyprenyldiphosphate synthases (e.g., Coq1 polypeptides) during ubiquinone biosynthesis. According to the present invention, ubiquinone production in a host organism may be adjusted by modifying the expression or activity of one or more proteins involved in isoprenoid biosynthesis as discussed above.

As discussed herein, two different pathways can produce the ubiquinoid precursor para-hydroxybenzoate—the first, the "shikimate pathway" is utilized in prokaryotes and yeast, involves synthesis of para-hydroxybenzoate (PHB) through chorismate. Biosynthesis of para-hydroxybenzoate from chorismate occurs by the action of chorismate pyruvate lyase. For example, as discussed herein, enzymes of the shikimate pathway, chorismate synthase, DAHP synthase, and transketolase are involved in this process. Representative examples of these enzymes are provided in Table 33 and Tables 35 through 37. In the second possible pathway, para-hydroxybenzoate is produced by derivation of tyrosine or phenylalanine. Biosynthesis of para-hydroxybenzate from tyrosine or phenylalanine occurs through a five step process in mammalian cells (see, for example FIG. 3).

Accordingly, ubiquinone (e.g., CoQ10 and/or $C_{5-9}$ quinone compounds) production in a host organism may be adjusted by modifying the expression or activity of one or more proteins involved in PHB biosynthesis. In some embodiments, such modification involves introduction of one or more heterologous PHB polypeptides into the host cell; alternatively or additionally, modifications may be made to the expression or activity of one or more endogenous or heterologous additional PHB polypeptide, and/or isoprenoid biosynthesis polypeptides. Given the considerable conservation of components of the PHB biosynthesis polypeptides, it is expected that heterologous PHB biosynthesis polypeptides will often function well even in significantly divergent organisms. Further, given the conservation of the pathways among organism, it is anticipated that heterologous polypeptides throughout the ubiquinone biosynthetic pathway will function together effectively. Furthermore, should it be desirable to introduce more than one heterologous PHB polypeptide and/or isoprenoid biosynthesis polypeptide, in many cases polypeptides from different source organisms will function well together. In some embodiments of the invention, a plurality of different heterologous PHB and/or isoprenoid biosynthesis polypeptides is introduced into the same host cell. In some embodiments, this plurality contains only polypeptides from the same source organism; in other embodiments the plurality includes polypeptides from different source organisms. In still other embodiments, modification of endogenous PHB and/or isoprenoid biosynthesis polypeptides are also utilized, either alone or in combination with heterologous polypeptides as discussed herein.

As noted herein, the isoprenoid biosynthesis pathway is also involved in the production of non-ubiquinone compounds, such as carotenoids, sterols, steroids, and vitamins, such as vitamin K or vitamin E. Proteins that act on isoprenoid biosynthesis pathway intermediates, and divert them into biosynthesis of non-ubiquinone compounds are therefore indirect inhibitors of ubiquinone biosynthesis (see, for example, FIG. 5, which illustrates points at which isoprenoid intermediates are channeled into other biosynthesis pathways). Such proteins are therefore considered ubiquinone biosynthesis competitor polypeptides. Reductions of the level or activity of such ubiquinone biosynthesis competitor polypeptides are expected to increase ubiquinone (e.g., CoQ10 and/or $C_{5-9}$ quinone compounds) production in host cells according to the present invention.

In some embodiments of the present invention, production or activity of endogenous ubiquinone biosynthesis competitor polypeptides may be reduced or eliminated in host cells. In some embodiments, this reduction or elimination of the activity of a ubiquinone biosynthesis competitor polypeptide can be achieved by treatment of the host organism with small molecule inhibitors of enzymes of the ergosterol biosynthetic pathway. Enzymes of the ergosterol biosynthetic pathway include, for example, squalene synthase (Erg9), squalene epoxidase (Erg1), 2,3-oxidosqualene-lanosterol cyclase (Erg7), cytochrome P450 lanosterol 14α-demethylase (Erg11), C-14 sterol reductase (Erg24), C-4 sterol methyl oxidase (Erg25), SAM:C-24 sterol methyltransferase (Erg6), C-8 sterol isomerase (Erg2), C-5 sterol desaturase (Erg3), C-22 sterol desaturase (Erg5), and C-24 sterol reductase (Erg4) polypeptides. Each of these enzymes is considered a ubiquinone biosynthesis competitor polypeptide. Regulators of these enzymes may also be considered ubiquinone biosynthesis competitor polypeptides (e.g., the yeast proteins Sut1 (Genbank Accession JC4374 GI:2133159) and Mot3 (Genbank Accession NP_013786 GI:6323715), which may or may not have homologs in other organisms.

In some embodiments of the invention, production or activity of endogenous ubiquinone biosynthesis competitor polypeptides may be reduced or eliminated in host cells. In some embodiments, this reduction or elimination of the activity of a ubiquinone biosynthesis competitor polypeptide can be achieved by treatment of the host organism with small molecule inhibitors of enzymes of the ergosterol biosynthetic pathway. Enzymes of the ergosterol biosynthetic pathway include, for example, squalene synthase, squalene epoxidase, 2,3-oxidosqualene-lanosterol cyclase, cytochrome P450 lanosterol 14α-demethylase, C-14 sterol reductase, C-4 sterol methyl oxidase, SAM:C-24 sterol methyltransferase, C-8 sterol isomerase, C-5 sterol desaturase, C-22 sterol desaturase, and C-24 sterol reductase. Each of these enzymes is considered a ubiquinone biosynthesis competitor polypeptide. Regulators of these enzymes may also be considered ubiquinone biosynthesis competitor polypeptides (e.g., the yeast proteins Sut1 (Genbank Accession JC4374 GI:2133159) and Mot3 (Genbank Accession NP_013786 GI:6323715), which may or may not have homologs in other organisms).

Known small molecule inhibitors of some ubiquinone biosynthesis competitor enzymes include, but are not limited to, zaragosic acid (including analogs thereof such as TAN1607A (Biochem Biophys Res Commun Feb. 15, 1996; 219(2):515-520)), RPR 107393 (3-hydroxy-3-[4-(quinolin-6-yl)phenyl]-1-azabicyclo[2-2-2]octane dihydrochloride; J Pharmacol Exp Ther. May 1997; 281(2):746-52), ER-28448 (5-{N-[2-butenyl-3-(2-methoxyphenyl)]-N-methylamino}-1,1-penthylidenebis(phosphonic acid) trisodium salt; Journal of Lipid Research, Vol. 41, 1136-1144, July 2000), BMS-188494 (The Journal of Clinical Pharmacology, 1998; 38:1116-1121), TAK-475 (1-[2-[(3R,5S)-1-(3-acetoxy-2,2-dimethylpropyl)-7-chloro-1,2,3,5-tetrahydro-2-oxo-5-(2,3-dimethoxyphenyl)-4,1-benzoxazepine-3-yl]acetyl]piperidin-4-acetic acid; Eur J Pharmacol. Apr. 11, 2003; 466(1-2):155-61), YM-53601 ((E)-2-[2-fluoro-2-(quinuclidin-3-ylidene)ethoxy]-9H-carbazole monohydrochloride; Br J Pharmacol. September 2000; 131(1):63-70), or squalestatin I that inhibit squalene synthase; terbinafine (e.g., LAMISIL®), naftifine (NAFTIN®), S-allylcysteine, garlic, resveratrol, NB-598 (e.g., from Banyu Pharmaceutical Co), and/or green tea phenols that inhibit squalene epoxidase (see, for example, *J. Biol Chem* 265:18075, 1990; *Biochem. Biophys. Res. Commun.* 268:767, 2000); various azoles that inhibit cytochrome P450 lanosterol 14α-demethylase; and fenpropimorph that inhibits the C-14 sterol reductase and the C-8 sterol isomerase. In other embodiments, heterologous ubiquinone biosynthesis competitor polypeptides may be utilized (whether functional or non-functional; in some embodiments, dominant negative mutants are employed).

One ubiquinone biosynthesis competitor polypeptide useful according to the present invention is squalene synthase which has been identified and characterized from a variety of organisms; representative examples of squalene synthase polypeptide sequences are included in Table 16. In some embodiments of the invention that utilize squalene synthase (or modifications of squalene synthase) source organisms include, but are not limited to, *Neurospora crassa, Xanthophyllomyces dendrorhous (Phaffia rhodozyma), Aspergillus niger, Saccharomyces cerevisiae, Mucor circinelloides, Rhotorula glutinis, Candida utilis, Mortierella alpina,* and *Yarrowia lipolytica.*

Another ubiquinone biosynthesis competitor polypeptide useful according to the present invention is anthranilate synthase, which has also been identified in a variety of organisms; representative anthranilate synthase polypeptides are provided in Table 32 and 32B. In some embodiments of the invention, anthranilate synthase polypeptide, or modifications thereof are utilized and adapted from source organisms including, but not limited to: *Kluyveromyces lactis, Candida glabrata, Saccharomyces cerevisiae, Yarrowia lipolytica, Debaryomyces hansenii, Candida albicans, Aspergillus fumigatus, Aspergillus oryzae, Aspergillus nidulans, Ustilago maydis, Neurospora crassa, Schizosaccharomyces pombe, Gibberella zeae,* and *Cryptococcus neoformans* var.

Similarly, yet another ubiquinone biosynthesis competitor polypeptide useful according to the invention is chorismate mutase, which has also been identified in a variety of organisms; representative chorismate mutase polypeptides are provided in Table 34. In some embodiments of the invention, chorismate mutase polypeptide, or modifications thereof are utilized and adapted from source organisms including, but not limited to: *Kluyveromyces lactis, Candida glabrata, Arabidopsis thaliana, Yarrowia lipolytica, Candida albicans, Aspergillus fumigatus, Aspergillus oryzae, Aspergillus nidulans, Ustilago maydis, Neurospora crassa, Schizosaccharomyces pombe, Gibberella zeae,* and *Pichia pastoris.*

Particularly for embodiments of the present invention directed toward production of CoQ10, it will often be desirable to utilize one or more genes from a natural CoQ10-producing organism. In general, where multiple heterologous polypeptides are to be expressed, it may be desirable to utilize the same source organism for all, or to utilize closely related source organisms.

Bacterial ubiquinogenic genes have already been demonstrated to be transferable to other organisms, and are therefore useful in accordance with the present invention (see, for example, Okada et al., *FEMS Lett.* 431:241-244 (1998)). In some embodiments of this invention, it may be desirable to fused sequences encoding specific targeting signals to bacterial ubiquinogenic genes. For example, in certain embodiments mitochondrial signal sequences are useful in conjunction with, e.g., bacterial ubiquinogenic polypeptides for effective targeting of polypeptides for proper functioning. Mitochondrial signal sequences are known in the art, and include, but are not limited to example, mitochondrial signal sequences provided in Table 22. In other embodiments, it may be desirable to utilize genes from other source organisms such as animals, plants, alga, or microalgae, fungi, yeast, insect, protozoa, and mammals.

The present invention contemplates not only introduction of heterologous ubiquinogenic polypeptides, but also adjustment of expression or activity levels of heterologous or endogenous ubiquinogenic polypeptides, including, for example, alteration of constitutive or inducible expression patterns so as to increase activity of ubiquinogenic polypeptides. For example, genetic modifications comprising alteration and/or addition of regulatory sequences (e.g., promoter elements, terminator elements) may be utilized to confer particular regulation of expression patterns. Such genetic modifications may be utilized in conjunction with endogenous genes (e.g., for regulation of endogenous ubiquinogenic polypeptide(s)); alternatively, such genetic modifications may be included so as to confer regulation of expression of heterologous polypeptides (e.g., ubiquinogenic polypeptide(s)).

To give but a few specific examples of strains engineered to produce CoQ10 (and optionally to be oleaginic) according to the present invention, in some embodiments, *Yarrowia lipolytica* cells are engineered to express a decaprenyl diphosphate synthase polypeptide(s) from a source organism. In some embodiments, the source organism is selected from the group consisting of *Silibacter pomeroyi* and *Loktanella vestfoldensis*. As is discussed herein, where the source organism is other than *Y. lipolytica*, nucleic acid sequences encoding the polypeptide(s) can be established with *Y. lipolytica* codon preferences and/or targeting sequences (e.g., mitochondrial targeting sequences). In some embodiments, one or more endogenous polyprenyl synthase genes (e.g., nonaprenyl diphosphate synthase) is/are disrupted or inactivated, and a decaprenyl diphosphate synthase gene from a different source organism is introduced. In some embodiments, the different source organism is selected from the group consisting of *Silibacter pomeroyi* and *Loktanella vestfoldensis.*

Alternatively or additionally, in some embodiments of the invention, host cells are engineered to produce CoQ10 by introducing or increasing expression or activity of one or more ubiquinone biosynthesis polypeptides, and in particular of one or more polypeptides involved in converting parahydroxybenzoic acid to CoQ10 (e.g., via a ubiquinol pathway). To give but one specific example, *Yarrowia lipolytica* cells are engineered to express a 4-hydroxybenzoate polyprenyltransferase polypeptide from source organism, for example selected from the group consisting of *Silibacter*

*pomeroyi* and *Bos taurus*. Sequences encoding the polypeptide(s) can optionally be established with *Y. lipolytica* codon preferences and/or targeting sequences (e.g., mitochondrial targeting sequences).

In some embodiments, CoQ10 production in cells, e.g., in *Yarrowia lipolytica* cells is enhanced by engineering the cells to increase production of para-hydroxybenzoic acid (PHB), for example by increasing expression or activity of one or more PHB polypeptides. In some embodiments, *Y. lipolytica* cells are engineered to express one or more of 3-deoxy-D-arabino-heptulosonate-7-phosphate (DAHP) and chorismate lyase polypeptides from a source organism. Where the source organism is other than *Y. lipolytica*, nucleic acid sequences encoding the polypeptide(s) can be established with *Y. lipolytica* codon preferences and/or targeting sequences (e.g., mitochondrial targeting sequences). In some embodiments, one or both of the DAHP and chorismate lyase polypeptides are from heterologous source organisms, which may be the same or different. In some embodiments, at least one source organism is *Erwinia carotovora*.

In some embodiments, host cells (e.g., *Yarrowia lipolytica*) engineered to increase production of para-hydroxybenzoic acid are further engineered to increase expression and/or activity of one or more ubiquinone biosynthesis polypeptides involved in converting para-hydroxybenzoic acid to a ubiquinone (e.g., via a ubiquinol pathway), and/or of one or more decaprenyl diphosphate synthase. To give but a couple of particular examples, such strains may be engineered to express a 4-hydroxybenzoate polyprenyltransferase polypeptide from source organism, for example selected from the group consisting of *Silibacter pomeroyi* and *Bos taurus* and/or to express a decaprenyl diphosphate synthase polypeptide(s) from a source organism, for example selected from the group consisting of *Silibacter pomeroyi* and *Loktanella vestfoldensis*.

Alternatively or additionally, in some specific embodiments, CoQ10 production is enhanced by engineering cells to reduce carbon flow into competing metabolic pathways such as, for example, the sterol pathway. To give but one specific example, in some embodiments of the invention, *Yarrowia lipolytica* cells are engineered to inactivate (e.g., partially) an endogenous gene (e.g., ERG9) encoding a squalene synthase polypeptide.

Yet further, in some particular embodiments, CoQ10 production is enhanced by engineering cells by expression of a truncated HMG CoA reductase polypeptide (e.g., from a source organism such as *Y. lipolytica*).

In some embodiments of the present invention, host cells are engineered to produce one or more ubiquinones other than CoQ10 in addition or as an alternative to CoQ10. Specifically, in some embodiments of the invention, host cells are engineered to produce one or more $C_{5-9}$ quinones.

That is, the present invention provides engineered host cells, e.g., fungal cells, that produce $C_{5-9}$ quinones as a result of the engineering. The present invention therefore provides engineered host cells containing a $C_{5-9}$ quinones production modification. Such a modification may comprise, for instance, introduction or activation of one or more $C_{5-9}$ quinones biosynthetic polypeptides within a host cell. Exemplary such polypeptides include, for example, pentaprenyl, hexaprenyl, heptaprenyl, octaprenyl, and/or solanesyl(nonaprenyl) biosynthesis polypeptides. Specific examples of each of these can be found, for example, in Tables 61-65.

To give but a few specific examples, in some embodiments of the present invention, *Yarrowia lipolytica* cells are engineered to express one or more polyprenyl diphosphate synthase genes (e.g., nonaprenyl diphosphate synthase, octaprenyl diphosphate synthase, heptaprenyl diphosphate synthase, hexaprenyl diphosphate synthase, pentaprenyl disphosphate synthase, etc.). In some embodiments, one or more endogenous polyprenyl synthase genes (e.g., nonaprenyl diphosphate synthase) is/are disrupted or inactivated, and a polyprenyl synthase gene from a different source organism is introduced. In some embodiments, the different source organism is selected from the group consisting of *Silibacter pomeroyi* and *Loktanella vestfoldensis*.

Vitamin K

Vitamin K is a generic term that refers to derivatives of 2-methyl-1,4-naphthoquinone that have coagulation activity. The two natural forms of vitamin K differ in the identity of their side chains at position 3. Vitamin $K_1$, also known as phylloquinone (based on its presence in plants), has a phytyl side chain in position 3; vitamin $K_2$, also known as menaquinone, has an isoprenyl side chain at position 3. Different forms of menaquinone, having side chains with different numbers of isoprene units (typically 4-13) are found in different types of cells.

Vitamin K has been found to be an important vitamin involved in the blood coagulation system, and is utilized as a hemostatic agent. Recently it has been suggested that vitamin K is involved in osteo-metabolism, and vitamin K is expected to be applied to the treatment of osteoporosis. Both phylloquinone and menaquinone have been approved as pharmaceuticals.

The daily requirement for vitamin K is about 1 ug/kg; an average diet typically contains about 75-150 ug/day. Vitamin K deficiency results in hypoprothrombinemia and defective coagulation. Primary vitamin K deficiency is uncommon in adults because of its general availability in the food chain, and potentially also because it can be produced by microbes inhabiting the human gastrointestinal tract. Vitamin K deficiency is observed in newborns, as breast milk contains very little and the newborn gut is sterile (i.e., not inhabited by vitamin K-producing organisms) for the first several days of life.

Vitamin K is considered an essential nutrient since mammals do not produce it and it is a dietary requirement. As depicted for example in FIG. 9, vitamin K is produced through precursor molecules chorismate and isoprenoids, similar to ubiquinone production, though biosynthesis proceeds through production of isochorismate, and prenyl addition does not occur until the final or next to last step in synthesis. Details of production of vitamin K, and the relevant enzymes involved are known in the art and can be adapted for use in combination with the provided methods and compositions. See, e.g., Meganathan, *Vitamins and Hormones* 61: 173-219, 2001.

The present invention provides engineered host cells, e.g., fungal cells, that produce vitamin K as a result of the engineering. That is, the present invention provides engineered host cells containing a Vitamin K production modification. Such a modification may comprise, for instance, introduction or activation of one or more Vitamin K biosynthetic polypeptides within a host cell. Exemplary such polypeptides include, for example, MenF, MenD, MenC, MenE, MenB, MenA, UbiE, and/or MenG polypeptides. Specific examples of each of these can be found, for example, in Tables 46-53.

Vitamin E

Vitamin E is a generic term for a family of structurally related compounds that have a 6-chromanol ring, an isoprenoid side chain, and the biologic activity of α-tocopherol. The term encompasses the eight known naturally occurring vitamin E compounds, the four tocopherols (α, β, γ, δ) and four tocotrienols (α, β, γ, δ), which all contain a hydrophilic chromanol ring and a hydrophobic side chain. The α, β, γ, and δ forms differ from one another in the number of methyl groups on the chromanol ring. Several synthetic vitamin E compounds have also been prepared, and still others are possible (see, for example, Bramley et al., *J. Sci Food Agric* 80:913, 2000). α-tocopherol is a potent antioxidant, and is generally considered to be the most active vitamin E compound in humans.

Vitamin E is commonly included in nutritional supplements and also in skin creams and lotions (based on a reported role in wound healing). Vitamin E deficiency is manifested differently in different species and in different individual cases, but can include reproductive disorders; abnormalities of muscle, liver, bone marrow, and/or brain function; red blood cell hemolysis; defective embryogenesis; exudative diathesis, a disorder of capillary permeability; and/or skeletal muscular dystrophy (with or without cardiomyopathy). Vitamin E is used to treat vitamin E deficiency, and is also suspected to be useful in the treatment of cancer (thanks to its antioxidant properties), cataracts and macular degeneration (particularly age-related), heart disease, neurological disorders (e.g., Alzheimer's Disease, Parkinson's Disease, etc.), immune disorders, inflammatory diseases, among other things.

The U.S. Dietary Reference Intake (DRI) Recommended Daily Amount (RDA) for a 25-year old male for Vitamin E is 15 mg/day. This is approximately 15 IU/day Specifically, The natural form of alpha-tocopherol: RRR-alpha-tocopherol maintain 1.5 IU/mg.

Figure 10A:
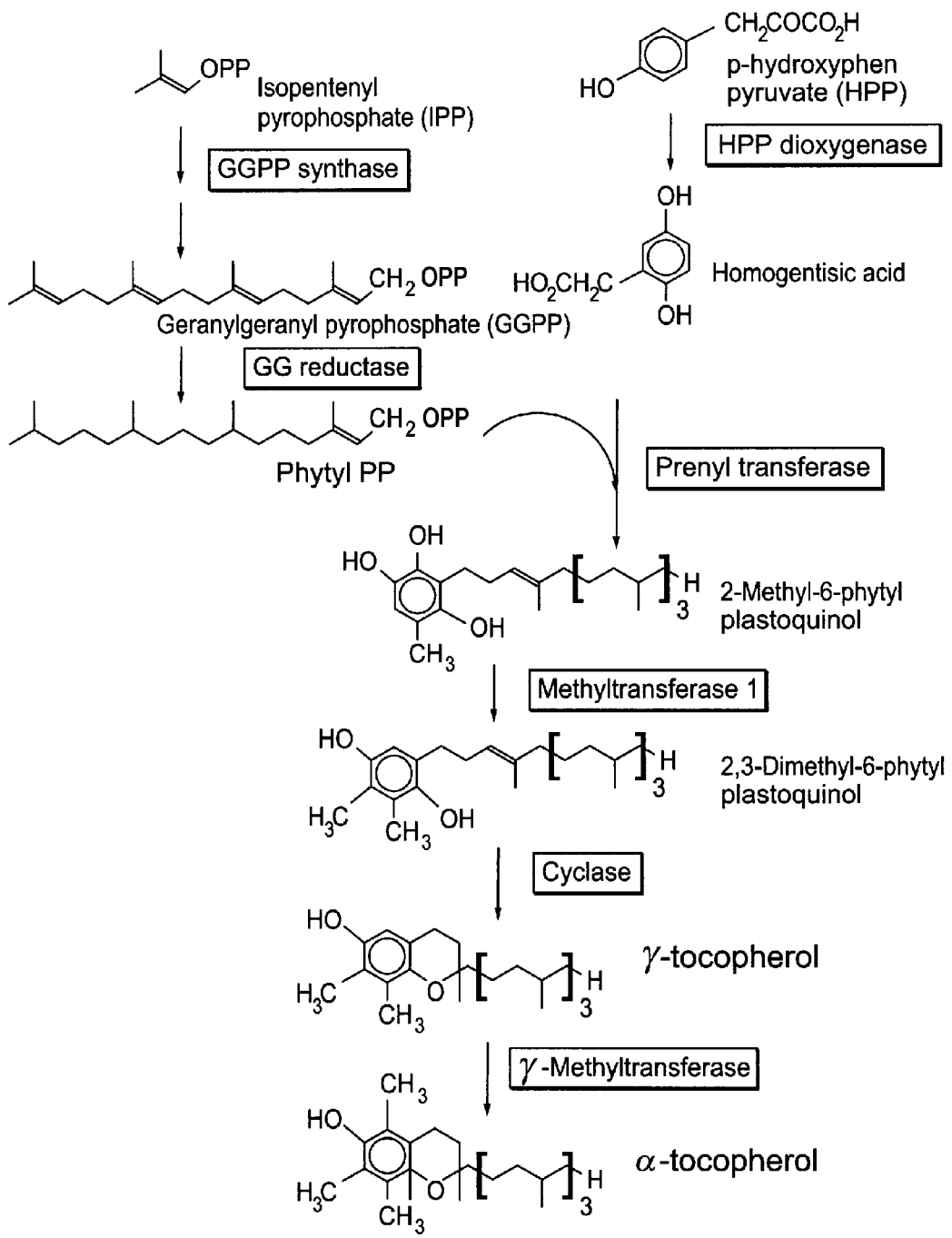
FIG. 10, Panels A-C, depict vitamin E biosynthesis pathways. Panel A shows synthesis of γ- and α-tocopherols from isopentenyl pyrophosphate and p-hydroxyphenpyruvate through action of geranylgeranylpyrophosphate synthase, geranylgeranyl reductase, p-hydroxyphenpyruvate dioxygenase, prenyl transferase, methyltransferase I, cyclase, and γ-methyltransferase enzyme activities. Panel B depicts the tocopherol biosynthetic pathway in plants. Dashed arrows represent multiple steps. Enzymes are indicated by circled numbers as follows: 1) HGA phytyltransferase; 2) p-hydroxyphenyl pyruvate dioxygenase; 3) HGA dioxygenase; 4) geranylgeranyl diphosphate reductase, 5) geranylgeranyl diphosphate synthase; 6) 1-deoxy-D-xylulose-5-phosphate synthase; 7) 2-methyl4-phytyl-1,4-benzoquinol methyltransferase; 8) tocopherol cyclase; and 9) γ-tocopherol methyltransferase. Panel C depicts synthesis of α, β, γ, and δ tocopherols.
Figure 10B:
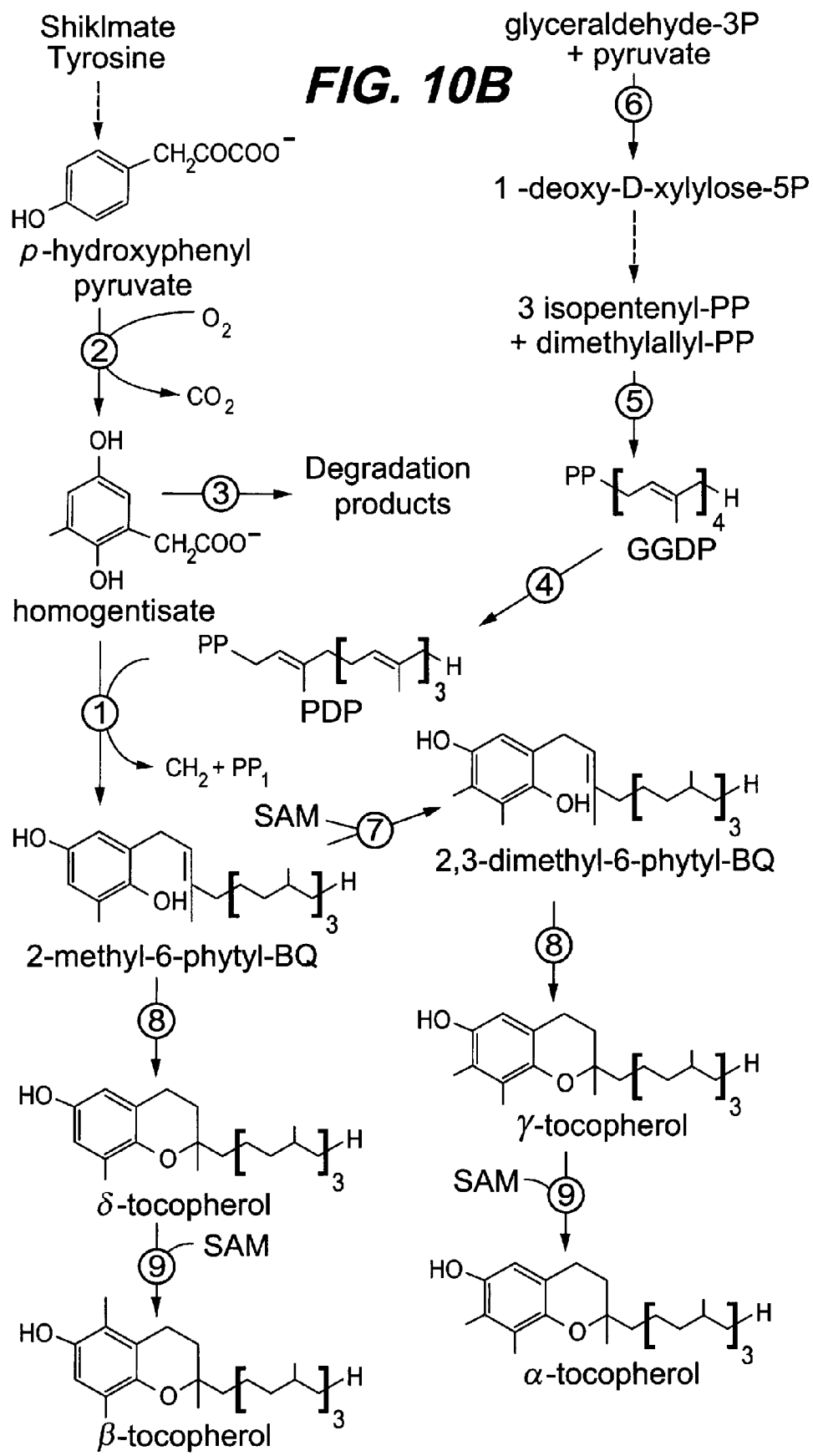
Figure 10C:
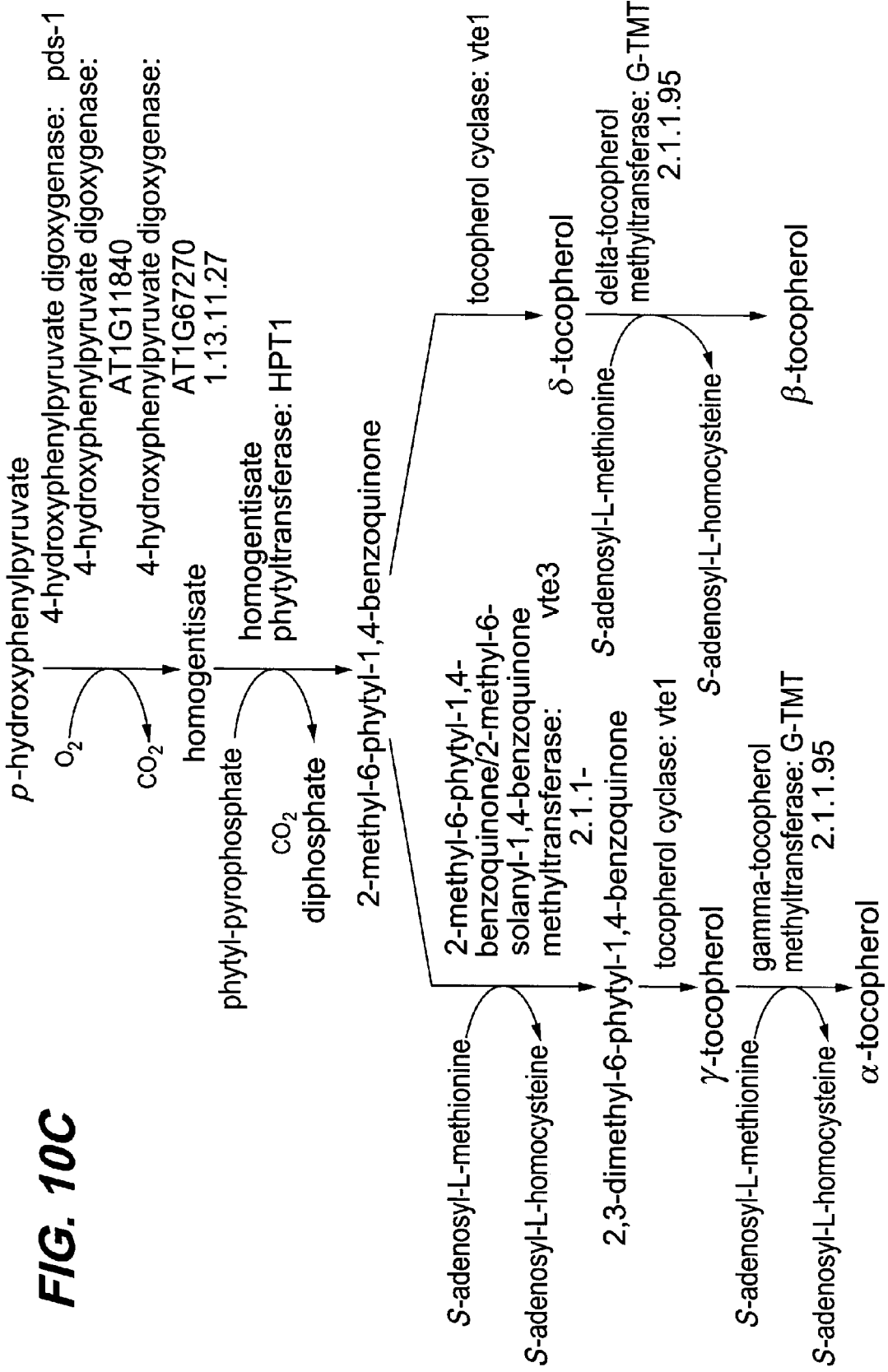
Figure 12B:
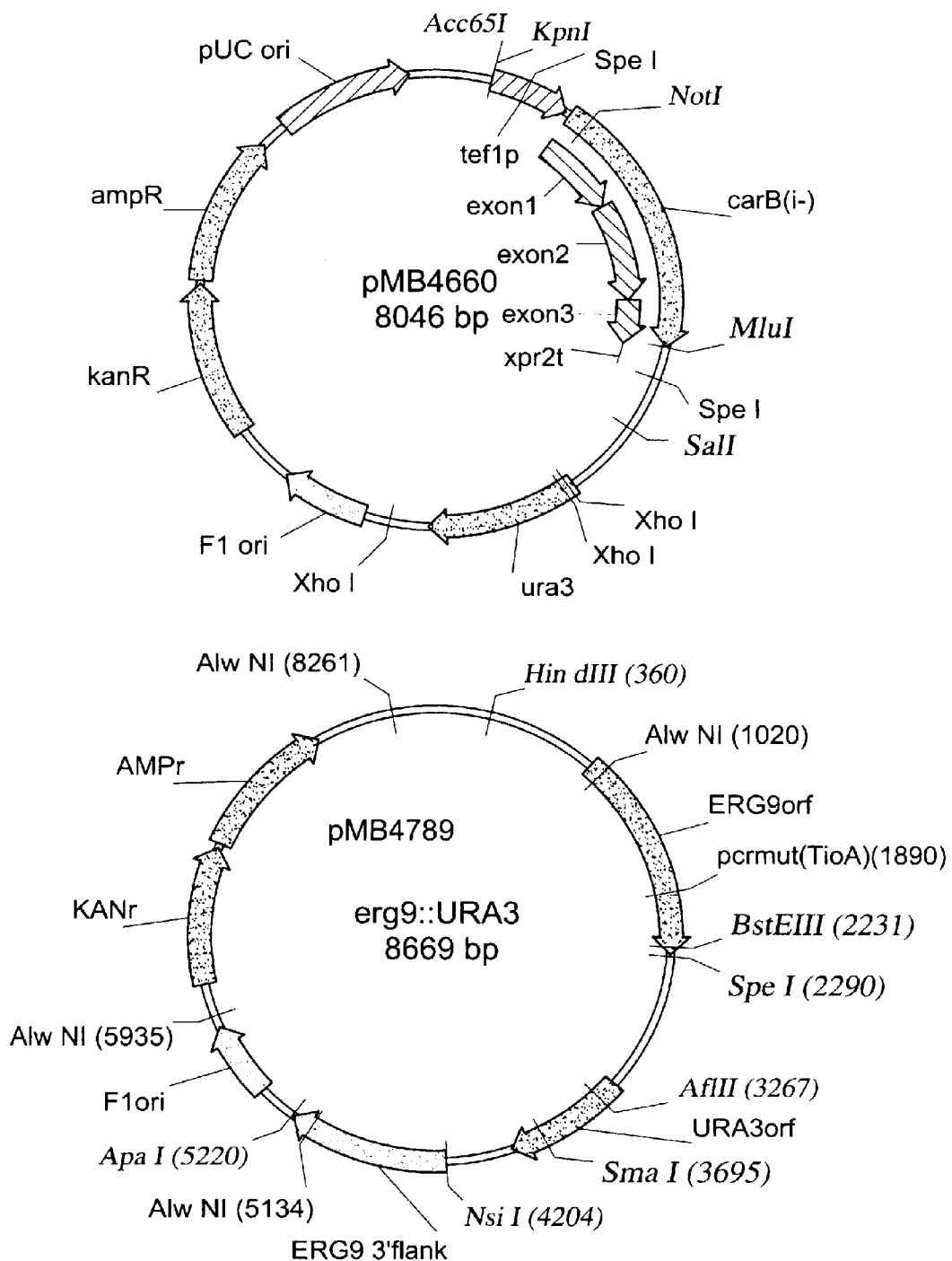
FIG. 12, Panels A-M depict schematic representations of plasmids generated and described in detail in the exemplification
Figure 12C:
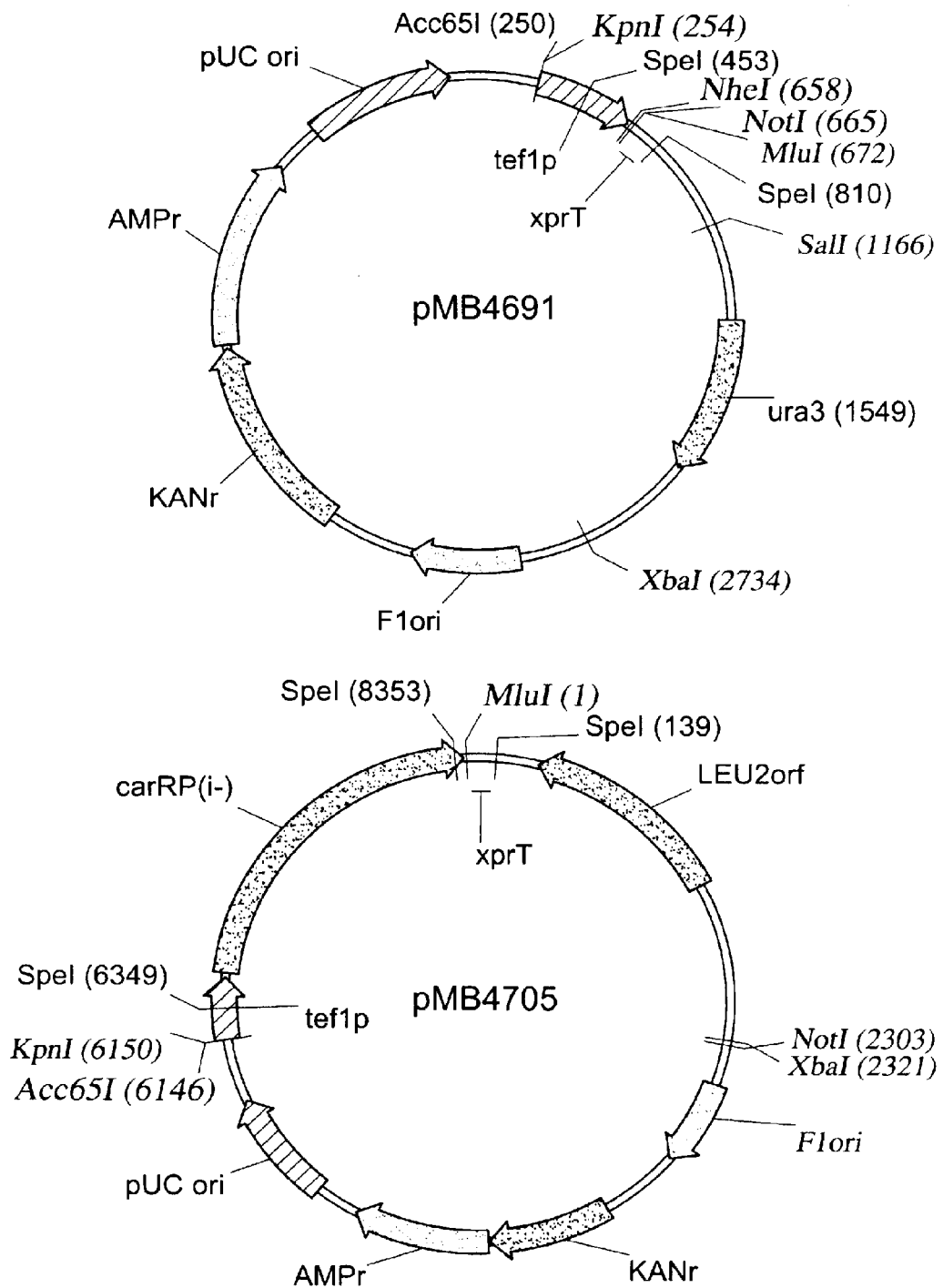
Figure 12D:
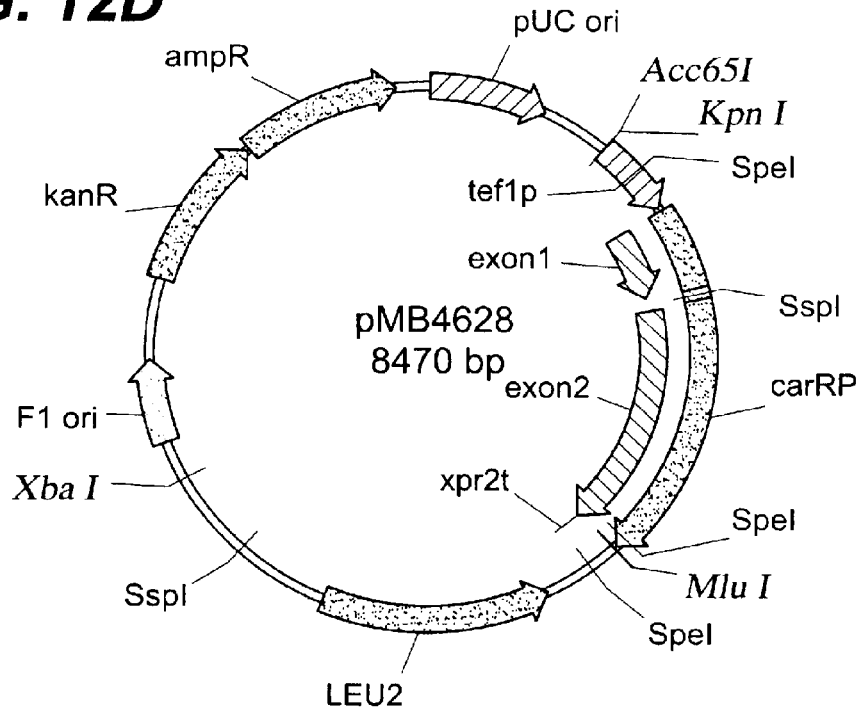
Figure 12E:
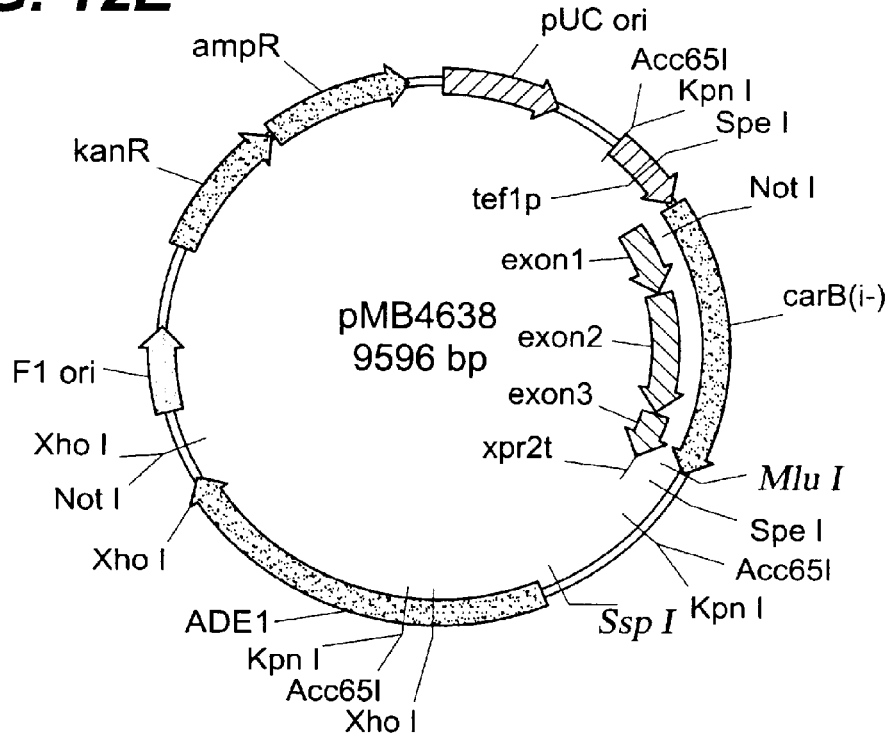
Figure 12F:
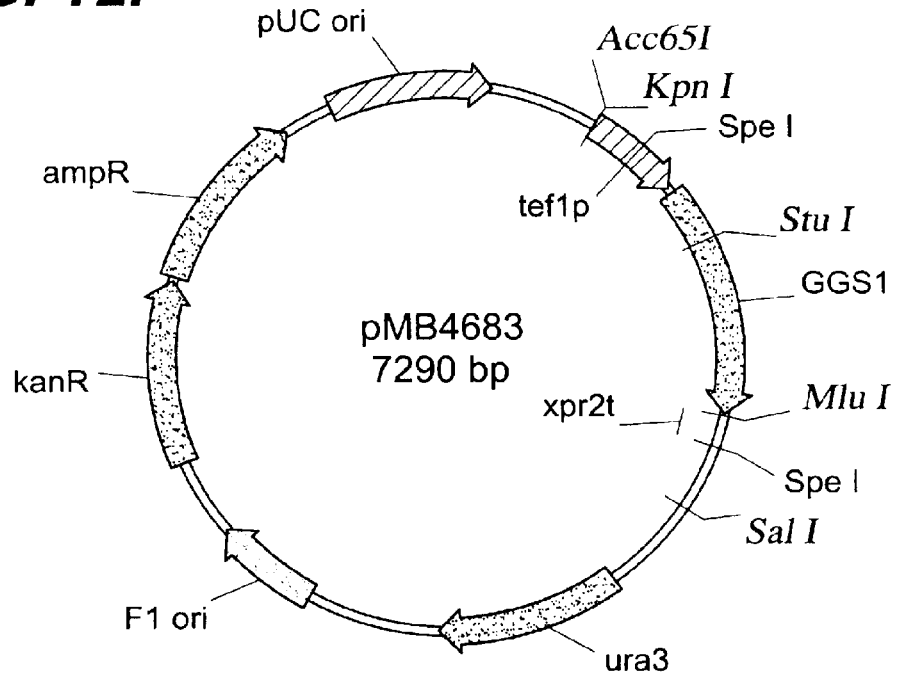
Figure 12G:
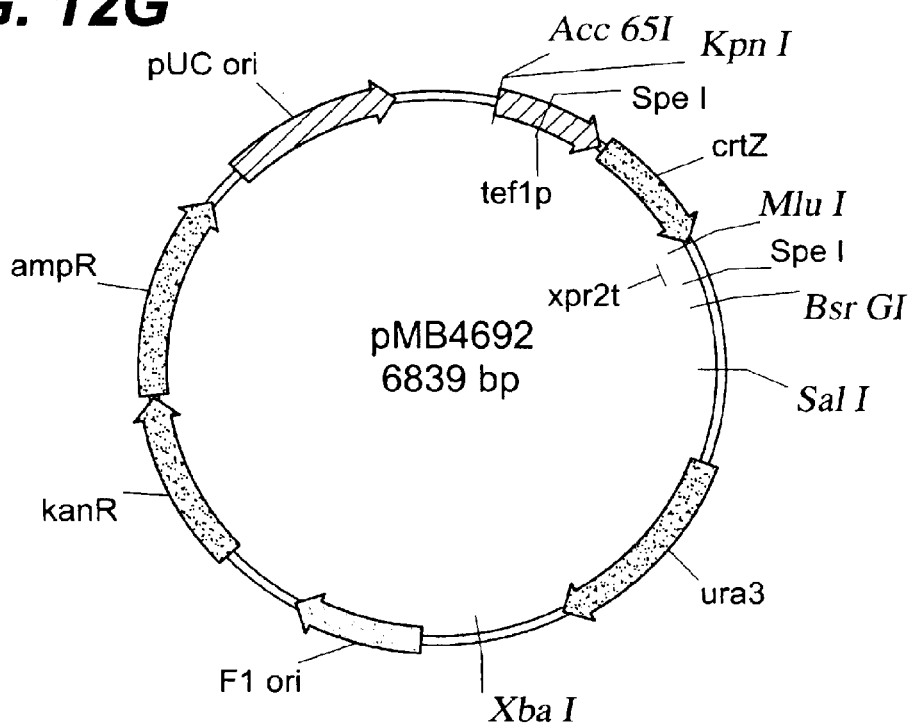
Figure 12H:
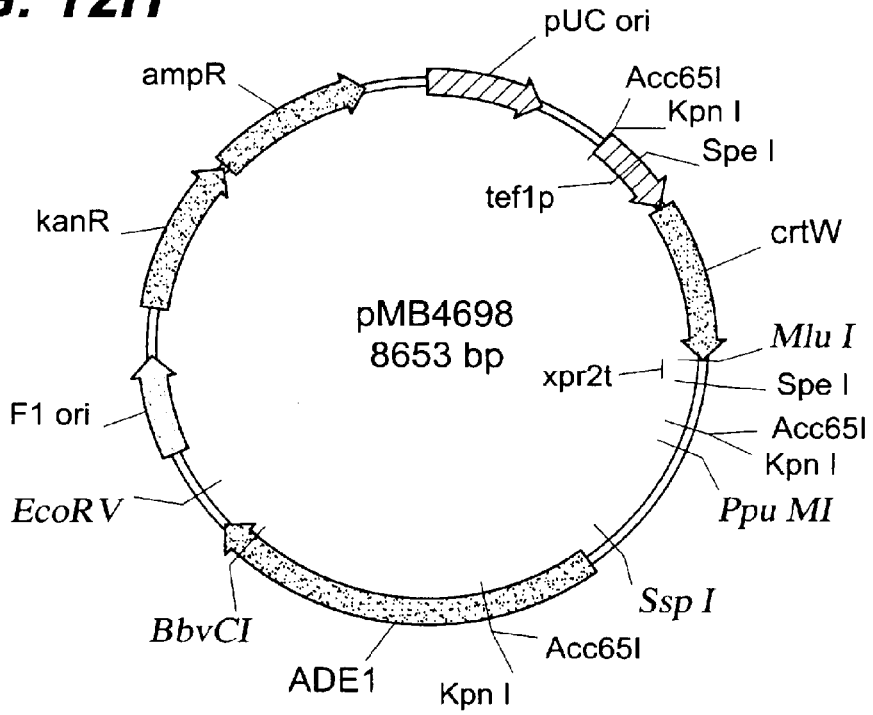
Figure 12I:
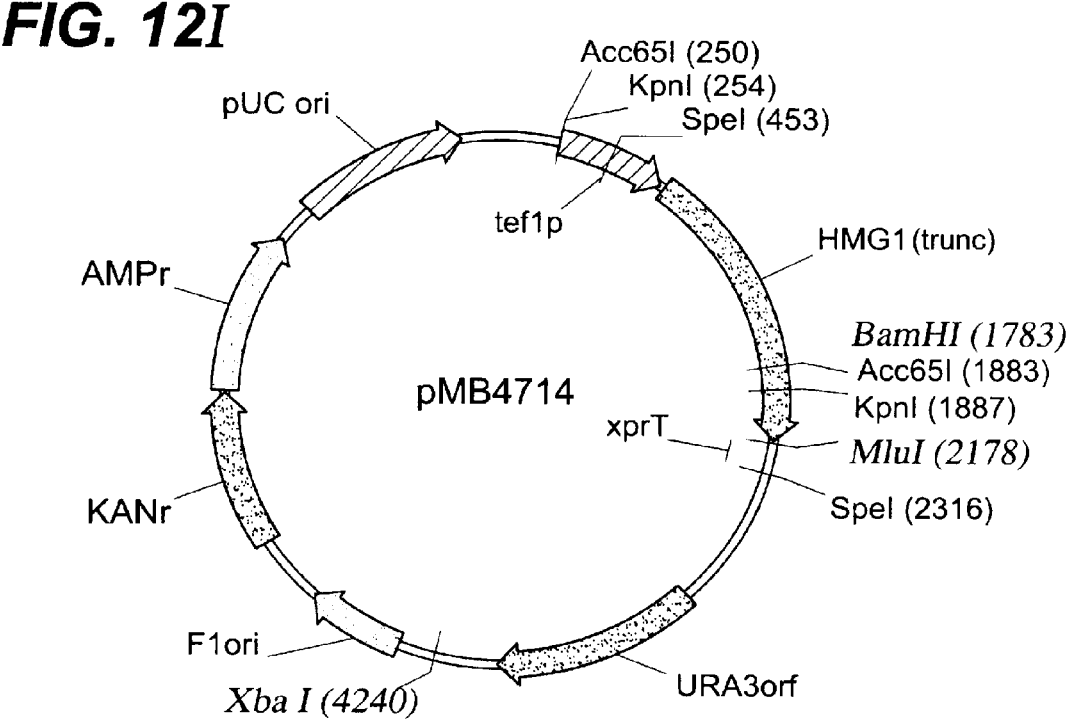
Figure 12J:
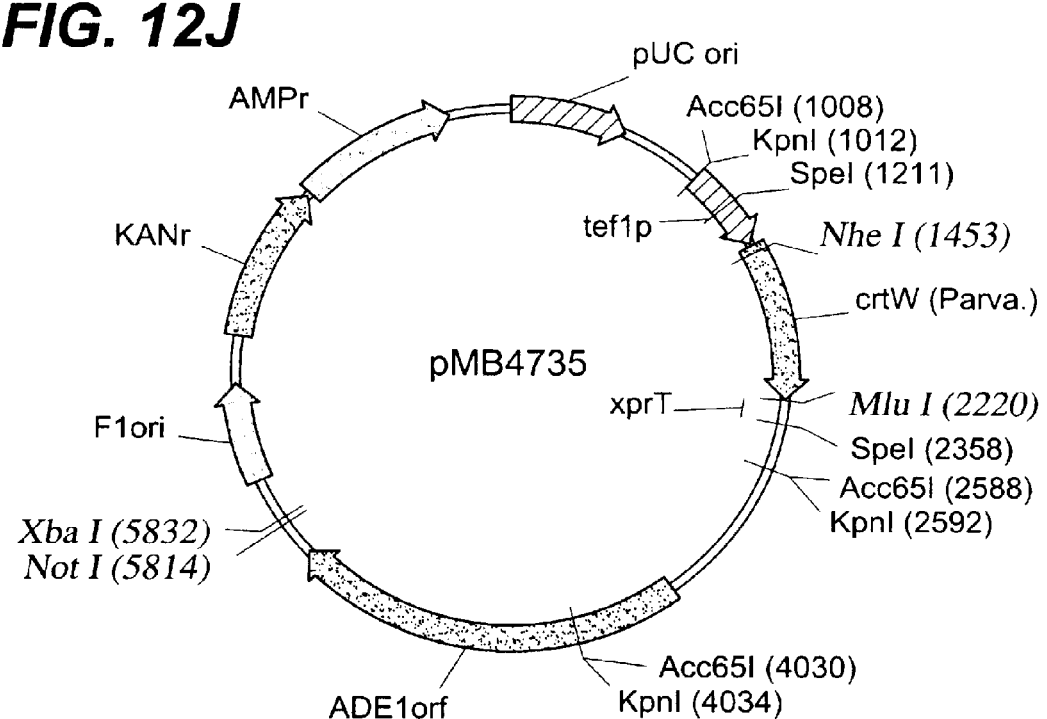
Figure 12K:
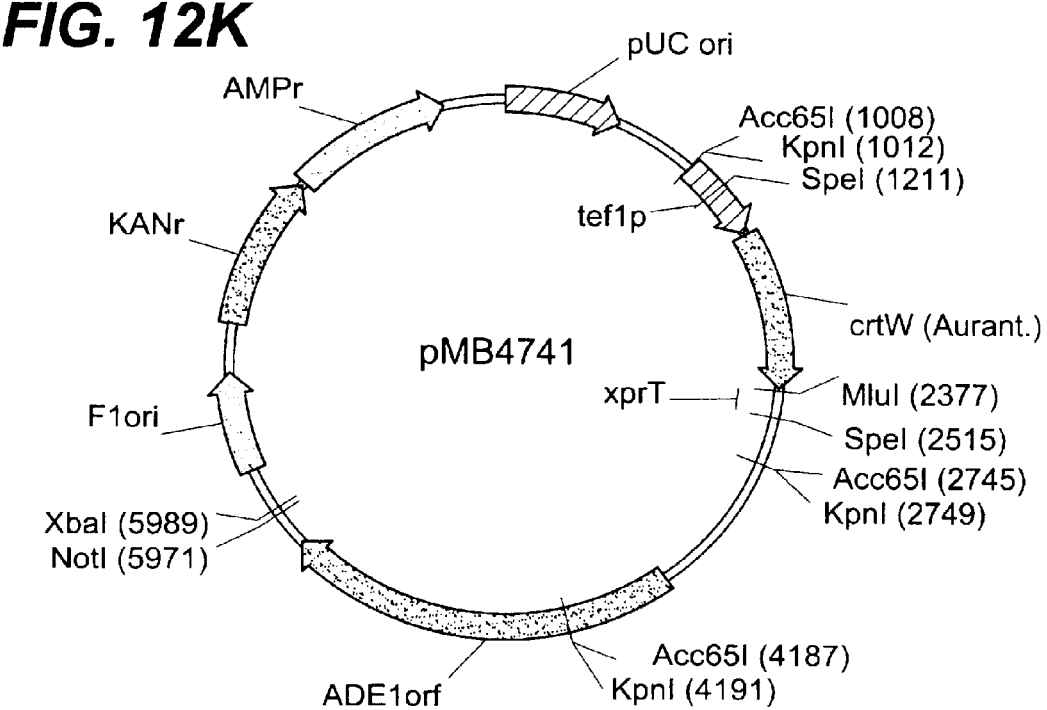
Figure 12L:
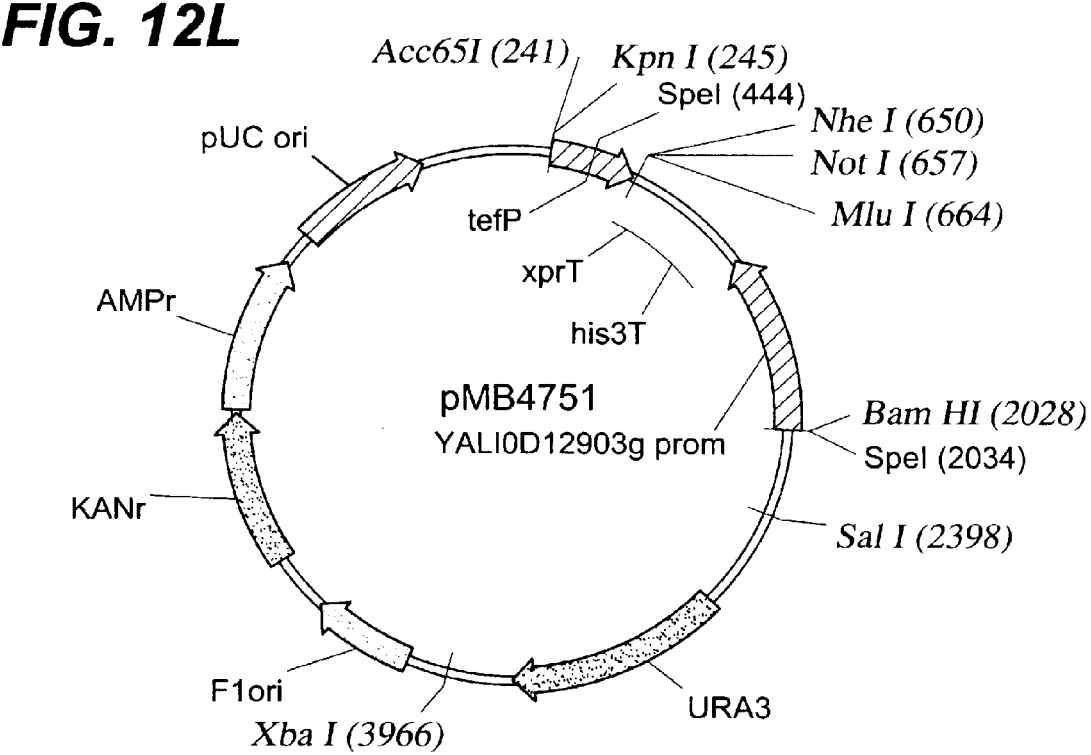
Figure 12M:
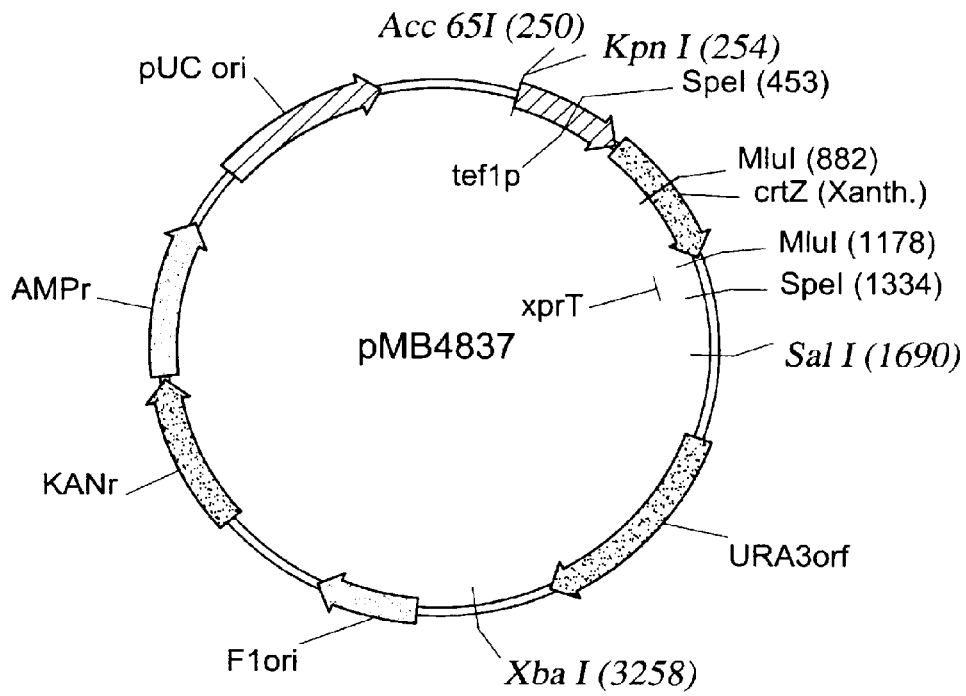

Vitamin E compounds are synthesized by higher plants and cyanobacteria by two pathways: the isoprenoid pathway and the homogentisic acid formation pathway. The overall synthesis is depicted in FIG. 10, Panels A-C. As can be seen, the first step is formation of the homogentisic head group (HGA), which is produced from p-hydroxyphenylpyruvic acid (HPP) by the enzyme p-hydroxyphenylpyruvic acid dioxygenase (HPPDase). This is a complex reaction involving the addition of two oxygen atoms as well as the decarboxylation and rearrangement of the HPP side chain.

In the next step, HGS is prenylated and decarboxylated to form 2-methyl-6-phytylplastoquinol. This step also represents the commitment step for production of tocopherols and/or tocotrienols, as 2-methyl-6-phytylplastoquinol represents the common intermediate in the synthesis of all tocopherols. The present invention provides host cells that have been engineered to accumulate 2-methyl-6-phytlplastoquinol. In some embodiments, the host cells are (or have been engineered to be) oleaginous or lipid-accumulating. In some embodiments, produced 2-methyl-6-phytylplastoquinol accumulates in lipid bodies within the engineered host cells.

In the final steps of tocopherol synthesis, methylation and ring cyclization reactions convert the 2-methyl-6-phytylplastoquinol into various tocopherols.

It is expected in accordance with the present invention that availability of tocopherol precursors and/or intermediates may well affect the rate and/or extent of tocopherol (or other vitamin E compound) production and/or accumulation by and/or within cells. The present invention therefore encompasses engineering host cells to adjust the rate or amount of one or more tocopherol precursors and/or intermediates.

The present invention provides engineered host cells, e.g., fungal cells, that produce vitamin E as a result of the engineering. The present invention specifically provides engineered host cells, e.g., fungal cells, that produce larger amounts of vitamin E that an otherwise identical non-engineered host cell. That is, the present invention provides engineered host cells containing a Vitamin E production modification. Such a modification may comprise, for instance, introduction or activation of one or more Vitamin E biosynthetic polypeptides within a host cell. Exemplary such polypeptides include, for example, tyrA, pds1(hppd), VTE1, HPT1(VTE2), VTE3, VTE4, and/or GGH polypeptides. Specific examples of each of these can be found, for example, in Tables 54-60.

Production and Isolation of Quinone Derived Compounds

Accumulation of lipid bodies in oleaginous organisms is generally induced by growing the relevant organism under conditions of carbon excess and nitrogen or other nutrient (e.g., phosphate and/or magnesium) limitation. Specific conditions for inducing such accumulation have previously been established for a number of different oleaginous organisms (see, for example, Wolf (ed.) *Nonconventional yeasts in biotechnology* Vol. 1, Springer-Verlag, Berlin, Germany, pp. 313-338; *Lipids* 18(9):623, 1983; *Indian J. Exp. Biol.* 35(3): 313, 1997; *J. Ind. Microbiol. Biotechnol.* 30(1):75, 2003; *Bioresour Technol.* 95(3):287, 2004, each of which is incorporated herein by reference in its entirety).

In general, it will be desirable to cultivate inventive modified host cells under conditions that allow accumulation of at least about 20% of their dry cell weight as lipid. In other embodiments, the inventive modified host cells are grown under conditions that permit accumulation of at least about 15%, 16%, 17%, 18%, 19%, 20%, 21%, 22%, 23%, 24%, 25%, 30%, 35%, 40%, 45%, 50%, 55%, 60%, 65%, 70%, 75%, or even 80% of their dry cell weight as lipid. In certain embodiments, the host cells utilized are cells which are naturally oleaginous and induced to produce lipid to the desired levels. In other embodiments, the host cells are cells which naturally produce lipid, but have been engineered to increase production of lipid such that desired levels of lipid production and accumulation are achieved.

In certain embodiments, the host cells of the invention are not naturally oleaginous, but have been engineered to produce lipid such that desired levels of lipid production are obtained. Those of ordinary skill in the art will appreciate that, in general, growth conditions that are effective for inducing lipid accumulation in a source organism may also be useful for inducing lipid accumulation in a host cell into which a source organism's oleaginic polypeptides have been introduced. Of course, modifications may be required in light of characteristics of the host cell, which modifications are within the skill of those of ordinary skill in the art.

It will also be appreciated by those of ordinary skill in the art that it will often be desirable to ensure that production of a desired quinone derived compound by an inventive modified host cell occurs at an appropriate time in relation to the induction of oleaginy such that the compound(s) accumulate(s) in the lipid bodies. In some embodiments, it will be desirable to induce production of a particular quinone derived compound (e.g., a ubiquinone, α-tocopherol, phylloquinone and/or menaquinone) in a host cell which does not naturally the particular compound, such that detectable levels of the compound are produced. In certain embodiments, host cells that do not naturally produce a particular quinone derived compound are capable of producing one or more other quinone derived compounds (e.g., cells that do not produce CoQ10 may produce one or more of CoQ5, CoQ6, CoQ7, CoQ8, CoQ9, etc). In additional embodiments, it will be desirable to increase production levels of a particular quinone derived compound in a host cell which does naturally produce low levels of that compound, such that increased detectable levels of the compound are produced. In certain aspects, the host cells which do naturally produce a particular compound (e.g., CoQ10) also produce additional quinone derived compound(s) (e.g., CoQ6, CoQ8); in other aspects, the cells which naturally produce the particular compound do not produce additional quinone derived compound(s).

In certain embodiments of the invention, it will be desirable to accumulate one or more quinone derived compounds (i. e., considering the total amount of all produced quinone derived compounds together or considering a particular quinone derived compound) to levels that are greater than at least about 1% of the dry weight of the cells. In some embodiments, the total quinone derived compound accumulation will be to a level at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells.

In some embodiments of the invention, a particular quinone derived compound may not accumulate to a level as high as 1% of the total dry weight of the cells; appropriately engineered cells according to the present invention, and any lipid bodies and/or quinone derived compound(s) they produce, remain within the scope of the present invention. Thus, in some embodiments, the cells accumulate a given quinone derived compound to a level below about 1% of the dry weight of the cells. In some embodiments, the quinone derived compound accumulates to a level below about 0.9%, 0.8%, 0.7%, 0.6%, 0.5%, 0.4%, 0.3%, 0.2%, 0.1%, 0.05%, or lower, of the dry cell weight of the cells.

In some embodiments of the invention, one or more quinone derived compound(s) accumulate both within lipid bodies and elsewhere in the cells. In some embodiments, quinone derived compound(s) accumulate primarily within lipid bodies. In some embodiments, quinone derived compound (s) accumulate substantially exclusively within lipid bodies. In some embodiments, at least about 10%, 15%, 20%, 25%, 30%, 35%, 40%, 45%, 50%, 55%, 60%, 65%, 70%, 75%, 80%, 85%, 90%, 95% or more of a desired produced quinone derived compound(s) accumulates in lipid bodies.

In some embodiments of the invention, modified host cells are engineered to produce one or more quinone derived compound(s) characterized by negligible solubility in water (whether hot or cold) and detectable solubility in one or more oils. In some embodiments, such compounds have a solubility in oil below about 0.2%. In some embodiments, such compounds have a solubility in oil within the range of about <0.001%-0.2%.

The present invention therefore provides engineered host cells (and methods of making and using them) that contain lipid bodies and that further contain one or more quinone derived compounds accumulated in the lipid bodies, where the compounds are characterized by a negligible solubility in water and a solubility in oil within the range of about <0.001%-0.2%; 0.004%-0.15%; 0.005-0.1%; or 0.005-0.5%. For example, in some embodiments, such compounds have a solubility in oil below about 0.15%, 0.14%, 0.13%, 0.12%, 0.11%, 0.10%. 0.09, 0.08%, 0.07%, 0.06%, 0.05%, 0.04%, 0.03%, 0.02%, 0.01%, 0.05%, or less. In some embodiments, the compounds show such solubility in an oil selected from the group consisting of sesame; soybean; apricot kernel; palm; peanut; safflower; coconut; olive; cocoa butter; palm kernel; shea butter, sunflower; almond; avocado; borage; carnauba; hazel nut; castor; cotton seed; evening primrose; orange roughy; rapeseed; rice bran; walnut; wheat germ; peach kernel; babassu; mango seed; black current seed; jojoba; macadamia nut; sea buckthorn; sasquana; tsubaki, mallow; meadowfoam seed; coffee; emu; mink; grape seed; thistle; tea tree; pumpkin seed; kukui nut; and mixtures thereof.

Also, it should be noted that, the absolute and/or relative amounts of quinone derived compounds produced in accordance with the present invention can sometimes be altered by adjustment of growth conditions, for example to modulate the isoprenoid biosynthesis pathway and/or one or more downstream pathways. For example, controlling the concentration of dissolved oxygen in a culture during cultivation may regulate relative production levels of CoQ10.

Inventive modified cells, that have been engineered to produce one or more quinone derived compounds and/or to accumulate lipid (including to be oleaginous), can be cultured under conditions that achieve ubiquinone (e.g. CoQ10 and/or $C_5$-$C_9$ quinone compounds) production and/or oleaginy.

In some embodiments, it will be desirable to control growth conditions in order to maximize production of a particular quinone derived compound or quinone derived compounds and/or to optimize accumulation of the particular quinone derived compound(s) in lipid bodies. In some embodiments it will be desirable to control growth conditions to adjust the relative amounts of different quinone derived compound products produced.

In some embodiments, it will be desirable to limit accumulation of a particular intermediate, for example ensuring that substantially all of a particular intermediate compound is converted so that accumulation is limited. For example, particularly in situations where a downstream enzyme may be less efficient than an upstream enzyme and it is desirable to limit accumulation of the product of the upstream enzyme (e.g., to avoid its being metabolized via a competitive pathway and/or converted into an undesirable product), it may be desirable to grow cells under conditions that control (e.g., slow) activity of the upstream enzyme so that the downstream enzyme can keep pace.

Those of ordinary skill in the art will appreciate that any of a variety of growth parameters, including for example amount of a particular nutrient, pH, temperature, pressure, oxygen concentration, timing of feeds, content of feeds, etc can be adjusted as is known in the art to control growth conditions as desired.

To give but a few examples, in some embodiments, growth and/or metabolism is/are limited by limiting the amount of biomass accumulation. For example, growth and/or metabolism can be limited by growing cells under conditions that are limiting for a selected nutrient. The selected limiting nutrient can then be added in a regulated fashion, as desired. In some embodiments, the limiting nutrient is carbon, nitrogen (e.g., via limiting ammonium or protein), phosphate, magnesium, or combinations thereof. In some embodiments, the limiting nutrient is carbon.

In some embodiments, use of a limiting nutrient can be utilized to control metabolism of a particular intermediate and/or to adjust relative production of particular quinone derived compounds. In some embodiments, this result can be achieved by controlling metabolism of a particular intermediate as discussed above; in some embodiments, it can be achieved, for example, by limiting progress through the quinone biosynthesis pathway so that a desired quinone derived compound product is not converted to a downstream compound. For example, nutrient limitation (e.g. phosphate limitation) may slow the overall rate of flux through the quinone derived compound biosynthesis pathway and may be utilized to change the ratio of one quinone derived compound versus another.

In some embodiments, cells are grown in the presence of excess carbon source and limiting nitrogen, phosphate, and/or magnesium to induce oleaginy. In some embodiments cells are grown in the presence of excess carbon source and limiting nitrogen. In some embodiments, the carbon:nitrogen ratio is within the range of about 200:1, 150:1, 125:1, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, or less. Those of ordinary skill in the art are aware of a wide variety of carbon sources, including, for example, glycerol, glucose, galactose, dextrose, any of a variety of oils (e.g., olive, canola, corn, sunflower, soybean, cottonseed, rapeseed, etc., and combinations thereof) that may be utilized in accordance with the present invention. Combinations of such may also be utilized. For example, common carbon source compositions contain oil: glucose in a ratios within the range of about 5:95 to 50:50 (e.g. about 5:95, about 10:90, about 15:85, about 20:80, about 25:75, about 30:70, about 35:65, about 40:60, about 45:55, about 50:50).

Those of ordinary skill in the art are also aware of a variety of different nitrogen sources (e.g., ammonium sulfate, proline, sodium glutamate, soy acid hydrolysate, yeast extract-peptone, yeast nitrogen base, corn steep liquor, etc, and combinations thereof) that can be utilized in accordance with the present invention.

In some embodiments, cultures are grown at a selected oxygen concentration (e.g., within a selected range of oxygen concentrations). In some embodiments, oxygen concentration may be varied during culture. In some embodiments, oxygen concentration may be controlled during some periods of culture and not controlled, or controlled at a different point, during others. In some embodiments, oxygen concentration is not controlled. In some embodiments, cultures are grown at an oxygen concentration within the rage of about 5-30%, 5-20%, 10-25%, 10-30%, 15-25%, 15-30%, including at about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or more. In some embodiments, oxygen concentration is maintained above about 20%, at least for some period of the culture.

In some embodiments, cells are grown via fed-batch fermentation. In some embodiments, feed is continued until feed exhaustion and/or the feed is controlled to initiate or increase once a certain level of dissolved oxygen is detected in the culture medium (e.g., about 5%, 6%, 7%, 8%, 9%, 10%, 11%, 12%, 13%, 14%, 15%, 16%, 17%, 18%, 19%, 20%, 21%, 22%, 23%,24%, 25%,26%, 27%, 28%, 29%, 30%, 31%, 32%, 33%, 34%,35%, 36%, 37%, 38%, 39%, 40%, or more dissolved oxygen). The feed rate can be modulated to maintain the dissolved oxygen at a specific level (e.g., about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or more dissolved oxygen).

In some embodiments, inventive modified cells are grown in a two-phase feeding protocol in which the first phase is designed to maintain conditions of excess carbon and limiting oxygen, and the second phase results in conditions of excess oxygen and limiting carbon.

In some embodiments, inventive modified cells are cultivated at constant temperature (e.g., between about 20-40, or 20-30° C., including for example at about 20, 20.5, 21, 21.5, 22, 22.5, 23, 23.5, 24, 24.5, 25, 25.5, 26, 26.5, 27, 27.5, 28, 28.5, 29, 29.5, 30° C. or above) and/or pH (e.g., within a range of about 4-7.5, or 4-6.5, 3.5-7, 3.54, 4-4.5, 4.5-5, 5-5.5, 5.5-6, 6-6.5, 6.5-7, etc., including at about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, or 6.5, 6.6, 6.7, 6.8, 6.9, 7.0, 7.1, 7.2, 7.3, 7.4, 7.5 or above); in other embodiments, temperature and/or pH may be varied during the culture period, either gradually or in a stepwise fashion.

In some embodiments, the temperature at which inventive cells are cultivated is selected so that production of one or more particular carotenoid compound(s) is adjusted (e.g., so that production of one or more particular compound(s) is increased and/or production of one or more other compound(s) is decreased). In some embodiments, the temperature at which inventive cells are cultivated is selected so that the ratio of one quinone derived compound to another, is adjusted. To give but one example, in some embodiments, a temperature is selected to be sufficiently low that levels of one quinone derived compound are reduced and the level of at least one other quinone derived compound(s) is increased.

In some embodiments, cultures are grown at about pH 5.5 and or at a temperature between about 28-30° C. In some embodiments, it may be desirable to grow inventive modified cells under low pH conditions, in order to minimize growth of other cells. In some embodiments, it will be desirable to grow inventive modified cells under relatively higher temperature conditions in order to slow growth rate and/or increase the ultimate dry cell weight output of quinone derived compounds (e.g. CoQ10, $C_5$-$C_9$ quinones, vitamin K compounds, vitamin E compounds).

One advantage provided by the present invention is that, in addition to allowing the production of high levels of one or more quinone derived compounds, certain embodiments of the present invention allow produced compounds to be readily isolated because they accumulate in the lipid bodies within oleaginous organisms. Methods and systems for isolating lipid bodies have been established for a wide variety of oleaginous organisms (see, for example, U.S. Pat. Nos. 5,164, 308; 5,374,657; 5,422,247; 5,550,156; 5,583,019; 6,166,231; 6,541,049; 6,727,373; 6,750,048; and 6,812,001, each of which is incorporated herein by reference in its entirety). In brief, cells are typically recovered from culture, often by spray drying, filtering or centrifugation.

Of course, it is not essential that lipid bodies be specifically isolated in order to collect quinone derived compounds produced according to the present invention. Any of a variety of approaches can be utilized to isolate and/or purify quinone derived compounds. Many useful extraction and/or purification procedures for lipophilic agents generally, are known in the art (see, for example, EP670306, EP719866, U.S. Pat. No. 4,439,629, U.S. Pat. No. 4,680,314, U.S. Pat. No. 5,310,554, U.S. Pat. No. 5,328,845, U.S. Pat. No. 5,356,810, U.S. Pat. No. 5,422,247, U.S. Pat. No. 5,591,343, U.S. Pat. No. 6,166, 231, U.S. Pat. No. 6,750,048, U.S. Pat. No. 6,812,001, U.S. Pat. No. 6,818,239, U.S. Pat. No. 7,015,014, US2003/0054070, US2005/0266132, each of which is incorporated herein by reference).

In many typical isolation procedures, cells are disrupted (e.g., mechanically, chemically [e.g., by exposure to a mild caustic agent such as a detergent or 0.1 N NaOH, for example at room temperature or at elevated temperature], etc.) to allow access of intracellular quinone derived compound(s) to an extraction solvent, and are then extracted one or more times. Cells may optionally be concentrated (e.g., to at least about 100 g/L or more, including to at least about 120 g/l, 150 g/l, 175 g/L, 200 g/L or more) and/or dried (e.g., with a spray dryer, Blaw Knox double drum dryer, single drum vacuum dryer, etc.), prior to exposure to extraction solvent (and/or prior to disruption or homogenization). Disruption can, of course, be performed prior to and/or during exposure to extraction solvent. After extraction, solvent is typically removed (e.g., by evaporation, for example by application of vacuum, change of temperature, etc.).

In some instances, cells are homogenized and then subjected to supercritical liquid extraction or solvent extraction. Typical liquids or solvents utilized in such extractions include, for example, organic or non-organic liquids or solvents. To give but a few specific examples, such liquids or solvents may include acetone, carbon dioxide (e.g., supercritical carbon dioxide, acetone, heptane, octane, ethanol), chloroform, ethanol, ethyl acetate, heptane, hexane, hexane:ethyl acetate, isopropanol, methanol, methylene chloride, isopropanol, ethyl acetateoctane, tetrahydrofuran (THF), different types of oils (e.g., soybeen, rapeseed, etc.), and combinations thereof. Particular solvents may be selected, for example, based on their ability to solubilize particular quinone derived compounds or sets of quinone derived compounds (e.g., all quinone derived compounds), and/or based on regulatory or other considerations (e.g., toxicity, cost, ease of handling, ease of removal, ease of disposal, etc.). For example, more polar quinone derived compounds may be extracted more efficiently into extraction solvents with increased polarity. In some embodiments, hexane is used as a solvent. In other embodiments, hexane:ethyl acetate is utilized.

In some embodiments, combinations of solvents may be utilized. In some embodiments, combinations of a relatively polar solvent (e.g., alcohols, acetone, chloroform, methylene chloride, ethyl acetate, etc.) and a relatively non-polar solvent (e.g., hexane, oils, etc.) are utilized for extraction. Those of ordinary skill in the art will readily appreciate that different ratios of polar to non-polar solvent may be employed as appropriate in a particular situation. Just to give a few examples, common ratios include 1:1, 2:1, 3:1, 3:2, 95:5, 90:10, 85:15, 80:20, 75:25, 70:30, 65:45, 60:40, 55:45, and 50:50. It will be appreciated that solvents or solvent mixtures of different polarities may be more effective at extracting particular quinone derived compounds (e.g., based on their polarities and/or as a function of other attributes of the host cell material from which they are being extracted). Those of ordinary skill in the art are well able to adjust the overall polarity of the extracting solvent, for instance by adjusting the relative amounts of polar and non-polar solvents in a solvent blend, in order to achieve more efficient extraction.

Extraction may be performed under any of a variety of environmental conditions, including any of a variety of temperatures. For example, extraction may be performed on ice, at room temperature, or at any of a variety of other temperatures. For example, a solvent may be maintained at a selected temperature (e.g., about 4, 25, 28, 30, 37, 68, 70, 75, 80, 85, 90, 95, or 100° C.) in order to improve or adjust extraction of a particular desired quinone derived compound.

Extraction typically yields a crude oil suspension. In some embodiments, the crude oil suspension contains some intact host cells but is at least about 95% free of intact host cells. In some embodiments, the crude oil suspension is at least about 96%, 97%, 98%, or 99% or more free of intact host cells. In some embodiments, the suspension is substantially free of water-soluble cell components (e.g., nucleic acids, cell wall or storage carbohydrates, etc.). In some embodiments, the suspension contains less than about 5%, 4%, 3%, 2%, or 1% or less water-soluble cell components.

Extraction conditions that yield a crude oil suspension will enrich for lipophilic components that accumulate in the lipid bodies within oleaginous organisms. In general, the major components of the lipid bodies consist of triacylglycerols, ergosteryl esters, other steryl esters, free ergosterol, phospholipids, and some proteins, which often function in the synthesis or regulation of the levels of other lipid body components. C16 and C18 (e.g. C16:0, C16:1, C18:0, C18:1, and C18:2) are generally the major fatty acids present in lipid bodies, mainly as components of triacylglycerol and steryl esters.

In some embodiments of the invention, the crude oil suspension contains at least about 2.5% by weight quinone derived compound(s); in some embodiments, the crude oil suspension contains at least about 5% by weight quinone derived compound(s), at least about 10% by weight quinone derived compound(s), at least about 20% by weight quinone derived compound(s), at least about 30% by weight quinone derived compound(s), at least about 40% by weight quinone derived compound(s), or at least about 50% by weight quinone derived compound(s).

The crude oil suspension may optionally be refined as known in the art. Refined oils may be used directly as feed or food additives. Alternatively or additionally, quinone derived compounds (e.g. CoQ10) can be isolated from the oil using conventional techniques.

Given the sensitivity of quinones generally to oxidation, many embodiments of the invention employ oxidative stabilizers (e.g., tocopherols, vitamin C; ethoxyquin; vitamin E, BHT, BHA, TBHQ, etc., or combinations thereof) during and/or after quinone derived compound isolation. When the desired product is the reduced ubiquinol form, then it may be advantageous to further add conventional reducing agents (e.g. sodium dithionite, ascorbic acid). Alternatively or additionally, microencapsulation, for example with proteins, may be employed to add a physical barrier to oxidation and/or to improve handling (see, for example, U.S. Patent Application 2004/0191365).

Extracted quinone derived compounds may be further isolated and/or purified, for example, by crystallization, washing, recrystallization, and/or other purification strategies. In some embodiments, carotenoid crystals are collected by filtration and/or centrifugation. Isolated or purified quinone derived compounds may be dried and/or formulated for storage, transport, sale, and/or ultimate use. To give but a few specific examples, quinone derived compounds may be prepared as a cold-water dispersible powder, as a suspension of crystals in oil (e.g., vegetable oil, e.g., about 5%-30% w/w), etc.

Uses

Quinone derived compounds (e.g., ubiquinones, vitamin K compounds, and/or vitamin E compounds) produced according to the present invention can be utilized in any of a variety of applications, for example exploiting biological or nutritional (e.g., metabolic, anti-oxidant, anti-proliferative, etc.) properties.

For example, according to the present invention, one or more quinone derived compounds may be used in pharmaceutical and/or nutraceutical applications for treatment and/or prevention of disorders such as cardiovascular disorders (including, congestive heart failure, myocardial infarction and cardiac surgery patients, angina, hypertension, etc), metabolic disorders, diabetes, pain, aging, neurodegenerative disorders (e.g., Parkinson's and Huntington's disorders), inflammatory disorders and cancers. Additionally, supplements of certain quinone derived compounds (including, e.g., CoQ10) have been proposed to improve performance (e.g., athletic performance). See, for example, Choi, et al., *Appl.*

*Microbiol, Biotechnol,* 68: 9-15, 2005; Kawamukai, *J. Biosci. Bioeng,* 94:511-517, 2002; Ernster and Dallner, *Biochim. Biophys. Acta.,* 1271: 195-204, 1995; U.S. Pat. No. 6,806,076; U.S. Pat. No. 6,867,024; U.S. Pat. No. 6,686,485; U.S. Pat. No. 6,417,233; U.S. Patent Publication No. 2006/0010519; U.S. Patent Publication No. 2004/0034107; U.S. Patent Publication No. 2003/0236239; U.S. Patent Publication No. 2003/0167556; U.S. Patent Publication No. 2002/0058712), nutritional supplement (see for example, U.S. Pat. No. 6,686,485; U.S. Pat. No. 6,080,788, U.S. Patent Publication No. 2004/0082536) food supplements (see, for example, U.S. Patent Publication Nos. 2005/011226 and 2004/0115309, cosmetics (as anti-oxidants and/or as cosmetics, including fragrances; see for example U.S. Patent Publication No. 2005/0084505; U.S. Patent Publication No. 2003/0167556), etc. The contents of each of the foregoing journal and patent publications are hereby incorporated by reference. Quinone derived compound(s) produced herein can also be co-administered with an HMG CoA reductase inhibitor (e.g. a statin such as atorvastatin, simvastatin, rosuvastatin, etc.)

It will be appreciated that, in some embodiments of the invention, one or more quinone derived compound(s) produced by manipulated host cells as described herein are incorporated into a final product (e.g., food or feed supplement, pharmaceutical, cosmetic, etc.) in the context of the host cell. For example, host cells may be lyophilized, freeze dried, frozen or otherwise inactivated, and then whole cells may be incorporated into or used as the final product. The host cells may also be processed prior to incorporation in the product to, e.g., increase bioavailability (e.g., via lysis). Alternatively or additionally, a final product may incorporate only a portion of a host cell (e. g., fractionated by size, solubility), separated from the whole. For example, in some embodiments of the invention, lipid bodies are isolated from host cells and are incorporated into or used as the final product.

For instance, inventive compound-containing lipid bodies (e.g., from engineered cells, and particularly from engineered fungal cells) may be substituted for the plant oil bodies described in U.S. Pat. No. 6,599,513 (the entire contents of which are hereby incorporated by reference) and incorporated into emulsions or emulsion formulations, as described thereon. In other embodiments, a ubiquinone itself is isolated and reformulated into a final product.

Preparations of one or more quinone derived compounds, including formulations, dosing, supplements (e.g., dietary supplements), have been described and are known in the art. For example, see citations relating to pharmaceutical preparations, nutritional supplement, and food additives described above. Additionally, see, for example, U.S. Pat. No. 6,906,106, U.S. Pat. No. 6,867,024; U.S. Pat. No. 6,740,338; U.S. Pat. No. 6,300,377; U.S. Patent Publication No. 2003/0105168, U.S. Patent Publication No. 2004/0014817; U.S. Patent Publication No. 2005/0019268; U.S. Patent Publication No. 2004/0152612; U.S. Patent Publication No. 2003/0167556; U.S. Patent Publication No. 2005/0153406; U.S. Patent Publication No. 2005/0181109; U.S. Patent Publication No. 2006/0010519; International Patent Publication No. WO05069916A2, and International Patent Publication No. WO05092123A1, each of which is incorporated herein by reference.

The amount of any particular quinone derived compound incorporated into a given product may vary dramatically depending on the product, and the particular compound(s) involved. Amounts may range, for example, from less than 0.01% by weight of the product, to more than 1%, 10%, 20%, 30% or more; in some cases the compound may comprise 100% of the product. Thus, the amount of quinone derived compound incorporated into a given product may be, for example, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%.

In some embodiments of the invention, one or more produced quinone derived compound is incorporated into a component of food or feed (e. g., a food supplement, food additive). Types of food products into which quinone derived compound(s) can be incorporated according to the present invention are not particularly limited, and include beverages such as teas, juices, and liquors; confections such as jellies and biscuits; fat-containing foods and beverages such as dairy products; processed food products such as rice and soft rice (or porridge); infant formulas; or the like. In some embodiments of this aspect of the invention, it may be useful to incorporate the quinone derived compound within bodies of edible lipids as it may facilitate incorporation into certain fat-containing food products.

Examples of feedstuffs into which one or more quinone derived compounds produced in accordance with the present invention may be incorporated include, for instance, pet foods such as cat foods, dog foods and the like, feeds for aquarium fish or cultured fish, etc., feed for farm-raised animals (including livestock and further including fish raised in aquaculture). Food or feed material into which the quinone derived compound (s) produced in accordance with the present invention is incorporated is preferably palatable to the organism which is the intended recipient. This food or feed material may have any physical properties currently known for a food material (e. g., solid, liquid, soft).

In some embodiments of the invention, produced quinone derived compound is incorporated into a cosmetic product. Examples of such cosmetics include, for instance, skin cosmetics (e. g., lotions, emulsions, liquids, creams and the like), lipsticks, anti-sunburn cosmetics, makeup cosmetics, fragrances, products for daily use (e. g., toothpastes, mouthwashes, bad breath preventive agents, solid soaps, liquid soaps, shampoos, conditioners), etc.

In some embodiments, produced quinone derived compound is incorporated into a pharmaceutical. Examples of such pharmaceuticals include, for instance, various types of tablets, capsules, drinkable agents, troches, gargles, etc. In some embodiments, the pharmaceutical is suitable for topical application. Dosage forms are not particularly limited, and include capsulae, oils, granula, granula subtilae, pulveres, tabellae, pilulae, trochisci, or the like. Oils and oil-filled capsules may provide additional advantages both because of their lack of ingredient decomposition during manufacturing, and because inventive compound-containing lipid droplets may be readily incorporated into oil-based formulations.

Pharmaceuticals according to the present invention may be prepared according to techniques established in the art including, for example, the common procedure as described in the United States Pharmacopoeia, for example.

In still other embodiments, produced quinone derived compound is incorporated into a nutritional supplement or nutraceutical. Examples of such nutraceuticals, include, for instance, various types of tablets, capsules, drinkable agents, troches, gargles, etc. In some embodiments, the nutraceutical is suitable for topical application. Dosage forms are, as in pharmaceutical products, not particularly limited and include any of the same types of dosages as pharmaceuticals.

Quinone derived compound(s) produced according to the present invention (whether isolated or in the context of lipid droplets or of cells, e.g., fungal cells) may be incorporated into products as described herein by combination with any of a variety of agents. For instance, such quinone derived compound (s) may be combined with one or more binders or fillers. In some embodiments, inventive products will include one or more chelating agents, pigments, salts, surfactants, moisturizers, viscosity modifiers, thickeners, emollients, fragrances, preservatives, etc., and combinations thereof.

Useful surfactants include, for example, anionic surfactants such as branched and unbranched alkyl and acyl hydrocarbon compounds, sodium dodecyl sulfate (SDS); sodium lauryl sulfate (SLS); sodium lauryl ether sulfate (SLES); sarconisate; fatty alcohol sulfates, including sodium, potassium, ammonium or triethanolamine salts of $C_{10}$ to $C_{18}$ saturated or unsaturated forms thereof; ethoxylated fatty alcohol sulfates, including alkyl ether sulfates; alkyl glyceryl ether sulfonate, alpha sulpho fatty acids and esters; fatty acid esters of isethionic acid, including Igepon A; acyl (fatty) N-methyltaurides, including Igepon T; dialkylsulfo succinate esters, including $C_8$, $C_{10}$ and $C_{12}$ forms thereof; Miranot BT also referred to as lauroamphocarboxyglycinate and sodium tridecath sulfate; N-acylated amino acids, such as sodium N-lauroyl sarconisate or gluconate; sodium coconut monoglyceride sulfonate; and fatty acid soaps, including sodium, potassium, DEA or TEA soaps.

Among the cationic surfactants that are useful are monoalkyl trimethyl quartenary salts; dialkyl dimethyl quartenary salts; ethoxylated or propoxylated alkyl quaternary ammonium salts, also referred to in the art as ethoquats and propoquats; cetyl benzylmethylalkyl ammonium chloride; quaternized imidazolines, which are generally prepared by reacting a fat or fatty acid with diethylenetriamine followed by quaternization, and non-fat derived cationic polymers such as the cellulosic polymer, Polymer JR (Union Carbide).

Further useful cationic surfactants include lauryl trimethyl ammonium chloride; cetyl pyridinium chloride; and alkyltrimethylammonium bromide. Cationic surfactants are particularly useful in the formulation of hair care products, such as shampoos, rinses and conditioners.

Useful nonionic surfactants include polyethoxylated compounds and polypropoxylated products. Examples of ethoxylated and propoxylated non-ionic surfactants include ethoxylated anhydrohexitol fatty esters, for example Tween 20; mono- and diethanolamides; Steareth-20, also known as Volpo20; polyethylene glycol fatty esters (PEGs), such as PEG-8-stearate, PEG-8 distearate; block co-polymers, which are essentially combinations of hydrophylic polyethoxy chains and lipophilic polypropoxy chains and generically known as Poloaxamers.

Still other useful non-ionic surfactants include fatty esters of polyglycols or polyhydric alcohols, such as mono and diglyceride esters; mono- and di-ethylene glycol esters; diethylene glycol esters; sorbitol esters also referred to as Spans; sucrose esters; glucose esters; sorbitan monooleate, also referred to as Span80; glyceryl monostearate; and sorbitan monolaurate, Span20 or Arlacel 20.

Yet other useful nonionic surfactants include polyethylene oxide condensates of alkyl phenols and polyhydroxy fatty acid amide surfactants which may be prepared as for example disclosed in U.S. Pat. No. 2,965,576.

Examples of amphoteric surfactants which can be used in accordance with the present invention include betaines, which can be prepared by reacting an alkyldimethyl tertiary amine, for example lauryl dimethylamine with chloroacetic acid. Betaines and betaine derivatives include higher alkyl betaine derivatives including coco dimethyl carboxymethyl betaine; sulfopropyl betaine; alkyl amido betaines; and cocoamido propyl betaine. Sulfosultaines which may be used include for example, cocoanidopropyl hydroxy sultaine. Still other amphoteric surfactants include imidazoline derivatives and include the products sold under the trade name "Miranol" described in U.S. Pat. No. 2,528,378 which is incorporated herein by reference in its entirety. Still other amphoterics include phosphates for example, cocamidopropyl PG-dimonium chloride phosphate and alkyldimethyl amine oxides.

Suitable moisturizers include, for example, polyhydroxy alcohols, including butylene glycol, hexylene glycol, propylene glycol, sorbitol and the like; lactic acid and lactate salts, such as sodium or ammonium salts; $C_3$ and $C_6$ diols and triols including hexylene glycol, 1,4 dihydroxyhexane, 1,2,6-hexane triol; aloe vera in any of its forms, for example aloe vera gel; sugars and starches; sugar and starch derivatives, for example alkoxylated glucose; hyaluronic acid; lactamide monoethanolamine; acetamide monoethanolamine; glycolic acid; alpha and beta hydroxy acids (e.g. lactic, glycolic salicylic acid); glycerine; pantheol; urea; vaseline; natural oils; oils and waxes (see: the emollients section herein) and mixtures thereof.)

Viscosity modifiers that may be used in accordance with the present invention include, for example, cetyl alcohol; glycerol, polyethylene glycol (PEG); PEG-stearate; and/or Keltrol.

Appropriate thickeners for use in inventive products include, for example, gelling agents such as cellulose and derivatives; Carbopol and derivatives; carob; carregeenans and derivatives; xanthane gum; sclerane gum; long chain alkanolamides; bentone and derivatives; Kaolin USP; Veegum Ultra; Green Clay; Bentonite NFBC; etc.

Suitable emollients include, for example, natural oils, esters, silicone oils, polyunsaturated fatty acids (PUFAs), lanoline and its derivatives and petrochemicals.

Natural oils which may be used in accordance with the present invention may be obtained from sesame; soybean; apricot kernel; palm; peanut; safflower, coconut; olive; cocoa butter; palm kernel; shea butter; sunflower; almond; avocado; borage; carnauba; hazel nut; castor; cotton seed; evening primrose; orange roughy; rapeseed; rice bran; walnut; wheat germ; peach kernel; babassu; mango seed; black current seed; jojoba; macadamia nut; sea buckthorn; sasquana; tsubaki; mallow; meadowfoam seed; coffee; emu; mink; grape seed; thistle; tea tree; pumpkin seed; kukui nut; and mixtures thereof.

Esters which may be used include, for example, $C_8$-$C_{30}$ alkyl esters of $C_8$-$C_{30}$ carboxylic acids; $C_1$-$C_6$ diol monoesters and diesters of $C_8$-$C_{30}$ carboxylic acids; $C_{10}$-$C_{20}$ alcohol monosorbitan esters, $C_1$-$C_{20}$ alcohol sorbitan di- and tri-esters; $C_{10}$-$C_{20}$ alcohol sucrose mono-, di-, and tri-esters and $C_{10}$-$C_{20}$ fatty alcohol esters of $C_2$-$C_6$ 2-hydroxy acids and mixtures thereof. Examples of these materials include isopropyl palmitate; isopropyl myristate; isopropyl isononate; $C_{12}$/$C_{14}$ benzoate ester (also known as Finesolve); sorbitan palmitate, sorbitan oleate; sucrose palmitate; sucrose oleate; isostearyl lactate; sorbitan laurate; lauryl pyrrolidone carboxylic acid; panthenyl triacetate; and mixtures thereof.

Further useful emollients include silicone oils, including non-volatile and volatile silicones. Examples of silicone oils that may be used in the compositions of the present invention are dimethicone; cyclomethycone; dimethycone-copolyol; aminofunctional silicones; phenyl modified silicones; alkyl modified silicones; dimethyl and diethyl polysiloxane; mixed $C_1$-$C_{30}$ alkyl polysiloxane; and mixtures thereof. Additionally useful silicones are described in U.S. Pat. No. 5,011,681 to Ciotti et al., incorporated by reference herein.

A yet further useful group of emollients includes lanoline and lanoline derivatives, for example lanoline esters.

Petrochemicals which may be used as emollients in the compositions of the present invention include mineral oil; petrolatum; isohexdecane; permethyl 101; isododecanol; $C_{11}$-$C_{12}$ Isoparrafin, also known as Isopar H.

Among the waxes which may be included in inventive products are animal waxes such as beeswax; plant waxes such as carnauba wax, candelilla wax, ouricurry wax, Japan wax or waxes from cork fibres or sugar cane. Mineral waxes, for example paraffin wax, lignite wax, microcrystalline waxes or ozokerites and synthetic waxes may also be included.

Exemplary fragrances for use in inventive products include, for instance, linear and cyclic alkenes (i.e. terpenes); primary, secondary and tertiary alcohols; ethers; esters; ketones; nitrites; and saturated and unsaturated aldehydes; etc.

Examples of synthetic fragrances that may be used in accordance with the present invention include without limitation acetanisole; acetophenone; acetyl cedrene; methyl nonyl acetaldehyde; musk anbrette; heliotropin; citronellol; sandella; methoxycitranellal; hydroxycitranellal; phenyl ethyl acetate; phenylethylisobutarate; gamma methyl ionone; geraniol; anethole; benzaldehyde; benzyl acetate; benzyl salicate; linalool; cinnamic alcohol; phenyl acetaldehyde; amyl cinnamic aldehyde; caphore; p-tertiary butyl cyclohexyl acetate; citral; cinnamyl acetate; citral diethyl acetal; coumarin; ethylene brasslate; eugenol; 1-menthol; vanillin; etc.

Examples of natural fragrances of use herein include without limitation lavandin; heliotropin; sandlewood oil; oak moss; pathouly; ambergris tincture; ambrette seed absolute; angelic root oil; bergamont oil; benzoin Siam resin; buchu leaf oil; cassia oil; cedarwood oil; cassia oil; castoreum; civet absolute; chamomile oil; geranium oil; lemon oil; lavender oil; Ylang Ylang oil; etc.

A list of generally used fragrance materials can be found in various reference sources, for example, "Perfume and Flavor Chemicals", Vols. I and II; Steffen Arctander Allured Pub. Co. (1994) and "Perfumes: Art, Science and Technology"; Muller, P. M and Lamparsky, D., Blackie Academic and Professional (1994) both incorporated herein by reference.

Suitable preservatives include, among others, (e.g., sodium metabisulfite; Glydant Plus; Phenonip; methylparaben; Germall 115; Germaben II; phytic acid; sodium lauryl sulfate (SLS); sodium lauryl ether sulfate (SLES); Neolone; Kathon; Euxyl and combinations thereof), anti-oxidants (e.g., butylated hydroxytoluened (BHT); butylated hydroxyanisol (BHA); ascorbic acid (vitamin C); tocopherol; tocopherol acetate; phytic acid; citric acid; pro-vitamin A.

In some embodiments, inventive products will comprise an emulsion (e.g., containing inventive lipid bodies), and may include one or more emulsifying agents (e.g., Arlacel, such as Alacel 165; Glucamate; and combinations thereof) and/or emulsion stabilizing agents. In some embodiments, inventive products will include one or more biologically active agents other than the ubiquinone(s). To give but a few examples, inventive cosmetic or pharmaceutical products may include one or more biologically active agents such as, for example, sunscreen actives, anti-wrinkle actives, anti-aging actives, whitening actives, bleaching actives, sunless tanning actives, anti-microbial actives, anti-acne actives, anti-psoriasis actives, anti-eczema actives, antioxidants, anesthetics, vitamins, protein actives, etc.

Engineering Production of Multiple Isoprenoid Compounds

In certain embodiments of the invention, it may be desirable to generate engineered organisms that accumulate one or more other compounds in addition to the quinone derived compound described herein, and further to accumulate such other compound(s), optionally together with the quinone derived compound(s), in lipid bodies. For example, certain inventive engineered organisms may accumulate quinone derived compound together with at least one other compound derived from an isoprenoid precursor. In some embodiments, the other compound derived from an isoprenoid precursor will be one or more quinone derived compound discussed herein (e.g., a ubiquinone, vitamin K, vitamin E). Alternatively or additionally, in some embodiments the other compound derived from an isoprenoid precursor will be one or more carotenoids. Production of carotenoids in oleaginous organisms is described in U.S. Provisional Application No. 60/663,621, filed Mar. 18, 2005, and is also described in U.S. patent application Ser. No. 11/385,580, entitled Production of Carotenoids in Oleaginous Yeast and Fungi, filed Mar. 20, 2006.

In some embodiments of the invention, host cells are engineered to produce at least two compounds selected from the group consisting of a ubiquinone (e.g. CoQ10, a $C_{5-9}$ quinone), vitamin K, vitamin E, and carotenoids. In some such embodiments, host cells are engineered to produce a least one compound selected from the group consisting of a ubiquinone (e.g. CoQ10, a $C_{5-9}$ quinone), vitamin K, vitamin E, and at least one other compound. Such host cells are particularly useful for producing mixtures or combination products that contain a ubiquinone and/or vitamin K. Such host cells are also useful for producing combination products including one or more carotenoids.

In some embodiments of the invention, host cells are engineered to produce at least one quinone derived compound and at least one carotenoid. Carotenoids, which have an isoprene backbone consisting of 40 carbon atoms, have antioxidant effects as well as use in coloring agents. Carotenoids such as β-carotene, astaxanthin, and cryptoxanthin are believed to possess cancer preventing and immunopotentiating activity.

The carotenoid biosynthesis pathway branches off from the isoprenoid biosynthesis pathway at the point where GGPP is formed. Up to and including formation of FPP, and potentially GGPP, is as described above for production of a ubiquinone. The commitment step in carotenoid biosynthesis is the formation of phytoene by the head-to-head condensation of two molecules of GGPP, catalyzed by phytoene synthase (often called crtB). A series of dehydrogenation reactions, each of which increases the number of conjugated double bonds by two, converts phytoene into lycopene via neurosporene. The pathway branches at various points, both before and after lycopene production, so that a wide range of carotenoids can be generated. For example, action of a cyclase enzyme on lycopene generates γ-carotene; action of a desaturase instead produces 3,4-didehydrolycopene. γ-carotene is converted to β-carotene through the action of a cyclase. β-carotene can be processed into any of a number of products, including astaxanthin (via echinone, hydroxyechinone, and phoenicoxanthin).

Carotenoid production in a host organism may be adjusted by modifying the expression or activity of one or more proteins involved in carotenoid biosynthesis. In some embodiments of the invention, it will be desirable to utilize as host cells organisms that naturally produce one or more carotenoids. In some such cases, the focus will be on increasing production of a naturally-produced carotenoid, for example by increasing the level and/or activity of one or more proteins involved in the synthesis of that carotenoid and/or by decreasing the level or activity of one or more proteins involved in a competing biosynthetic pathway. Alternatively or additionally, in some embodiments it will be desirable to generate production of one or more carotenoids not naturally produced by the host cell.

In some embodiments of the invention, it will be desirable to introduce one or more carotenogenic modifications into a host cell. In certain embodiments the carotenogenic modification may confer expression of one or more heterologous carotenogenic polypeptides into a host cell. As will be apparent to those of ordinary skill in the art, any of a variety of heterologous polypeptides may be employed; selection will consider, for instance, the particular carotenoid whose production is to be enhanced. Still further, selection will consider the complementation and/or ability of the selected polypeptide to function in conjunction with additional oleaginic and/or quinonogenic modifications of a cell such that each of oleaginy, ubiquinone biosynthesis and carotenoid biosynthesis are effectuated to the desired extent.

Proteins involved in carotenoid biosynthesis include, but are not limited to, phytoene synthase, phytoene dehydrogenase, lycopene cyclase, carotenoid ketolase, carotenoid hydroxylase, astaxanthin synthase (a single multifunctional enzyme found in some source organisms that typically has both ketolase and hydroxylase activities), carotenoid epsilon hydroxylase, lycopene cyclase (beta and epsilon subunits), carotenoid glucosyltransferase, and acyl CoA:diacyglycerol acyltransferase. Representative example sequences for carotenoid biosynthesis polypeptides are provided in Tables 17-21 and Tables 38-41.

Alternatively or additionally, modified carotenoid ketolase polypeptides that exhibit improved carotenoid production activity may be utilized in accordance with the present invention. For example, carotenoid ketolase polypeptides comprising one more mutations to corresponding to those identified Sphingomonas sp. DC18 which exhibited improved astaxanthin production (Tao et al. 2006 Metab Eng. Jun. 27, 2006) and *Paracoccus* sp. strain N81106 which exhibited altered carotenoid production (Ye et al. *Appl Environ Microbiol* 72:5829, 2006).

In some embodiments of the invention, potential source organisms for carotenoid biosynthesis polypeptides include, but are not limited to, genera of naturally oleaginous or non-oleaginous fungi that naturally produce carotenoids. These include, but are not limited to, *Botrytis, Cercospora, Fusarium (Gibberella), Mucor, Neurospora, Phycomyces, Puccina, Rhodotorula, Sclerotium, Trichoderma*, and *Xanthophyllomyces*. Exemplary species include, but are not limited to, *Neurospora crassa, Xanthophyllomyces dendrorhous (Phaffia rhodozyma), Mucor circinelloides,* and *Rhodotorula glutinis*. Of course, carotenoids are produced by a wide range of diverse organisms such as plants, algae, yeast, fungi, bacteria, cyanobacteria, etc. Any such organisms may be source organisms for carotenoid biosynthesis polypeptides according to the present invention.

It will be appreciated that the particular carotenogenic modification to be applied to a host cell in accordance with the present invention will be influenced by which carotenoid(s) is desired to be produced. For example, isoprenoid biosynthesis polypeptides are relevant to the production of most carotenoids. Carotenoid biosynthesis polypeptides are also broadly relevant. Carotenoid ketolase activity is particularly relevant for production of canthaxanthin, as carotenoid hydroxylase activity is for production of lutein and zeaxanthin, among others. Both carotenoid hydroxylase and ketolase activities (and/oror astaxanthin synthase) are particularly useful for production of astaxanthin.

Bacterial carotenogenic genes have already been demonstrated to be transferable to other organisms, and are therefore particularly useful in accordance with the present invention (see, for example, Miura et al., *Appl. Environ. Microbiol.* 64:1226, 1998). In other embodiments, it may be desirable to utilize genes from other source organisms such as plant, alga, or microalgae; these organisms provide a variety of potential sources for ketolase and hydroxylase polypeptides Still additional useful source organisms include fungal, yeast, insect, protozoal, and mammalian sources of polypeptides.

In certain embodiments of the present invention, cells are engineered to produce at least one sterol compound together with the at least one quinone derived compound. The commitment step in sterol biosynthesis is the conversion of farnesyl pyrophosphate into presqualene pyrophosphate. Farnesyl pyrophosphate (FPP) is produced from isopentenyl pyrophosphate (IPP), for example in a process that involves isomerization of IPP into dimethylallyl pyrophosphate (DMAPP), followed by three sequential condensation reactions with additional molecules of FPP generate the ten-carbon molecule geranyl pyrophosphate (GPP), followed by the fifteen-carbon molecule farnesyl pyrophosphate (FPP). FPP can either enter the sterol biosynthesis pathway by conversion into presqualene pyrophosphate, or alternatively can be diverted toward biosynthesis of carotenoids and other compounds (e.g., a ubiquinone, vitamin E, vitamin K, etc.) by conversion into the twenty-carbon compound geranylgeranyl pyrophosphate (GGPP). In many instances, FPP appears to be the predominant substrate used by polyprenyldiphosphate synthases (Coq1 polypeptides) during biosynthesis of ubiquinones.

Once the sterol biosynthesis pathway has been entered, presqualene pyrophosphate is then converted to squalene by the same enzyme that performed the farnesyl pyrophosphate→presqualene pyrophosphate conversion. Squalene is then converted into a variety of different sterol compounds, including, but not limited to, lanosterol, zymosterol, ergosterol, 7-dehydrocholesterol (provitamin D3), and vitamin D compounds. The vitamin $D_2$ biosynthetic pathway and the vitamin $D_3$ biosynthetic pathway share some common reactions, and there can be multiple points at which a vitamin $D_2$ intermediate can be converted into a vitamin $D_3$ intermediate (see, for example, FIG. 1).

In some embodiments, the sterol compound whose production is engineered is selected from the group consisting of squalene, lanosterol, zymosterol, ergosterol, and vitamin D compounds (e.g., 7-dehydrocholesterol (provitamin D3)).

In some embodiments of the present invention, host cells are engineered to produce squalene in addition to one or more quinone derived compounds. In some embodiments, squalene production is enhanced in a cell by introduction of one or more sterologenic modifications that increases levels of IPP, FPP and/or squalene itself. In some embodiments, squalene production is enhanced in a cell by increasing the level and/or activity of one or more squalene biosynthesis polypeptides (e.g., one or more isoprenoid biosynthesis polypeptides, an FPP synthase polypeptide, and/or a squalene synthase polypeptide). Alternatively or additionally, in some embodiments, squalene production is enhanced in a cell by decreasing the level and/or activity of one or more sterol biosynthesis competitor polypeptides that diverts one or more intermediates away from squalene production and/or that metabolizes squalene itself.

For example, in some embodiments of the present invention, squalene production in a host cell is increased by introducing or increasing expression and/or activity of one or more squalene synthase polypeptides in the cell. Representative examples of squalene synthase polypeptide sequences are included in Table 16. In some embodiments of the invention that utilize squalene synthase (or modifications of squalene synthase) source organisms include, but are not limited to, *Neurospora crassa, Aspergillus niger, Saccharomyces cerevi-* siae, *Mucor circinelloides, Candida utilis, Mortierella alpina, Phaffia rhodozyma*, and *Yarrowia lipolytica*.

In some embodiments of the invention, squalene production in a host cell is increased by reducing the level or activity of one or more squalene biosynthesis competitor. polypeptides, including for example one or more vitamin D biosynthesis polypeptides (e.g., which act to metabolize squalene). For instance, in some embodiments, the level or activity of one or more polypeptides active in the ergosterol biosynthetic pathway (see below) is reduced or eliminated.

In some embodiments, the sterol compound produced in addition to one or more quinone derived compounds according to the present invention is lanosterol. In some embodiments, lanosterol production is enhanced in a cell by introduction of one or more sterologenic modifications that increases levels of IPP, FPP and/or lanosterol itself. In some embodiments, lanosterol production is enhanced in a cell by increasing the level and/or activity of one or more lanosterol biosynthesis polypeptides (e.g., one or more isoprenoid biosynthesis polypeptides, an FPP synthase polypeptide, squalene synthase polypeptide, squalene epoxidase polypeptide, or 2,3-oxidosqualene-lanosterol cyclase polypeptide). Alternatively or additionally, in some embodiments, lanosterol production is enhanced in a cell by decreasing the level and/or activity of one or more sterol biosynthesis competitor polypeptides that diverts one or more intermediates away from lanosterol production and/or that metabolizes lanosterol itself.

For example, in some embodiments of the present invention, lanosterol production in a host cell is increased by introducing or increasing expression and/or activity of one or more squalene synthase polypeptide, squalene epoxidase polypeptide, or 2,3-oxidosqualene-lanosterol cyclase polypeptide in the cell. Representative examples of squalene synthase polypeptide, squalene epoxidase polypeptide, and 2,3-oxidosqualene-lanosterol cyclase polypeptide sequences are included in Table 16, 83, and 85. In some embodiments of the invention that utilize squalene synthase polypeptide, squalene epoxidase polypeptide, or 2,3-oxidosqualene-lanosterol cyclase polypeptide (or modifications of these polypeptides) source organisms include, but are not limited to, *Neurospora crassa, Aspergillus niger, Saccharomyces cerevisiae, Phaffia rhodozyma, Mucor circinelloides, Candida utilis, Mortierella alpina*, and *Yarrowia lipolytica*.

In some embodiments of the invention, lanosterol production in a host cell is increased by reducing the level or activity of one or more vitamin D biosynthesis polypeptides (e.g., which act to metabolize squalene). For instance, in some embodiments, the level or activity of one or more polypeptides active in the ergosterol biosynthetic pathway (see below).

In some embodiments of the present invention, host cells are engineered to produce zymosterol in addition to one or more quinone derived compounds. In some embodiments, zymosterol production is enhanced in a cell by introduction of one or more sterologenic modifications that increases levels of IPP, FPP and/or zymosterol itself. In some embodiments, zymosterol production is enhanced in a cell by increasing the level and/or activity of one or more zymosterol biosynthesis polypeptides (e.g., one or more isoprenoid biosynthesis polypeptides, an FPP synthase polypeptide, squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, or C-4 sterol methyl oxidase polypeptide). Alternatively or additionally, in some embodiments, zymosterol production is enhanced in a cell by decreasing the level and/or activity of one or more sterol biosynthesis competitor polypeptides that diverts one or more intermediates away from lanosterol production and/or that metabolizes lanosterol itself.

For example, in some embodiments of the present invention, zymosterol production in a host cell is increased by introducing or increasing expression and/or activity of one or more squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, or C-4 sterol methyl oxidase polypeptide in the cell. Representative examples of squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, or C-4 sterol methyl oxidase polypeptide sequences are included in Tables 16, and tables 86-99. In some embodiments of the invention that utilize squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, or C-4 sterol methyl oxidase polypeptide (or modifications of these polypeptides) source organisms include, but are not limited to, *Neurospora crassa, Aspergillus niger, Saccharomyces cerevisiae, Phaffia rhodozyma, Mucor circinelloides, Candida utilis, Mortierella alpina*, and *Yarrowia lipolytica*.

In some embodiments of the invention, zymosterol production in a host cell is increased by reducing the level or activity of one or more vitamin D biosynthesis polypeptides (e.g., which act to metabolize squalene). For instance, in some embodiments, the level or activity of one or more polypeptides active in the ergosterol biosynthetic pathway (see below).

In some embodiments of the present invention, host cells are engineered to produce ergosterol in addition to one or more quinone derived compounds. In some embodiments, ergosterol production is enhanced in a cell by introduction of one or more sterologenic modifications that increases levels of IPP, FPP and/or ergosterol itself. In some embodiments, ergosterol production is enhanced in a cell by increasing the level and/or activity of one or more ergosterol biosynthesis polypeptides (e.g., one or more isoprenoid biosynthesis polypeptides, an FPP synthase polypeptide, squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, C-4 sterol methyl oxidase polypeptide, SAM:C-24 sterol methyltransferase polypeptide, C-8 sterol isomerase polypeptide, C-5 sterol desaturase polypeptide, C-22 sterol desaturase polypeptide, or C-24 sterol reductase polypeptide. Alternatively or additionally, in some embodiments, ergosterol production is enhanced in a cell by decreasing the level and/or activity of one or more sterol biosynthesis competitor polypeptides that diverts one or more intermediates away from ergosterol production and/or that metabolizes ergosterol itself.

For example, in some embodiments of the present invention, ergosterol production in a host cell is increased by introducing or increasing expression and/or activity of one or more squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, C4 sterol methyl oxidase polypeptide, SAM:C-24 sterol methyltransferase polypeptide, C-8 sterol isomerase polypeptide, C-5 sterol desaturase polypeptide, C-22 sterol desaturase polypeptide, or C-24 sterol reductase polypeptide in the cell. Representative examples of squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, C4 sterol methyl oxidase polypeptide, SAM:C-24 sterol methyltransferase polypeptide, C-8 sterol isomerase polypeptide, C-5 sterol desaturase polypeptide, C-22 sterol desaturase polypeptide, or C-24 sterol reductase polypeptide sequences are included in Table 16, and tables 86-99. In some embodiments of the invention that utilize squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, C-4 sterol methyl oxidase polypeptide, SAM:C-24 sterol methyltransferase polypeptide, C-8 sterol isomerase polypeptide, C-5 sterol desaturase polypeptide, C-22 sterol desaturase polypeptide, or C-24 sterol reductase polypeptide (or modifications of these polypeptides) source organisms include, but are not limited to, *Neurospora crassa*, *Aspergillus niger*, *Saccharomyces cerevisiae*, *Mucor circinelloides*, *Candida utilis*, *Mortierella alpina*, and *Yarrowia lipolytica*.

In some embodiments of the invention, ergosterol production in a host cell is increased by reducing the level or activity of one or more vitamin D biosynthesis polypeptides (e.g., which act to metabolize squalene). For instance, in some embodiments, the level or activity of one or more polypeptides (see below).

In some embodiments, the sterol compound produced in addition to one or more quinone derived compounds in accordance with the present invention is a vitamin D compound. Vitamin D compounds are a group of steroid compounds including vitamin $D_3$ (cholecalciferol), vitamin $D_2$ (ergocalciferol), their provitamins, and certain metabolites (see, for example, FIG. 10A-B). Vitamins $D_3$ and $D_2$ can be produced from their respective provitamins (e.g., 7-dehydrocholesterol and ergosterol) by ultraviolet irradiation (e.g., by the action of sunlight). The most biologically active form of vitamin D is 1,25-dihydroxy vitamin $D_3$, which is also known as calcitriol. Calcitriol is produced by hydroxylation of vitamin $D_3$ at the 25 position, followed by hydroxylation to generate calcitriol.

In some embodiments, vitamin D production is enhanced in a cell by introduction of one or more sterologenic modifications that increases levels of IPP, FPP and/or squalene. In some embodiments, vitamin D production is enhanced in a cell by increasing the level and/or activity of one or more vitamin D biosynthesis polypeptides (e.g., one or more isoprenoid biosynthesis polypeptides, an FPP synthase polypeptide, a squalene synthase polypeptide, and/or one or more polypeptides involved in converting squalene into a particular vitamin D compound of interest [e.g., 7-dehydrocholesterol and/or calcitriol]). Alternatively or additionally, in some embodiments, vitamin D production is enhanced in a cell by decreasing the level and/or activity of one or more sterol biosynthesis competitor polypeptides that diverts one or more intermediates away from vitamin D production. In some embodiments of the invention, production of a particular vitamin D compound (e.g., 7-dehydrocholesterol and/or calcitriol) is enhanced by decreasing the level and/or activity of one or more polypeptides that diverts a relevant intermediate toward an alternative vitamin D compound (e.g., ergosterol, vitamin $D_2$).

To give but one particular example of a sterologenic modification that can be employed in accordance with the present invention to increase production of one or more vitamin $D_3$ compounds (e.g., 7-dehydrocholesterol and/or calcitriol), in accordance with some embodiments of the present invention, the level and/or activity of one or more polypeptides that diverts a relevant intermediate toward a vitamin $D_2$ compound (e.g., ergosterol, vitamin $D_2$), and away from vitamin $D_3$ compounds, can be inhibited or destroyed. In some embodiments of the invention, where multiple heterologous polypeptides are to be expressed (e.g., because one or more activities of interest require two or more polypeptide chains and/or because multiple activities of interest are being engineered), it may be desirable to utilize the same source organism for all, or to utilize closely related source organisms; in other embodiments, heterologous polypeptides may be from different source organisms. In some embodiments, two or more versions of a particular heterologous polypeptide, optionally from different source organisms, may be introduced into and/or engineered within, a single host cell.

Having now generally described the invention, the same will be more readily understood through reference to the following exemplification which is provided by way of illustration, and is not intended to be limiting of the present invention.

EXEMPLIFICATION

Table 42 describes the *Yarrowia lipolytica* strains used in the following exemplification:

TABLE 42

*Yarrowia lipolytica* strains.

| | | |
|---|---|---|
| NRRL Y-1095 | Wild type diploid | Derived from strain |
| ATCC76861 | MATB ura2-21 lyc1-5 LYS1-5B | |
| ATCC76982 | MATB ade1 leu2-35 lyc1-5 xpr2 | |
| ATCC201249 | MATA ura3-302 leu2-270 lys8-11 PEX17-HA | |
| MF346 | MATA ura2-21 | ATCC76861 × ATCC201249 |
| MF350 | MATB ura2-21 leu2-35 ade1 | ATCC76982 × MF346 |
| MF358 | MATB ade1 | ATCC76982 × MF346 |
| MF454 | MATB ura3-302 ade1 leu2-270 | ATCC201249 × MF358 |

(The genotypes at LYC1, LYS1, XPR2, and PEX17 were not determined in crosses nor verified for ATCC strains.)

All basic molecular biology and DNA manipulation procedures described herein are generally performed according to Sambrook et al. or Ausubel et al. (Sambrook J, Fritsch E F, Maniatis T (eds). 1989. *Molecular Cloning: A Laboratory Manual*. Cold Spring Harbor Laboratory Press: New York; Ausubel F M, Brent R, Kingston R E, Moore D D, Seidman J G, Smith J A, Struhl K (eds). 1998. *Current Protocols in Molecular Biology*. Wiley: N.Y.). The GPD1 and TEF1 promoters are from *Y. lipolytica* as is the XPR2 terminator.

Plasmids were generated for construction of CoQ10 producing strains. The following subparts describe production of plasmids encoding ubiquinogenic polypeptides. General plasmid construction for expression vectors are described in Table 43, and further constructions in the text. All PCR amplifications used NRRL Y-1095 genomic DNA as template unless otherwise specified. The URA5 gene described below is allelic with the ura2-21 auxotrophy above in Table 42.

TABLE 43

Plasmids

| Plasmid | Backbone | Insert | Oligos or source |
|---|---|---|---|
| pMB4529 | pCR2.1 | 3.4 kb ADE1 PCR product | MO4475 & MO4476 |
| pMB4534 | pCR2.1 | 2.1 kb LEU2 PCR product | MO4477 & MO4478 |
| pMB4535 | pCR2.1 | 1.2 kb URA5 PCR product | MO4471 & MO4472 |
| pMB4589 | pMB4535 (KpnI + SpeI) | 1.2 kb GPD1 promoter (KpnI + NotI); 0.14 kb XPR2 terminator (NotI + SpeI) | MO4568 & MO4591; MO4566 & MO4593 |
| pMB4590 | pMB4535 (KpnI + SpeI) | 0.4 kb TEF1 promoter (KpnI + NotI); 0.14 kb XPR2 terminator (NotI + SpeI) | MO4571 & MO4592; MO4566 & MO4593 |
| pMB4597 | pMB4534 (Acc65I + SpeI) | GPD1 promoter & XPR2 terminator (Acc65I + SpeI) | From pMB4589 |
| pMB4603 | pMB4597 (RsrII + MluI) | Residual backbone & TEF1 promoter (RsrII + MluI) | From pMB4590 |
| pMB4616 | pMB4529 (RsrII + SpeI) | Residual backbone & GPD1 promoter & XPR2 terminator (RsrII + SpeI) | From pMB4589 |
| pMB4629 | pMB4616 (RsrII + MluI) | Residual backbone & TEF1 promoter (RsrII + MluI) | From pMB4590 |
| pMB4631 | pMB4603 (KpnI + NheI) | 1.2 kb GPD1 promoter (KpnI + NheI); | MO4568 & MO4659 |
| pMB4637 | pMB4629 (NheI + MluI) | 1.5 kb hmg1$^{trunc}$ ORF (XbaI + MluI) | MO4657 & MO4658 |
| pMB4662 | pMB4631 (SpeI + XhoI) | 1.8 kb URA3 fragment (SpeI + BsaI) | MO4684 & MO4685 |
| pMB4691 | pMB4662 (Acc65I + MluI) | 0.4 kb TEF1 promoter (Acc65I + MluI) | From pMB4629 |

TABLE 44

Oligonucleotides referenced in Table 43

```
MO4471  5'CTGGGTGACCTGGAAGCCTT

MO4472  5'AAGATCAATCCGTAGAAGTTCAG

MO4475  5'AAGCGATTACAATCTTCCTTTGG

MO4476  5'CCAGTCCATCAACTCAGTCTCA

MO4477  5'GCATTGCTTATTACGAAGACTAC

MO4478  5'CCACTGTCCTCCACTACAAACAC

MO4566  5'CACAAACTAGTTTGCCACCTACAAGCCAGAT

MO4568  5'CACAAGGTACCAATGTGAAAGTGCGCGTGAT

MO4571  5'CACAAGGTACCAGAGACCGGGTTGGCGG

MO4591  5'CACAAGCGGCCGCGCTAGCATGGGGATCGATCTCTTATAT

MO4592  5'CACAAGCGGCCGCGCTAGCGAATGATTCTTATACTCAGAAG

MO4593  5'CACAAGCGGCCGCACGCGTGCAATTAACAGATAGTTTGCC

MO4659  5'CACAAGCTAGCTGGGGATGCGATCTCTTATATC

MO4684  5'  CATTCACTAGTGGTGTGTTCTGTGGAGCATTC

MO4685  5'  CACACGGTCTCATCGAGGTGTAGTGGTAGTGCAGTG

MO4657  5'CACACTCTAGACACAAAAATGACCCAGTCTGTGAAGGTGG

MO4658  5'CACACACGCGTACACCTATGACCGTATGCAAAT
```

Example 1

Biosynthesis of CoQ10 in *Yarrowia lipolytica*

Decaprenyl diphosphate synthases ("dpdpS") based on the amino acid sequence of those found in *Silicibacter pomeroyi* and in *Loktanella vestfoldensis* are expressed in *Yarrowia lipolytica*, using nucleotide sequences with the appropriate *Yarrowia* codon bias, and with *Yarrowia* mitochondrial targeting sequences. Insertion of the expression cassette results in the disruption of the native COQ1 gene, encoding nonaprenyl diphosphate synthase.

To construct the mitochondrial leader sequence encoding DNA of NADH:ubiquinone oxidoreductases (complex I) ["NUAM"], four oligos were annealed and treated sequentially with Klenow fragment and ligase:

```
MO4859:  5'-TCTAGACACAAAAATGCTCTCGAGAAACCTCAGCAAGTT
         TG

MO4860:  5'-GTGGTTGCTGGCCGGATGAGACCGGCTCGAGCAAACTTG
         CT

MO4861:  5'-CAGCAACCACATCCACACACACCCGACTATTCTCTGTCT
         CC

MO4862:  5'-GGATCCCGTCTCGGACAGACGTCGGGCGGAGACAGAG.
```

The resulting fragment was subsequently amplified with MO4859 and MO4862 using Pfu polymerase and the product was phosphorylated and ligated to pBluescriptSKII⁻ cut with EcoRV to create pMB4776. The mitochondrial leader sequence of NUAM is thereby encoded within the resultant XbaI-BsmBI (underline) fragment:

(NUAM1dr):
tctagacacaaaaatgctctcgagaaacctcagcaagtttgctcgagccg gtctcatccggccagcaaccacatccacacacacccgactattctctgtc tccgcccgacgtctgtccgagacgggatcc To construct the mitochondrial leader sequence encoding DNA of the native *Y. lipolytica* Coq1 protein, *Y. lipolytica* genomic DNA was amplified with MO4857 (5'-CGGATC-CCGTCTCGGACATTTCTTGCGACACAATG) and MO4858 (5'-CTCTAGACACAAAAATGCTGAGAGTCG-GACGAAT) and the 0.25 kb product was phosphorylated and ligated to pBluescriptSKII⁻ cut with EcoRV to create pMB4750. The mitochondrial leader sequence of Coq1 is thereby encoded within the resultant XbaI-BsmBI (underline) fragment:

(Coq1ldr):
ctctagacacaaaaatgctgagagtcggacgaattggcaccaagaccta gccagcagcagcctgcgtttcgtggcaggtgctcggcccaaatccacgct caccgaggccgtgctggagaccacagggctgctgaaaaccacgcccaaa accccgagtggtctggagccgtcaagcaggcatctcgtctggtggagacc gacactccgatccgagaccgttttccattgtgtcgcaagaaatgtccga gacgggatccg.

To construct a cassette encoding the decaprenyl diphosphate synthase (dpdpS) from *Silicibacter pomeroyi*, the following sequence was synthesized de novo:

(Sp-dpdpS):
GGATCCCGTCTCTTGTCTGATGCCAAAGTCTCTACAAAGCCTCACGAGAT

GCTCGCTGCCACACTCTCTCAGGAAATGGCCGCTGTCAACGCCCTTATTC

GAACCCGTATGGCTTCTGAACACGCCCCTAGAATCCCCGAAGTTACAGCC

CACCTCGTCGAAGCCGGCGGAAAACGATTGCGACCTATGCTGACACTTGC

TGCTGCCCGACTGTGTGGATACCAGGGCGAAGATCATGTCAAACTGGCTG

CCACTGTTGAATTTATTCACACTGCTACACTTTTGCACGATGATGTCGTG

GACGAGTCTGGACAAAGACGTGGACGACCTACTGCTAATCTTCTTTGGGA

TAACAAGTCCTCTGTTCTTGTGGGCGACTATCTTTTTGCACGATCGTTCC

AGCTGATGGTCGAAACCGGTTCCCTTCGAGTGCTTGACATCCTCGCTAAC

GCTGCCGCGACAATTGCCGAAGGTGAAGTGCTCCAGATGACCGCTGCTTC

CGATCTTAGAACTGATGAATCCGTTTACCTTCAGGTCGTTCGAGGTAAAA

CTGCCGCTCTTTTTTCTGCTGCTACTGAAGTTGGTGGTGTTATTGCCGGA

GTCCCCGAAGCCCAAGTTTCGAGCACTTTTTGAATACGGTGATGCGCTGG

GAATTGCATTTCAGATTGCTGATGACCTCCTCGACTACCAAGGTGATGCT

AAGGCCACTGGAAAGAATGTTGGAGATGACTTCAGAGAAAGAAAACTCAC

ATTGCCTGTTATTAAAGCCGTCGCTCAAGCTACTGATGAGGAACGAGCGT

TTTGGGTTAGAACTATTGAAAAGGGAAAGCAAGCTGAAGGAGATCTTGAA

CAGGCTCTCGCTCTCATGGAAAAATACGGAACACTTGCCGCAACCAGAGC

CGATGCGCATGCTTGGGCCGAAAAAGCACGAACCGCCCTCGAACTGTTGC

CGAATCACGAAATCAGAACAATGCTCTCCGACCTCGCCGATTATGTCGTT

GCTAGATTGTCTTAAACGCGT.

To construct a cassette encoding the decaprenyl diphosphate synthase (dpdpS) from *Loktanella vestfoldensis*, the following sequence was synthesized de novo:

(Lv-dpdpS):
GGATCCCGTCTCTTGTCTCTTGATCACGCTGCCACCAAACCTCATGAACA

ACTTGCCGCCGCCCTTGCCGACGACCTTACCGCAGTTAACGCTATGATTA

GAGACCGAATGGCCAGCGAACATGCCCCCAGAATTCCACAAGTTACCGCA

CACCTCGTTGAAGCCGGAGGTAAAAGACTTCGTCCAATGCTGACCCTTGC

CGCCGCCCGTATGTGTGGCTACGACGGACCTTACCACATCCACCTTGCAG

CCACCGTTGAGTTCATTCACACCGCCACCTTGCTCCATGACGATGTTGTT

GATGAGTCCTCCCAACGTCGTGGTCGACCTACCGCTAATCTTCTGTGGGA

TAATACCTCTTCTGTTTTGGTTGGAGACTACCTCTTTGCACGATCTTTTC

AGTTGATGGTTGAGACCGGATCGCTTCGAGTTCTTGACATCCTGGCCAAT

GCTTCTGCTACCATCGCCGAAGGTGAGGTTCTGCAACTTACCGCCGCCGC

TGACCTTGCAACTACCGAGGACATTTACATCAAAGTTGTTCGAGGAAAGA

CTGCTGCACTCTTTTCTGCTGCTATGGAAGTTGGTGGAGAAATCGCCGGT

CAGGACCCGGCTATTAAACAGGCTCTCTTTGACTACGGCGACGCTCTCGG

AATTTCTTTTCAGATTGTTGATGACCTGTTGGATTACGGTGGAACAAAAG

CTACAGGAAAGAACGTTGGTGATGACTTCCGAGAAAGAAAGCTCACCCTC

CCTGTTATTCGTGCCGTTGCTGCTGCTGATGCTGATGAAAGAGCTTTTTG

GGAACGAACAATTCAAAAAGGAAGACAACAAGATGGAGACCTGGACCATG

CAATTGCCCTTCTTCATAGACACGGAACCCTTGAATCCACACGACAAGAC

GCAATCCTTTGGGCCGCTAAAGCTAAAGAAGCACTCGGAGTTATCCCGGA

CCATGCTCTTAAAACCATGCTCGTTGACCTTGCTGACTACGTTGTTGCTC

GACTCACCTAAACGCGT.

A NUAM1dr-Sp-dpdpS fusion capable of being expressed in *Y. lipolytica* was constructed by ligating the XbaI-BsmBI NUAM1dr fragment together with the BsmBI-MluI Sp-dpdpS fragment into pMB4691 cut with NheI and MluI, to create pMB4799.

A NUAM1dr-Lv-dpdpS fusion capable of being expressed in *Y. lipolytica* was constructed by ligating the XbaI-BsmBI NUAM1dr fragment together with the BsmBI-MluI Lv-dpdpS fragment into pMB4691 cut with NheI and MluI, to create pMB4797.

A Coq1ldr-Sp-dpdpS fusion capable of being expressed in *Y. lipolytica* was constructed by ligating the XbaI-BsmBI Coq1ldr fragment together with the BsmBI-MluI Sp-dpdpS fragment into pMB4691 cut with NheI and MluI, to create pMB4798.

A Coq1ldr-Lv-dpdpS fusion capable of being expressed in *Y. lipolytica* was constructed by ligating the XbaI-BsmBI Coq1ldr fragment together with the BsmBI-MluI Lv-dpdpS fragment into pMB4691 cut with NheI and MluI, to create pMB4796.

To effect the disruption of the native COQ1 gene and its replacement by the fusions described above, *Y. lipolytica* genomic DNA was amplified with two pairs of primers:

```
5'-CACACGGTACCGGTATAGGCACAAGTGC [MO4848]
with

5'-CACTCGGATCCGTACGTCTGTGGTGCTGTGGT [MO4856],
and

5'-CACACGGATCCGCTAGCTCTGAGAAACCTCACCATG [MO4850]
with

5'-CACACTCTAGATTTTCTTGGCCATGAACGGT [MO4851],
``` yielding a fragment of approximately 0.7 kb and 0.85 kb in length, respectively. Fragment MO4848/4856 was cleaved with Acc65I and BamHI, fragment MO4850/4851 was cleaved with BamHI and XbaI, and pBluescriptSKII⁻ was cleaved with XbaI and Acc65I. These three segments were ligated together to yield plasmid pMB4747.

The 3.6 (or 3.7) kb Acc65I-XbaI fragments from pMB4796, pMB4797, pMB4798, and pMB4799 containing various tef-dpdpS constructs and the URA3 marker were each ligated to pMB4747 cleaved with BsiWI and NheI. The resulting plasmids, pMB4800 (Coq1ldr-Lv-dpdpS), pMB4801 (NUAMldr-Lv-dpdpS), pMB4802 (Coq1ldr-Sp-dpdpS), pMB4803 (NUAMldr-Sp-dpdpS), are cleaved with Acc65I and XbaI and the 5.1 (or 5.3) kb fragment containing various coq1-tef1p-dpdpS-URA3-coq1 sequences is used to transform *Y. lipolytica* strain MF454 (MATB ura3 leu2 ade1) to uracil prototrophy. Transformants were checked by PCR for confirmation of homologous integration based gene replacement which confirmed the presence of the heterologous dpdpS and the absence of the wild type *Y. lipolytica* COQ1 allele. The strains were designated MF975 (MATB ura3 leu2 ade1 coq1ΔNUAMldr-Lv-dpdpS-URA3), MFL976 (MATB ura3 leu2 ade1 coq1ΔNUAMldr-Lv-dpdpS-URA3) as duplicate and MF977 (MATB ura3 leu2 ade1 coq1ΔNUAMldr-Sp-dpdpS-URA3). Strains were analyzed for ubiquinone by TLC and HPLC analysis as described in subsequent examples.

Example 2

Increased CoQ10 Production Resulting from Enhanced PHB-Polyprenyltransferase Activity 4-hydroxybenzoate polyprenyl transferases ("phbPPt") based on the amino acid sequence of those found in *Silicibacter pomeroyi* and in *Bos taurus* are expressed in *Yarrowia lipolytica*, using nucleotide sequences with the appropriate *Yarrowia* codon bias, and in the case of the *S. pomeroyi* sequence, with *Yarrowia* mitochondrial targeting sequences.

The following sequences are synthesized de novo:

```
G: Yarrowia lipolytica Coq1 signal sequence. +
Silicibacter pomeroyi phbPPt
5'-TTCTAGACACAAAAATGCTGCGAGTGGGCCGAATCGGCACCAAGACC
CTGGCCTCTTCTTCTCTGCGATTCGTGGCCGGCGCCCGACCCAAGTCTAC
CCTGACCGAGGCCGTGCTGGAGACCACCGGCCTGCTGAAGACCACCCCC
AGAACCCCGAGTGGTCTGGCGCCGTGAAGCAGGCCTCTCGACTGGTGGAG
ACCGACACCCCCATCCGAGACCCCTTCTCTATCGTGTCTCAGGAGATGCA
GGGCCAGGCCCCCACCCCCGACGGCCAGGTGGCCGACGCCGTGACCGGCA
ACTGGGTGGACATCCACGCCCCCGCCTGGTCTCGACCCTACCTGCGACTG
TCTCGAGCCGACCGACCCATCGGCACCTGGCTGCTGCTGATCCCCTGTTG
GTGGGGCCTGGCCCTGGCCATGCTGGACGGCCAGGACGCCCGATGGGGCC
ACCTGTGGATCGCCCTGGGCTGTGCCATCGGCGCCTTCCTGATGCGAGGC
GCCGGCTGTACCTGGAACGACATCACCGACCGAGAGTTCGACGGCCGAGT
GGAGCGAACCCGATCTCGACCCATCCCCTCTGGCCAGGTGTCTGTGCGAA
TGGCCGTGGTGTGGATGATCGCCCAGGCCCTGCTGGCCCTGATGATCCTG
CTGACCTTCAACCGAATGGCCATCGCCATGGGCGTGCTGTCTCTGCTGCC
CGTGGCCGTGTACCCCTTCGCCAAGCGATTCACCTGGTGGCCCCAGGTGT
TCCTGGGCCTGGCCTTCAACTGGGGCGCCCTGCTGGCCTGGACCGCCCAC
TCTGGCTCTCTGGGCTGGGGCGCCCTGTTCCTGTACCTGGCCGGCATCGC
CTGGACCCTGTTCTACGACACCATCTACGCCCACCAGGACACCGAGGACG
ACGCCCTGATCGGCGTGAAGTCTACCGCCCGACTGTTCGGCGCCCAGACC
CCCCGATGGATGTCTTACTTCCTGGTGGCCACCGTGTCTCTGATGGGCAT
CGCCGTGTTCGAGGCCGCCCTGCCCGACGCCTCTATCCTGGCCCTGGTGC
TGGCCCTGGCCGGCCCCTGGGCCATGGGCTGGCACATGGCCTGGCAGCTG
CGAGGCCTGGACCTGGACGACAACGGCAAGCTGCTGCAGCTGTTCCGAGT
GAACCGAGACACCGGCCTGATCCCCCTGATCTTCTTCGTGATCGCCCTGT
TCGCCTAACGCGT H: Bos taurus phpPPt
5'-TTCTAGACACAAAAATGCTGGGCTCTTGTGGCGCCGGCCTGGTGCGA
GGCCTGCGAGCCGAGACCCAGGCCTGGCTGGGGCACCCGAGGCCGATC
TCTGGCCCTGGTGCACGCCGCCCGAGGCCTGCACGCCGCCAACTGGCAGC
CCTCTCCCGGCCAGGGCCCCCGAGGCCGACCCCTGTCTCTGTCTGCCGCC
GCCGTGGTGAACTCTGCCCCCCGACCCCTGCAGCCCTACCTGCGACTGAT
GCGACTGGACAAGCCCATCGGCACCTGGCTGCTGTACCTGCCCTGTACCT
GGTCTATCGGCCTGGCCGCCGACCCCGGCTGTCTGCCCGACTGGTACATG
CTGTCTCTGTTCGGCACCGGCGCCGTGCTGATGCGAGGCGCCGGCTGTAC
CATCAACGACATGTGGGACCGAGACTACGACAAGAAGGTGACCCGAACCG
CCTCTCGACCCATCGCCGCCGGCGACATCTCTACCTTCCGATCTTTCGTG
TTCCTGGGCGGCCAGCTGACCCTGGCCCTGGGCGTGCTGCTGTGTCTGAA
CTACTACTCTATCGCCCTGGGCGCCGCCTCTCTGCTGCTGGTGGACCACCT
ACCCCCTGATGAAGCGAATCACCTACTGGCCCCAGCTGGCCCTGGGCCTG
ACCTTCAACTGGGGCGCCCTGCTGGGCTGGTCTGCCGTGAAGGGCTCTTG
TGACCCCTCTGTGTGTCTGCCCCTGTACTTCTCTGGCATGATGTGGACCC
TGATCTACGACACCATCTACGCCCACCAGGACAAGAAGGACGACGCCCTG
ATCGGCCTGAAGTCTACCGCCCTGCTGTTCCGAGAGGACACCAAGAAGTG
GCTGTCTGGCTTCTCTGTGGCCATGCTGGGCGCCCTGTCTCTGGTGGGCG
TGAACTCTGGCCAGACCATGCCCTACTACACCCCCTGGCCGCCGTGGGC
GCCCACCTGGCCCACCAGATCTACACCCTGGACATCAACCGACCCGAGGA
CTGTTGGGAGAAGTTCACCTCTAACCGAACCATCGGCCTGATCATCTTCC
TGGGCATCGTGCTGGGCAACCTGTGTAAGGCCAAGGAGACCGACAAGACC
CGAAGAACATCGAGAACCGAATGGAGAACTAACGCGT
```

The above sequences are cleaved with MluI and XbaI, and inserted into NheI- and MluI-cleaved pM4603, placing the genes under the control of the *Y. lipolytica* TEF1 promoter, and adjacent to a functional *Y. lipolytica* LEU2 gene. These plasmids are designated tef-transS (from sequence G) and tef-transB (from sequence H).

These plasmids can be used to transform *Y. lipolytica* strain MF454, ML975, MF976, or MF977 to leucine prototrophy by cleaving with enzymes that lie within plasmid backbone sequences to favor nonhomologous integration events. Transformants can be checked by Southern analysis for confirmation of ectopic integration. Production of CoQ10 can be assessed using HPLC or TLC analysis.

Example 3

Extraction of Ubiquinone from *Yarrowia lipolytica* Cells

Shake-flask testing was conducted using 20 ml cultures containing YPD medium (1% yeast extract, 2% peptone, 2% glucose) in 125 ml flasks grown at 30° C. *Y. lipolytica* cells were harvested from 24 hour cultures, and extractions are performed to determine ubiquinone form and quantity. Entire culture was pelleted and washed with 50 ml $H_2O$. Pelleted cells may be frozen at −80° C. and stored. 0.5 ml of cubic zirconium beads was added to cell pellets, along with 1 ml ice-cold extraction solvent (a 50/50 v/v mix of hexane and ethyl acetate containing 0.01% butylhydroxytoluene (BHT)). The mixture was then agitated (Mini-BeadBeater-8, BioSpec Products, Inc.) at maximum speed for 5 minutes at 4° C. The mixture was then spun at maximum speed for 2 minutes, and the supernatant collected and deposited in a cold 16 ml glass vial. The remaining cell debris was re-extracted at least three times, without the addition of zirconium beads; all supernatants were pooled in the 16 ml glass vial. A Speed Vac was used to concentrate the supernatant (room temperature in dark), and the samples were stored at −20° C. or −80° C. until immediately before TLC and HPLC analysis. Prior to TLC analysis, the samples were resuspended in 50 µl ice-cold solvent and then transferred to a cold amber vial. In an alternative similar protocol, *Y. lipolytica* cells can be harvested from 72-96 hour 20 ml cultures grown in 125 ml flasks grown at 30° C. 1.8 ml of culture is placed into a pre-weighed tube with a hole poked in the top. Cells are pelleted and washed with 1 ml H$_2$O. The washing procedure is repeated and then cells are lyophilized overnight. After drying to completion, the tube is weighed in order to calculate dry cell weight. 1 ml from the same shake flask culture is placed into a screw-cap tube for ubiquinone extraction. Cells are pelleted and washed once with 1 ml H$_2$O and once with 1 M potassium phosphate solution, pH 7.1. Pelleted cells may be frozen at –80° C. and stored. Cubic zirconium beads addition and extraction is performed as describe above. Following extraction, the glass vial is spun for 5 minutes at 2000 rpm at 4° C. in a Sorvall tabletop centrifuge, and the supernatant is transferred to a new cold 16 ml glass vial. A Speed Vac is used to concentrate the supernatant (room temperature in dark), and the samples are stored at –20° C. or –80° C. until immediately before HPLC analysis. Prior to HPLC analysis, the samples are resuspended in 1 ml ice-cold solvent and then transferred to a cold amber vial. Throughout the extraction protocols, care is taken to avoid contact with oxygen, light, heat, and acids.

Example 4a

Purification of Ubiquinones from Crude Extract by Thin Layer Chromatography (TLC)

Ubiquinone containing samples from the primary extraction in example 3 were spotted to immobilized silica gel plates next to the primary standards (Coenzyme Q9 (Sigma 275970) and Coenzyme Q10 (Sigma 27595)) and resolved in a 80:40:1 hexanes:diethyl ether:acetic acid solvent mixture. Ubiquinone containing bands were identified by UV shadowing and migration with the purified ubiquinone standard and excised from the TLC plate. Samples were extracted from the silica gel with 50 µl acetone followed by mixing, centrifugation, decanting and drying before HPLC analysis.

Example 4b

Quantification of Ubiquinone Production by HPLC

Ubiquinone-containing samples are resuspended in ice-cold extraction solvent (a 50/50 v/v mix of hexane and ethyl acetate containing 0.01% butylhydroxytoluene (BHT)). An Alliance 2795 HPLC (Waters) equipped with a Waters XBridge C18 column (3.5 µm, 2.1×50 mm) and Thermo Basic 8 guard column (2.1×10 mm) is used to resolve ubiquinone at 25° C.; authentic ubiquinone samples are used as standards. Ubiquinone molecules were detected at 275 nm (alternatively, they can also be detected at 405 nm), and retention times include CoQ10 (4.272 min) and CoQ9 (4.164 min). The mobile phases and flow rates are shown in Table 45 (Solvent A=Ethyl Acetate; Solvent B=Water; Solvent C=Methanol; Solvent D=Acetonitrile). The injection volume was 10 µL. The detector was a Waters 996 photodiode array detector. A peak corresponding to Coenzyme Q10 was observed in strains MF975, MF976, and MF977.

The retention times for additional lipophilic molecules include astaxanthin (1.159 min), zeaxanthin (1.335), β-apo-8'-carotenal (2.86 min), ergosterol (3.11 min), lycopene (3.69 min), β-Carotene (4.02 min), and phytoene (4.13 min). Astaxanthin, zeaxanthin, β-apo-8'-carotenal, lycopene and β-Carotene are detected at 475 nm, whereas ergosterol and phytoene are detected at 286 nm.

TABLE 45

Mobile Phases and Flow Rates for Ubiquinone Resolution

| Time (min) | Flow (mL/min) | % A | % B | % C | % D | Curve |
|---|---|---|---|---|---|---|
|  | 0.50 | 0.0 | 20.0 | 0.0 | 80.0 |  |
| 3.00 | 1.00 | 20.0 | 0.0 | 0.0 | 80.0 | 6 |
| 4.50 | 1.00 | 80.0 | 0.0 | 20.0 | 0.0 | 6 |
| 5.50 | 1.00 | 0.0 | 0.0 | 60.0 | 40.0 | 6 |
| 6.50 | 1.00 | 0.0 | 0.0 | 80.0 | 20.0 | 6 |
| 7.50 | 1.00 | 0.0 | 0.0 | 100.0 | 0.0 | 6 |
| 8.50 | 1.00 | 0.0 | 0.0 | 100.0 | 0.0 | 6 |
| 9.50 | 1.00 | 0.0 | 20.0 | 0.0 | 80.0 | 6 |
| 10.50 | 0.50 | 0.0 | 20.0 | 0.0 | 80.0 | 6 |

Example 5

Engineering of PHB Biosynthetic Pathway Genes Results in Increased Para-Hydroxybenzoic Acid Production Production of para-hydroxybenzoic acid (PHB) is increased by overexpression of a heterologous 3-deoxy-D-arabino-heptulosonate-7-phosphate (DAHP) synthase and a heterologous chorismate lyase (UbiC). Both genes are codon-optimized variants of the *Erwinia carotovora* coding sequences. The DAHP synthase is based on the amino acid sequence of that found in *Erwinia* is expressed in *Yarrowia lipolytica*, using nucleotide sequences with the appropriate *Yarrowia* codon bias, and containing a P148L substitution. The P148L substitution can be employed to alleviate tyrosine-mediated allosteric regulation of the *Erwinia* DAHP synthase. The following sequences are synthesized:

```
J: DAHP E. carotovora (optimized)(AroF with P148L
substitution)
5'-TTCTAGACACAAAAATGCAGAAGGACTCTCTGAACAACATCAACATC
TCTGCCGAGCAGGTGCTGATCACCCCCGACGAGCTGAAGGCCAAGTTCCC
CCTGAACGACGTGGAGCAGCGAGACATCGCCCAGGCCCGAGCCACCATCG
CCGACATCATCCACGGCCGAGACGACCGACTGCTGATCGTGTGTGGCCCC
TGTTCTATCCACGACACCGACGCCGCCCTGGAGTACGGCCGACGACTGCA
GCTGCTGGCCGCCGAGCTGAACGACCGACTGTACATCGTGATGCGAGTGT
ACTTCGAGAAGCCCCGAACCACCGTGGGCTGGAAGGGCCTGATCAACGAC
CCCTTCATGGACGGCTCTTTCGACGTGGAGTCTGGCCTGCACATCGCCCG
AGGCCTGCTGCTGCAGCTGGTGAACATGGGCCTGCCCCTGGCCACCGAGG
CCCTGGACCTGAACTCTCCCCAGTACCTGGGCGACCTGTTCTCTTGGTCT
GCCATCGGCGCCCGAACCACCGAGTCTCAGACCCACCGAGAGATGGCCTC
TGGCCTGTCTATGCCCGTGGGCTTCAAGAACGGCACCGACGGCTCTCTGG
GCACCGCCATCAACGCCATGCGAGCCGCCGCCATGCCCCACCGATTCGTG
GGCATCAACCAGACCGGCCAGGTGTGTCTGCTGCAGACCCAGGGCAACGG
CGACGGCCACGTGATCCTGCGAGGCGGCAAGACCCCCAACTACTCTGCCA
GGACGTGGCCGAGTGTGAGAAGCAGATGCAGGAGGCCGGCCTGCGACCCG
CCCTGATGATCGACTGTTCTCACGGCAACTCTAACAAGGACTACCGACGA
CAGCCCCTGGTGGTGGAGTCTGCCATCGAGCAGATCAAGGCCGGCAACCG
ATCTATCATCGGCCTGATGCTGGAGTCTCACCTGAACGAGGGCTCTCAGT
CTTCTGAGCAGCCCCGATCTGACATGCGATACGGCGTGTCTGTGACCGAC
GCCTGTATCTCTTGGGAGTCTACCGAGACCCTGCTGCGATCTGTGCACCA
GGACCTGTCTGCCGCCCGAGTGAAGCACTCTGGCGAGTAACGCGT K: Chorismate lyase E. carotovora (optimized)
(UbiC)
5'-TTCTAGACACAAAAATGTCTGACGACGCCTCTACCCTGCTGCGAACC
ATCTCTTGGTTCACCGAGCCCCCCTCTGTGCTGCCCGAGCACATCGGCGA
CTGGCTGATGGAGACCTCTTCTATGACCCAGCGACTGGAGAAGTACTGTG
CCCAGCTGCGAGTGACCCTGTGTCGAGAGGGCTTCATCACCCCCCAGATG
CTGGGCGAGGAGCGAGACCAGCTGCCCGCCGACGAGCGATACTGGCTGCG
AGAGGTGGTGCTGTACGGCGACGACCGACCCTGGCTGTTCGGCCGAACCA
TCGTGCCCCAGCAGACCCTGGAGGGCTCTGGCGCCGCCCTGACCAAGATC
```

```
GGCAACCAGCCCCTGGGCCGATACCTGTTCGAGCAGAAGTCTCTGACCCG
AGACTACATCCACACCGGCTGTTGTGAGGGCCTGTGGGCCCGACGATCTC
GACTGTGTCTGTCTGGCCACCCCCTGCTGCTGACCGAGCTGTTCCTGCCC
GAGTCTCCCGTGTACTACACCCCCGGCGACGAGGGCTGGCAGGTGATCTA
ACGCGT
```

The above sequences are cleaved with MluI and XbaI. Sequence J is inserted into NheI- and MluI-cleaved pMB4603, and sequence K is inserted into NheI- and MluI-cleaved pMB4691, placing the genes under the control of the *Y. lipolytica* TEF1 promoter, and adjacent to a functional *Y. lipolytica* LEU2 (J) or URA43 (K) gene. These plasmids are designated tef-aroF P148L (from sequence J) and tef-ubiC (from sequence K). They can be integrated sequentially, by cleavage of tef-aroF P148L with SspI and of tef-ubiC with SalI, into the genome of *Y. lipolytica* strain ATCC201249 (MATA ura3 leu2 lys8), and screened for confirmation of homologous integration as well as for increased PHB and ubiquinone production.

Example 6

Production of CoQ10 in *Yarrowia lipolytica* Strains Harboring Multiple Exogenous Ubiquinogenic Pathway Genes The PHB overproducing strain produced in Example 5 is mated with COQ10-producing strains described in Example 1 or Example 2, and diploids are selected on minimal medium. Upon meiosis and sporulation, haploid recombinants may be selected that harbor all four heterologous genes: AroF P148L, ubiC, dpdpS, and phbPPt. Genotypes of selected segregants can be confirmed by Southern blotting and polymerase chain reaction (PCR) analysis. Furthermore, increased production of CoQ10 in the selected recombinants is assessed as described in prior examples. In addition, segregants can be chosen that also harbor an ade1 auxotrophy to facilitate further manipulation.

Example 7

Decreasing Carbon Flow to the Competing Sterol Pathway Results in Enhanced Ubiquinone Production In order to partially inactivate the ERG9 gene encoding squalene synthase, the neighboring FOL3 gene is disrupted, resulting in a folinic acid requirement. This strain is then transformed with a mutagenized fragment of DNA partially spanning the two genes, and Fol+ transformants are screened for decreased squalene synthase activity.

The following oligonucleotides are synthesized:

```
5'-CCTTCTAGTCGTACGTAGTCAGC[L];

5'-CCACTGATCTAGAATCTCTTTCTGG[M].
```

They are used to amplify a 2.3 kb fragment from *Y. lipolytica* genomic DNA spanning most of the FOL3 gene, using Pfu polymerase. The fragment is cleaved with XbaI and phosphorylated, and ligated into pBluescriptSK⁻ (GenBank accession number X52330) that has been cleaved with KpnI, treated with T4 DNA polymerase (T4pol) in the presence of dNTPs, and subsequently cleaved with XbaI. The resultant plasmid, designated BS-fol3, is then cleaved with Acc65I and EcoRI, treated with T4pol as above, and ligated to the 3.4 kb EcoRV-SpeI ADEI fragment (treated with T4pol) from pMB4529.

The resulting plasmid, pBSfol3ΔAde, can be cleaved with BsiWI and XbaI to liberate a 5.5 kb fragment that is used to transform the ade1 CoQ10-overproducing strains described above to adenine prototrophy. Ade+ transformants are screened for a folinic acid requirement; and for homologous integration by PCR analysis.

Strains that harbor the resultant fol3ΔADEI allele can be transformed with a 3.5 kb DNA fragment generated by mutagenic PCR amplification using the primers:

```
5'-GGCTCATTGCGCATGCTAACATCG[N];

5'-CGACGATGCTATGAGCTTCTAGACG[P],
``` and *Y. lipolytica* genomic DNA as template. This fragment contains the N-terminal three-quarters of the FOL3 ORF and the C-terminal nine-tenths of the ERG9 ORF. Fol+ Ade⁻ transformants are screened for decreased squalene synthase activity by sensitivity to agents such as zaragozic acid, itraconazole, or fluconazole, or by resistance to reactive oxygen species-generating agents such as antimycin.

In addition, the above fragment could be cloned, and altered in such a way as to remove the 3'-untranslated region of ERG9. Replacement of the fol3ΔADEI disruption by this fragment results in decreased expression of squalene synthase [Schuldiner et al. (2005), Cell 123:507-519][Muhlrad and Parker (1999), RNA 5:1299-1307], which can be confirmed as described above. This approach may also be used in a Fol+ Ade⁻ strain, using the ADEI marker to disrupt the ERG9 3'-UTR.

Partially defective ERG9 alleles can also be identified in *S. cerevisiae* using plasmid shuffling techniques [Boeke et al. (1987), Methods Enzymol. 154:164-175], and using drug sensitivities as a phenotype. Defective genes can be transferred to *Y. lipolytica* using standard molecular genetic techniques.

Example 8

Expression of a Truncated Form of HMG-CoA Reductase to Elevate CoQ10 Production

In order to further increase CoQ10 production, carbon flow through the isoprenoid pathway is enhanced by introducing a truncated variant of the *Y. lipolytica* HMG-CoA reductase gene, which also encodes a 77 amino acid leader sequence derived from *S. cerevisiae* Hmg1.

The following oligonucleotides are synthesized:

```
5'-TTCTAGACACAAAAATGGCTGCAGACCAATTGGTGA[Q];

5'-CATTAATTCTTCTAAAGGACGTATTTTCTTATC[R];

5'-GTTCTCTGGACGACCTAGAGG[S];

5'-CACACACGCGTACACCTATGACCGTATGCAAAT[T].
```

Q and R are used to amplify a 0.23 kb fragment encoding Met-Ala followed by residues 530 to 604 of the Hmg1 protein of *S. cerevisiae*, using genomic DNA as template. S and T are used to amplify a 1.4 kb fragment encoding the C-terminal 448 residues of the Hmg1 protein of *Y. lipolytica*, using genomic DNA as template. These fragments are ligated to the appropriate cloning vector, and the resultant plasmids, designated pQR and pST, are verified by sequencing. The QR fragment is liberated with XbaI and AseI, and the ST fragment is liberated with MaeI and MluI. These fragments are then ligated to the ADE1 tef1p expression vector pMB4629 cut with NheI and MluI.

The resulting plasmid, pTefHMG, can be cleaved with SnaBI, BbvcI, or Bsu36I to direct integration at the ade1 locus, or with BamHI to direct integration at the HMG1 locus, of the CoQ10-producing strains described above, restoring them to adenine prototrophy. Ade+ transformants are screened for increased CoQ10 production.

Alternatively, the native HMG1 gene from *Y. lipolytica* may be modified through truncation, and without *S. cerevisiae* sequences, by amplifying *Y. lipolytica* genomic DNA with primer T above and

T2

```
5'-CACACTCTAGACACAAAAATGACCCAGTCTGTGAAGGTGG
``` yielding a 1.5 kb fragment that is cleaved with XbaI and MluI and ligated to pMB4629 cut with NheI and MluI to create pMB4637. pMB4637 may be cut with SnaBI, Bsu36I, or BbvCI to direct integration at the ade1 locus, or with BamHI to direct integration at the HMG1 locus, of the CoQ10-producing strains described above, restoring them to adenine prototrophy. Ade+ transformants are screened for increased CoQ10 production.

Example 9

Constructing an Oleaginous Strain of *Saccharomyces cerevisiae*

Genes encoding the two subunits of ATP-citrate lyase from *N. crassa*, the AMP deaminase from *Saccharomyces cerevisiae*, and the cytosolic malic enzyme from *M. circinelloides* are overexpressed in *S. cereviseae* strains in order to increase the total lipid content. Similar approaches to enhance lipid production could be employed in other host organisms such as *Xanthophyllomyces dendrorhous* (*Phaffia rhodozyma*), using the same, homologous, or functionally similar oleaginic polypeptides.

Qiagen RNAEasy kits (Qiagen, Valencia, Calif.) are used to prepare messenger RNA from lyophilized biomass prepared from cultures of *N. crassa*. Subsequently, RT-PCR is performed in two reactions containing the mRNA template and either of the following primer pairs.

```
acl1:
1fwd:  5'  CACACGGATCCTATAatgccttccgcaacgaccg
1rev:  5'  CACACACTAGttaaatttggacctcaacacgaccc acl2:
2fwd:  5'  CACACGGATCCAATATAAatgtctgcgaagagcatcctcg
2rev:  5'  CACACGCATGCttaagcttggaactccaccgcac
```

The resulting fragment from the acl1 reaction is cleaved with SpeI and BamHI, and that from the acl2 reaction is cleaved with BamHI and SphI, and both are ligated together into YEp24 that has been digested with NheI and SphI, creating the plasmid "p12". The bidirectional GAL1-10 promoter is amplified from *S. cerevisiae* genomic DNA using the primers.

```
gal10:
5'  CACACGGATCCaattttcaaaaattcttacttttttttggatggac gal1:
5'  CACACGGATCCttttttctccttgacgttaaagtatagagg,
``` and the resulting 0.67 kb fragment is cleaved with BamHI and ligated in either orientation to BamHI-digested "p12" to create "p1gal2" and "p2gal1", containing GAL1-acl1/GAL10-acl2 and GAL10-acl1/GAL1-acl2, respectively (Genbank accession: acl1: CAB91740.2; acl2: CAB91741.2).

In order to amplify the *S. cereviseae* gene encoding AMP deaminase and a promoter suitable for expressing this gene, *S. cerevisiae* genomic DNA is amplified using two primer pairs in separate reactions:

```
AMD1 ORF:
AMD1FWD:
5'  CACACGAGCTCAAAAatggacaatcaggctacacagag

AMD1rev:
5'  CACACCCTAGGtcactttcttcatggttctcttgaaattg

GAL7p:
gal7prox:
5'  CACACGAGCTCggaatattcaactgttttttttatcatgttgatg gal7dist:
5'  CACACGGAtccttcttgaaaatatgcactctatatcttttag,
```

The resulting fragment from the AMD1 reaction (2.4 kb) is cleaved with SacI and AvrII, and that from the GAL7 reaction (0.7 kb) is cleaved with BamHI and SphI, and both are ligated together into YEp13 that has been digested with NheI and BamHI, creating the plasmid "pAMPD". This plasmid carries the *S. cerevisiae* gene, AMD1, encoding AMP deaminase, under the control of the galactose-inducible GAL7 promoter.

Messenger RNA is prepared from lyophilized biomass of *M. circinelloides*, as described above, and the mRNA template is used in a RT-PCR reaction with two primers:

```
MAEfwd:
5'  CACACGCTAGCTACAAAatgttgtcactcaaacgcatagcaac

MAErev:
5'  CACACGTCGACttaatgatctcggtatacgagaggaac,
``` and the resulting fragment is cleaved with NheI and SalI, and ligated to XbaI- and XhoI-digested pRS413TEF (Mumberg, D. et al. (1995) Gene, 156:119-122), creating the plasmid "pTEFMAE", which contains sequences encoding the cytosolic NADP+-dependant malic enzyme from *M. circinelloides* (E.C. 1.1.1.40; mce gene; Genbank accession: AY209191) under the control of the constitutive TEF1 promoter.

The plasmids "p1gal2", "pAMPD", and "pTEFMAE" are sequentially transformed into a strain of *S. cereviseae* to restore prototrophy for uracil ("p1gal2"), leucine ("pAMPD"), and histidine ("pTEFMAE") (Guthrie and Fink Methods in Enzymology 194:1-933, 1991). The resulting transformants are tested for total lipid content following shake flask testing (e.g., 20 ml cultures in 125 ml flasks grown at 30° C. for 72-96 hour cultures) in either synthetic complete (SC) medium lacking uracil, leucine and histidine or in a 2-step fermentation process. In the 2-step process, 1.5 ml of cells from an overnight 2 ml roll tube culture containing SC medium lacking uracil, leucine and histidine are centrifuged, washed in distilled water, and resuspended in 20 ml of a nitrogen-limiting medium suitable for lipid accumulation (30 g/L glucose, 1.5 g/L yeast extract, 0.5 g/L NH$_4$Cl, 7 g/L KH$_2$PO$_4$, 5 g/L Na$_2$HPO$_4$-12H$_2$O, 1.5 g/L MgSO$_4$-7H$_2$O, 0.08 g/L FeCl$_3$-6H$_2$O, 0.01 g/L ZnSO$_4$-7H$_2$O, 0.1 g/L CaCl$_2$-2H$_2$O, 0.1 mg/L MnSO$_4$-5H$_2$O, 0.1 mg/L CuSO$_4$-5H$_2$O, 0.1 mg/L Co(NO$_3$)$_2$-6H$_2$O; pH 5.5 (J Am Oil Chem Soc 70:891-894 (1993)).

Intracellular lipid content of the modified and control *S. cerevisiae* strains is analyzed using the fluorescent probe, Nile Red (J Microbiol Meth (2004) 56:331-338). In brief, cells diluted in buffer are stained with Nile Red, excited at 488 nm, and the fluorescent emission spectra in the wavelength region of 400-700 nm are acquired and compared to the corresponding spectra from cells not stained with Nile Red. To confirm results from the rapid estimation method, the total lipid content is determined by gas chromatographic analysis of the total fatty acids directly transmethylesterified from dried cells, as described (Appl Microbiol Biotechnol. 2002 November; 60(3):275-80). Yeast strains expressing multiple oleaginic polypeptides produce elevated total lipid (for example, in the range of 17% and 25% dry cell weight basis) following growth in YPD and lipid accumulation medium when compared to non-transformed *S. cerevisiae* strains which may, for example, produce in the range of 6% and 10% total lipid after growth in YPD and lipid accumulation medium.

Example 10

*Y. lipolytica* Oleaginic and Isoprenoid Biosynthesis Genes

FIG. 11 is a list of *Y. lipolytica* genes representing various polypeptides (e.g. oleaginic and isoprenoid biosynthesis peptides) useful in the fungal strains and methods described herein. The Genbank accession number and GI number is given for each polypeptide in addition to oligo pairs which can be used to amplify the coding region for each gene from *Y. lipolytica* genomic DNA or cDNA. Resulting PCR fragments can be cleaved with restriction enzyme pairs (e.g. depending on what site is present within the oligo sequence, XbaI/MluI or NheI/MluI or XbaI/AscI or NheI/AscI) and inserted into expression vectors (e.g. fungal expression vectors including *Y. lipolytica* expression vectors such as MB4629 and MB4691 described herein).

The DNA and proteins they encode of the *Y. lipolytica* genes represented in FIG. 11 are as follows (intron sequence is underlined):

YALI0F30481g
DNA:
atgtcgcaaccccagaacgttggaatcaaagccctcgagatctacgtgcc
ttctcgaattgtcaaccaggctgagctcgagaagcacgacggtgtcgctg
ctggcaagtacaccattggtcttggtcagaccaacatggcctttgtcgac
gacagagaggacatctattcctttgccctgaccgccgtctctcgactgct
caagaacaacaacatcgaccctgcatctattggtcgaatcgaggttggta
ctgaaaccttctggacaagtccaagtccgtcaagtctgtgctcatgcag
ctctttggcgagaacagcaacattgagggtgtggacaacgtcaacgcctg
ctacggaggaaccaacgccctgttcaacgctatcaactgggttgagggtc
gatcttgggacggccgaaacgccatcgtcgttgccggtgacattgccctc
tacgcaaagggcgctgcccgacccaccggaggtgccggctgtgttgccat
gctcattggccccgacgctcccctggttcttgacaacgtccacggatctt
acttcgagcatgcctacgatttctacaagcctgatctgacctccgagtac
ccctatgttgatggccactactccctgacctgttacacaaaggccctcga
caaggcctacgctgcctacaacgcccgagccgagaaggtcggtctgttca
aggactccgacaagaagggtgctgaccgatttgactactctgccttccac
gtgcccacctgcaagcttgtcaccaagtcttacgctcgacttctctacaa
cgactacctcaacgacaagagcctgtacgagggccaggtccccgaggagg
ttgctgccgtctcctacgatgcctctctcaccgacaagaccgtcgagaag
accttccttggtattgccaaggctcagtccgccgagcgaatggccttc -continued
tctccagggacccaccaacaccggtaacatgtacaccgcctctgtgtacg
cttctctcatctctctgctgacttttgtccccgctgagcagctgcagggc
aagcgaatctctctcttctcttacggatctggtcttgcttccactcttt
ctctctgaccgtcaagggagacatttctcccatcgtcaaggcctgcgact
tcaaggctaagctcgatgaccgatccaccgagactcccgtcgactacgag
gctgccaccgatctccgagagaaggcccacctcaagaagaactttgagcc
ccagggagacatcaagcacatcaagtctggcgtctactacctcaccaaca
tcgatgacatgttccgacgaaagtacgagatcaagcagtag Protein:
Msqpqnvgikaleiyvpsrivnqaelekhdgvaagkytiglgqtnmafvd
drediysfaltavsrllknnnidpasigrievgtetlldksksvksvlmq
lfgensniegvdnvnacyggtnalfnainwvegrswdgrnaivvagdial
yakgaarptggagcvamligpdaplvldnvhgsyfehaydfykpdltsey
pyvdghysltcytkaldkayaaynaraekvglfkdsdkkgadrfdysafh
vptcklvtksyarllyndylndkslyegqvpeevaavsydasltdktvek
tflgiakaqsaermapslqgptntgnmytasvyaslislltfvpaeqlqg
krislfsygsglastlfsltvkgdispivkacdfkaklddrstetpvdye
aatdlrekahlkknfepqgdikhiksgvyyltniddmfrrkyeikq YALI0B16038g
DNA:
atggactacatcatttcggcgccaggcaaagtgattctatttggtgaaca
tgccgctgtgtttggtaagcctgcgattgcagcagccatcgacttgcgaa
catacctgcttgtcgaaaccacaacatccgacaccccgacagtcacgttg
gagtttccagacatccacttgaacttcaaggtccaggtggacaagctggc
atctctcacagcccagaccaaggccgaccatctcaattggtcgactccca
aaactctggataagcacattttcgacagcttgtctagcttggcgcttctg
gaagaacctgggctcactaaggtccagcaggccgctgttgtgtcgttctt
gtacctctacatccacctatgtccccttctgtgtgcgaagattcatcaa
actgggtagttcgatcaacgctgcctatcggcgcgggcctgggctcttcc
gcatccatttgtgtctgtttggctgcaggtcttctggttctcaacggcca
gctgagcattgaccaggcaagagatttcaagtccctgaccgagaagcagc
tgtctctggtggacgactggtccttcgtcggtgaaatgtgcattcacggc
aaccccgtcgggcatcgacaatgctgtggctactcagggaggtgctctgtt
gttccagcgacctaacaaccgagtccctcttgttgacattcccgagatga
agctgctgcttaccaatacgaagcatcctcgatctaccgcagacctggtt
ggtggagtcggagttctcactaaagagtttggctccatcatggatcccat
catgacttcagtaggcgagattctccaaccaggccatggagatcatttcta
gaggcaagaagatggtggaccagtctaaccttgagattgagcagggtatc
ttgcctcaacccacctctgaggatgcctgcaacgtgatggaagatggagc
tactcttcaaaagttgagagatatcggttcggaaatgcagcatctagtga
gaatcaatcacggcctgcttatcgctatgggtgtttcccacccgaagctc
gaaatcattcgaactgcctccattgtccacaacctgggtgagaccaagct
cactggtgctggaggaggaggttgcgccatcactctagtcacttctaaag
acaagactgcgacccagctggaggaaaatgtcattgctttcacagaggag
atggctacccatggcttcgaggtgcacgagactactattggtgccagagg
agttggtatgtgcattgaccatccctctctcaagactgttgaagccttca
agaaggtggagcgggcggatctcaaaaacatcggtccctggacccattag Protein:
mdyiisapgkvilfgehaavfgkpaiaaaidlrtyllvetttsdtptvtl
efpdihlnfkvqvdklasltaqtkadhlnwstpktldkhifdslsslall
eepgltkvqqaavvsflylyihlcppsvcedssnwvvrstlpigaglgss
asicvclaagllvlngqlsidqardfksltekqlslvddwsfvgemcihg
npsgidnavatqggallfqrpnnrvplvdipemkllltnthprstadlv
ggvgvltkefgsimdpimtsvgeisnqameiisrgkkmvdqsnleieqgi
lpqptsedacnvmedgatlqklrdigsemqhlvrinhglliamgvshpkl
eiirtasivhnlgetkltgaggggcaitlvtskdktatqleenviaftee
mathgfevhettigargvgmcidhpslktveafkkveradlknigpwth YALI0E06193g
DNA:
atgaccacctattcggctccgggaaaggccctcctttgcggcggttattt
ggttattgatccggcgtattcagcatacgtcgtgggcctctcggcgcgta
tttacgcgacagtttcggcttccgaggcctccaccacctctgtccatgtc
gtctctccgcagtttgacaagggtgaatggacctacaactacacgaacgg
ccagctgacggccatcggacacaacccatttgctcacgcggccgcattca
ccgttctgcattacgttcctcctcgaaacctccacatcaacatcagcatc
aaaagtgacaacgcgtaccactcgcaaattgacagcacgcagagaggcca
gtttgcataccacaaaaaggcgatccacgaggtgcctaaaacgggcctcg
gtagctccgctgctcttaccaccgttcttgtggcagctttgctcaagtca
tacggcattgatcccttgcataacacccaacctcgttcacaacctgtccca
ggttgcacactgctcgcacagaagaagattgggtctggatttgacgtgg
cttcggccgtttgtggctctctagtctatagacgtttcccggcggagtcc
gtgaacatggtcattgcagctgagggacctcgcgaatacggggctctgttg
agaactaccgttaatcaaaagtggaaggtgactctgaaccatccttctt
gccgccgggaatcagcctgcttatggagacgtccagggaggatctgaga
ctccaggtatggtggccaaggtgatggcatggcgaaaagcaaagccccga
gaagccgagatggtgtggagagatctcaacgctgccaacatgctcatggt
caagttgttcaacgacctgcgcaagctctctctcactaacaacgaggcct -continued
```
acgaacaacttttggccgaggctgctcctctcaacgctctaaagatgata
atgttgcagaaccctctcggagaactagcacgatgcattatcactattcg
aaagcatctcaagaagatgacacgggagactggtgctgctattgagccgg
atgagcagtctgcattgctcaacaagtgcaacacttatagtggagtcatt
ggaggtgttgtgcctggagcaggaggctacgatgctatttctcttcggt
gatcagctctacggtgaacaatgtcaagcgagagagccagggagtccaat
ggatggagctcaaggaggagaacgagggtctgcggctcgagaagggttc
aagtag
```

Protein:
```
mttysapgkallcggylvidpaysayvvglsariyatvsaseasttsvhv
vspqfdkgewtynytngqltaighnpfahaavntvlhyvpprnlhinisi
ksdnayhsqidstqrgqfayhkkaihevpktglgssaalttvlvaallks
ygidplhnthlvhnlsgvahcsaqkkigsgfdvasavcgslvyrrfpaes
vnmviaaegtseygallrttvnqkwkvtlepsflppgisllmgdvqggse
tpgmvakvmawrkakpreaemvwrdlnaanmlmvklfndlrklsltnnea
yeqllaeaaplnalkmimiqnplgelarciitirkhlkkmtretgaaiep
deqsallnkcntysgviggvvpgaggydaisllvissstvnnvkresqgvq
wmelkeeneglrlekgtk
```

YALI0F05632g
DNA:
```
atgatccaccaggcctccaccaccgctccggtgaacattgcgacactcaa
gtactggggcaagcgagaccctgctctcaatctgcccactaacaactcca
tctccgtgactttgtcgcaggatgatctgcggacccctcaccacagcctcg
tgttccctcgattcacccaggacgagctgtggctcaatggcaagcagga
ggacgtgagcggcaaacgtctggttgcgtgtttccgagagctgcgggctc
tgcgacacaaatggaggactccgactcttctctgcctaagctggccgat
cagaagctcaagatcgtgtccgagaacaacttcccccaccgccgctggtct
cgcctcatcggctgctggctttgccgcgctgatccgagccgttgcaaatc
tctacgagctccaggagaccccggagcagctgtccattgtggctcgacag
gctctggatccgcctgtcgatctctctacggaggctacgtggcatggga
aatgggcaccgagtctgacggaagcgactcgcgagcggtccagatcgcca
ccgccgaccactggcccgagatgcgagccgccatcctcgtgtctctgccg
acaagaaggacaacgtcgtccactaccgtatgcaggtgactgtgcaact
tctccccctcttcaaggagcgagtcaccactgtggttcccgagcggtttgc
ccagatgaagagtcgattctggaccgagactttcccccacctttgccgagc
tcaccatgcgagactcaaaccagttccacgccacctgtctggactcgtat
cctccattttctacctcaacgacgtgtcgcagccttccattcgggtagt
tgaggccatcaacaaggctgccggagccaccattgccgcctacacctttg
atgctgaccccaactgtgtcatctactacgaggacaagaacgaggagctg
gttctggggtgctctcaaggccattctgggccgtgtggagggatgggaaga
gcaacagtctgtggacgccaagaagattgatgttgacgagcggtggagt
ccgagctggccaacgaattcagcgggtgatcctaccaagggtggagga
gatcccgtgaagaccgctgagtcgcttatcaacgaggatggttctctgaa
gaacagcaagtag
```

Protein:
```
mihqastapvniatlkywgkrdpalnlptnnsisvtlsqddlrtlttas
cspdftqdelwlngkqedvsgkrlvacfrelralrhkmedsdsslpklad
qklkivsennfptaaglassaagfaaliravanlyelqetpeqlsivarq
gsgsacrslyggyvawemgtesdgsdsravqiatadhwpemraailvvsa
dkkdtsstgmqvtvhtsplfkervttvvperfaqmkksildrdfptfae
ltmrdsnqfhatcldsyppifylndvsrasirvveainkaagatiaaytf
dagpncviyyedkneelvlgalkailgrvegwekhqsvdakkidvderwe
selangiqrviltkvggdpvktaeslinedgslknsk
```

YALI0F04015g
DNA:
```
Atgacgacgtcttacagcgacaaaatcaagagtatcagcgtgagctctgt
ggctcagcagtttcctgaggtggcgccgattgcgacgtgtccaaggcta
gccggcccagcacggagtcgtcggactcgtcggcaagctatttgatggc
cacgacgaggagcagatcaagctgatggacgagatctgtgtggtgctgga
ctgggacgacaagccgattggcggcgcgtccaaaaagtgctgtcatctga
tggacaacatcaacgacggactggtgcatcggggcctttccgtgttcatg
ttcaacgaccgcggtgagctgctctgcagcagcgggcggcggaaaaaat
caccctttgccaacatgtggaccaacacgtgctgctcgcatcctctggcgg
tgccagcgagatgggcggtctggatctggagtccccgatccaggggcc
aaaaacgccgcggttccggcagacaagttccatttcctccaccgatcccactacgccg
cgccctcctcgggccctgggcgcagcacgagattgactacattctgtt
gtccggggcgacccgagctcaagtggtggcaacaggtcgcgatac
cgtgtgggtgtcgcagcaggcgtcaaggactcaagtatggccgatcccaagc
tggttttcacccttggttccggctcatttgtgagcaggcgctgtttccc
tggtgggaccagttggacaatctgcccgcgggcgatgacgagattcggc
gtggatcaagtag
```

Protein:
```
mttsysdkiksisvssvaqqfpevapiadvskasrpstessdssaklfdg
hdeeqiklmdeicvvldwddkpiggaskkcchlmdnindglvhrafsvfm
fndrgellllqqraaekitfanmwtntccshplavpsemggldlesriqqa
```

-continued
```
knaavrklehelgidpkavpadkfhfltrihyaapssgpwgeheidyilf
vrgdpelkvvanevrdtvwvsqqglkdmmadpklvftpwfrliceqalfp
wwdqldnlpagddeirrwik
```

YALI0E05753
DNA:
```
atgtccaaggcgaaattcgaaagcgtgttccccccgaatctccgaggagct
ggtgcagctgctgcgagacgagggtctgcccaggatgccgtgcagtggt
tttccgactccacttcagtacaactgtgtgggtggaaagctcaaccgaggc
ctgtctgtggtcgacacctaccagctactgaccggcaagaaggagctcga
tgacgaggagtactaccgactcgcgctgctcggctggctgattgagctgc
tgcaggcgttttcctcgtgtcggacgacattatggatgagtccaagacc
cgacgaggccagccctgctggtacctcaagcccaaggtcggcatgattgc
catcaacgatgcttttcatgctagagagtgcatcactacattctgcttaaga
agcatttccgacaggagaagtactacattgaccttgtcgagctgttccac
gacatttcgttcaagaccgagctgggccagctggtggatcttctgactgc
ccccgaggatgaggttgatctcaaccggttctctctggacaagcactcct
ttattgtcgatacaagactgcttactactccttctacctgcccgttgtt
ctagccatgtacgtggccggcattaccaacccccaaggacctgcagcaggc
catgatgtgctgatccctctcggagagtacttccaggtccaggacgact
accttgacaactttggagaccccgagttcattggtaagatcggcaccgac
atccaggacaacaagtgctcctggctcgtgtaacaaagcccttcaagaggc
caccccgagcagcgacagatcctcgaggacaactacggcgtcaaggaca
gtccaaggagctcgtcatcaagaaactgtatgatgacatgaagattgag
caggactaccttgactacgaggaggagggttgttggcgacatcaagaagaa
gatcgagcaggttgacgagagccgaggcttcaagaaggaggtgctcaacg
cttttcctcgccaagatttacaagcgacagaagtag
```

Protein:
```
mskakfesvfpriseelvqllrdeglpqdavqwfsdslqyncvggklnrg
lsvvdtyqlltgkkelddeeyyrlallgwliellqafflvsddimdeskt
rrgqpcwylkpkvgmiaindafmlesgiyillkkhfrqekyyidlvelfh
disfktelgqlvdlltapedevdlnrfsldkhsfivryktayysfylpvv
lamyvagitnpkdlqqamdvliplgeyfqvqddyldnfgdpefigkigtd
iqdnkcswlvnkalqkatpeqrqilednygvkdkskelvikklyddmkie
qdyldyeeevvgdikkkieqvdesrgfkkevlnaflakiykrqk
```

YALI0E18634g
DNA:
```
atgttacgactacgaaccatgcgacccacacagaccagcgtcagggcggc
gcttgggccaccgccgcggcccgaaacatgtcctcctccagccctcca
gcttcgaatactcgtcctacgtcaagggcacgcgggaaatcggccaccga
aaggcgcccacaaactcgtgcggttgagggcccatctacgtgggctt
cgacgcattcgtcttctcaacctgccgcatctcaacaagggctcgggat
tccccctcaacgagccgacgggaattcagactcagtggtcttctgccctct
gccgaagccaccctggaggaacaggtcgaccgagcataccaacaattcaa
aaagtgcgactcccttagccaaaaacgggttctgcacctcgctcaagt
tccaaaacgaggtgctctactacgccctgctgctcaagcacgttaaggag
gtcttcccatcatctataccgactcagggagaagccattgaacagta
ctcgcggctgttccggcggcccgaaggctgcttcctcgacatcaccagtc
cctacgacgtggaggagctgtgggagcgttggagaccatgacgacatt
gactacattgtcgtgactgactccgaggtattctcggaattggaagacca
aggagtgggcggtattggtatttccatcgccaagctggctctcatgactc
tatgtgctggagtcaacccctcacgagtcattcctgtggttctggatacg
ggaaccaacaaccaggagctgctcacgaccccctgtatctcggccgacg
aatgccccgagtgcgaggaaagcagtacgacgacttcatcgacaactttg
tgcactctgcccgaaggctgtatcccaaggcggtgatccattctcgaggc
tttgggctcgctaacgcacacaagatcctcgacaagtatcgaccggagat
ccctgcttcaacgacgacatccaggcactggagccgtcactttggcct
ccatccggccgctctcaagggtcgtggcaaaaatatcacagatactcga
attcgtctacgagctggttcgccggcatgggtattgctgaacagtt
ctatgataacctggttgccaggtctcgacgacaagactcgcgacaaa
acatctttctcatggaccgaccgggtctactgaccaccgcacttaccgac
gagcagatgagcgacgtgcagaagccgtttgcaaggacaaggccaatta
cgagggagtggacaccaaggcgtggacacgtggttgctgccgtcaagc
cccatattctcattggatgttccactcagccggcgcctttaacgagaag
gtcgtcaaggagatgctcaaacacaccctgacccatcattctccctct
ttcaaccccaacacgtcttcatgaggctgtccctgcagatctgtaagt
ggacgacgcaagctctggttgccaccgggtcgcctttgacccagtc
aacggcaaggacgtctgagaacaataactgctttgttttccccggaat
cgggctgggagccattctgtctcgataaagctcatccacaccatgat
tgctgctgcacggatgcctgccgaacagcccccattctcaagaacc
acgacgagggagtacttcccgacgtagctctcatccagatcatttcggc
cgggtggcactgccgtggtcttcaggccaaggctgagggcctagccac
tgtcgaggaagagctcaagcccggcaccaaggaacatgcagattcccg
acaactttgacgagtgtctcgcctgggtcgagactcagatgtggcggcc
gtctaccggcctctcatccatgtgcgggattacgactag
```

Protein:
```
mlrlrtmrptqtsvraalgptaaarnmssspssfeyssyvkgtreighr
kapttrlsvegpiyvgfdgirllnlphlnkgsgfplnerrefrlsgllps
```

-continued aeatleeqvdrayqqfkkcgtplakngfctslkfqnevlyyalllkhvke
vfpiiytptqgeaieqysrlfrrpegcflditspydveerlgafgdhddi
dyivvtdsegilgigdqgvggigisiaklalmtlcagvnpsrvipvvldt
gtnnqellhdplylgrrmprvrgkqyddfidnfvqsarrlypkavihfed
fglanahkildkyrpeipcfnddiqgtgavtlasitaalkvlgknitdtr
ilvygagsagmgiaeqvydnlvaqgldqktarqniflmdrpgllttaltd
eqmsdvqkpfakdkanyegvdtktlehvvaavkphiligcstqpgafnek
vvkemlkhtprpiilplsnptrlheavpadlykwtdgkalvatgspfdpv
ngketsennncfvfpgiglgailsrsklitntmiaaaieclaeqapilkn
hdegvlpdvaliqiisarvatavvlqakaeglatveeelkpgtkehvqip
dnfdeclawvetqmwrpvyrplihvrdyd YALI0E11495g
DNA:
atgccgcagcaagcaatggatatcaagggcaaggccaagtctgtgcccat
gcccgaagaagacgacctggactcgcattttgtgggtcccatctctcccc
gacctcacggagcagacgagattgctggcacgtgggctgcgaagacgacg
aagacgagcttgaagaactgggaatgctgggccgatctgcgtccaacgca
ttctcttacgcggaagaacgccacctcatcgaggttgatgccaagtacag
agctcttcatggccatctgcctcatcagcactctcagagtcccgtgtcca
gatcttcgtcatttgtgcgggccgaaatgaaccacccccctcccccaccc
tccagccacacccaccaacagccagaggacgatgacgcatccactcgatc
tcgatcgtcgtctcgagcttctggacgcaagttcaacagaaacagaacca
agtcgtcgatcttcgctgagcaagggtctccagcagctcaacatgaccga
tcgctcgaagaagagccctacgagagcgatgacgatgcccgactatctgc
ggagacgacattgtctatgatgctgtacccagaaagacacctgcaagccat
atctcctactctcaaacgcacccgcaccaaggacgacatgaagaacatgt
ccatcaacgacgtcaaaatcaccaccaccacagaagatcctcttgtggcc
caggagctgccatgatgttcgaaaaggtgcagtactgccgagacctccg
agacaagtaccaaaccgtgcgctacagaaggacggagacaaccccaagg
atgacaagacactggaaaatttaccccgagcctccaccaccctcctgg
cacgagaccgaaaagcgattccgaggctcgtccaaaaaggagcaccaaaa
gaaagacccgacaatggatgaattcaaattcgaggactgcgaaatcccg
gacccaacgacatggtcttcaagcgagatcctacctgtgctctatcaggtc
tatgaggatgaaagctctctcaacgaaaataagccgttgttgccatccc
ctcaatccgacgattactacatggatctggaggatctcattgtggcttcgt
ctgacggacctgccaagtcttttgcttccgacgactgcaatatctagaa
gccaagtggaacctctactacctgctcaacgagtacacggagacaaccga
gtccaagacaaccccatcgagactttacaacgtacgaaaggtgaca
cccacgttcaccactcgcctgcatgaaccagaagcatctgctgcgattc
atcaaatacaagatgaagaactgccctgatgaagtttgtcatccaccgaga
cggtcgggagctgacactctcccaggtgttttgagtcacttaacttgactg
cctacgacctgtctatcgataccttgatatgcatgctcacaaggactcg
ttccatcgatttgacaagttcaacctcaagtacaaccctgtcggtgagtc
tcgactgcgagaaatctcctaaagaccgacaactacatccaggtcgat
acctagctgagatcacaaaggaggtgttccaggatctcgagaactcgaag
taccagatggcggagtaccgtatttccatctacggtcggtccaaggacga
gtgggacaagctggctgctgggtgctggacacaaacaatcgttttcgccca
atgttcggtggtgatccaggtgcctcgactgtacgacatttacaagaag
gctggtctggttaacacctttgccgacattgtgcagaacgtctttgagcc
tcttttcgaggtcaccaaggatcccagtacccatcccaagctgcacgtgt
tcctgcagcgagttgtgggctttgactctgtcgatgacgagtcgaagctg
gaccgacgtttccaccgaaagttcccaactgcagcatactgggacagcgc
acagaaccctccctactcgtactggcagtactatctatacgccaacatgg
cctccatcaacacctggagacgacgtttgggctatacttacttttgagttg
cgacccatgctggagacgctggtgacccagacgcatcttctctgtcacttta
tctggttgctcagggtatcaaccacggtatctgttgcgaaaggtgcctt
tcattcagtaccttactacctggaccagatcccattgccatgtctcct
gtgtccaacaatgcgctgttcctcacgttcgacaagaaccccttctactc
atacttcaagcgggtctcaacgtgtccttgtcatcgagatgatcctctgc
agtttgcttacactaaggaggctctgattgaggagtactctgtggctgcg
ctcatttacaagctttccaacgtggatatgtgtgagcttgctcgaaactc
ggtactgcaatctggctttgagcgaatcatcaaggagcattggatcggcg
aaaactacgagatccatggcccgagggcaacaccatccagaagacaaac
gtgcccaatgtcgtctggccttccgagacgagactttgacccacgagct
tgctctggtggacaagtaccaatcttgaggagtttgagcggctgcatg
gttaa Protein:
mpqqamdikgkaksvpmpeeddldshfvgpisprphgadeiagyvgcedd
edeleelgmlgrsasthfsyaeerhlievdakyralhghlphqhsqspvs
rsssfvraemnhpppppsshthqqpeddasslrsrsssagrkfhrnr
tksgsslskglqqlnmtgsleeepyesdddarlsaeddivydatqkdtck
pispsptlkrtrtkddmknmsindvkitttttedplvaqelsmmfekvqy
crdlrdkyqtvslqkdgdnpkddkthwkiypeppppswhetekrfrgsskkeh
qkkdfpmdefkfedceipgpndmvflcrdptcvyqvyedesslnenkpfv
aipsirdyymdledlivassdgpaksfafrrlqyleakwnlyyllneyte
ttesktnphrdfynvrkvdthvhhsacmnqkhllrfikykmkncpdevvi
hrdgreltlsqvfeslnltaydlsidtldmhahkdsfhrfdkfnlkynpv
gesrlreiflktdnyiqgrylaeitkevfqdlenskyqmaeyrisiygrs
kdewdklaawvldnklfspnvrwliqvprlydiykkaglvntfadivqnv feplfevtkdpsthpklhvflqrvvgfdsvddeskldrrfhrkfptaayw
dsaqnppysywqyylyanmasintwrqrlgyntfelrphageagdpehll
ctylvaqginhgillrkvpfiqylyyldqipiamspvsnnalfltfdknp
fysyfkrglnvslssddplqfaytkealieeysvaaliyklsnvdmcela
rnsvlqsgferiikehwigenyeihgpegntiqktnvpnvrlafrdetlt
helalvdkytnleeferlhg YALI0D16753g
DNA:
atgttccgaacccgagttaccggctccaccctgcgatccttctccacctc
cgctgcccgacagcacaaggttgtcgtcctggcgccaacggaggcattg
gccagccctgtctctgctgctcaagctcaacaagaacgtgaccgacctc
ggtctgtacgatctgcgaggcgcccccggcgttgctgccgatgtctccca
catcccaccaactccaccgtggccggctactctcccgacaacaacggca
ttgccgaggccctcaagggcgccaagtcggtgctgatccccgccggtgtc
ccccgaaagccccggcatgaccgagacgatctgttcaacaccaacgcctc
cattgtgcgagacctggccaaggccgtcggtgagcacgcccccgacgcct
ttgtcggagtcattgctaaccccgtcaactccaccgtcccccattgtcgcc
gaggtgctcaagtccaagggcaagtacgacccccaagaagctcttcggtgt
caccaccctcgacgtcatccgagccgagcgattcgtctcccagctcgagc
acaccaaccccaccaaggagtacttcccggttgttggcggccactccggt
gtcaccattgtcccctcgtgtccagtccgaccaccccgacattgccgg
tgaggctcgagacaagctccaccgaatccagtttggcggtgacgaggttg
tcaaggccaaggacggtgccggatccgcaccctttccatggcccaggct
gccgccgattcgccgactctctcctccgagggtgtcaacggcgagaagga
cgttgttgagccccacttttcgtcgactctcctctgttcaaggtgagggca
tcgacttcttctccaccaaggtcactcttgcctcaacggtgttgaggag
atccaccccatcggaaaggtcaacgagtacgaggagaagctcatcgaggc
tgccaaggccgatctcaagaagaacattgagaagggtgtcaactttgtca
agcagaaccccttaa Protein:
mfrtrvtgstlrsfstsaarqhkvvvlganggigqplslllklnknvtdl
glydlrgapgvaadvshiptnstvagyspdnngiaealkgaklvlipagv
prkpgmtrddlfntnasivrdlakavgehapdafvgvianpvnstvpiva
evlkskgkydpkklfgvttldviraerfvsqlehtnptkeyfpvvgshsg
vtivpivsqsdhpdiageardklvhriqfggdevvkakdgagsatlsmaq
aaarfadsllrgvngekdvveptfvdsplfkgegidffstkvtlgpngve
eihpigkvneyeeklieaakadlkkniekgvnfvkqnp YALI0D16247g
DNA:
atgacacaaacgcacaatctgttttcgccaatcaaagtgggctcttcgga
gctccagaaccggatcgttctcgcacccttgactcgaaccagagctctgc
ccggaaacgtgcctcggatcttgccacagagtactacgcacaaagagca
gcatctccaggcactctcctcatcaccgaggccacatacatctcccccgg
atctgctggatgcccattccaggagacggaatcgttccgggcatcgtga
gtgacgagcagctcgaagcatgaaaaaggtgttcaaggccgtgcacgac
cgaggatccaaaatctacgtccagctgtgggacattggacgtgtcgcatg
gtaccacaagctgcaggaactgggcaactactccctacaggcccctcag
ctatcctcagaagggagggaggagcagcgacatctcaaggctctgactcac
tgggagatcaagggcaaggtggccctctacgtcaacgctgccaagaaccc
cattgcgcaggcgctgatggcgtcgagatccactcggccaacggctacc
ttcccgacacatttctgagaagcgcctccaaccaacgaacagacgaatat
ggaggaagatcagaaccgggcccgattctcgctggagattgtcgacgc
tatcaccgaggccattgagacgacaaaaccgccatccgtctgtctccct
ggtccacttttccaggacattgaggtgaatgacaccgagaccccgcacag
ttcacatacctgtttgagcagctgcagaagcgagccgacgagggaaagca
gctggcctacgtgcatgtagttgagccccgactgtttggtcccccgagc
cctgggccaccaatgagcctttcagaaaaatttggaagggtaacttcatt
agagcaggtggatacgagacagagactgctcttgaggatgcagacaagtc
agacaacccctgattgcctttggtcgagacttcattgccaatcctgatc
tcgtccaacgccttcaagaataacgagcctttggccaagtacgacagaaca
accttctacgttccaggtgccaagggctacactgattaccctgcgtacaa
gatgtaa Protein:
mtqthnlfspikvgsselqnrivlapltrtralpgnvpsdlateyyaqra
aspgtllliteatyispgsagvpipdgivpgiwsdeqleawkkvfkavhd
rgskiyvqlwdigrvawyhklqelgnyfptgpsaipmkgeesehlkalth
weikgkvalyvnaaknaiaagadgveihsangylpdttlrsasnqrtdey
ggsienrarfsleivdaiteaigadktairlspwstfqdievndtetpaq
ftylfeqlqkradegkqlayvhvveprlfgppepwatnepfrkiwkgnfi
raggydretaledadksdntliafgrdfianpdlvqrlknneplakydrt
tfyvpgakgytdypaykm YALI0A15972g
DNA:
atggaagccaaccccgaagtccagaccgatatcatcacgctgacccggtt
cattctgcaggaacagaacaaggtgggcgcgtcgtccgcaatccccaccg
gagacttcactctgctgctcaactcgctgcagtttgccttcaagttcatt -continued
```
gcccacaacatccgacgatcgaccctggtcaacctgattggcctgtcggg
aaccgccaactccaccggcgacgaccagaagaagctggacgtgatcggag
acgagatcttcatcaacgccatgaaggcctccggtaaggtcaagctggtg
gtgtccgaggagcaggaggacctcattgtgtttgagggcgacggccgata
cgccgtggtctgcgaccccatcgacggatcctccaacctcgacgccggcg
tctccgtcggcaccattttcggcgtctacaagctccccgagggctcctcc
ggatccatcaaggacgtgctccgacccggaaggagatggttgccgccggc
tacaccatgtacggtgcctccgccaacctggtgctgtccaccggaaacgg
ctgcaacggcttcactctcgatgacctctgggagagttcatcctgaccca
ccccgatctcaagctccccgatctgcgatccatctactccgtcaacgagg
gtaactcctccctgtggtccgacaacgtcaaggactacttcaaggccctc
aagttccccgaggacggctccaagcccactcggcccgatacattggctc
catggtcgccgacgtgcaccgaaccattctctacggaggtatgtttgcct
accccgccgactccaagtccaagaagggcaagctccgacttttgtacgag
ggtttccccatggcctacatcattgagcaggccggcggtcttgccatcaa
cgacaacggcgagcgaatcctcgatcggtccccaccgagatccacgagc
gatccggcgtctggctgggctccaagggcgagattgagaaggccaagaag
taccttctgaaatga
```

Protein:
meanpevqtdiitltrfilqeqnkvgassaiptgdftlllnslqfafkfi
ahnirrstlvnliglsgtanstgddqkkldvigdeifinamkasgkvklv
vseeeqedlivfegdgryavvcdpidgssnldagvsvgtifgvyklpegss
gsikdvlrpgkemvaagytmygasanlvlstgngcngftlddplgefilt
hpdlklpdlrsiysvnegnsslwsdnvkdyfkalkfpedgskpysaryig
smvadvhrtilyggmfaypadskskkgklrllyegfpmayiieqagglai
ndngerildlvpteihersgvwlgskgeiekakkyllk YALIOE11099g
DNA:
```
atgcgactcactctgccccgacttaacgccgcctacattgtaggagccgc
ccgaactcctgtcggcaagttcaacggagccctcaagtccgtgtctgcca
ttgacctcggtatcaccgctgccaaggccgctgtccagcgatccaaggtc
cccgccgaccagattgacgagtttctgtttggccaggtgctgaccgccaa
ctccggccaggcccccgcccgacaggtggttatcaaggaggcttcccccg
agtccgtcgaggccaccaccatcaacaaggtgtgctcttccggcctcaag
accgtggctctggctgccaggccatcaaggccggcgaccgaaacgttat
cgtggccggtggaatggagtccatgtccaacacccctactactccggtc
gaggtcttgtttcggcaaccagaagctggagactccatcgtcaaggac
ggtctctgggacccctacaacaacatccacatgggcaactgctgcgagaa
caccaacaagcgagacggcatcaccgagagcagcaggacgagtacgcca
tcgagtcctaccgacgggccaacgagtccatcaagaacggcgccttcaag
gatgagattgtccccgttgagatcaagacccgaagaggcaccgtgactgt
ctccgaggacgaggagcccaagggacgcaacgccgagaagctcaagggcc
tcaagcctgtctttgacaagcagggctccgtcactgccggtaacgcctcc
cccatcaacgatggtgcttctgccgttgtcgttgcctctggcaccaaggc
caaggagctcggtaccccgtgctcgccaagattgtctcttacgcagact
cgccaccgccccattgacttaccattgctccctctctgcccattccc
gccgcctcaagaaggctggccttaccaagacgacattgccctctggaa
gatcaacgaggccttctccggtgtcgctctcgccaacctcatgcgactcg
gaattgacaagtccaaggtcaacgtcaaggagggtgctgttgctctccgc
caccccattggtgcctccggtaaccgaatcttttgtgacttttgtcaacgc
cctcaaggagggcgagtacggagttgccgccatctgcaacggtggaggag
cttccaccgccatcgtcatcaagaaggtctcttctgtcgagtag
```

Protein:
mrltlprlnaayivgaartpvgkfngalksvsaidlgitaakaavqrskv
padqidefllfgqvltansgqaparqvvikggfpesveattinkvcssglk
tvalaaqaikagdrnvivaggmesmsntpyysgrglvfgnqkledsivkd
glwdpynnihmgnccentnkrdgitreqqdeyaiesyrranesikngafl
cdeivpveiktrkgtvtvsedeepkganaeklkglkpvfdkqgsvtagna
spindgasavvvasgtkakelgtpvlakivsyadaatapidftiapslai
paallkkagltkddialweineafsgvalanlmrlgidksjvnvkggaval
ghpigasgnrifvtlvnalkegeygvaaicngggastaivikkvssve YALIOE34793g
DNA:
```
atgtctgccaacgagaacatctcccgattcgacgcccctgtgggcaagga
gcaccccgcctacgagctcttccataaccacacacgatctttcgtctatg
gtctccagcctcgagcctgccaggatgctggactttcgacttcatcgta
agcgagagaaccccctcgtggccggtgtcatctatccctcggcggccag
ttcgtcaccaagatgtactggggcaccaaggagactcttccctgtcta
ccagcaggtcgagaaggccgctgcaaagcacccgaggtcgatgtcgtcgt
caactttgcctcctctcgatccgtctactcctctaccatggagctgctcg
agtaccccagttccgaaccatcgccattattgccgagggtgtccccgag
cgacgagcccgagagatcctccacaaggcccaagaaggggtgactgaccat
cattggttccgctccggcgaggtcaccaactgcatgctcgagctcaaggt
ccgttgcctactgccaagtccggaggaatgtccaagctgagcaacaac
attatctctcacaccaccgacggtgtctacgagggtattgctattggtgt
tgaccgataccctggtactaccttcattgaccatatcctgcgatacgagg
ccgaccccaagtgtaagatcatcgtcctccttggtgaggttggtggtgtt
```

```
gaggagtaccgagtcatcgaggctgttaagaacggccagatcaagaagcc
catcgtcgcttgggccattggtacttgtgcctccatgttcaagactgagg
ttcagttcggccacgccggctccatggccaactccgacctggagactgcc
aaggctaagaacgccgccatgaagtctgctggcttctacgtccccgatac
cttcgaggacatgcccgaggtccttgccgagctctacgagaagatggtcg
ccaagggcgagctgtctcgaatctctgagcctgaggtcccccaagatcccc
attgactactcttgggccaggagcttggtcttatcggaaagcccgctgc
tttcatctccactatttccgatgaccgaggccaggagctctgtacgctg
gcatgcccatttccgaggttttcaaggaggacattggtatcggcggtgtc
atgtctctgctgttccgacgagcttgcccgactacgcctccattc
ttgagatgtcttctcatgcttactgctgaccacgtccccgccgtatccggt
gccatgaacaccattatcaccacccgagctggtaaggatctcatttcttc
cctggttgctggtctcctgaccattggtacccgattcggaggtgctcttg
acggtgctgccaccgagttcaccactgcctacgacaaggtctgtcccc
cgacagttcgttgataccatgcgaaagcagaacaagctgattcctggtat
tggccatcgagtcaagtctcgaaacaacccgatttccgagtcgagcttg
tcaaggactttgttaagaagaacttcccctccacccagctgctcgactac
gccctttgctgtcgaggaggtcaccacctccaagaaggacaacctgattct
gaacgttgacggtgctattgctgtttcttttgtcgatctcatgcgatctt
gcggtgcctttactgtggaggagactgaggactacctcaagaacggtgtc
tcaacggtctgttcgttctcggtcgatccattggtctcattgcccaccat
ctgcatcagaagcgactcaagaccggtctgtaccgacatccttgggacga
tatcaccttacctggttggccaggaggctatccagaagaagcgagtcgaga
tcagcgccggcgacgtttccaaggccaagactcgatcatag
```

Protein:
msanenisrfdapvgkehpayelfhnhtrsfvyglqpracqgmldfdfic
krenpsvagviypfggqfvtkmywgtketllpvyqqvekaaakhpevdvv
vnfassrsvyssstmelleypqfrtiaiiaegvperrareilhkaqkkgvt
iigpatvggikpgcfkvgntggmmdnivasklyrpgsvayvsksggmsne
lnniishttdgvyegiaiggdrypgttfidhilryeadpkckiivllgev
ggveeyrvieavkngqikkpivawaigtcasmtktevqfghagsmansdl
etakaknaamksagfyvpdtfedmpevlaelyekmvakgelsrisepevp
kipidyswaqelglirkpaafistisddrgqellyagmpisevfkedigi
ggvmsllwfrrrlpdyaskflemvlmtadhgpavsgamntiittragkd
lisslvaglltigtrfggaldgaatefttaydkglsprqfvdtmrkqnkl
ipgighrvksrnnpdfrvelvkdfvkknfpstqlldyalaveevttskkd
nlilnvdgaiavsfvdlmrscgaftveetedylkngvlnglfvlgrsigl
iahhldqkrlktglyrhpwdditylvgqeaiqkkrveisagdvskaktrs YALI0D24431g
DNA:
```
atgtcagcgaaatccattcacgaggccgacggcaagccctgctcgcaca
ctttctgtccaaggcgcccgtgtgggccgagcagcagcccatcaacacgt
tgaaatgggcacacccaagctggcgtctctgacgttcgaggacggcgtg
cccccgagcagatcttcgccgccgctgaaaagacctacccctggctgct
ggagctccgcgcccaagtttgtgccaagcccgaccagctcatcaagcgac
gaggcaaggccgggctgctggtactcaacaagtcgtgggaggagtgcaag
ccctggatcgccgagcgggccgccaagcccatcaacgtggagggcattga
cggagtgctgcgaacgttcctggtcgagccctttgtgccccacgaccaga
agcacgatacatcaacatccactccgtgcgagagggcgactggatc
ctcttctaccacggaggagtcgacgtcggcgacgtggacgccaaggc
cgccaagatcctcatccccgttgacattgagaacgagtaccctccaacg
ccacgctcaccaaggagctgctggcacacgtgcccgaggaccagaccag
accctgctcgacttcatcaaccggctctacgccgtctacgtcgatctga
gtttacgtatctgctggagatcaacccccctgtcgtgatccccaccgcccagg
gcgtcgaggtccactacctggatcttgccggcaagctcgaccagaccgca
gagtttgagtgcggccccaagtgggctgctgcgcggtcccccgccgctct
gggccaggtcgtcaccattgacgccggctccaccaaggtgtccatcgacg
ccggccccgccatggtcttccccgctccctttggtcgagagctggtg
gaggagcgtacattgcggagcgatcgttccaagaccggagcttctctgaa
gctgactgttctcaatgccaagggccgaatctggaccctgtggctggtg
gaggagcctccgtcgtctacgccgacgccattgcgtctgccggctttgct
gacgagctcgccaactacggcgagtactctggcgctccaacgagaccca
gacctacgagtacgccaaaaccgtactggatctcatgacccggggcgacg
ctcaccccgagggcaaggtactgttcattggcggaggaatcgccaacttc
acccaggttggatccaccttcaagggcatcatccggacctctcgggacta
ccagtcttctctgcacaaccacaaggtgaagattacgtgcgacgaggcg
gtcccactggcaggggtctgcggttgatcaagtcggctggcgacgagc
tgaatctgcccatggagattacggccccgacatgcacgtgtcggtatt
gttcctttggctctgcttggaaagcggccaagaatgtcaagcctttgg
caccggacctttctactgaggcttccactcctctcggagtttaa
```

Protein:
Msaksiheadgkallahflskapvwaeqqpintfemgtpklasltfedgv
apeqifaaaektypwllesgakfvakpdqlikrrgkagllvlnksweeck
pwiaeraakpinvegidgvlrtflvepfvphdqkheyyinihsvregdwi
lfheggvdvgdvdakaakilipvdieneypsnatltkellahvpedqhqt
lldfinrlyavyvdlqftyleinplvviptaggvevhyldlagkldqtae
fecgpkwaaarspaalgqvvtidagstkvsidagpamvfpapfgrelske
eayiaeldsktgaslkltvlnakgriwtivagggasvvyadaiasagfad

YALI0E14190g

DNA:
atggttattatgtgtgtgggacctcagcacacgcatcatcccaacacagg
gtgcagtatatatagacagacgtgttccttcgcaccgttcttcacatatc
aaaacactaacaaattcaaaag<u>tgagtatcatggtggggagtcaattgatt
gctcgggagttgaacaggcaacaatggcatgcacagggccagtgaaggc
agactgcagtcgctgcacatggatcgtggttctgagcgttgctatcaaa
agggtcaattacctcacgaaacacagctggatgttgtgcaatcgtcaatg
aaaaacccgacacaatgcaagatctctttgcgcgcattgccatcgctgtt
gccatcgctgtcgccaatcgccaatgccggctgcggattattatccctacct
tgttccccgcttccgcacaaccggcgatgtctttgtatcatgaactctcg
aaactaactcagtggttaaagctgtcgttgccggagccgctggtggtatt</u>
ggccagccccttctcttctcctcaaactctctccttacgtgaccgagct
tgctctctacgatgtcgtcaactcccccggtgttgccgctgacctctccc
acatctccaccaaggctaaggtcactggctacctccccaaggatgacggt
ctcaagaacgctctgaccggcgccaacattgtcgttatccccgccggtat
ccccccgaaagcccggtatgacccgagacgatctgttcaagatcaacgctg
gtatcgtccgagatctgtcaccggtgtcgcccagtacgccctcgacgcc
tttgtgctcatcatctccaaccccgtcaactctaccgtccctattgctgc
cgaggtcctcaagaagcacaacgtcttcaaccctaagaagctcttccgtg
tcaccacccttgacgttgtccgagcccagaccttcaccgccgctgttgtt
ggcgagtctgacccaccaagctcaacatccccgtcgttggtggccactc
cggagacaccattgtccctctcctgtctctgaccaagcctaaggtcgaga
tccccgccgacaagctcgacgacctcgtcaagcgaatccagttggtggt
gacgaggttgtccaggctaaggacggtcttggatccgctaccctctccat
ggcccaggctggttccgatttgccgaggctgtcctcaagggtgccgctg
gtgagaagggcatcatcgagcccgctacatctacctgacggtgatggc
acctccgacatcaagcgagaggtcggtgtcgccttcttctctgtccctgt
cgagttcggccctgagggtgccgctaaggcttacaacatccttccggagg
ccaacgactacgagaagaagcttctcaaggtctccatcgacggtctttac
ggcaacattgccaagggcgaggagttcattgttaaccctcctcctgccaa
gtaa Protein:
vvkavvagaaggigqplslllklspyvtelalydvvnspgvaadlshist
kakvtgylpkddglknaltganivvipagiprkpgmtrddlfkinagivr
dlvtgvaqyapdafvliisnpvnstvpiaaevlkkhnvfhpkklfgvttl
dvvraqtftaavvgesdptklnipvvgghsgdtivpllsltkpkveipad
klddlvkriqfggdevvqakdglgsatlsmaqagfrfaeavlkgaagekg
iiepayiyldgidgtsdikrevgvaffsvpvefgpegaakaynilpeand
yekkllkvsidglygniakgeefivnpppak

YALI0E22649g

DNA:
atgactggcaccttacccaagttcggcgacggtgaaccaccattgtggttc
tggagcctccggcgacctcgctaagaagaagacc<u>gtgagtattgaaccag
actgaggtcaattgaagagtaggagagtctgagaactatcgacggacctg
attgtgctctggaccactcaattgactcgttgagacccccaatgggtct
ggctagccgagtcgttgacttgttgactgttgagcccagaaccccaac
ttttgccaccatacaccgccatcaccatgacacccagatgtgcgtgcgta
tgtgagagtcaattgttccgtggcaaggcacagcttattccaccgtgtc
cttgcacaggtggtctttacgctctcccactctatccgagcaataaaagc
ggaaaaacagcagcaagtcccaacagacttctgctccgaataaggcgtct
agcaagtgtgcccaaaactcaattcaaaaatgtcagaaacctgatatcaa
cccgtctttcaaaagctaaccccagttccccgccctcttcggccttttaccg</u>
aaacggcctgctgccaaaaatgttgaaatcatcggctacgcacggtcga
aaatgactcaggaggagtaccacgagcgaatcagccactacttcaagacc
cccgacgaccagtccaaggagcaggccaagaagtccttgaaaacacctg
ctacgtccagggcccttacgacggtgccgagggctaccagcgactgaatg
aaaagattgaggagtttggagaagaagaagcccgagccccactaccgtct
ttctacctggctctgccccagcgtcttccttgaggctgccaaggtct
gaagaagtatgctacccggcgagggcaaggcccgaatcatcatcgaga
gcccttggccacgacctggcctcgtcacgagagctccaggacggcctt
gctcctctcgaaggagtctggaaatgttccgaatcgaacactacctcgg
aaggagatggtcaagaaccctcaacattgtcgatttggcaaccagttcc
tgtccgccgtgtgggacaagaacaccattttccaacgtccagatctccttc
aaggagccctttggcactgagggccgaggtggatacttcaacgacatgga
atcatccgacgttattcgaaccatctgttgcaggttctgtccattct
agccatggagcgacccgtcacttttcggcgccgaggacattcgagatgaga
aggtcaaggtgctccgatgtgtcgacattctcaacattgacgacgtcatt
ctcggccagtacggccctctgaagacggaaagaagcccggatacaccga
tgacgatgcgttcccgatgactccgcccgagctgtgacctttgctgctca
atctcgagatcgacccaacgacgatgggaggtgttccttttcatcctcga
gccgtaaggctctgacgagggcaaggtcgagatccgagtcagttccg
agacgtgaccaagggcgttgtggaccatcgtcctcgaaatgagctcgtca
tccgaatccagccctccgagtccatctacatgaagatgaactccaagctg
cctggccttactgccaagaacattgtcaccgacctggatctgacctacaa
ccgacgatactcggacgtgcgaatccctgaggcttacgagtctctcattc
tggactgcctcaagggtgaccacaccaactttgtgcgaaacgacgagctg
gacatttcctggaagattttcaccgatctgctgcacaagattgacgagga
caagagcattgtgcccgagaagtacgcctacggctctcgtggccccgagc
gactcaagcagtggctccgagaccgaggctacgtgcgaaacggcaccgag
ctgtaccaatggcctgtcaccaagggctcctcgtga Protein:
mtgtlpkfgdgtttivvlgasgdlakkktfpalfglyrngllpknveiigy
arskmtqeeyherishyfktpddqskeqakkflentcyvqgpydgaegyq
rlnekieefekkkpephyrlfylalppsvfleaanglkkyvypgegkari
iiekpfghdlassrelqdglaplwkeseifridhylgkemvknlnilrfg
nqflsavvdkntisrivqisfkepfgtegrggyfndigiirdviqnhllq
vlsilamerpvtfgaedirdekvkvlrcvdilniddvilgqygpsedgkk
pgytdddgvpddsravtfaalhlqihndrwegvpfilragkaldegkvei
rvqfrdvtkgvvdhlprnelvirigpsesiymkmnsklpgltaknivtdl
dltynrrysdvripeayeslildclkgdhtnfvrndeldiswkiftdllh
kidedksivpekyaygsrgperlkqwlrdrgyvrngtelyqwpvtkgss

YALI0B15598g

DNA:
atgactgacacttcaaacatcaa<u>gtgagtattgccgcacacaattgcaat
caccgccgggctctacctcctcagctctcgacgtcaatgggccagcagcc
gccatttgaccccaattacactggttgtgtaaaaccctcaaccacaatcg
cttatgctcaccacagactacgacttaaccaagtcatgtcacaggtcaaa
aagtaaagtcagcgcaacaccccctcaatctcaacacacttttgctaact
caggcctgtcgctgacattgcctccatcggtctcgccgtcatgggccaga
acctgatcctcaacatggccgaccacggtaagtatcaattgactgcaagac
gcaccagcagatacagagcataccagcaatcgctcctctgataatcgcc
attgtaacactacgttggttagatgatctcaaggtcgttgctggttccatg
cacttccacttgctcatatgaaggagagtcaaactctattttgataagtgtc
ctctcccatccccgaaatgtcgcattgttgctaacaataggctacgaggt</u>
tgttgctacaaccgaaccacctccaaggtcgaccacttcctcgagaacg
aggccaagggtgagtatccgtccagctatgctgtttacagccattgaccc
cacccttcccccacaattgctacgtcaccattaaaaaacaaaattaccggt
<u>atcggcaagctagacttcatgcaacctacgcaggggtaacaagttgagtt
tcagccgtgcaccttacaggaaaaccagtcatacgccgaggcagtgtgaa
agcgaaagcacacagcctacggtgattgattgcattttttttgacatagga
gggaaacacgtgacatggcaagtgcccaacacgaatactaacaaacagga</u>
aagtccattattggtgctcactctatcaaggagctgtgtgctctgctgaa
gcgaccccgacgaatcattctgctcgttaaggccggtgctgctgtcgatt
ctttcatcgaacagctcctgccctatctcgataaggggtgatatcatcatt
gacggtggtaactcccccatccccgactccaaccgacgatacgaggagt
taacgagaaggaatcctctttgttggttccggtgtttccggcggtgagg
agggtgcccgatacggtccctccatcatgcccggtgaaacaaggaggcc
tggccccacattaagaagattttccaggacatctctgctaaggctgatgg
tgagccctgctgtgactgggtcggtgacgctggtgccggccactttgtca
agatggttcacaacgcgtattgagtatggtgatcagcagcttatctgcgag
gcttacgacctcatgaagcgaggtgctggtttcaccaatgaggagattgg
agacgttttcgccaagtggaacaacggtatcctcgactccttcctcattg
agatcacccgagacatcttcaagtacgacgacggctctggaactcctctc
gttgagaagatctccgacactgctggccagaagggtactggaaagtggac
cgctatcaacgctcttgaccttggtatgcccgtcaccctgatcggtgagg
ccgtcttcgctcgatgcctttctgccctcaagcaggagcgtgtccgagct
tccaaggtcttcgatggccccgagcccgtcaagttcactggtgacaagaa
ggagtttgtcgaccagctcgagcagggccctttacgcctccaagatcatct
cttacgcccaggtttcatgcttatccgagaggccgccaagacctacggc
tgggagctcaacaacgccggtattgccctcatgtggcgaggtggttgcat
catccgatccgtcttccttgctgacatcaccaaggcttaccgacaggacc
caacctcgagaacctgctgttcaacgacttcttcaagaacgccatctcc
aaggccaacccctcttggcgagctaccgtggccaaggctgtcacctgggg
tgttcccactcccgccttgcctcggctctggctttctacgacggttacc
gatctgccaagctcccccgctaacctgctccaggcccagcgagactacttc
ggcgcccacacctaccagctcctcgatggtgatggaaagtggatccacac
caactggaccggcgaggtggtgaggtttcttcttccacttacgatgctt
aa Protein:
mtdtsnikpvadialigavmgqnlilnmadhgyevvaynrttskvdhfl
eneakgksiigahsikelcallkrprriillvkagaavdsfieqllpyld
kgdiiidggnshfpdsnrryeelnekgilfvgsgvsggeegarygpsimp
ggnkeawphikkifqdisakadgepccdwvgdagaghfvkmvhngieygd
mqliceaydlmkrgagflneeigdvfakwnngildsflieitrdifkydd
gsgtplvekisdtagqkgtgkwtainaldlgmpvtligeavfarclsalk
qervraskvldgpepvkftgdkkefvdqleqalyaskiisyaqfmlire
aaktygwelnnagialmwrggciirsvfladitkayrqdpnlenllfhdf
fknaiskanpswratvakavtwgvptpafasalafydgyrsaklpanllq
aqrdyfgahtyqlldgdgkwihtnwtgrggevsssstyda YALI0D06303g
DNA:
atgctcaaccttagaaccgcccttcgagctgtgcgaccgtcactctggt
gagtatctcggagcccgggacggctaccaacacacaagcaagatgcaaca
gaaaccggacttttttaaatgcggattgcggaaaatttgcatggcggcaac
gactcggagaaggagcgggacaattgcaatggcaggatgccattgacgag
ctgaggtgatgagagaccgggcctccgatgacgtggtggtgacgacagc
ccggctggtgttgccgggactgtctctgaaaagcaatttctctatctccg
gtctcaacagactccccttctctagctcaattggcattgtcttcagaagg
tgtcttagtggtatccccattgttatcttctttttccccaatgtcaatgtc
aatgtcaatggctccgacctctttcacattaacacggcgcaaacacagat
accacggaaccgactcaaacaaatccaaagagacgcagcggaataattgg
catcaacgaacgatttgggatactctggcgagaatgccgaaatatttcgc
ttgtcttgttgtttctcttgagtgagttgttttgtgaagtcgtttgaaaga
aggttcccaatgtcacaaaccataccaactcgttacagccagcttgtaat
ccccacctcttcaatacatactacgcagacccgatcctacgccacttcc
tggcctcttcaccggccagaagaactccaacggcaagtacactgtgtct
ctgattgagggagacggtatcggaaccgagatctccaaggctgtcaagga
catctaccatgccgccaaggtccccatcgactgggaggttgtcgacgtca
cccccactctggtcaacggcaagaccaccatccccgacagcgccattgag
tccatcaaccgaaacaaggttgccctcaagggtccctcgccaccccat
cggtaagggccacgtttccatgaacctgactctgcgacgaaccttcaacc
tgttcgccaacgtccgacattcctgtcaagtccgtcgtgggctacaagaccct
tacgagaacgtcgacaccctgctcatcgagagaacactgagggtgagta
ctccggtatcgagcacaccgtcgtccccggtgtcgttcagtccatcaagc
tgatcacccgagaggcttccgagcgagtcatccggtacgcttacgagtac
gccctgtcccgaggcatgaagaaggtccttgttgtcacaaggcctctat
tatgaaggtctccgatggtctttccttgaggttgctcgagagctcgcca
aggagtaccccctccattgacctttccgtcgagctgatcgacaacacctgt
ctgcgaatggtccaggacccccgctctctaccgagatgtcgtcatggtcat
gcccaaccttttacggtgacattctgtccgatcttgcctccggtcttatcg
gtggtcttggtctgaccccctccggtaacagtgggtgacgaggtctccatc
ttcgaggccgtccacggatccgctcccgacattgctggcaagggtcttgc
taaccccactgctctgctgctctcctccgtgatgatgctgcgacacatgg
gtctcaacgacaacgccaacatcgagcaggccgtcttcggcaccatt
gcttccggccccgagaaccgaaccaaggatcttaagggtaccgccaccac
ttctcactttgctgagcagattatcaagcgactcaagtag Protein:
mlnlrtalravrpvfltrsyatsvasftgqknsngkytvsliegdgigte
iskavkdiyhaakvpidwevvdvtptlvngkttipdsaiesinrnkvalk
gplatpigkghvsmnltlrrtfnlfanvrpcksvvgyktpyenvdtllir
entegeysgiehtvvpgvvqsiklitreaserviryayeyalsrgmkkvl
vvhkasimkvsdglflevarelakeypsidlsvelidntclrmvqdpaly
rdvvmvmpnlygdilsdlasgligglgltpsgnmgdevsifeavhgsapd
iagkglanptallllssvmmlrhmglndnatnieqavfgtiasgpenrtkd
lkgtattshfaeqiikrlk

Example 11

Regulatory Sequences

Sequences which consist of, consist essentially of, or comprise the following regulatory sequences (e.g. promoters and terminator sequences, including functional fragments thereof) may be useful to control expression of endogenous and heterologous genes in recombinant fungi described herein.

Met2 promoter
5'cctctcactttgtgaatcgtgaaacatgaatcttcaagccaagaatgt
taggcaggggaagctttctttcagactttttggaattggtcctcttttgg
acattattgacgatattattattttttcccgtccaatgttgaccttg
taagccattccggttctggagcgcatctcgtctgaaggagtcttcgtgtg
gctataactacaagcgttgtatggtggatcctatgaccgtctatataggg
caacttttgctcttgttcttcccctccttgagggacgtatggcaatgta
tgacaactatcgtagtgagcctctataacccattgaagtacaagtcctcc
acctttgctgccaaactcgcgagaaaaaaagtccaccaactccgccgggaa
atactggagaacacctctagacgtgggcttctgcacctgtggcttggg
tctgggttttgcgagctctgagccacaacctaaggacggtgtgattggga
gataagtagtcgttggttttctaatcgcacgtgatatgcaagccacactt
ataacacaatgaagacgagccgatgaactgcatgtcattgtacaggtgcg
gagagcaagaaactctggggcggaggtgaaagatgagacaaaaagcctca
ggtgcaaggtagggagttgatcaacgtcaaacacaaataatctaggttgt
taggcagctaaacatgtatataactgggctgccaccgagtgttacttgtc
attaacgtcgcattttcgcctacacaaaatttgggttactcgccactaca ctgctcaaatcttcagctgtgcaacaagctttcaggtcacacatagact
cgcataaggacccgggtcatctgttattctccactggtaaaccaatagtc
ctagctgatttgggtacagaagctcactttcacatcttttcatcttcttc
tacaaccatc Met3 promoter
5'atctgtgaggagcccctggcgtcactgtcgactgtgccggcattctg
atggtatttccagccccgcagttctcgagaccccgaacaaatgtgccac
acccttgccaaaatgacgaatacacggcgtcgcggccgggaatcgaactc
ttggcaccgccacaggagtgaaatttgaaatttgaaatttgaaaaataat
tcacatttttgagtttcaataatatatcgatgaccctcccaaaagacccaa
gtcgagacgcaaaaaacacccagacgacatggatgcggtcacgtgaccg
caaaaccgccccggaaatccgtttgtgacgtgttcaattccatctctat
gtttttctgcggtttctacgatgccgcaatggtggccaatgtgcgtttca
ctgccgtagtggctggaacaagccacaggggggtcgtcgggccaatcagac
ggtccctgacatggttctgcgccctaacccgggaactctaaccccgtgg
tggcgcaatcgctgtcttcatgtgctttatctcacgtgacggctggaatc
tggcagaagacggagtatgtacattttgtcgttggtcacgttatccctaa
aacgtggtgttttaaactggtcgaatgcttggcccagaacacaagaagaaa
aaaacgagacaacttgatcagtttcaacgccacagcaagcttgtcttcac
tgtggttggtcttctccacgccacaagcaacacgtacatgtcaattacgt
cagggtcttttaagttctgtggcttttgaaccagttataaagaaccaacc
acccttttttcaaagctaatcaagacggggaaatttttttttttgatattt
ttcgaca Met6 promoter
5'gatactgcagacggtgcattacttacccgtgtcgactgagagtctact
tggtacttggccctgtggctaagcagtatttgagcaacaatgcaatgcag
ttgctgactcggttccagatccccttgccccgatgtgtggaagcgttgtt
tttggggcaagggcatgtgggggctgcatcatactgtggctggggccgtt
ggaagagccgtcggcagcgagcctgagtcgcttctcggggcttattccc
ccgcctctaggtcagcggcggccgaagtgtcgtactcagctcgcctgta
cagtatgacgtgaccgaatagcctctggaaggttggagaagtacagtgca
aaaaaagttgcaaaatttcattttagcgttcgatccgacgtggcagttg
gacaatgaatcgatggagacatgatcatgggcagaaatagaaggtctcca
tgttcaatggcagtaccaattgagcaacagacgggtcgacaggcggcggg
cacaccatccgccctccacatggcgcaatcgtcagtgcagcgattcgtac
tcggattgcatcatgttgcaccgaaagttggggcccgcacgttggagagg
cgaggagccagggttagcttttggtgggggtccttttgttgtcacgtggcatc
agcgaatggcgtcctccaatcagggccgtcagcgaagtcggcgtgtgata
gtgcgtggggagcgaatagagtttctggggggggggcggcccaaaacgtga
aatccgagtacgcatgtagagtgtaaattgggtgtatagtgacattgttt
gactctgaccctgagagtaatatataatgtgtacgtgtcccctccgttg
gtcttctttttttctccttttctcctaaccaacacccaaactaatcaatc Met25 promoter
5'aagtcgtattaacataactttccttacattttttttaaagcacgtcact
atccacgtgacctagccacgcgataccaagtattcatccataatgacaca
ctcatgacgtccggaggacgtcatcatcgtccagtcacgtgccaaggcac
atgactaatcataacacccttatgactagcttctgaatcgctacacagttc
caattcgcaaataaactcgaaatgacgaaatgccataataaaaatgacga
aactcgagattgagagcagcacatgcactgaagtggtggcaaccagcgt
atccggagacacgacggatccagcaccatggaagctggccgaaaaagaga
tccccagcacattgagcaaccaagtcagctcaattgagtaacatcacaca
ctcagatcgagtctgatggtggtccctctttttgttccttcactttgaaaaat
aattgaaaataacaataacaataaaaataaaaacaaaataaaaaataaaaa
taaaaataaaaataaaaaaataaaaaaaccttgccgcattttagcgtcagc
cacccccgcattgacctgagtacgttggattgaccccgatcctgcacgt
cgagcgtggtcggccaaaaagcgcccgtggctggtgagtcagaaatagca
gggttgcaagagagagctgcgcaacgagcaataaacggtgtttttttcgc
ttctgtgctgcttagagtggaagccgacctcgccatgctcacgtgacc
attcacgtggttgcaaactccaccttagtatagccgtgtccctctcgcta
cccattatcgcatcgtactccagccacattttttttgttcccgctaaatc
cggaacctttatctgggtcacgtgaaattgcaatctcgacaggaggttata
cttatagagtgagacactccacgcaaggtgttgcaagtcaattgacacca
cctcacctcagactaacatccaca Pox2 promoter
5'gaatctgccccacatttttatctccgcttttgactgtttttctccccc
ctttcacactctgcttttggctacataaaccccgcaccgtttggaactct
gttggtccggggaagccgccgttaggtgtgtcagatggagagcgccagac
gagcagaaccggagcagcggatcgggggagggctgtcacgtgacgaag
ggcactgttgacgtggtgaatgtcgcccgttctcacgtgacccgtctcct
ctatatgtgtatccgcctcttttgtttggttttttttctgcttccccccc
ccccccccacccaatcacatgctcagaaagtagacatctgcatcgtcct
gcatgccatcccacaagacgaacaagtgataggccgagagccgaggacga
gtgagtgcacaagggtaggcgaatggacgattccgccaagtgagactg
gcgatcgggagaaggggtggtggtcatgggggatagaatttgtacaagtg
gaaaaaccactacgagtagcggatttgataccacaagtagcagagatata
cagcaatggtgggagtgcaagtatcggaatgtactgtacctcctgtactc
gtactcgtacggcactcgtagaaacggggcaatacggggagaagcgatc

```
gcccgtctgttcaatcgccacaagtccgagtaatgctcgagtatcgaagt
cttgtacctccctgtcaatcatggcaccactggtcttgacttgtctattc
atactggacaagcgccagagttaagcttgtagcgaatttcgccctcggac
atcaccccatacgacggacacacatgcccgacaaacagcctctcttattg
tagctgaaagtatattgaatgtgaacgtgtacaatatcaggtaccagcgg
gaggttacggccaaggtgataccggaataaccctggcttggagatggtcg
gtccattgtactgaagtgtccgtgtcgtttccgtcactgccccaattgga
catgtttgtttttccgatctttcgggcgccctctccttgtctcttgtctg
tctcctggactgttgctaccccatttctttggcctctggttcctcccgt
ctttcacgtcgtctatggttgcatggtttcccttatacttttccccacag
tcacatgttatggaggggtctagatggaggcctaattttgacgtgcaagg
ggcgaattgggcgagaaacacgtcgtggacatggtgcaaggcccgcagg
gttgattcgacgcttttccgcgaaaaaaacaagtccaaataccccgttt
attctccctcggctctcggtatttcacatgaaaactataacctagactac
acgggcaaccttaacccccagagtatacttatatataccaaagggatgggtcc
tcaaaaatcacacaagcaacg Yef3 (YALI0E13277g) promoter
5'cgccattcggttccttccagaccattccagatcaatccacctcttctt
atctcaggtgggtgtgctgacatcagaccccgtagccctttctcccagtgg
cgaacagcaggcataaaacagggccattgagcagagcaaacaaggtcggt
gaaatcgtcgaaaaagtcggaaaacggtgcaagaaattggagcgtcacc
tgccaccctccaggctctatataaagcattgccccaattgctaacgcttc
atatttacacctttggcacccagtccatccctccaataaaatgtactac
atgggacacaacaagagaggatgcgcgcccaaaccctaacctagcacatg
cacgatgattctctttgtctgtgaaaaaattccaccaaaatttccccatt
gggatgaaaccctaaccgcaaccaaaagtttttaactatcatcttgtacg
tcacggtttccgattcttctcttctctttcatcatcatcacttgtgacc Cam1 (YALI0C24420g) promoter
5'aactaccataagtaccgagaaatataggcaattgtacaaattgtccac
ctccttcacttacattaccgaaccatggccatatcaccaaaataccccga
gtgctaaaacacctccctccaaatgttctcttaccttccaccgaaaaccg
atcttattatcccaacgcttgttgtggcttgacgcgccgcacccgctggg
cttgccatttcgataccaatccaagaggaaaagctcatgagaaacattcg
gaatatcacgagaacggcctggcgaaccaacaggatattttttgaatataa
ttaccccctcgaatctagtcatatctatgtctactgtagacttgggcggca
tcatgatgtacattattttagcgtctggaaccctaaagttcacgtacaat
catgtgacaaacgaggctaaaaaatgtcaatttcgtatattagtgttatt
acgtggctcacatttccgaatcatctaccaccccccacctaaaaa YALI0D16467g promoter
5'tttttttaattttcatatttatttcatatttatttcatatttattt
tcatttatttattcatgtatttatttattactttttaagtattttaaact
cctcactaaaccgtcgattgcacaatattaaccttcattacacctgcagc
gtggttttgtggtcgttagccgaagtcttccaacgtgggtataagtagg
aacaattgggcgatttttgagccgtctaaatctctcgactcaattgat
ctgctgtcgaaaatccggctctctagctccttttccccgtccgctggagc
tcctcttcattgtgccgttttttccaacatttaactttgccaccaccacc
acccccactaccatcacccactcgatctctgttcgtgtcaccacgacttt
gtcttctcacacatactctgttgtgcaccacacattgcaa Tef4 (YALI0B12562g) promoter
5'gctacaatagctttattggccctattgagcacgctacaattcggtcca
gtatgtacaacgtctatgcgcactaacggccatacagtgagttacagcac
acccaaaagtaaccctgcctgacctgtctgcctgagacaggaagattaac
tcttgtagtgaccgagctcgataagactcaagccacacaatttttttata
gccttgcttcaagagtcgccaaaatgacattacacaactccacggaccgt
cggttccatgtccacacccttggatgggtaagcgctccacgcacgtacca
cgtgcattgagtttaaccacaaacataggtctgtgtcccagagttaccct
gctgcatcagccaagtcttgaaagcaaaatttcttgcacaattttttcctc
ttcttttcttcactgatcgcagtccaaacacaaaca YALI0D12903g promoter
5'gcgctctgatccacttgtatggctccaagttcagtgtaccaagtagtt
ggtgatgcagggagggatgtctctatccaccaataatgaactcatgggcg
aaattgtttctgttaaacactccaactgtcgtttaaatctcattctctt
tgcatttggactccattcgcttccgttgggccaatataatccatcgtaac
gtactttagatggaaatttagttacctgctacttgtctcaacacccaac
aggggctgttcgacagaggtaatagagcgtcaatgggttaataaaaacac
actgtcgattttcactcattgtctttatgatattacctgttttccgctgt
tatcaatgccgagcatcgtgttatatcttccaccccaactacttgcattt
acttaactattacctcaactatttacaccccgaattgttacctcccaata
agtaactttatttcaaccaatgggacgagagcatctctgagaacatcgat
ctatctctgtcaatattgcccagaatcgtcgaaaaaaaacaccaaaagg
tttacagcgccattataaatataaattcgttgtcaattccccgcaatgt
ctgttgaaatctcattttgagacctccaacattaccctctctccgtct
ggtcacatgacgtgactgcttcttcccaaaacgaacactcccaactcttc
cccccgtcagtgaaaagtatacatccgacctccaaatctttttcttcact
caac Tef1 (YALI0C09141g) promoter
5'agagacgggttggcggcgtattgtcccaaaaaacagccccaattgccc
caattgaccccaaattgacccagtagcgggcccaacccggcgagagccc
ccttcaccccacatatcaaacctccccggttcccacacttgccgttaag
ggcgtagggtactgcagtctggaatctacgcttgttcagactttgtacta
gtttctttgtctggccatccgggtaacccatgccggacgcaaaatagact
actgaaaatttttttgctttgtggttgggactttagccaagggtataaaa
gaccaccgtccccgaattaccttttcctcttctttttctctctctccttgtc
aactcacacccgaaatcgttaagcatttccttctgagtataagaatcat
tc Fba1 (YALI0E26004g) promoter
5'gctgcgctgatctggacaccacagaggttccgagcactttaggttgca
ccaaatgtcccaccaggtgcaggcagaaaaacgctggaacagcgtgtacag
tttgtcttagcaaaaagtgaaggcgctgaggtcgagcagggtggtgtgac
ttgttatagcctttagagctgcgaaagcgcgtatggatttggctcatcag
gccagattgagggtctgtggacacatgtcatgttagtgtacttcaatcgc
ccctggatatagccccgacaataggccgtggcctcattttttttgcttc
cgcacatttccattgctcggtacccacaccttgcttctcctgcacttgcc
aaccttaatactggtttacattgaccaacatcttacaagcggggggcttg
tctagggtatatataaacagtggctctcccaatcggttgccagtctcttt
tttcctttcttcccccacagattcgaaatctaaactacacatc Pox2 terminator:
5'gatgaggaatagacaagcgggtatttattgtatgaataaagattatgt
attgattgcaaaaaagtgcatttgtagatgtggtttattgtagagagtac
ggtatgactgtacgaacattaggagctacttctacaagtagatttttctta
acaagggtgaaatttactaggaagtacatgcatatttcgttagtagaatc
acaaaagaaatgtacaagcacgtactacttgtactccacaatgtggagtg
ggagcaaaaaaattggacgacaccggaatcgaaccggggacctcgcgcat
gctaagcgcatgtgataaccaactacaccagacgcccaagaacttttcttg
gtgattatggaatacgtggtctgctatatctcaattttgctgtaatgaat
cattagaattaaaaaaaaaacccccattttttgtgtgattgtcggccaagag
atggaacaggaagaatacgtgaacaagcgagcacgaatgccatatgctct
tctgaacaaccgagtccgaatccgatttgtgggtatcacatgtctcaagt
agctgaaatgtatttcgctagaataaaatgcagtagtatggacagtaggt
actgccagccagagaagtttttggaattgatacttgagtcattttttccat
tccccattccccattccaacacgctgactatatataaatattattgggtc
tgttttcttgtttatgtcgaaattatctgggttttactactgtgctcg
agtatagagtggcctgactggagaaaatgcagtagtatggacagtaggta
ctgccagccagagaagtttttggaattgatacttgagtcattttttccat
ccccattccccattccaacacaatcaactgtttctgaacattttccaaaa
cgcggagatgtatgtcacttggcactgcaagtctcgattcaaaatgcatc
tctttcagaccaaagtgtcatcagcttttgtttggccccaaattaccgcaa
atacttgtcgaaattgaagtgcaatacggcctcgtctgccatgaaacctg
cctattctcttcaaattggcgtcaggtttcacgtccagcattcctcgccc
agacagagttgctatggttgaatcgtgtactgttaatatatgtatgtatt
atactcgtactacgatatactgttcaatagagtctcttataatcgtacga
cgattctgggca
```

Example 12

Cultures Conditions, such as Limitation for Nitrogen, Magnesium or Phosphate, can Promote Lipid Accumulation in *Y. lipolytica*

12a. Strains Used to Analyze Lipid Accumulation during Growth Under Various Conditions.

Strains MF760, MF858, and MF921 were grown under an array of culture conditions, and then harvested cells were extracted and analyzed for total lipid content and levels of specific lipophilic metabolites. FIG. 12 depicts schematic representations of certain plasmids generated and described in this example. Strain MF760 has genotype MATB ura2::URA2/tef-GGS1 ChrA-1635618::tef-carB ur&3-302 ade1::?ADE1/tef-HMG1trunc leu2::?LEU2/tef-carRP (questions marks denote presumed loci of chromosomal integration). Strain MF760 harbors four insertion plasmids, pMB4637, pMB4591, pMB4705, and pMB4660, which encode native or heterologous genes required for synthesis of either isoprenoid metabolites in general, or carotenoid metabolites specifically. In all insertion plasmids, except pMB4789, described in this example, the *Y. lipolytica* TEF1 promoter and XPR2 terminator were the regulatory sequences used to control expression of genes of interest. Also, in some instances multiple URA3-containing plasmids can be utilized in the same strain, since 5-fluoroorotic acid can be used to select for Ura⁻ segregants following transformation with a URA3 plasmid. pMB4637 is an ADE1 plasmid that encodes a truncated variant of the *Y. lipolytica* HMG-CoA reductase. pMB4591 is a URA5 plasmid that encodes the *Y. lipolytica* geranylgeranylpyrophosphate synthase. pMB4705 is a LEU2 plasmid that encodes the phytoene synthase/lycopene cyclase (CarRP) from *Mucor circinelloides*. pMB4660 is a URA3 plasmid that encodes a phytoene dehydrogenase from *M. circinelloides*.

Strain MF858 has genotype MATB ura2::URA2/tef-GGS1 ChrA-1635618::tef-carB ura3-302::?URA3/tef-plasmid ade1::?ADE1/tef-HMG1trunc leu2::?LEU2/tef-carRP. Strain MF858 harbors the same four plasmids as MF760, and an addition control plasmid (pMB4691), which is a URA3 plasmid that contains regulatory sequences but no gene of interest.

Strain MF921 has genotype MATB erg9-3'UTR::URA3 ura2::URA2/tef-GGS1 ChrA-1635618::tef-carB ura3-302 ade1::?ADE1/tef-HMG1trunc leu2::?LEU2/tef-carRP. Strain MF921 harbors the same four plasmids as MF760, and an addition URA3 plasmid, pMB4789, which contains sequences for insertion into the 3' UTR of the native ERG9. Insertion into 3' UTR of ERG9 is presumed to result in a hypomorphic mutation to decrease squalene synthase activity.

12b. Lipid Accumulation in Media Containing Various Carbon:Nitrogen Ratios

Shake flask testing was conducted using carbon to nitrogen (C/N) ratios of 160, 80, 60, 40, 30, 20, and 10 with yeast nitrogen base being the base medium providing vitamins, trace elements and salts. Ammonium sulfate (which contains 21% nitrogen) was used as the nitrogen source and glucose (which contains 40% carbon) was used as the carbon source at a concentration of 30 g/L. The concentrations of ammonium sulfate corresponding to these ratios are: 0.36, 0.71, 0.95, 1.43, 1.91, 2.86, and 4.6 g/L, respectively. Uracil was supplemented at 0.2 mM. As controls, strains were also grown in yeast extract-peptone with 50 g/L of glucose (media in which lipids do not accumulate at high levels) and yeast extract-peptone with 5% olive oil (v/v) (media in which lipids accumulate at high levels). Strain MF760 (10-14 ml of culture) was harvested after 4 days of growth at 30° C., during which time the cultures were shaking at 250 rpm. Following harvesting, cells were washed three times with water, with the exception of the oil-grown cells which were washed three times in 0.5% BSA and one time with water before lipid extractions. Lipids were extracted as described in Folch J, Lees, M, and Stanley, G. H. S. *J. Biol. Chem.* 226: 497-509, 1957. In brief, cell pellets were resuspended in 6 ml of water. A 1 ml aliquot was transferred to a pre-weighed tube with a hole on the lid, spun down and the cell pellet lyophilized overnight to determine the dry cell weight. The remaining 5 ml were placed in a 15 ml Falcon tube and spun down. Cell pellets were frozen at −20° C. until extractions were performed. Two to three volumes of a Zymolyase solution (2 mg/ml Zymolyase 100T in 1M Sorbitol, 50 mM EDTA and 0.01% β-mercaptoethanol) was added to each cell pellet and placed at 37° C. with constant agitation for 1 hr. Two volumes of cubic zirconia beads were added to each tube and vortexed for 15-20 min. Samples were viewed under a microscope to ensure cell breakage before continuing with extractions. After cell breakage was complete, 6 ml of extraction solvent was added (a 2:1 mix of chloroform and methanol) and mixed. The mixture was spun down for 5 min at 3000 rpm and the organic layer was transferred to a clean tube. NaCl was added to the remaining aqueous layer to make it a 0.29% NaCl solution. 6 ml of extraction solvent was added and mixed, and the mixture was spun down for 5 min. The organic layers were pooled and filtered through a 0.2 μm filter to get rid of any cell debris. The extract was washed with 0.2 volumes of 0.29% NaCl solution and another 6 ml of extraction solvent added and mixed. Mixtures were spun and the organic layer was placed in a pre-weighed glass vial, the solvent was evaporated under a flow on nitrogen and the vial was weighed again to determine the weight of the lipid extracted. The dry cell weight is used to determine the percentage of lipid per dry cell weight. The lipid accumulation results are in the Table 66 below:

TABLE 66

Lipid accumulation under various carbon:nitrogen ratio growth conditions

|  | C/N Ratio | % lipid |
|---|---|---|
| YNB | 160 | 61 |
| 3% Glucose | 80 | 49 |
|  | 60 | 34 |
|  | 40 | 17 |
|  | 30 | 16 |
|  | 20 | 14 |
|  | 10 | 15 |
| YEP | 5% Glucose | 22 |
|  | 5% olive oil | 38 |

Other nitrogen sources tested were proline (12% nitrogen), sodium glutamate (7% nitrogen), soy acid hydrolysate (12% nitrogen), and yeast extract-peptone (26.8% nitrogen). All nitrogen sources tested at C/N ratios of 80 (with glucose as a carbon source), had significantly larger lipid bodies than at C/N ratios of 10 (also with glucose as a carbon source). Strains MF858 and MF921 were harvested after 4 days of growth at 30° C. (3% glucose was used as the carbon source). Cells were washed three times with water and lipids extracted as described above. Lipid accumulation data for soy hydrolysate, yeast extract-peptone and yeast nitrogen base, used as a control, are listed in Table 67 below.

TABLE 67

Lipid accumulation under different carbon and nitrogen conditions with various nitrogen sources

|  |  | % lipid | |
|---|---|---|---|
|  | C/N Ratio | MF858 | MF921 |
| Soy hydrolysate | 80 | 36 | 36 |
|  | 60 | 36 | 35 |
|  | 10 | 14 | 15 |
| Yeast Extract- | 80 | 37 | 37 |
| Peptone | 80 | 37 | 37 |
|  | 10 | 15 | 14 |
| Yeast Nitrogen | 80 | 37 | 38 |
| Base | 10 | 13 | 11 |

12c. Determination of Lipid Levels Under High Carbon and Phosphate or Magnesium Limiting Conditions.

To test whether other nutrient limitations, under high carbon conditions, will allow for higher lipid accumulation, phosphate or magnesium limiting conditions were tested. For phosphate limiting conditions, yeast nitrogen base medium without phosphate was prepared. Shake flask testing was performed using carbon to phosphate ratios ranging from 5376 down to 42. This range corresponds to 7.8 mg/L up to 1 g/L, respectively, and the latter concentration corresponds to that are commonly used in yeast nitrogen base medium. Glucose, at 30 g/L, was used at the carbon source. Potassium phosphate monobasic (containing 28.7% phosphate) was used as the phosphate source.

For magnesium limiting conditions, yeast nitrogen base medium without magnesium was prepared. Shake flask testing was conducted using carbon to magnesium ratios ranging from 31360 down to 245. This range corresponds to 0.375 mg/L up to 0.5 g/L, and the latter magnesium concentration corresponds to that commonly used in yeast nitrogen base. Glucose, at 30 g/L, was used as the carbon source. Magnesium sulfate (containing 9.8% magnesium) was used as the magnesium source.

Strains MF858 and MF921 were harvested after 4 days of growth at 30° C., during which time the cultures were shaking at 250 rpm. Cells were washed three times with water before lipid extraction. Lipids were extracted as described above. Lipid accumulation data is listed in the Table 68 below:

TABLE 68

Lipid accumulation in phosphate or magnesium limiting growth conditions

|  |  | % Lipid | |
| --- | --- | --- | --- |
|  | g/L | MF858 | MF921 |
| phosphate | 1 | 14 | 14 |
|  | 0.0625 | 18 | 20 |
|  | 0.0313 | 34 | 41 |
|  | 0.0156 | 62 | 63 |
|  | 0.0078 | 83 | 76 |
| magnesium | 0.5 | 12 | 11 |
|  | 0.0313 | NA | 16 |
|  | 0.0156 | NA | 25 |
|  | 0.0078 | NA | 42 |
|  | 0.0039 | 48 | 48 |

The following tables are referenced throughout the description. Each reference and information designated by each of the Genbank Accession and GI numbers are hereby incorporated by reference in their entirety.

Lengthy table referenced here

US08633009-20140121-T00001

Please refer to the end of the specification for access instructions.

Lengthy table referenced here

US08633009-20140121-T00002

Please refer to the end of the specification for access instructions.

Lengthy table referenced here

US08633009-20140121-T00003

Please refer to the end of the specification for access instructions.

Lengthy table referenced here

US08633009-20140121-T00004

Please refer to the end of the specification for access instructions.

Lengthy table referenced here

US08633009-20140121-T00005

Please refer to the end of the specification for access instructions.

Lengthy table referenced here

US08633009-20140121-T00006

Please refer to the end of the specification for access instructions.

Lengthy table referenced here

US08633009-20140121-T00007

Please refer to the end of the specification for access instructions.

Lengthy table referenced here

US08633009-20140121-T00008

Please refer to the end of the specification for access instructions.

Lengthy table referenced here

US08633009-20140121-T00009

Please refer to the end of the specification for access instructions.

Lengthy table referenced here

US08633009-20140121-T00010

Please refer to the end of the specification for access instructions.

Lengthy table referenced here

US08633009-20140121-T00011

Please refer to the end of the specification for access instructions.

Lengthy table referenced here
US08633009-20140121-T00012

Please refer to the end of the specification for access instructions.

Lengthy table referenced here
US08633009-20140121-T00013

Please refer to the end of the specification for access instructions.

Lengthy table referenced here
US08633009-20140121-T00014

Please refer to the end of the specification for access instructions.

Lengthy table referenced here
US08633009-20140121-T00015

Please refer to the end of the specification for access instructions.

Lengthy table referenced here
US08633009-20140121-T00016

Please refer to the end of the specification for access instructions.

Lengthy table referenced here
US08633009-20140121-T00017

Please refer to the end of the specification for access instructions.

Lengthy table referenced here
US08633009-20140121-T00018

Please refer to the end of the specification for access instructions.

Lengthy table referenced here
US08633009-20140121-T00019

Please refer to the end of the specification for access instructions.

Lengthy table referenced here
US08633009-20140121-T00020

Please refer to the end of the specification for access instructions.

Lengthy table referenced here
US08633009-20140121-T00021

Please refer to the end of the specification for access instructions.

Lengthy table referenced here
US08633009-20140121-T00022

Please refer to the end of the specification for access instructions.

Lengthy table referenced here
US08633009-20140121-T00023

Please refer to the end of the specification for access instructions.

Lengthy table referenced here
US08633009-20140121-T00024

Please refer to the end of the specification for access instructions.

Lengthy table referenced here
US08633009-20140121-T00025

Please refer to the end of the specification for access instructions.

Lengthy table referenced here
US08633009-20140121-T00026

Please refer to the end of the specification for access instructions.

Lengthy table referenced here
US08633009-20140121-T00027

Please refer to the end of the specification for access instructions.

Lengthy table referenced here
US08633009-20140121-T00028
Please refer to the end of the specification for access instructions.

Lengthy table referenced here
US08633009-20140121-T00029
Please refer to the end of the specification for access instructions.

Lengthy table referenced here
US08633009-20140121-T00030
Please refer to the end of the specification for access instructions.

Lengthy table referenced here
US08633009-20140121-T00031
Please refer to the end of the specification for access instructions.

Lengthy table referenced here
US08633009-20140121-T00032
Please refer to the end of the specification for access instructions.

Lengthy table referenced here
US08633009-20140121-T00033
Please refer to the end of the specification for access instructions.

Lengthy table referenced here
US08633009-20140121-T00034
Please refer to the end of the specification for access instructions.

Lengthy table referenced here
US08633009-20140121-T00035
Please refer to the end of the specification for access instructions.

Lengthy table referenced here
US08633009-20140121-T00036
Please refer to the end of the specification for access instructions.

Lengthy table referenced here
US08633009-20140121-T00037
Please refer to the end of the specification for access instructions.

Lengthy table referenced here
US08633009-20140121-T00038
Please refer to the end of the specification for access instructions.

Lengthy table referenced here
US08633009-20140121-T00039
Please refer to the end of the specification for access instructions.

Lengthy table referenced here
US08633009-20140121-T00040
Please refer to the end of the specification for access instructions.

Lengthy table referenced here
US08633009-20140121-T00041
Please refer to the end of the specification for access instructions.

Lengthy table referenced here
US08633009-20140121-T00042
Please refer to the end of the specification for access instructions.

Lengthy table referenced here
US08633009-20140121-T00043
Please refer to the end of the specification for access instructions.

Lengthy table referenced here
US08633009-20140121-T00044
Please refer to the end of the specification for access instructions.

Lengthy table referenced here
US08633009-20140121-T00045
Please refer to the end of the specification for access instructions.

Lengthy table referenced here
US08633009-20140121-T00046
Please refer to the end of the specification for access instructions.

Lengthy table referenced here
US08633009-20140121-T00047
Please refer to the end of the specification for access instructions.

Lengthy table referenced here
US08633009-20140121-T00048
Please refer to the end of the specification for access instructions.

Lengthy table referenced here
US08633009-20140121-T00049
Please refer to the end of the specification for access instructions.

Lengthy table referenced here
US08633009-20140121-T00050
Please refer to the end of the specification for access instructions.

Lengthy table referenced here
US08633009-20140121-T00051
Please refer to the end of the specification for access instructions.

Lengthy table referenced here
US08633009-20140121-T00052
Please refer to the end of the specification for access instructions.

Lengthy table referenced here
US08633009-20140121-T00053
Please refer to the end of the specification for access instructions.

Lengthy table referenced here
US08633009-20140121-T00054
Please refer to the end of the specification for access instructions.

Lengthy table referenced here
US08633009-20140121-T00055
Please refer to the end of the specification for access instructions.

Lengthy table referenced here
US08633009-20140121-T00056
Please refer to the end of the specification for access instructions.

Lengthy table referenced here
US08633009-20140121-T00057
Please refer to the end of the specification for access instructions.

Lengthy table referenced here
US08633009-20140121-T00058
Please refer to the end of the specification for access instructions.

Lengthy table referenced here
US08633009-20140121-T00059
Please refer to the end of the specification for access instructions.

Lengthy table referenced here
US08633009-20140121-T00060
Please refer to the end of the specification for access instructions.

Lengthy table referenced here
US08633009-20140121-T00061
Please refer to the end of the specification for access instructions.

Lengthy table referenced here
US08633009-20140121-T00062
Please refer to the end of the specification for access instructions.

Lengthy table referenced here
US08633009-20140121-T00063
Please refer to the end of the specification for access instructions.

Lengthy table referenced here
US08633009-20140121-T00064
Please refer to the end of the specification for access instructions.

Lengthy table referenced here
US08633009-20140121-T00065
Please refer to the end of the specification for access instructions.

Lengthy table referenced here
US08633009-20140121-T00066
Please refer to the end of the specification for access instructions.

Lengthy table referenced here
US08633009-20140121-T00067
Please refer to the end of the specification for access instructions.

Lengthy table referenced here
US08633009-20140121-T00068
Please refer to the end of the specification for access instructions.

Lengthy table referenced here
US08633009-20140121-T00069
Please refer to the end of the specification for access instructions.

Lengthy table referenced here
US08633009-20140121-T00070
Please refer to the end of the specification for access instructions.

Lengthy table referenced here
US08633009-20140121-T00071
Please refer to the end of the specification for access instructions.

Lengthy table referenced here
US08633009-20140121-T00072
Please refer to the end of the specification for access instructions.

Lengthy table referenced here
US08633009-20140121-T00073
Please refer to the end of the specification for access instructions.

Lengthy table referenced here
US08633009-20140121-T00074
Please refer to the end of the specification for access instructions.

Lengthy table referenced here
US08633009-20140121-T00075
Please refer to the end of the specification for access instructions.

| | |
|---|---|
| Lengthy table referenced here<br>US08633009-20140121-T00076<br>Please refer to the end of the specification for access instructions. | Lengthy table referenced here<br>US08633009-20140121-T00084<br>Please refer to the end of the specification for access instructions. |
| Lengthy table referenced here<br>US08633009-20140121-T00077<br>Please refer to the end of the specification for access instructions. | Lengthy table referenced here<br>US08633009-20140121-T00085<br>Please refer to the end of the specification for access instructions. |
| Lengthy table referenced here<br>US08633009-20140121-T00078<br>Please refer to the end of the specification for access instructions. | Lengthy table referenced here<br>US08633009-20140121-T00086<br>Please refer to the end of the specification for access instructions. |
| Lengthy table referenced here<br>US08633009-20140121-T00079<br>Please refer to the end of the specification for access instructions. | Lengthy table referenced here<br>US08633009-20140121-T00087<br>Please refer to the end of the specification for access instructions. |
| Lengthy table referenced here<br>US08633009-20140121-T00080<br>Please refer to the end of the specification for access instructions. | Lengthy table referenced here<br>US08633009-20140121-T00088<br>Please refer to the end of the specification for access instructions. |
| Lengthy table referenced here<br>US08633009-20140121-T00081<br>Please refer to the end of the specification for access instructions. | Lengthy table referenced here<br>US08633009-20140121-T00089<br>Please refer to the end of the specification for access instructions. |
| Lengthy table referenced here<br>US08633009-20140121-T00082<br>Please refer to the end of the specification for access instructions. | Lengthy table referenced here<br>US08633009-20140121-T00090<br>Please refer to the end of the specification for access instructions. |
| Lengthy table referenced here<br>US08633009-20140121-T00083<br>Please refer to the end of the specification for access instructions. | Lengthy table referenced here<br>US08633009-20140121-T00091<br>Please refer to the end of the specification for access instructions. |

Lengthy table referenced here

US08633009-20140121-T00092

Please refer to the end of the specification for access instructions.

Lengthy table referenced here

US08633009-20140121-T00093

Please refer to the end of the specification for access instructions.

Lengthy table referenced here

US08633009-20140121-T00094

Please refer to the end of the specification for access instructions.

Equivalents

Those skilled in the art will recognize, or be able to understand that the foregoing description and examples are illustrative of practicing the provided invention. Those skilled in the art will be able to ascertain using no more than routine experimentation, many variations of the detail presented herein may be made to the specific embodiments of the invention described herein without departing from the spirit and scope of the present invention.

LENGTHY TABLES

The patent contains a lengthy table section. A copy of the table is available in electronic form from the USPTO web site (http://seqdata.uspto.gov/?pageRequest=docDetail&DocID=US08633009B2). An electronic copy of the table will also be available from the USPTO upon request and payment of the fee set forth in 37 CFR 1.19(b)(3).

What is claimed is:

1. An engineered *Y. lipolytica* strain comprising:
a combination of two or more quinonogenic modifications selected from the group consisting of:
  a. increased expression or activity of a GGPP synthase polypeptide;
  b. increased expression or activity of a truncated HMG CoA reductase polypeptide;
  c. increased expression or activity of a 4-hydroxybenzoate polyprenyl transferase polypeptide;
  d. increased expression or activity of a decaprenyl diphosphate synthase polypeptide;
  e. increased expression or activity of a DAHP synthase polypeptide;
  f. increased expression or activity of a chorismate lyase polypeptide;
  g. increased expression or activity of a shikimate pathway polypeptide;
  h. increased expression or activity of a chorismate mutase polypeptide;
  i. increased expression or activity of a transketolase polypeptide;
  j. increased expression or activity of an FPP synthase polypeptide;
  k. increased expression or activity of an IPP isomerase polypeptide;
  l. increased expression or activity of an HMG-CoA synthase polypeptide;
  m. increased expression or activity of a mevalonate kinase polypeptide;
  n. increased expression or activity of a phosphomevalonate kinase polypeptide;
  o. increased expression or activity of a mevalonate pyrophosphate decarboxylate polypeptide;
  p. increased expression or activity of a cytosolic malic enzyme polypeptide;
  q. increased expression or activity of a malate dehydrogenase polypeptide;
  r. increased expression or activity of an AMP deaminase polypeptide;
  s. increased expression or activity of a glucose 6 phosphate dehydrogenase polypeptide;
  t. increased expression or activity of a malate dehydrogenase homolog2 polypeptide;
  v. increased expression or activity of a GND1-6-phosphogluconate dehydrogenase polypeptide;
  w. increased expression or activity of a isocitrate dehydrogenase polypeptide;
  x increased expression or activity of a IDH2-isocitrate dehydrogenase polypeptide;
  y. increased expression or activity of a fructose 1,6 bisphosphatase polypeptide;
  z. increased expression or activity of an Erg10-acetoacetyl CoA thiolase polypeptide;
  aa. increased expression or activity of an ATP citrate lyase subunit 2 polypeptide;
  bb. increased expression or activity of an ATP citrate lyase subunit 1 polypeptide;
  cc. increased expression or activity of a chorsimate synthase polypeptide;
  dd. decreased expression or activity of a squalene synthase polypeptide;
  ee. decreased expression or activity of a prenyldiphosphate synthase polypeptide; and
  ff. decreased expression or activity of a PHB polyprenyltransferase polypeptide;
wherein as a result of the combination of two or more quinonogenic modifications the engineered *Y. lipolytica* strain produces at least one quinone derived compound to at least about 1% of its dry cell weight; and
wherein the engineered strain can accumulate lipid to at least about 20% of its dry cell weight.

2. The engineered *Y. lipolytica* strain of claim 1, wherein the combination of two or more quinonogenic modifications comprises:

a. increased expression or activity of a GGPP synthase polypeptide;
b. increased expression or activity of a 4-hydroxybenzoate polyprenyl transferase polypeptide;
c. increased expression or activity of a decaprenyl diphosphate synthase polypeptide;
d. increased expression or activity of a DAHP synthase polypeptide; and
e. increased expression or activity of a chorismate lyase polypeptide.

3. The engineered *Y. lipolytica* strain of claim 1, further comprising at least one oleaginic modification.

* * * * *

UNITED STATES PATENT AND TRADEMARK OFFICE
CERTIFICATE OF CORRECTION

PATENT NO. : 8,633,009 B2  Page 1 of 4
APPLICATION NO. : 12/293237
DATED : January 21, 2014
INVENTOR(S) : Bailey et al.

It is certified that error appears in the above-identified patent and that said Letters Patent is hereby corrected as shown below:

In the Claims

On the last page of the patent, Col. 103, Line 30, correct Claim 1 "x" from:

"1. An engineered *Y. lipolytica* strain comprising:
   a combination of two or more quinonogenic modifications selected from the group consisting of:
   a. increased expression or activity of a GGPP synthase polypeptide;
   b. increased expression or activity of a truncated HMG CoA reductase polypeptide;
   c. increased expression or activity of a 4-hydroxybenzoate polyprenyl transferase polypeptide;
   d. increased expression or activity of a decaprenyl diphosphate synthase polypeptide;
   e. increased expression or activity of a DAHP synthase polypeptide;
   f. increased expression or activity of a chorismate lyase polypeptide;
   g. increased expression or activity of a shikimate pathway polypeptide;
   h. increased expression or activity of a chorismate mutase polypeptide;
   i. increased expression or activity of a transketolase polypeptide;
   j. increased expression or activity of an FPP synthase polypeptide;
   k. increased expression or activity of an IPP isomerase polypeptide;
   l. increased expression or activity of an HMG-CoA synthase polypeptide;
   m. increased expression or activity of a mevalonate kinase polypeptide;
   n. increased expression or activity of a phosphomevalonate kinase polypeptide;
   o. increased expression or activity of a mevalonate pyrophosphate decarboxylate Signed and Sealed this
Eighth Day of April, 2014

Michelle K. Lee
*Deputy Director of the United States Patent and Trademark Office*

CERTIFICATE OF CORRECTION (continued)
U.S. Pat. No. 8,633,009 B2 polypeptide;

p.    increased expression or activity of a cytosolic malic enzyme polypeptide;

q.    increased expression or activity of a malate dehydrogenase polypeptide;

r.    increased expression or activity of an AMP deaminase polypeptide;

s.    increased expression or activity of a glucose 6 phosphate dehydrogenase polypeptide;

t.    increased expression or activity of a malate dehydrogenase homolog2 polypeptide;

v.    increased expression or activity of a GND1-6-phosphogluconate dehydrogenase polypeptide;

w.    increased expression or activity of a isocitrate dehydrogenase polypeptide;

x    increased expression or activity of a IDH2-isocitrate dehydrogenase polypeptide;

y.    increased expression or activity of a fructose 1,6 bisphosphatase polypeptide;

z.    increased expression or activity of an Erg10-acetoacetyl CoA thiolase polypeptide;

aa.    increased expression or activity of an ATP citrate lyase subunit 2 polypeptide;

bb.    increased expression or activity of an ATP citrate lyase subunit 1 polypeptide;

cc.    increased expression or activity of a chorsimate synthase polypeptide;

dd.    decreased expression or activity of a squalene synthase polypeptide;

ee.    decreased expression or activity of a prenyldiphosphate synthase polypeptide; and ff.    decreased expression or activity of a PHB polyprenyltransferase polypeptide;

wherein as a result of the combination of two or more quinonogenic modifications the engineered *Y. lipolytica* strain produces at least one quinone derived compound to at least about 1% of its dry cell weight; and wherein the engineered strain can accumulate lipid to at least about 20% of its dry cell weight."

to read:

-- 1. An engineered *Y. lipolytica* strain comprising:

a combination of two or more quinonogenic modifications selected from the group consisting of:

a.    increased expression or activity of a GGPP synthase polypeptide;

b. increased expression or activity of a truncated HMG CoA reductase polypeptide;

c. increased expression or activity of a 4-hydroxybenzoate polyprenyl transferase polypeptide;

d. increased expression or activity of a decaprenyl diphosphate synthase polypeptide;

e. increased expression or activity of a DAHP synthase polypeptide;

f. increased expression or activity of a chorismate lyase polypeptide;

g. increased expression or activity of a shikimate pathway polypeptide;

h. increased expression or activity of a chorismate mutase polypeptide;

i. increased expression or activity of a transketolase polypeptide;

j. increased expression or activity of an FPP synthase polypeptide;

k. increased expression or activity of an IPP isomerase polypeptide;

l. increased expression or activity of an HMG-CoA synthase polypeptide;

m. increased expression or activity of a mevalonate kinase polypeptide;

n. increased expression or activity of a phosphomevalonate kinase polypeptide;

o. increased expression or activity of a mevalonate pyrophosphate decarboxylate polypeptide;

p. increased expression or activity of a cytosolic malic enzyme polypeptide;

q. increased expression or activity of a malate dehydrogenase polypeptide;

r. increased expression or activity of an AMP deaminase polypeptide;

s. increased expression or activity of a glucose 6 phosphate dehydrogenase polypeptide;

t. increased expression or activity of a malate dehydrogenase homolog2 polypeptide;

v. increased expression or activity of a GND1-6-phosphogluconate dehydrogenase polypeptide;

w. increased expression or activity of a isocitrate dehydrogenase polypeptide;

x. increased expression or activity of a IDH2-isocitrate dehydrogenase polypeptide;

y. increased expression or activity of a fructose 1,6 bisphosphatase polypeptide;

z. increased expression or activity of an Erg10-acetoacetyl CoA thiolase polypeptide;

aa. increased expression or activity of an ATP citrate lyase subunit 2 polypeptide;

CERTIFICATE OF CORRECTION (continued)
U.S. Pat. No. 8,633,009 B2 bb.        increased expression or activity of an ATP citrate lyase subunit 1 polypeptide;

cc.        increased expression or activity of a chorsimate synthase polypeptide;

dd.        decreased expression or activity of a squalene synthase polypeptide;

ee.        decreased expression or activity of a prenyldiphosphate synthase polypeptide; and ff.        decreased expression or activity of a PHB polyprenyltransferase polypeptide;

wherein as a result of the combination of two or more quinonogenic modifications the engineered *Y. lipolytica* strain produces at least one quinone derived compound to at least about 1% of its dry cell weight; and wherein the engineered strain can accumulate lipid to at least about 20% of its dry cell weight. --